US011732046B2

(12) United States Patent
Yoles et al.

(10) Patent No.: US 11,732,046 B2

(45) **Date of Patent: *Aug. 22, 2023**

(54) MODIFIED ANTI-PD-L1 ANTIBODY AND METHODS AND USES FOR TREATING A NEURODEGENERATIVE DISEASE

(71) Applicants: ImmunoBrain Checkpoint, Inc., Dover, DE (US); Yeda Research and Development Co. Ltd., Rehovot (IL)

(72) Inventors: Ester Yoles, Beit-Gamliel (IL); Berit Olsen Krogh, Valby (DK); Allan Jensen, Valby (DK); Jan Egebjerg, Valby (DK); Carol David, Rehovot (IL); Kuti Baruch, Ness Ziona (IL); Michal Eisenbach-Schwartz, Rehovot (IL)

(73) Assignees: ImmunoBrain Checkpoint, Inc., Dover, DE (US); Yeda Research and Development Co. Ltd., Rehovot (IL)

( * ) Notice: Subject to any disclaimer, the term of this patent is extended or adjusted under 35 U.S.C. 154(b) by 298 days.

This patent is subject to a terminal disclaimer.

(21) Appl. No.: 17/222,370

(22) Filed: Apr. 5, 2021

(65) Prior Publication Data

US 2021/0221893 A1 Jul. 22, 2021

Related U.S. Application Data

(63) Continuation of application No. 16/852,508, filed on Apr. 19, 2020, now Pat. No. 10,995,141.

(Continued)

(30) Foreign Application Priority Data

Apr. 19, 2019 (EP) .................................... 19170438

(51) Int. Cl.

| | |
|---|---|
| *C07K 16/28* | (2006.01) |
| *A61P 25/00* | (2006.01) |
| *A61K 39/00* | (2006.01) |

(52) U.S. Cl.

CPC .... *C07K 16/2827* (2013.01); *A61K 2039/505* (2013.01); *C07K 2317/515* (2013.01); *C07K 2317/56* (2013.01)

(58) Field of Classification Search

None

See application file for complete search history.

(56) References Cited

U.S. PATENT DOCUMENTS

| | | | |
|---|---|---|---|
| 7,563,869 | B2 | 7/2009 | Honjo et al. |
| 8,008,449 | B2 | 8/2011 | Korman et al. |

(Continued)

FOREIGN PATENT DOCUMENTS

| | | | |
|---|---|---|---|
| EP | 2320940 | B1 | 3/2015 |
| EP | 1575484 | B1 | 7/2015 |

(Continued)

OTHER PUBLICATIONS

Nebbia, et al., Upregulation of the Tim-3/Galectin-9 Pathway of T Cell Exhaustion in Chronic Hepatitus B Virus Infection, PLoS ONE 7(10): e47648, pp. 1-15 (2012).

(Continued)

*Primary Examiner* — Aurora M Fontainhas

(74) *Attorney, Agent, or Firm* — UltimatEdge IP Law Group, P.C.; Dean G. Stathakis

(57) ABSTRACT

The present specification discloses modified anti-PD-L1 antibodies that abolishes Fc-related effector function and enhances clearance rate while maintaining therapeutic efficacy for neurodegenerative disease modification. The present specification also discloses nucleic acid sequences and expression constructs encoding such modified anti-PD-L1

(Continued)

antibodies as well as methods of making such modified anti-PD-L1 antibodies. In addition, the present specification discloses methods of treatment and uses that employ an administration regime of the disclosed anti-PD-L1 antibodies that ensures the antibodies are present for only a specific period of time and then are sufficiently cleared from the body to ensure treatment efficacy is maintained.

19 Claims, 30 Drawing Sheets

Specification includes a Sequence Listing.

Related U.S. Application Data

(60) Provisional application No. 62/836,247, filed on Apr. 19, 2019.

(56) References Cited

U.S. PATENT DOCUMENTS 8,552,154 B2 10/2013 Freeman et al.
8,629,098 B2 1/2014 Fahmy et al.
8,709,416 B2 4/2014 Langermann et al.
8,735,553 B1 5/2014 Li et al.
8,779,105 B2 7/2014 Korman et al.
8,900,587 B2 12/2014 Carven et al.
8,927,697 B2 1/2015 Davis et al.
8,945,561 B2 2/2015 Davis
8,952,136 B2 2/2015 Carven et al.
8,993,731 B2 3/2015 Tyson
9,085,625 B2 7/2015 Labrijn et al.
9,394,365 B1 7/2016 Eisenbach-Schwartz et al.
9,512,225 B2 12/2016 Eisenbach-Schwartz et al.
9,512,227 B2 12/2016 Eisenbach-Schwartz et al.
9,534,052 B2 1/2017 Eisenbach-Schwartz et al.
9,567,399 B1 2/2017 Campbell et al.
9,617,338 B1 4/2017 Campbell et al.
9,856,318 B2 1/2018 Eisenbach-Schwartz et al.
9,982,047 B2 5/2018 Eisenbach-Schwartz et al.
9,982,048 B2 5/2018 Eisenbach-Schwartz et al.
9,982,049 B2 5/2018 Eisenbach-Schwartz et al.
9,982,050 B2 5/2018 Eisenbach-Schwartz et al.
9,982,051 B2 5/2018 Eisenbach-Schwartz et al.
10,144,778 B2 12/2018 Eisenbach-Schwartz et al.
10,214,585 B2 2/2019 Eisenbach-Schwartz et al.
10,519,237 B2 12/2019 Eisenbach-Schwartz et al.
10,618,963 B2 4/2020 Eisenbach-Schwartz et al.
2004/0033497 A1 2/2004 Alarcon-Riquelme et al.
2010/0061992 A1 3/2010 Anderson et al.
2014/0004081 A1 1/2014 Cobbold et al.
2014/0023614 A1 1/2014 Barawkar et al.
2014/0044738 A1 2/2014 Langermann et al.
2014/0093511 A1 4/2014 Lonberg et al.
2014/0099254 A1 4/2014 Chang et al.
2014/0127227 A1 5/2014 Chang
2014/0212446 A1 7/2014 Riley et al.
2014/0220021 A1 8/2014 Shibayama et al.
2014/0227180 A1 8/2014 Govindan et al.
2014/0234296 A1 8/2014 Sharma et al.
2014/0234331 A1 8/2014 Korman et al.
2014/0271540 A1 9/2014 Stogniew et al.
2014/0271677 A1 9/2014 Palese et al.
2014/0294759 A1 10/2014 Chu et al.
2014/0294765 A1 10/2014 Cojocaru et al.
2014/0294852 A1 10/2014 Korman et al.
2014/0302070 A1 10/2014 Chen et al.
2014/0314714 A1 10/2014 Honjo et al.
2014/0328833 A1 11/2014 Korman et al.
2014/0335048 A1 11/2014 Stogniew et al.
2014/0335093 A1 11/2014 Olive
2014/0341920 A1 11/2014 Noelle
2014/0348743 A1 11/2014 Korman et al.
2014/0348786 A1 11/2014 Berzofsky et al.
2014/0356363 A1 12/2014 Zhou et al.
2014/0377250 A1 12/2014 Bantia
2014/0377253 A1 12/2014 Harding et al.
2014/0377334 A1 12/2014 Irvine et al.
2015/0004175 A1 1/2015 Kaech et al.
2015/0017194 A1 1/2015 Akahata et al.
2015/0018516 A1 1/2015 Govindan et al.
2015/0079109 A1 3/2015 Li et al.
2015/0086584 A1 3/2015 Gilboa et al.
2015/0118222 A1 4/2015 Levy et al.
2015/0118234 A1 4/2015 Honjo et al.
2015/0132290 A1 5/2015 Fuchs et al.
2015/0152180 A1 6/2015 Davis et al.
2015/0165021 A1 6/2015 Mashal et al.
2015/0166661 A1 6/2015 Chen et al.
2015/0183875 A1 7/2015 Cobbold et al.
2015/0203560 A1 7/2015 Grewal et al.
2015/0203579 A1 7/2015 Papadopoulos et al.
2015/0210769 A1 7/2015 Freeman et al.
2015/0216970 A1 8/2015 Grogan et al.
2015/0218274 A1 8/2015 Sabatos-Peyton et al.
2018/0179287 A1 6/2018 Kuenkele et al.

FOREIGN PATENT DOCUMENTS

WO 2005046719 A1 5/2005
WO 2006121168 A1 11/2006
WO 2007005874 A2 1/2007
WO 2011056300 A1 5/2011
WO 2011110604 A1 9/2011
WO 2012075291 A1 6/2012
WO 2013022738 A1 2/2013
WO 2014022332 A1 2/2014
WO 2014037952 A1 3/2014
WO 2014045305 A1 3/2014
WO 2014059251 A1 4/2014
WO 2014066527 A2 5/2014
WO 2014071402 A1 5/2014
WO 2014074852 A1 5/2014
WO 2014127917 A1 8/2014
WO 2014134355 A1 9/2014
WO 2014144791 A2 9/2014
WO 2014144885 A2 9/2014
WO 2014179664 A2 11/2014
WO 2014183066 A2 11/2014
WO 2014186035 A1 11/2014
WO 2014206107 A1 12/2014
WO 2014209804 A1 12/2014
WO 2015009856 A2 1/2015
WO 2015018528 A1 2/2015
WO 2015024042 A1 2/2015
WO 2015024060 A1 2/2015
WO 2015026684 A1 2/2015
WO 2015036394 A1 3/2015
WO 2015058573 A1 4/2015
WO 2015063187 A1 5/2015
WO 2015082499 A2 6/2015
WO 2015084721 A1 6/2015
WO 2015085210 A1 6/2015
WO 2015085847 A1 6/2015
WO 2015095895 A1 6/2015
WO 2015103072 A1 7/2015
WO 2015103602 A1 7/2015
WO 2015117002 A1 8/2015
WO 2015136541 A2 9/2015
WO 2017009829 A1 1/2017
WO 2017042633 A2 3/2017
WO 2017220569 A1 12/2017
WO 2017220990 A1 12/2017

OTHER PUBLICATIONS

Newell, et al., Imaging Resolution and Transient Clinical Improvement Following Cyclophosphamide Treatment of a Cerebral Amyloid Angiopathy-Related Lesion, Alzheimer's & Dementia 8(4): S775-S776 (2012).

Ohaegbulam, et al., Human Cancer Immunotherapy with Antibodies to the PD-1 and PD-L1 Pathway, Trends Mol. Med. 21(1): 24-33(2015).

(56) References Cited

OTHER PUBLICATIONS

Pardoll, et al., The Blockade of Immune Checkpoints in Cancer Immunotherapy, Nat. Rev. Cancer 12: 252-264 (2012).
Peng, et al., PD-1 Blockade Enhances T-Cell Migration to Tumors by Elevating IFN-gamma Inducible Chemokines, Cancer Res. 72(20): 5209-5218 (2012).
Pere, et al., A CCR4 Antagonist Combined with Vaccines Induces Antigen-Specific CD8+ T Cells and Tumor Immunity Against Self Antigens, Blood 118: 4853-4862 (2011).
Qin, et al., MicroRNA-126 Regulates the Induction and Function of CD4(+) Foxp3(+) Regulatory T Cells through PI3K/AKT Pathway, J. Cell. Mol. Med. 17: 252-264 (2013).
Quiroga, et al., Inducible Costimulator: A Modulator of IFN-gamma Production in Human Tuberculosis, J. Immunol. 176: 5965-5974 (2006).
Raposo, et al., Central Nervous System Repair Requires Both Effector and Regulatory T Cells with Distinct Temporal and Spatial Profiles, J. Neuroimmunol. 275: 206, Abstract 115 (2014).
Raynor, et al., Homeostasis and Function of Regulatory T Cells in Aging, Curr. Opin. Immunol. 24: 482-487 (2012).
Reines, et al., Rofecoxib No Effect on Alzheimer's Disease in a 1-Year, Randomized, Blinded, Controlled Study, Neurol. 62: pp. 66-71 (2004).
Reiss, et al., Harnessing the Power of the Immune System via Blockade of PD-1 and PD-L1: A Promising New Anticancer Strategy, Immunother. 6(4): 459-475 (2014).
Ren, et al., Programmed Death-1 Pathway Limits Central Nervous System Inflammation and Neurologic Deficits in Murine Experimental Stroke, Stroke 42: 2578-2583 (2011).
Rosenkranz, et al., Higher Frequency of Regulatory T cells in the Elderly and Increased Suppressive Activity in Neurodegeneration, J. Neuroimmunol. 188: 117-127 (2007).
Sakthivel, Attenuation of Immune-Mediated Influenza Pneumonia by Targeting the Inducible Co-Stimulator (ICOS) Molecule on T Cells, PLoS ONE 9(7): e100970, pp. 1-11 (2014).
Sakuishi, et al., Targeting Tim-3 and PD-1 Pathways to Reverse T cell Exhaustion and Restore Anti-Tumor Immunity, J. Exp. Med. 207: 2187-2194 (2010).
Salama, et al., Critical Role of the Programmed Death-1 (PD-1) Pathway in Regulation of Experimental Autoimmune Encephalomyelitis, J. Exp. Med. 198(1): 71-78 (2003).
Saresella, et al., A Potential Role for the PD1/PD-L1 Pathway in the Neuroinflammation of Alzheimer's Disease, Neurobiol. Aging 33: 624.e11-624e22 (2012).
Saresella, et al., PD1 Negative and PD1 Positive CD4+ T Regulatory Cells in Mild Cognitive Impairment and Alzheimer's Disease, J. Alzheimers Dis. 21: 927-938 (2010).
Schreiber, et al., Cancer Immunoediting: Integrating Immunity's Roles in Cancer Suppression and Promotion, Science 331: 1565-1570 (2011).
Schwartz, et al., Breaking Peripheral Immune Tolerance to CNS Antigens in Neurodegenerative Diseases Boosting Autoimmunity to Fight-Off Chronic Neuroinflammation, J. Autoimmun. 54: 8-14 (2014).
Schwartz, et al., The Resolution of Neuroinflammation in Neurodegeneration: Leukocyte Recruitment via the Choroid Plexus, EMBO J. 33(1): 7-22.(2014).
Schwartz, et al., Therapeutic T Cell-Based Vaccination for Neurodegenerative Disorders, The Role of CD4+ CD25+ Regulatory T cells, Ann. NY Acad. Sci. 1051: 701-708 (2005).
Sharpe, et al., The B7-CD28 Superfamily, Nat. Rev. Immunol. 2: 116-126 (2002).
Shecter, et al., Infiltrating Blood-Derived Macrophages are Vital Cells Playing an Anti-inflammatory Role in Recovery from Spinal Cord Injury in Mice, PLoS Med, 6(1): e1000113, pp. 1-17 (2009).
Shevchenko, et al., Low-Dose Gemcitabine Depletes Regulatory T Cells and Improves Survival in the Orthotopic Panc02 Model of Pancreatic Cancer, Int. J. Cancer 133: 98-107 (2013).
Shimmura-Tomita, et al., Galectin-9-Mediated Protection from Allo-Specific T Cells as a Mechanism of Immune Privilege of Corneal Allografts, PLoS ONE 8(5): e63620, pp. 1-11. (2013).
Simpson, et al., Fc-Dependent Depletion of Tumor-Infiltrating Regulatory T Cells Co-Defines the Efficacy of Anti-CTLA-4 Therapy Against Melanoma, J. Exp. Med. 210: 1695-1710 (2013).
Simpson, et al., Regulation of CD4 T Cell Activation and Effector Function by Inducible Costimulator (ICOS), Curr. Opin. Immunol. 22: 326-332 (2010).
Smith, et al., The Microbial Metabolites, Short-Chain Fatty Acids, Regulate Colonic Treg Cell Homeostasis, Science 341: 569-573 (2013).
Terme, et al., Modulation of Immunity by Antiangiogenic Molecules in Cancer, Clin. Develop. Imunol. 2012(492920): 1-8 (2012).
Thomas-Schoemann, et al., Arsenic Trioxide Exerts Antitumor Activity through Regulatory T cell Depletion Mediated by Oxidative Stress in a Murine Model of Colon Cancer, J. Immunol. 189: 5171-5177 (2012).
Voo, et al., Antibodies Targeting Human OX40 Expand Effector T Cells and Block Inducible and Natural Regulatory T Cell Function, J. Immunol. 191: 3641-3650 (2013).
Wainwright, et al., Targeting Tregs in Malignant Brain Cancer: Overcoming IDO, Frontiers Immunol. 4(16): 1-17 (2013).
Wang, et al., ]TIM-3-Galectin-9 Pathway Involves the Suppression Induced by CD4+CD25+ Regulatory T Cells, Immunobiol. 214: 342-349 (2009).
Wang, et al., PD1 Blockade Reverses the Suppression of Melanoma Antigen-Specific CTL by CD4+CD25 Hi Regulatory T Cells, Int. Immunol. 21(9): 1065-1077 (2009).
Wang, et al., Down-Modulation of Programmed Death 1 Alters Regulatory T Cells and Promotes Experimental Autoimmune Encephalomyelitis, J. Neurosci. Res. 88: 7-15 (2010).
Ward, et al., The Soluble Isoform of CTLA-4 as a Regulator of T-Cell Responses, Eur. J. Immunol. 43: 1274-1285 (2013).
Webster, et al., Frontiers in Genetics, 5(88): 1-23 (2014).
Weiskopf, et al., Improving Macrophage Responses to Therapeutic Antibodies by Molecular Engineering of SIRPalpha Variants, Oncoimmunol. 2(9): e25773-1-e25773-3 (2013).
WIPO, PCT Form ISA237 Written Opinion of the International Searching Authority for International Patent Application Serial No. PCT/IB2016/001433, pp. 7 (dated May 26, 2017).
WIPO, PCT Form ISA210 International Search Report for International Patent Application Serial No. PCT/IB2016/001433, pp. 5 (dated May 26, 2017).
WIPO, PCT Form ISA210 International Search Report for International Patent Application Serial No. PCT/IL2015/050265, pp. 6 (dated Sep. 28, 2015).
WIPO, PCT Form ISA210 International Search Report for International Patent Application Serial No. PCT/IL2016/050750, pp. 5 (dated Nov. 4, 2016).
WIPO, PCT Form ISA237 Written Opinion of the International Searching Authority for International Patent Application Serial No. PCT/IL2015/050265, pp. 10 (dated Sep. 28, 2015).
WIPO, PCT Form ISA237 Written Opinion of the International Searching Authority for International Patent Application Serial No. PCT/IL2016/050750, pp. 9 (dated Nov. 4, 2016).
Zha, et al., Chronic Thoracic Spinal Cord Injury Impairs CD8+ T-Cell Function by Up-Regulating Programmed Cell Death-1 Expression, J. Neuroinflamm. 11(65): 1-18 (2014).
Zhao, et al., Regulation of Neuroinflammation through Programmed Death-1/Programed Death Ligand Signaling in Neurological Disorders, Frontiers Cell. Neurosci. 8(271): 1-7 (2014).
Zheng, et al., New Approaches to Treating Alzheimer's Disease, Pers. Med. Chem. 7: 1-8 (2015).
Zhu, et al., p300 Exerts an Epigenetic Role in Chronic Neuropathic Pain through its Acetyltransferase Activity in Rats Following Chronic Constriction Injury (CCI), Mol. Pain 8(84): 1-11 (2012).
Adapt-FS Research Group, Follow-Up Evaluation of Cognitive Function in the Randomized Alzheimer's Disease Anti-inflammatory Prevention Trial and its Follow-Up Study, Alzheimer's & Dementia 11: 216-225 (2015).

(56) References Cited

OTHER PUBLICATIONS

Adapt-FS Research Group, Naproxen and Celecoxib do not Prevent AD in Early Results from Randomized Controlled Trial, Neurol. 68: 1800-1808 (2007).
Aisen, et al., Effects of Rofecoxib or Naproxen vs Placebo on Alzheimer Disease Progression, A Randomized Controlled Trial, JAMA 289(21): 2819-2826 (2003).
Anderson, et al., Lag-3, Tim-3, and TIGIT: Co-Inhibitory Receptors with Specialized Functions in Immune Regulation, Immun. Rev. 44: 989-1004 (2016).
Angelov, et al., Therapeutic Vaccine for Acute and Chronic Motor Neuron Diseases: Implications for Amyotrophic Lateral Sclerosis, PNAS 100(8): 4790-4795 (2013).
Arvanitakis, et al., Relation of NSAIDs to Incident AD, Change in Cognitive Function, and AD Pathology, Neurol. 70: 2219-2225 (2008).
Avidan, et al., Vaccination with Autoantigen Protects Against Aggregated [beta]-Amyloid and Glutamate Toxicity by Controlling Microglia: Effect of CD4 +CD25 + T cells, Eur. J. Immunol. 34(12): 3434-3445 (2004).
Bai, et al., All-trans Retinoic Acid Down-Regulates Inflammatory Responses by Shifting the Treg/Th17 Profile in Human Ulcerative and Murine Colitis, J. Leukoc. Biol. 86: 959-969 (2009).
Baruch, et al., Aging-Induced Type 1 Interferon Response at the Choroid Plexus Negatively Affects Brain Function, Science 346(1): 89-93 (2014).
Baruch, et al., Breaking Immune Tolerance by Targeting Foxp3+ Regulatory T Cells Mitigates Alzheimer's Disease Pathology, Nat. Commun. 6(7967): 1-12 (2015).
Baruch, et al., Cerebral Nitric Oxide Represses Choroid Plexus NFkB-Dependent Gateway Activity for Leukocyte Trafficking, EMBO J. 34(13): 1816-1828 (2015).
Baruch, et al., CNS-Specific Immunity at the Choroid Plexus Shifts toward Destructive Th2 Inflammation in Brain Aging, PNAS 110(6): 2264-2269 (2013).
Baruch, et al., CNS-Specific T Cells Shape Brain Function via the Choroid Plexus, Brain Behav. Immun. 34: 11-16 (2013).
Baruch, et al., PD-1 Immune Checkpoint Bblockade Reduces Pathology and Improves Memory in Mouse Models of Alzheimer's Disease, Nat. Med. 22(2): 135-139 (2016).
Baruch, et al., Therapeutic potential of PD-1 immune checkpoint blockade in Alzheimer's disease, manuscript, Dept. of Neurobiology, Weizmann Institute of Science, 1-12.
Bodhankar, et al., PD-L 1 Enhances CNS Inflammation and Infarct Volume Following Experimental Stroke in Mice in Opposition to PD-1 , J. Neuroinflam. 10(1): 1-15 (2013).
Bodhankar, et al., Targeting Immune Co-Stimulatory Effects of PD-L1 and PD-L2 Might Represent an Effective Therapeutic Strategy in Stroke, Frontiers Cell. Neurosci. 8(228): 1-14 (2014).
Bowers, et al., Virtual Ligand Screening of the p300/CBP Histone Acetyltransferase: Identification of a Selective Small Molecule Inhibitor, Chem. Biol. 17: 471-482 (2010).
Brestoff, et al., Commensal Bacteria at the Interface of Host Metabolism and the Immune System, Nat. Immunol. 14(7): 676-684 (2013).
Butovsky, et al., Glatiramer Acetate Fights Against Alzheimer's Disease by Inducing Dendritic-Like Microglia Expressing Insulin-Like Growth Factor 1, PNAS 103(31): 11784-11789 (2006).
Butovsky, et al., Selective Ablation of Bone Marrow-Derived Dendritic Cells Increases Amyloid Plaques in a Mouse Alzheimer's Disease Model, Eur. J. Neurosci. 26(2): 413-416 (2007).
Colombo, et al., Regulatory-T-cell Inhibition Versus Depletion: The Right Choice in Cancer Immunotherapy, Nat. Rev. Cancer 7: 880-887 (2007).
Coyne, et al., Adding Fuel to the Fire: Immunogenic Intensification, Hum. Vacc. Immunother. 10: 3306-3312 (2014).
Dalotto-Moreno, et al., Targeting Galectin-1 Overcomes Breast Cancer-Associated Immunosuppression and Prevents Metastatic Disease, Cancer Res. 73(3): 1107-1117 (2013).
Duraiswamy, et al., Dual Blockade of PD-1 and CTLA-4 Combined with Tumor Vaccine Effectively Restores T-cell Rejection Function in Tumors—Response, Cancer Res. 74(2): 633-634 (2014).
Finnefrock, et al., PD-1 Blockade in Rhesus Macaques: Impact on Chronic Infection and Prophylactic Vaccination, J Immunol. 182(2): 980-987 (2009).
Francisco, et al., The PD-1 Pathway in Tolerance and Autoimmunity, Immunol. Rev. 236: 219-242 (2010).
Galvin, et al., Blocking Retinoic Acid Receptor-alpha Enhances the Efficacy of a Dendritic Cell Vaccine Against Tumours by Suppressing the Induction of Regulatory T Cells, Cancer Immunol. Immunother. 62: 1273-1282 (2013).
Ghiringhelli, et al., Production of Adenosine by Ectonucleotidases: A Key Factor in Tumor Immunoescape, J. Biomed Biotech. 2012(473712): 1-9 (2012).
Guo, et al., Alzheimer's Disease and Retinal Neurodegeneration, Curr. Alzheimer Res. 7: 1-12 (2010).
He, et al., The Role of Regulatory T Cells in Neurodegenerative Diseases, WIREs Syst. Biol. Med. 5: 153-180 (2013).
Heylmann, et al., Human CD4+CD25+ Regulatory T Cells are Sensitive to Low Dose Cyclophosphamide Implications for the Immune Response, PLoS ONE, 8(12): e83384, pp. 1-10 (2013).
Hezareh, et al., Effector Function Activities of a Panel of Mutants of a Broadly Neutralizing Antibody against Human Immunodeficiency Virus Type 1, J. Virol. 75(24): 12161-12168 (2001).
Hirayama, et al., Overcoming Regulatory T-cell Suppression by a Lyophilized Preparation of *Streptococcus pyogenes*, Eur. J. Immunol. 43: 989-1000 (2013).
Intlekofer, et al., Preclinical Rationale for CTLA-4 and PD-1 Blockage as Cancer Immunotherapy, J. Leukoc. Biol. 94(1): 25-39(2013).
Jin, et al., Role of PD-1 in Regulating T-Cell Immunity, Curr. Top. Microbiol. Immunol. 350: 17-37 (2011).
Joller, et al., Immune Checkpoints in Central Nervous System Autoimmunity, Immunol. Rev. 248: 122-139 (2012).
Ju, et al., The TIM-3/Galectin-9 Pathway Involves in the Homeostatis of Hepatic Tregs in a Mouse Model of Concanavalin A-Induced Hepatitis, Mol. Immunol. 58: 85-91 (2014).
Kawamoto, et al., Expression and Function of Inducible Co-Stimulator in Patients with Systemic Lupus Erythematosus: Possible Involvement in Excessive Interferon-γ and Anti-Double-Stranded DNA Antibody Production, Arthritis Res. Ther. 8(3): 1-14 (2006).
Keimowitz, Dementia Improvement with Cytotoxic Chemotherapy a Case of Alzheimer Disease and Multiple Myeloma, Arch. Neurol. 54(4): 485-488 (1997).
Kenanova, et al., Tailoring the Pharmacokinetics and Positron Emission Tomography Imaging Properties of Anti-Carcinoembryonic Antigen Single-Chain Fv-Fc Antibody Fragments, Cancer Res. 65(2): 622-631 (2005).
Kim, et al., Pan-Bcl-2 Inhibitor, GX15-070 (Obatoclax), Decreases Human T Regulatory lymphocytes while Preserving Effector T Lymphocytes: A Rationale for its Use in Combination Immunotherapy, J. Immunol. 192: 2622-2633 (2014).
Kroner, et al., PD-1 Regulates Neural Damage in Oligodendroglia-Induced Inflammation, PLoS ONE 4(2): e4405, pp. 1-9 (2009).
Kunis, et al., IFN-gamma-Dependent Activation of the Brain's Choroid Plexus for CNS Immune Surveillance and Repair, Brain 136: 3427-3440 (2013).
Kunis, et al., Immunization with a Myelin-Derived Antigen Activates the Brain's Choroid Plexus for Recruitment of Immunoregulatory Cells to the CNS and Attenuates Disease Progression in a Mouse Model of ALS, J. Neurosci. 35 (16): 6381-6393 (2015).
Leitner, et al., TIM-3 Does not Act as a Receptor for Galectin-9, PLoS Pathog. 9(3): e1003253 pp. 12 (2013).
Leung, et al., The CD28-B7 Family in Anti-Tumor Immunity: Emerging Concepts in Cancer Immunitherapy, Immune Network 14(6): 265-276 (2014).
Liu, et al., Inhibition of p300 Impairs Foxp3(+) T Regulatory Cell Function and Promotes Antitumor Immunity, Nat. Med. 19(9): 1173-1177 (2013).
Mcdermott, et al., PD-1 as a Potential Target in Cancer Therapy, Cancer Med. 2(5): 662-673 (2013).

(56) References Cited

OTHER PUBLICATIONS

Mellman, et al., Immunotherapy Comes of Age, Nature 480: 480-489 (2011).
U.S. Appl. No. 14/797,894, filed Jul. 13, 2015, 2016/0000909, U.S. Pat. No. 9,856,318.
U.S. Appl. No. 14/850,794, filed Sep. 10, 2015, 2016/0008463, U.S. Pat. No. 10,214,585.
U.S. Appl. No. 14/957,065, filed Dec. 2, 2015, U.S. Pat. No. 9,394,365.
U.S. Appl. No. 15/125,249, filed Sep. 12, 2016, 2017/0240634, U.S. Pat. No. 10,144,778.
U.S. Appl. No. 15/190,160, filed Jun. 22, 2016, U.S. Pat. No. 9,512,225.
U.S. Appl. No. 15,202,493, filed Jul. 5, 2016, U.S. Pat. No. 9,512,227.
U.S. Appl. No. 15,212,231, filed Jul. 16, 2016, 2016/0319021, U.S. Pat. No. 9,534,052.
U.S. Appl. No. 15/261,945, filed Sep. 10, 2016, 2017/0029508, U.S. Pat. No. 10,519,237.
U.S. Appl. No. 15,698,800, filed Sep. 8, 2017, 2018/0009893, U.S. Pat. No. 10,618,963.
U.S. Appl. No. 15,821,570, filed Nov. 22, 2017, 2018/0118826, U.S. Pat. No. 9,982,047.
U.S. Appl. No. 15,821,595, filed Nov. 22, 2017, 2018/0111997, U.S. Pat. No. 9,982,048.
U.S. Appl. No. 15/821,603, filed Nov. 22, 2017, 2018/0105592, U.S. Pat. No. 9,982,049.
U.S. Appl. No. 15/821,672, filed Nov. 22, 2017, 2018/0111998, U.S. Pat. No. 9,982,050.
U.S. Appl. No. 15/821,678, filed Nov. 22, 2017, 2018/0111999, U.S. Pat. No. 9,982,051.
U.S. Appl. No. 16/145,641, filed Sep. 28, 2018, 2019/0022198.
U.S. Appl. No. 16/167,226, filed Oct. 22, 2018, 2019/0011237, U.S. Pat. No. 10,961,309.
U.S. Appl. No. 16/284,081, filed Feb. 25, 2019, 2019/0185563, U.S. Pat. No. 10,981,989.
U.S. Appl. No. 16,728,587, filed Dec. 27, 2019, 2020/0140553.
U.S. Appl. No. 16,728,642, filed Dec. 27, 2019, 2020/0140555.
U.S. Appl. No. 16/852,508, filed Apr. 19, 2020, 2020/0332011, U.S. Pat. No. 10,995,141.
U.S. Appl. No. 17,186,960, filed Feb. 26, 2021.
U.S. Appl. No. 17/187,011, filed Feb. 26, 2021.
WIPO, PCTForm IB373 International Preliminary Report on Patentability for International Patent Application Serial No. PCT/IL2015/050265, pp. 12 (dated Sep. 22, 2016).

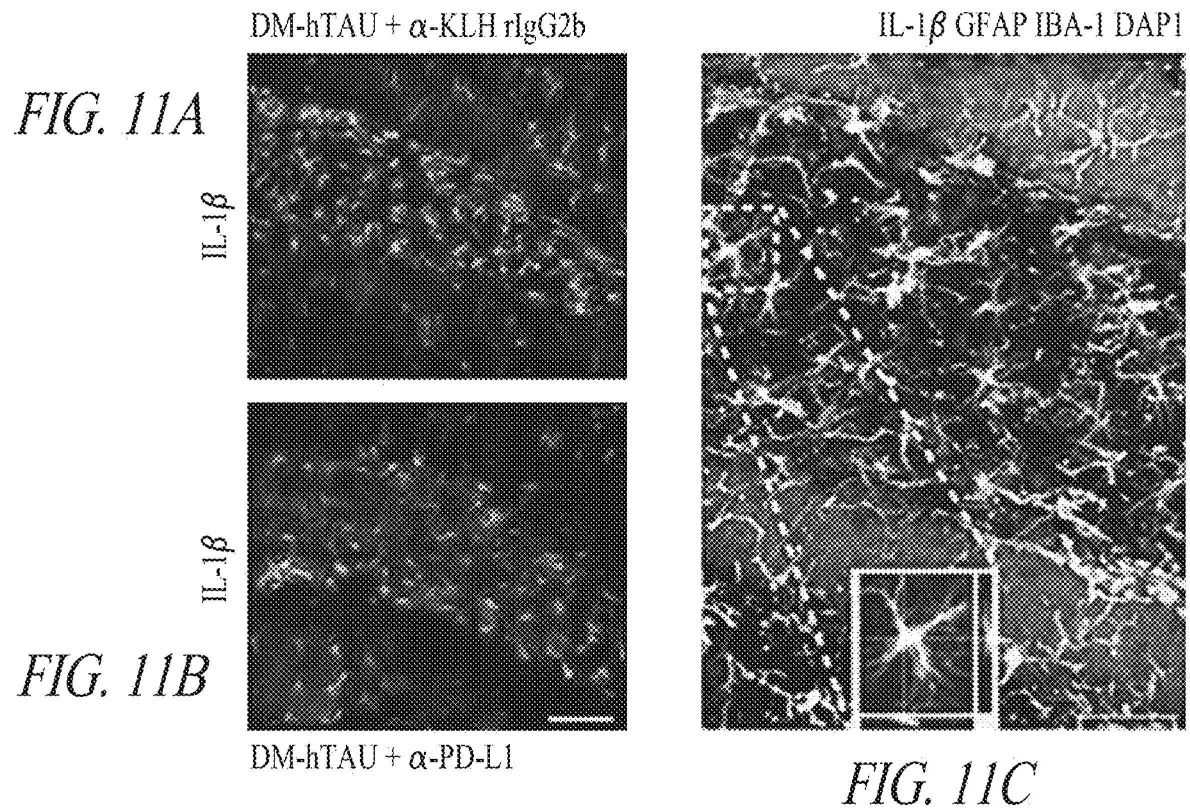
FIG. 11A
FIG. 11B
FIG. 11C
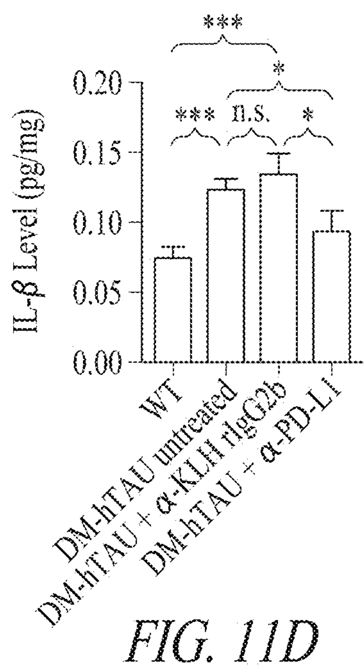
FIG. 11D
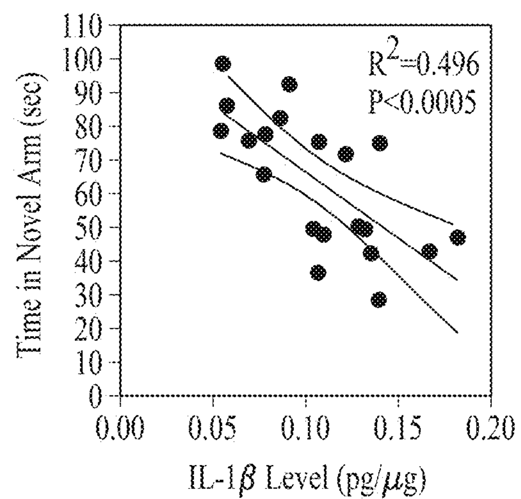
FIG. 11E

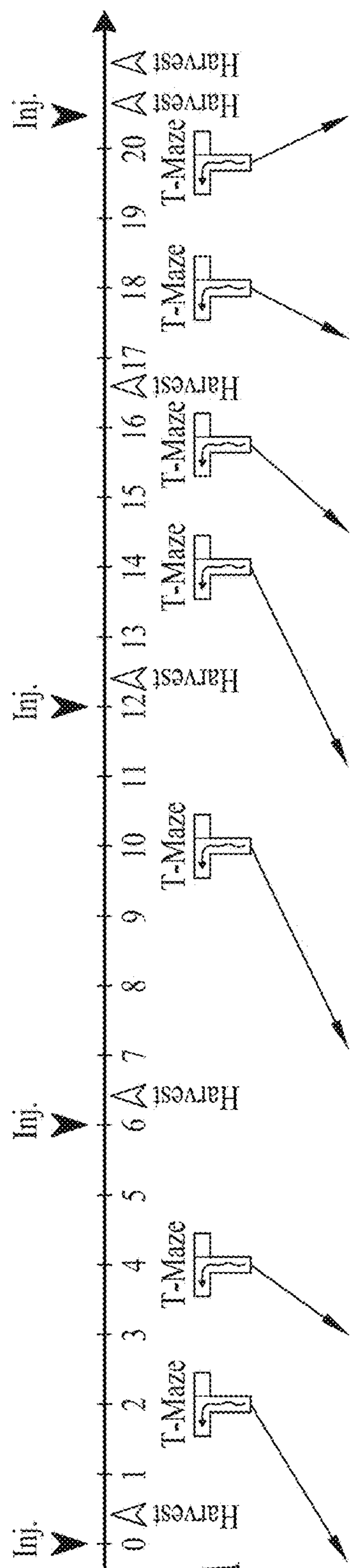
K257T/P301S
DM-Tau
6-7months old
Time (weeks)
Inj.
Harvest
T-Maze
FIG. 28A
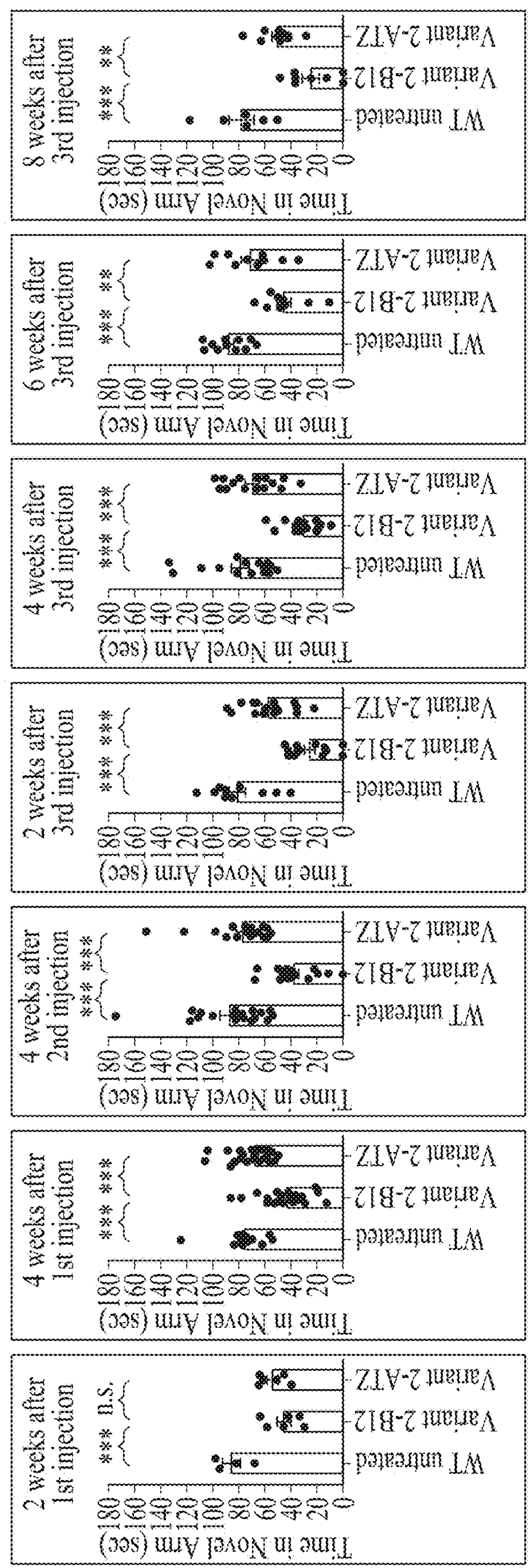
Time in Novel Arm (sec)
WT untreated
Variant 2-B12
Variant 2-ATZ
2 weeks after 1st injection
4 weeks after 1st injection
4 weeks after 2nd injection
2 weeks after 3rd injection
4 weeks after 3rd injection
6 weeks after 3rd injection
8 weeks after 3rd injection
n.s.
FIG. 28B
FIG. 28C
FIG. 28D
FIG. 28E
FIG. 28F
FIG. 28G
FIG. 28H Positive Control Antibody Target cell Lysis (%)

Conc. (μg/ml)

Variant 2-G09

Target cell Lysis (%)

Conc. (μg/ml)

```
                        SEQUENCE LISTING

<160> NUMBER OF SEQ ID NOS: 108

<210> SEQ ID NO 1
<211> LENGTH: 290
<212> TYPE: PRT
<213> ORGANISM: Homo sapiens

<400> SEQUENCE: 1

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175
```

```
Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290


<210> SEQ ID NO 2
<211> LENGTH: 122
<212> TYPE: PRT
<213> ORGANISM: Homo sapiens

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser
        115                 120


<210> SEQ ID NO 3
<211> LENGTH: 8
<212> TYPE: PRT
<213> ORGANISM: Homo sapiens

<400> SEQUENCE: 3

Gly Phe Thr Phe Asp Asp Tyr Ala
1               5


<210> SEQ ID NO 4
<211> LENGTH: 5
<212> TYPE: PRT
<213> ORGANISM: Homo sapiens

<400> SEQUENCE: 4

Asp Tyr Ala Met His
1               5
```

<210> SEQ ID NO 5
<211> LENGTH: 8
<212> TYPE: PRT
<213> ORGANISM: Homo sapiens

<400> SEQUENCE: 5

Ile Ser Trp Lys Ser Asn Ile Ile
1               5

<210> SEQ ID NO 6
<211> LENGTH: 17
<212> TYPE: PRT
<213> ORGANISM: Homo sapiens

<400> SEQUENCE: 6

Gly Ile Ser Trp Lys Ser Asn Ile Ile Gly Tyr Ala Asp Ser Val Lys
1               5                   10                  15

Gly

<210> SEQ ID NO 7
<211> LENGTH: 15
<212> TYPE: PRT
<213> ORGANISM: Homo sapiens

<400> SEQUENCE: 7

Ala Arg Asp Ile Thr Gly Ser Gly Ser Tyr Gly Trp Phe Asp Pro
1               5                   10                  15

<210> SEQ ID NO 8
<211> LENGTH: 13
<212> TYPE: PRT
<213> ORGANISM: Homo sapiens

<400> SEQUENCE: 8

Asp Ile Thr Gly Ser Gly Ser Tyr Gly Trp Phe Asp Pro
1               5                   10

<210> SEQ ID NO 9
<211> LENGTH: 107
<212> TYPE: PRT
<213> ORGANISM: Homo sapiens

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Pro Leu Ile
        35                  40                  45

Tyr Val Ala Ser Ser Leu Gln Ser Gly Val Pro Ser Ser Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Pro Ile
                85                  90                  95

Thr Phe Gly Gln Gly Thr Arg Leu Glu Ile Lys
            100                 105

<210> SEQ ID NO 10
<211> LENGTH: 6
<212> TYPE: PRT

<213> ORGANISM: Homo sapiens

<400> SEQUENCE: 10

Gln Ser Ile Ser Ser Tyr
1 5

<210> SEQ ID NO 11
<211> LENGTH: 11
<212> TYPE: PRT
<213> ORGANISM: Homo sapiens

<400> SEQUENCE: 11

Arg Ala Ser Gln Ser Ile Ser Ser Tyr Leu Asn
1 5 10

<210> SEQ ID NO 12
<211> LENGTH: 3
<212> TYPE: PRT
<213> ORGANISM: Homo sapiens

<400> SEQUENCE: 12

Val Ala Ser
1

<210> SEQ ID NO 13
<211> LENGTH: 7
<212> TYPE: PRT
<213> ORGANISM: Homo sapiens

<400> SEQUENCE: 13

Val Ala Ser Ser Leu Gln Ser
1 5

<210> SEQ ID NO 14
<211> LENGTH: 9
<212> TYPE: PRT
<213> ORGANISM: Homo Sapiens

<400> SEQUENCE: 14

Gln Gln Ser Tyr Ser Asn Pro Ile Thr
1 5

<210> SEQ ID NO 15
<211> LENGTH: 9
<212> TYPE: PRT
<213> ORGANISM: Homo sapiens

<400> SEQUENCE: 15

Gln Gln Ser Tyr Ser Asn Pro Ile Thr
1 5

<210> SEQ ID NO 16
<211> LENGTH: 107
<212> TYPE: PRT
<213> ORGANISM: Homo sapiens

<400> SEQUENCE: 16

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

```
Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 17
<211> LENGTH: 97
<212> TYPE: PRT
<213> ORGANISM: Homo sapiens

<400> SEQUENCE: 17

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Glu Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Gly Glu Val Thr His Gln Gly Leu Ser Ser
                85                  90                  95

Pro


<210> SEQ ID NO 18
<211> LENGTH: 107
<212> TYPE: PRT
<213> ORGANISM: Homo sapiens

<400> SEQUENCE: 18

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Arg Lys Val Asp Asn Ala Leu Gln
        35                  40                  45

Ser Gly Asn Ser Gln Glu Ser Val Thr Glu Gln Glu Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 19
<211> LENGTH: 107
<212> TYPE: PRT
<213> ORGANISM: Homo sapiens

<400> SEQUENCE: 19

Arg Thr Val Ala Ala Pro Ser Val Phe Ile Phe Pro Pro Ser Asp Glu
1               5                   10                  15
```

```
Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 20
<211> LENGTH: 107
<212> TYPE: PRT
<213> ORGANISM: Homo sapiens

<400> SEQUENCE: 20

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Asn Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 21
<211> LENGTH: 214
<212> TYPE: PRT
<213> ORGANISM: Homo sapiens

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Pro Leu Ile
        35                  40                  45

Tyr Val Ala Ser Ser Leu Gln Ser Gly Val Pro Ser Ser Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 22
<211> LENGTH: 204
<212> TYPE: PRT
<213> ORGANISM: Homo sapiens

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Pro Leu Ile
        35                  40                  45

Tyr Val Ala Ser Ser Leu Gln Ser Gly Val Pro Ser Ser Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Glu Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Gly Glu Val Thr His Gln Gly Leu Ser Ser Pro
        195                 200


<210> SEQ ID NO 23
<211> LENGTH: 214
<212> TYPE: PRT
<213> ORGANISM: Homo sapiens

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30
```

```
Leu Asn Trp Tyr Gln Gln Lys Pro Gly Lys Ala Pro Lys Pro Leu Ile
        35                  40                  45

Tyr Val Ala Ser Ser Leu Gln Ser Gly Val Pro Ser Ser Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Arg Lys Val Asp Asn Ala Leu Gln Ser Gly Asn Ser Gln
145                 150                 155                 160

Glu Ser Val Thr Glu Gln Glu Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 24
<211> LENGTH: 214
<212> TYPE: PRT
<213> ORGANISM: Homo sapiens

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Pro Leu Ile
        35                  40                  45

Tyr Val Ala Ser Ser Leu Gln Ser Gly Val Pro Ser Ser Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Leu Tyr
```

```
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 25
<211> LENGTH: 214
<212> TYPE: PRT
<213> ORGANISM: Homo sapiens

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Pro Leu Ile
        35                  40                  45

Tyr Val Ala Ser Ser Leu Gln Ser Gly Val Pro Ser Ser Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Asn Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 26
<211> LENGTH: 104
<212> TYPE: PRT
<213> ORGANISM: Homo sapiens

<400> SEQUENCE: 26

Pro Lys Ala Asn Pro Thr Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Gly Ser Pro Val Lys
        35                  40                  45

Ala Gly Val Glu Thr Thr Lys Pro Ser Lys Gln Ser Asn Asn Lys Tyr
    50                  55                  60

Ala Ala Ser Ser Tyr Leu Ser Leu Thr Pro Glu Gln Trp Lys Ser His
```

```
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100


<210> SEQ ID NO 27
<211> LENGTH: 106
<212> TYPE: PRT
<213> ORGANISM: Homo sapiens

<400> SEQUENCE: 27

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105


<210> SEQ ID NO 28
<211> LENGTH: 106
<212> TYPE: PRT
<213> ORGANISM: Homo sapiens

<400> SEQUENCE: 28

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Pro Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105


<210> SEQ ID NO 29
<211> LENGTH: 106
<212> TYPE: PRT
<213> ORGANISM: Homo sapiens

<400> SEQUENCE: 29

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30
```

```
Phe Tyr Pro Gly Ala Val Lys Val Ala Trp Lys Ala Asp Gly Ser Pro
        35                  40                  45

Val Asn Thr Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ser
            100                 105


<210> SEQ ID NO 30
<211> LENGTH: 106
<212> TYPE: PRT
<213> ORGANISM: Homo sapiens

<400> SEQUENCE: 30

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Asn Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105


<210> SEQ ID NO 31
<211> LENGTH: 106
<212> TYPE: PRT
<213> ORGANISM: Homo sapiens

<400> SEQUENCE: 31

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105


<210> SEQ ID NO 32
<211> LENGTH: 211
<212> TYPE: PRT
<213> ORGANISM: Homo sapiens
```

<400> SEQUENCE: 32

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Pro Leu Ile
        35                  40                  45

Tyr Val Ala Ser Ser Leu Gln Ser Gly Val Pro Ser Ser Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Pro Ile
                85                  90                  95

Thr Phe Gly Gln Gly Thr Arg Leu Glu Ile Lys Pro Lys Ala Asn Pro
            100                 105                 110

Thr Val Thr Leu Phe Pro Pro Ser Ser Glu Glu Leu Gln Ala Asn Lys
        115                 120                 125

Ala Thr Leu Val Cys Leu Ile Ser Asp Phe Tyr Pro Gly Ala Val Thr
    130                 135                 140

Val Ala Trp Lys Ala Asp Gly Ser Pro Val Lys Ala Gly Val Glu Thr
145                 150                 155                 160

Thr Lys Pro Ser Lys Gln Ser Asn Asn Lys Tyr Ala Ala Ser Ser Tyr
                165                 170                 175

Leu Ser Leu Thr Pro Glu Gln Trp Lys Ser His Arg Ser Tyr Ser Cys
            180                 185                 190

Gln Val Thr His Glu Gly Ser Thr Val Glu Lys Thr Val Ala Pro Thr
        195                 200                 205

Glu Cys Ser
    210
```

<210> SEQ ID NO 33
<211> LENGTH: 213
<212> TYPE: PRT
<213> ORGANISM: Homo sapiens

<400> SEQUENCE: 33

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Pro Leu Ile
        35                  40                  45

Tyr Val Ala Ser Ser Leu Gln Ser Gly Val Pro Ser Ser Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Pro Ile
                85                  90                  95

Thr Phe Gly Gln Gly Thr Arg Leu Glu Ile Lys Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140
```

```
Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210


<210> SEQ ID NO 34
<211> LENGTH: 213
<212> TYPE: PRT
<213> ORGANISM: Homo sapiens

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Pro Leu Ile
        35                  40                  45

Tyr Val Ala Ser Ser Leu Gln Ser Gly Val Pro Ser Ser Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Pro Ile
                85                  90                  95

Thr Phe Gly Gln Gly Thr Arg Leu Glu Ile Lys Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Pro
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Lys Ser Tyr
            180                 185                 190

Ser Cys Gln Val Thr His Glu Gly Ser Thr Val Glu Lys Thr Val Ala
        195                 200                 205

Pro Thr Glu Cys Ser
    210


<210> SEQ ID NO 35
<211> LENGTH: 213
<212> TYPE: PRT
<213> ORGANISM: Homo sapiens

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30
```

```
Leu Asn Trp Tyr Gln Gln Lys Pro Gly Lys Ala Pro Lys Pro Leu Ile
        35                  40                  45

Tyr Val Ala Ser Ser Leu Gln Ser Gly Val Pro Ser Ser Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Pro Ile
                85                  90                  95

Thr Phe Gly Gln Gly Thr Arg Leu Glu Ile Lys Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Lys Val Ala Trp Lys Ala Asp Gly Ser Pro Val Asn Thr Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Ala Glu Cys Ser
    210


<210> SEQ ID NO 36
<211> LENGTH: 213
<212> TYPE: PRT
<213> ORGANISM: Homo sapiens

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Pro Leu Ile
        35                  40                  45

Tyr Val Ala Ser Ser Leu Gln Ser Gly Val Pro Ser Ser Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Pro Ile
                85                  90                  95

Thr Phe Gly Gln Gly Thr Arg Leu Glu Ile Lys Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Val Ser Asp Phe Asn Pro Gly Ala
    130                 135                 140

Val Thr Val Ala Trp Lys Ala Asp Gly Ser Pro Val Lys Val Gly Val
145                 150                 155                 160

Glu Thr Thr Lys Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
```

```
            180                 185                 190

Ser Cys Arg Val Thr His Glu Gly Ser Thr Val Glu Lys Thr Val Ala
        195                 200                 205

Pro Ala Glu Cys Ser
    210


<210> SEQ ID NO 37
<211> LENGTH: 213
<212> TYPE: PRT
<213> ORGANISM: Homo sapiens

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Pro Leu Ile
        35                  40                  45

Tyr Val Ala Ser Ser Leu Gln Ser Gly Val Pro Ser Ser Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Pro Ile
                85                  90                  95

Thr Phe Gly Gln Gly Thr Arg Leu Glu Ile Lys Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Val Ser Asp Phe Tyr Pro Gly Ala
    130                 135                 140

Val Thr Val Ala Trp Lys Ala Asp Gly Ser Pro Val Lys Val Gly Val
145                 150                 155                 160

Glu Thr Thr Lys Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Arg Val Thr His Glu Gly Ser Thr Val Glu Lys Thr Val Ala
        195                 200                 205

Pro Ala Glu Cys Ser
    210


<210> SEQ ID NO 38
<211> LENGTH: 451
<212> TYPE: PRT
<213> ORGANISM: Homo sapiens

<400> SEQUENCE: 38

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
```

```
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450
```

<210> SEQ ID NO 39
<211> LENGTH: 452
<212> TYPE: PRT
<213> ORGANISM: Homo sapiens

<400> SEQUENCE: 39

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Ala
225                 230                 235                 240

Gly Ala Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
```

```
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 40
<211> LENGTH: 452
<212> TYPE: PRT
<213> ORGANISM: Homo sapiens

<400> SEQUENCE: 40

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320
```

```
Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 41
<211> LENGTH: 451
<212> TYPE: PRT
<213> ORGANISM: Artificial Sequence
<220> FEATURE:
<223> OTHER INFORMATION: anti-PD-L1 antibody heavy chain with L239A,
      L240A, and K327A variants

<400> SEQUENCE: 41

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220
```

```
Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Ala Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450


<210> SEQ ID NO 42
<211> LENGTH: 451
<212> TYPE: PRT
<213> ORGANISM: Artificial Sequence
<220> FEATURE:
<223> OTHER INFORMATION: anti-PD-L1 antibody heavy chain with L239A,
      L240A, H315A and K327A variants

<400> SEQUENCE: 42

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
```

```
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu Ala Gln Asp Trp Leu Asn
305                 310                 315                 320

Gly Lys Glu Tyr Lys Cys Ala Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450


<210> SEQ ID NO 43
<211> LENGTH: 451
<212> TYPE: PRT
<213> ORGANISM: Artificial Sequence
<220> FEATURE:
<223> OTHER INFORMATION: anti-PD-L1 antibody heavy chain with L239A,
      L240A, K327A and H440Q variants

<400> SEQUENCE: 43

Glu Val Gln Leu Val Glu Ser Gly Gly Gly Leu Val Gln Pro Gly Arg
1               5                   10                  15
```

```
Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Ala Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn Gln Tyr Thr Gln Lys Ser Leu Ser Leu
```

```
        435                 440                 445

Ser Pro Gly
    450


<210> SEQ ID NO 44
<211> LENGTH: 451
<212> TYPE: PRT
<213> ORGANISM: Artificial Sequence
<220> FEATURE:
<223> OTHER INFORMATION: anti-PD-L1 antibody heavy chain with L239A,
      L240A, H315A, K327A and H440Q variants

<400> SEQUENCE: 44

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu Ala Gln Asp Trp Leu Asn
305                 310                 315                 320

Gly Lys Glu Tyr Lys Cys Ala Val Ser Asn Lys Ala Leu Pro Ala Pro
                325                 330                 335
```

```
Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn Gln Tyr Thr Gln Lys Ser Leu Ser Leu
        435                 440                 445

Ser Pro Gly
    450


<210> SEQ ID NO 45
<211> LENGTH: 448
<212> TYPE: PRT
<213> ORGANISM: Homo sapiens

<400> SEQUENCE: 45

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255
```

```
Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 46
<211> LENGTH: 448
<212> TYPE: PRT
<213> ORGANISM: Homo sapiens

<400> SEQUENCE: 46

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
```

```
            180                 185                 190

Val Thr Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Met Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

```
<210> SEQ ID NO 47
<211> LENGTH: 448
<212> TYPE: PRT
<213> ORGANISM: Homo sapiens

<400> SEQUENCE: 47

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110
```

```
Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 48
<211> LENGTH: 448
<212> TYPE: PRT
<213> ORGANISM: Homo sapiens

<400> SEQUENCE: 48

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45
```

```
Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ser Val Glu Trp Glu Ser
    370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 49
<211> LENGTH: 451

<212> TYPE: PRT
<213> ORGANISM: Homo sapiens

<400> SEQUENCE: 49

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val Leu Leu
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu Leu Leu Asn His Tyr Thr Gln Lys Ser Leu Ser Leu Ser
        435                 440                 445

Leu Gly Lys
    450


<210> SEQ ID NO 50
<211> LENGTH: 449
<212> TYPE: PRT
<213> ORGANISM: Homo sapiens

<400> SEQUENCE: 50

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
```

```
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys


<210> SEQ ID NO 51
<211> LENGTH: 449
<212> TYPE: PRT
<213> ORGANISM: Homo sapiens

<400> SEQUENCE: 51

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Gly Ile Ser Trp Lys Ser Asn Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Ser Cys Pro Ala Pro Glu Phe Leu Gly Gly Pro
```

225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser Gln Glu Asp
260 265 270

Pro Glu Val Gln Phe Asn Trp Tyr Val Asp Gly Val Glu Val His Asn
275 280 285

Ala Lys Thr Lys Pro Arg Glu Glu Gln Phe Asn Ser Thr Tyr Arg Val
290 295 300

Val Ser Val Leu Thr Val Val His Gln Asp Trp Leu Asn Gly Lys Glu
305 310 315 320

Tyr Lys Cys Lys Val Ser Asn Lys Gly Leu Pro Ser Ser Ile Glu Lys
325 330 335

Thr Ile Ser Lys Ala Lys Gly Gln Pro Arg Glu Pro Gln Val Tyr Thr
340 345 350

Leu Pro Pro Ser Gln Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Arg Leu Thr Val Asp Lys
405 410 415

Ser Arg Trp Gln Glu Gly Asn Val Phe Ser Cys Ser Val Met His Glu
420 425 430

Ala Leu His Asn His Tyr Thr Gln Lys Ser Leu Ser Leu Ser Leu Gly
435 440 445

Lys

<210> SEQ ID NO 52
<211> LENGTH: 449
<212> TYPE: PRT
<213> ORGANISM: Hono sapiens

<400> SEQUENCE: 52

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Thr Pro Gly Lys Gly Leu Glu Trp Val
35 40 45

Ser Gly Ile Ser Trp Lys Ser Asn Ile Ile Gly Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Leu Tyr Tyr Cys
85 90 95

Ala Arg Asp Ile Thr Gly Ser Gly Ser Tyr Gly Trp Phe Asp Pro Trp
100 105 110

Gly Gln Gly Thr Leu Val Thr Val Ser Ser Ala Ser Thr Lys Gly Pro
115 120 125

Ser Val Phe Pro Leu Ala Pro Cys Ser Arg Ser Thr Ser Glu Ser Thr
130 135 140

Ala Ala Leu Gly Cys Leu Val Lys Asp Tyr Phe Pro Glu Pro Val Thr 145 150 155 160

Val Ser Trp Asn Ser Gly Ala Leu Thr Ser Gly Val His Thr Phe Pro
165 170 175

Ala Val Leu Gln Ser Ser Gly Leu Tyr Ser Leu Ser Ser Val Val Thr
180 185 190

Val Pro Ser Ser Ser Leu Gly Thr Lys Thr Tyr Thr Cys Asn Val Asp
195 200 205

His Lys Pro Ser Asn Thr Lys Val Asp Lys Arg Val Glu Ser Lys Tyr
210 215 220

Gly Pro Pro Cys Pro Pro Cys Pro Ala Pro Glu Phe Glu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser Gln Glu Asp
260 265 270

Pro Glu Val Gln Phe Asn Trp Tyr Val Asp Gly Val Glu Val His Asn
275 280 285

Ala Lys Thr Lys Pro Arg Glu Glu Gln Phe Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Gly Leu Pro Ser Ser Ile Glu Lys
325 330 335

Thr Ile Ser Lys Ala Lys Gly Gln Pro Arg Glu Pro Gln Val Tyr Thr
340 345 350

Leu Pro Pro Ser Gln Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Arg Leu Thr Val Asp Lys
405 410 415

Ser Arg Trp Gln Glu Gly Asn Val Phe Ser Cys Ser Val Met His Glu
420 425 430

Ala Leu His Asn His Tyr Thr Gln Lys Ser Leu Ser Leu Ser Leu Gly
435 440 445

Lys

<210> SEQ ID NO 53
<211> LENGTH: 449
<212> TYPE: PRT
<213> ORGANISM: Homo sapiens

<400> SEQUENCE: 53

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Thr Pro Gly Lys Gly Leu Glu Trp Val
35 40 45

Ser Gly Ile Ser Trp Lys Ser Asn Ile Ile Gly Tyr Ala Asp Ser Val
50 55 60

Lys Gly Arg Phe Thr Ile Ser Arg Asp Asn Ala Lys Asn Ser Leu Tyr

```
65                  70                  75                  80

Leu Gln Met Asn Ser Leu Arg Ala Glu Asp Thr Ala Leu Tyr Tyr Cys
                85                  90                  95

Ala Arg Asp Ile Thr Gly Ser Gly Ser Tyr Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Pro Val Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys
```

<210> SEQ ID NO 54
<211> LENGTH: 329
<212> TYPE: PRT
<213> ORGANISM: Artificial Sequence
<220> FEATURE:

```
<223> OTHER INFORMATION: anti-PD-L1 heavy chain constant region with
      L239A, L240A, and K327A variants

<400> SEQUENCE: 54

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325


<210> SEQ ID NO 55
<211> LENGTH: 329
<212> TYPE: PRT
<213> ORGANISM: Artificial Sequence
<220> FEATURE:
<223> OTHER INFORMATION: anti-PD-L1 heacy chain constant region with
      L239A, L240A, H315A, and K327A variants

<400> SEQUENCE: 55
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

Ala Gln Asp Trp Leu Asn Gly Lys Glu Tyr Lys Cys Ala Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

```
<210> SEQ ID NO 56
<211> LENGTH: 329
<212> TYPE: PRT
<213> ORGANISM: Artificial Sequence
<220> FEATURE:
<223> OTHER INFORMATION: anti-PD-L1 heavy chain constant region with
      L239A, L240A, K327A, and H440Q variants

<400> SEQUENCE: 56

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn Gln Tyr Thr
305                 310                 315                 320

Gln Lys Ser Leu Ser Leu Ser Pro Gly
                325


<210> SEQ ID NO 57
<211> LENGTH: 329
<212> TYPE: PRT
<213> ORGANISM: Artificial Sequence
<220> FEATURE:
<223> OTHER INFORMATION: anti-PD-L1 heavy chain constant region with
      L239A, L240A, H315A, K327A, and H440Q variants

<400> SEQUENCE: 57

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
```

```
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

Ala Gln Asp Trp Leu Asn Gly Lys Glu Tyr Lys Cys Ala Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn Gln Tyr Thr
305                 310                 315                 320

Gln Lys Ser Leu Ser Leu Ser Pro Gly
                325


<210> SEQ ID NO 58
<211> LENGTH: 1356
<212> TYPE: DNA
<213> ORGANISM: Artificial Sequence
<220> FEATURE:
<223> OTHER INFORMATION: Codon optimized nucleic acid sequence encoding
      anti-PD-L1 antibody heavy chain with L239A, L240A and K327A
      variants

<400> SEQUENCE: 58

gaggtgcagc tggtggagtc tgggggaggc ttggtccagc ctgggaggtc cctgagactc      60

tcctgtgcag cctctggatt cacctttgat gattatgcca tgcactgggt ccgccagact     120

ccagggaagg gcctggagtg ggtctcagga attagttgga aaagtaacat cattggatac     180

gcggactccg tgaagggccg attcaccatc tccagagaca acgccaagaa ctccctgtat     240

cttcaaatga acagcctgag agccgaggac acggctttgt attactgtgc aagagatatt     300

accggatccg gctcttacgg ctggttcgac ccctggggcc agggaaccct ggtcaccgtc     360

tcctcagcct ccaccaaggg cccatcggtc ttccccctgg caccctctag caagagcacc     420
```

-continued

```
tctgggggca cagcggccct gggctgcctg gtcaaggact acttccccga accggtgacg    480

gtgtcgtgga actcaggcgc cctgaccagc ggcgtgcaca ccttcccggc tgtcctacag    540

tcctcaggac tctactccct cagcagcgtg gtgaccgtgc cctccagcag cttgggcacc    600

cagacctaca tctgcaacgt gaatcacaag cccagcaaca ccaaggtgga caagcgggtt    660

gagcccaaat cttgtgacaa aactcacaca tgcccaccgt gcccagcacc tgaagccgcc    720

gggggaccgt cagtcttcct cttcccccca aaacccaagg acaccctcat gatctcccgg    780

acccctgagg tcacatgcgt ggtggtggac gtgagccacg aagaccctga ggtcaagttc    840

aactggtacg tggacggcgt ggaggtgcat aatgccaaga caaagccgag agaggagcag    900

tacaacagca cgtaccgtgt ggtcagcgtc ctcaccgtcc tgcaccagga ctggctgaat    960

ggcaaggagt acaagtgcgc cgtctccaac aaagccctcc cagcccccat cgagaaaacc   1020

atctccaaag ccaaagggca gccccgagaa ccacaggtgt acaccctgcc cccatcccgg   1080

gaggagatga ccaagaacca ggtcagcctg acctgcctgg tcaaaggctt ctatcccagc   1140

gacatcgccg tggagtggga gagcaatggg cagccggaga acaactacaa gaccacgcct   1200

cccgtgctgg actccgacgg ctccttcttc ctctattcta agctcaccgt ggacaagagc   1260

aggtggcagc aggggaacgt cttctcatgc tccgtgatgc atgaggctct gcacaaccac   1320

tacacgcaga agagcctctc cctgtctccc gggtga                            1356
```

<210> SEQ ID NO 59
<211> LENGTH: 1356
<212> TYPE: DNA
<213> ORGANISM: Artificial Sequence
<220> FEATURE:
<223> OTHER INFORMATION: Codon optimized nucleic acid sequence encoding anti-PD-L1 antibody heavy chain with L239A, L240A, H315A and K327A variants

<400> SEQUENCE: 59

```
gaggtgcagc tggtggagtc tgggggaggc ttggtccagc ctgggaggtc cctgagactc     60

tcctgtgcag cctctggatt cacctttgat gattatgcca tgcactgggt ccgccagact    120

ccagggaagg gcctggagtg ggtctcagga attagttgga aaagtaacat cattggatac    180

gcggactccg tgaagggccg attcaccatc tccagagaca acgccaagaa ctccctgtat    240

cttcaaatga acagcctgag agccgaggac acggctttgt attactgtgc aagagatatt    300

accggatccg gctcttacgg ctggttcgac ccctggggcc agggaaccct ggtcaccgtc    360

tcctcagcct ccaccaaggg cccatcggtc ttccccctgg caccctctag caagagcacc    420

tctgggggca cagcggccct gggctgcctg gtcaaggact acttccccga accggtgacg    480

gtgtcgtgga actcaggcgc cctgaccagc ggcgtgcaca ccttcccggc tgtcctacag    540

tcctcaggac tctactccct cagcagcgtg gtgaccgtgc cctccagcag cttgggcacc    600

cagacctaca tctgcaacgt gaatcacaag cccagcaaca ccaaggtgga caagcgggtt    660

gagcccaaat cttgtgacaa aactcacaca tgcccaccgt gcccagcacc tgaagccgcc    720

gggggaccgt cagtcttcct cttcccccca aaacccaagg acaccctcat gatctcccgg    780

acccctgagg tcacatgcgt ggtggtggac gtgagccacg aagaccctga ggtcaagttc    840

aactggtacg tggacggcgt ggaggtgcat aatgccaaga caaagccgag agaggagcag    900

tacaacagca cgtaccgtgt ggtcagcgtc ctcaccgtcc tggctcagga ctggctgaat    960

ggcaaggagt acaagtgcgc cgtctccaac aaagccctcc cagcccccat cgagaaaacc   1020

atctccaaag ccaaagggca gccccgagaa ccacaggtgt acaccctgcc cccatcccgg   1080
```

```
gaggagatga ccaagaacca ggtcagcctg acctgcctgg tcaaaggctt ctatcccagc   1140

gacatcgccg tggagtggga gagcaatggg cagccggaga acaactacaa gaccacgcct   1200

cccgtgctgg actccgacgg ctccttcttc ctctattcta agctcaccgt ggacaagagc   1260

aggtggcagc aggggaacgt cttctcatgc tccgtgatgc atgaggctct gcacaaccac   1320

tacacgcaga agagcctctc cctgtctccc gggtga                             1356
```

<210> SEQ ID NO 60
<211> LENGTH: 1356
<212> TYPE: DNA
<213> ORGANISM: Artificial Sequence
<220> FEATURE:
<223> OTHER INFORMATION: Codon optimized nucleic acid sequence encoding anti-PD-L1 antibody heavy chain with L239A, L240A, K327A and H440Q variants

<400> SEQUENCE: 60

```
gaggtgcagc tggtggagtc tgggggaggc ttggtccagc ctgggaggtc cctgagactc     60

tcctgtgcag cctctggatt cacctttgat gattatgcca tgcactgggt ccgccagact    120

ccagggaagg gcctggagtg ggtctcagga attagttgga aaagtaacat cattggatac    180

gcggactccg tgaagggccg attcaccatc tccagagaca acgccaagaa ctccctgtat    240

cttcaaatga acagcctgag agccgaggac acggctttgt attactgtgc aagagatatt    300

accggatccg gctcttacgg ctggttcgac ccctggggcc agggaaccct ggtcaccgtc    360

tcctcagcct ccaccaaggg cccatcggtc ttccccctgg caccctctag caagagcacc    420

tctgggggca cagcggccct gggctgcctg gtcaaggact acttccccga accggtgacg    480

gtgtcgtgga actcaggcgc cctgaccagc ggcgtgcaca ccttcccggc tgtcctacag    540

tcctcaggac tctactccct cagcagcgtg gtgaccgtgc cctccagcag cttgggcacc    600

cagacctaca tctgcaacgt gaatcacaag cccagcaaca ccaaggtgga caagcgggtt    660

gagcccaaat cttgtgacaa aactcacaca tgcccaccgt gcccagcacc tgaagccgcc    720

gggggaccgt cagtcttcct cttcccccca aaacccaagg acaccctcat gatctcccgg    780

acccctgagg tcacatgcgt ggtggtggac gtgagccacg aagaccctga ggtcaagttc    840

aactggtacg tggacggcgt ggaggtgcat aatgccaaga caaagccgag agaggagcag    900

tacaacagca cgtaccgtgt ggtcagcgtc ctcaccgtcc tgcaccagga ctggctgaat    960

ggcaaggagt acaagtgcgc cgtctccaac aaagccctcc cagcccccat cgagaaaacc   1020

atctccaaag ccaaagggca gccccgagaa ccacaggtgt acaccctgcc cccatcccgg   1080

gaggagatga ccaagaacca ggtcagcctg acctgcctgg tcaaaggctt ctatcccagc   1140

gacatcgccg tggagtggga gagcaatggg cagccggaga acaactacaa gaccacgcct   1200

cccgtgctgg actccgacgg ctccttcttc ctctattcta agctcaccgt ggacaagagc   1260

aggtggcagc aggggaacgt cttctcatgc tccgtgatgc atgaggctct gcacaaccag   1320

tacacgcaga agagcctctc cctgtctccc gggtga                             1356
```

<210> SEQ ID NO 61
<211> LENGTH: 1356
<212> TYPE: DNA
<213> ORGANISM: Artificial Sequence
<220> FEATURE:
<223> OTHER INFORMATION: Codon optimized nucleic acid sequence encoding anti-PD-L1 antibody heavy chain with L239A, L240A, H315A, K327A and H440 variants

<400> SEQUENCE: 61
gaggtgcagc tggtggagtc tggggggaggc ttggtccagc ctgggaggtc cctgagactc 60
tcctgtgcag cctctggatt cacctttgat gattatgcca tgcactgggt ccgccagact 120
ccagggaagg gcctggagtg ggtctcagga attagttgga aaagtaacat cattggatac 180
gcggactccg tgaagggccg attcaccatc tccagagaca acgccaagaa ctccctgtat 240
cttcaaatga acagcctgag agccgaggac acggctttgt attactgtgc aagagatatt 300
accggatccg gctcttacgg ctggttcgac ccctggggcc agggaaccct ggtcaccgtc 360
tcctcagcct ccaccaaggg cccatcggtc ttccccctgg caccctctag caagagcacc 420
tctgggggca cagcggccct gggctgcctg gtcaaggact acttccccga accggtgacg 480
gtgtcgtgga actcaggcgc cctgaccagc ggcgtgcaca ccttcccggc tgtcctacag 540
tcctcaggac tctactccct cagcagcgtg gtgaccgtgc cctccagcag cttgggcacc 600
cagacctaca tctgcaacgt gaatcacaag cccagcaaca ccaaggtgga caagcgggtt 660
gagcccaaat cttgtgacaa aactcacaca tgcccaccgt gcccagcacc tgaagccgcc 720
gggggaccgt cagtcttcct cttcccccca aaacccaagg acaccctcat gatctcccgg 780
acccctgagg tcacatgcgt ggtggtggac gtgagccacg aagaccctga ggtcaagttc 840
aactggtacg tggacggcgt ggaggtgcat aatgccaaga caaagccgag agaggagcag 900
tacaacagca cgtaccgtgt ggtcagcgtc ctcaccgtcc tggctcagga ctggctgaat 960
ggcaaggagt acaagtgcgc cgtctccaac aaagccctcc cagcccccat cgagaaaacc 1020
atctccaaag ccaaagggca gccccgagaa ccacaggtgt acaccctgcc cccatcccgg 1080
gaggagatga ccaagaacca ggtcagcctg acctgcctgg tcaaaggctt ctatcccagc 1140
gacatcgccg tggagtggga gagcaatggg cagccggaga acaactacaa gaccacgcct 1200
cccgtgctgg actccgacgg ctccttcttc ctctattcta agctcaccgt ggacaagagc 1260
aggtggcagc aggggaacgt cttctcatgc tccgtgatgc atgaggctct gcacaaccac 1320
tacacgcaga agagcctctc cctgtctccc gggtga 1356

<210> SEQ ID NO 62
<211> LENGTH: 1356
<212> TYPE: DNA
<213> ORGANISM: Artificial Sequence
<220> FEATURE:
<223> OTHER INFORMATION: Codon optimized nucleic acid sequence encoding anti-PD-L1 antibody heavy chain with L239A, L240A and K327A variants

<400> SEQUENCE: 62
gaagtgcagc tggtggaatc tggcggcgga ttggttcagc ctggcagatc cctgagactg 60
tcttgtgccg cctctggctt caccttcgac gactacgcta tgcactgggt ccgacagacc 120
cctggcaaag gactggaatg ggtgtccggc atctcctgga agtccaacat catcggctac 180
gccgactccg tgaagggcag attcaccatc tccagagaca acgccaagaa ctccctgtac 240
ctgcagatga acagcctgag agccgaggac accgctctgt actactgcgc cagagacatc 300
accggctccg gctcttacgg atggttcgat ccttggggcc agggcacact ggtcacagtg 360
tcctctgctt ccaccaaggg acccagcgtt ttccctctgg ctccatcctc caagtctacc 420
tctggcggaa cagctgctct gggctgcctg gtcaaggact actttcctga gcctgtgacc 480
gtgtcctgga actctggcgc tctgacatct ggcgtgcaca cctttccagc tgtgctgcag 540
tcctccggcc tgtactctct gtcctctgtc gtgaccgtgc cttccagctc tctgggaacc 600

```
cagacctaca tctgcaatgt gaaccacaag ccttccaaca ccaaggtgga caagagagtg    660

gaacccaagt cctgcgacaa gacccacacc tgtcctccat gtcctgctcc agaagctgct    720

ggcggccctt ccgtgtttct gttccctcca aagcctaagg acaccctgat gatctctcgg    780

acccctgaag tgacctgcgt ggtggtggat gtgtctcacg aggacccaga agtgaagttc    840

aattggtacg tggacggcgt ggaagtgcac aatgccaaga ccaagcctag agaggaacag    900

tacaactcca cctatagagt ggtgtccgtg ctgaccgtgc tgcaccagga ttggctgaac    960

ggcaaagagt acaagtgcgc cgtgtccaac aaggccctgc ctgctcctat cgaaaagacc   1020

atcagcaagg ccaagggcca gcctagggaa ccccaggttt acaccctgcc tccaagccgg   1080

gaagagatga ccaagaacca ggtgtccctg acctgcctcg tgaagggatt ctacccctcc   1140

gatatcgccg tggaatggga gtctaatggc cagccagaga acaactacaa gacaacccct   1200

cctgtgctgg actccgacgg ctcattcttc ctgtactcca agctgacagt ggacaagtcc   1260

agatggcagc agggcaacgt gttctcctgc tccgtgatgc acgaggccct gcacaatcac   1320

tacacacaga agtccctgtc tctgtcccct ggctga                              1356
```

```
<210> SEQ ID NO 63
<211> LENGTH: 1356
<212> TYPE: DNA
<213> ORGANISM: Artificial Sequence
<220> FEATURE:
<223> OTHER INFORMATION: Codon optimized nucleic acid sequence encoding
      anti-PD-L1 antibody heavy chain with L239A, L240A, H315A and K327A
      variants

<400> SEQUENCE: 63
```

```
gaagtgcagc tggtggaatc tggcggcgga ttggttcagc ctggcagatc cctgagactg     60

tcttgtgccg cctctggctt caccttcgac gactacgcta tgcactgggt ccgacagacc    120

cctggcaaag gactggaatg ggtgtccggc atctcctgga agtccaacat catcggctac    180

gccgactccg tgaagggcag attcaccatc tccagagaca acgccaagaa ctccctgtac    240

ctgcagatga acagcctgag agccgaggac accgctctgt actactgcgc cagagacatc    300

accggctccg gctcttacgg atggttcgat ccttggggcc agggcacact ggtcacagtg    360

tcctctgctt ccaccaaggg acccagcgtt ttccctctgg ctccatcctc caagtctacc    420

tctggcggaa cagctgctct gggctgcctg gtcaaggact actttcctga gcctgtgacc    480

gtgtcctgga actctggcgc tctgacatct ggcgtgcaca cctttccagc tgtgctgcag    540

tcctccggcc tgtactctct gtcctctgtc gtgaccgtgc cttccagctc tctgggaacc    600

cagacctaca tctgcaatgt gaaccacaag ccttccaaca ccaaggtgga caagagagtg    660

gaacccaagt cctgcgacaa gacccacacc tgtcctccat gtcctgctcc agaagctgct    720

ggcggccctt ccgtgtttct gttccctcca aagcctaagg acaccctgat gatctctcgg    780

acccctgaag tgacctgcgt ggtggtggat gtgtctcacg aggacccaga agtgaagttc    840

aattggtacg tggacggcgt ggaagtgcac aatgccaaga ccaagcctag agaggaacag    900

tacaactcca cctatagagt ggtgtccgtg ctgaccgtgc tggcccagga ttggctgaac    960

ggcaaagagt acaagtgcgc cgtgtccaac aaggccctgc ctgctcctat cgaaaagacc   1020

atcagcaagg ccaagggcca gcctagggaa ccccaggttt acaccctgcc tccaagccgg   1080

gaagagatga ccaagaacca ggtgtccctg acctgcctcg tgaagggatt ctacccctcc   1140

gatatcgccg tggaatggga gtctaatggc cagccagaga acaactacaa gacaacccct   1200
```

```
cctgtgctgg actccgacgg ctcattcttc ctgtactcca agctgacagt ggacaagtcc   1260

agatggcagc agggcaacgt gttctcctgc tccgtgatgc acgaggccct gcacaatcac   1320

tacacacaga agtccctgtc tctgtcccct ggctga                             1356


<210> SEQ ID NO 64
<211> LENGTH: 1356
<212> TYPE: DNA
<213> ORGANISM: Artificial Sequence
<220> FEATURE:
<223> OTHER INFORMATION: Codon optimized nucleic acid sequence encoding
      anti-PD-L1 antibody heavy chain with L239A, L240A, K327A and H440Q
      variants

<400> SEQUENCE: 64

gaagtgcagc tggtggaatc tggcggcgga ttggttcagc ctggcagatc cctgagactg     60

tcttgtgccg cctctggctt caccttcgac gactacgcta tgcactgggt ccgacagacc    120

cctggcaaag gactggaatg ggtgtccggc atctcctgga agtccaacat catcggctac    180

gccgactccg tgaagggcag attcaccatc tccagagaca acgccaagaa ctccctgtac    240

ctgcagatga acagcctgag agccgaggac accgctctgt actactgcgc cagagacatc    300

accggctccg gctcttacgg atggttcgat ccttggggcc agggcacact ggtcacagtg    360

tcctctgctt ccaccaaggg acccagcgtt ttccctctgg ctccatcctc caagtctacc    420

tctggcggaa cagctgctct gggctgcctg gtcaaggact actttcctga gcctgtgacc    480

gtgtcctgga actctggcgc tctgacatct ggcgtgcaca cctttccagc tgtgctgcag    540

tcctccggcc tgtactctct gtcctctgtc gtgaccgtgc cttccagctc tctgggaacc    600

cagacctaca tctgcaatgt gaaccacaag ccttccaaca ccaaggtgga caagagagtg    660

gaacccaagt cctgcgacaa gacccacacc tgtcctccat gtcctgctcc agaagctgct    720

ggcggccctt ccgtgtttct gttccctcca aagcctaagg acaccctgat gatctctcgg    780

acccctgaag tgacctgcgt ggtggtggat gtgtctcacg aggacccaga agtgaagttc    840

aattggtacg tggacggcgt ggaagtgcac aatgccaaga ccaagcctag agaggaacag    900

tacaactcca cctatagagt ggtgtccgtg ctgaccgtgc tgcaccagga ttggctgaac    960

ggcaaagagt acaagtgcgc cgtgtccaac aaggccctgc ctgctcctat cgaaaagacc   1020

atcagcaagg ccaagggcca gcctagggaa ccccaggttt acaccctgcc tccaagccgg   1080

gaagagatga ccaagaacca ggtgtccctg acctgcctcg tgaagggatt ctacccctcc   1140

gatatcgccg tggaatggga gtctaatggc cagccagaga acaactacaa gacaacccct   1200

cctgtgctgg actccgacgg ctcattcttc ctgtactcca agctgacagt ggacaagtcc   1260

agatggcagc agggcaacgt gttctcctgc tccgtgatgc acgaggccct gcacaatcag   1320

tacacacaga agtccctgtc tctgtcccct ggctga                             1356


<210> SEQ ID NO 65
<211> LENGTH: 1356
<212> TYPE: DNA
<213> ORGANISM: artificial Sequence
<220> FEATURE:
<223> OTHER INFORMATION: Codon optimized nucleic acid sequence encoding
      anti-PD-L1 antibody heavy chain with L239A, L240A, H315A, K327A
      and H440 variants

<400> SEQUENCE: 65

gaagtgcagc tggtggaatc tggcggcgga ttggttcagc ctggcagatc cctgagactg     60

tcttgtgccg cctctggctt caccttcgac gactacgcta tgcactgggt ccgacagacc    120
```

```
cctggcaaag gactggaatg ggtgtccggc atctcctgga agtccaacat catcggctac    180

gccgactccg tgaagggcag attcaccatc tccagagaca acgccaagaa ctccctgtac    240

ctgcagatga acagcctgag agccgaggac accgctctgt actactgcgc cagagacatc    300

accggctccg gctcttacgg atggttcgat ccttggggcc agggcacact ggtcacagtg    360

tcctctgctt ccaccaaggg acccagcgtt ttccctctgg ctccatcctc caagtctacc    420

tctggcggaa cagctgctct gggctgcctg gtcaaggact actttcctga gcctgtgacc    480

gtgtcctgga actctggcgc tctgacatct ggcgtgcaca cctttccagc tgtgctgcag    540

tcctccggcc tgtactctct gtcctctgtc gtgaccgtgc cttccagctc tctgggaacc    600

cagacctaca tctgcaatgt gaaccacaag ccttccaaca ccaaggtgga caagagagtg    660

gaacccaagt cctgcgacaa gacccacacc tgtcctccat gtcctgctcc agaagctgct    720

ggcggccctt ccgtgtttct gttccctcca aagcctaagg acaccctgat gatctctcgg    780

acccctgaag tgacctgcgt ggtggtggat gtgtctcacg aggacccaga agtgaagttc    840

aattggtacg tggacggcgt ggaagtgcac aatgccaaga ccaagcctag agaggaacag    900

tacaactcca cctatagagt ggtgtccgtg ctgaccgtgc tggcccagga ttggctgaac    960

ggcaaagagt acaagtgcgc cgtgtccaac aaggccctgc ctgctcctat cgaaaagacc   1020

atcagcaagg ccaagggcca gcctagggaa ccccaggttt acaccctgcc tccaagccgg   1080

gaagagatga ccaagaacca ggtgtccctg acctgcctcg tgaagggatt ctacccctcc   1140

gatatcgccg tggaatggga gtctaatggc cagccagaga acaactacaa gacaacccct   1200

cctgtgctgg actccgacgg ctcattcttc ctgtactcca agctgacagt ggacaagtcc   1260

agatggcagc agggcaacgt gttctcctgc tccgtgatgc acgaggccct gcacaatcag   1320

tacacacaga agtccctgtc tctgtcccct ggctga                             1356
```

```
<210> SEQ ID NO 66
<211> LENGTH: 470
<212> TYPE: PRT
<213> ORGANISM: Artificial Sequence
<220> FEATURE:
<223> OTHER INFORMATION: anti-PD-L1 antibody heavy chain with L239A,
      L240A and K327A variants and signal peptide C

<400> SEQUENCE: 66

Met Met Ser Phe Val Ser Leu Leu Leu Val Gly Ile Leu Phe His Ala
1               5                   10                  15

Thr Gln Ala Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Thr Pro Gly Lys Gly Leu
    50                  55                  60

Glu Trp Val Ser Gly Ile Ser Trp Lys Ser Asn Ile Ile Gly Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Leu
            100                 105                 110

Tyr Tyr Cys Ala Arg Asp Ile Thr Gly Ser Gly Ser Tyr Gly Trp Phe
        115                 120                 125

Asp Pro Trp Gly Gln Gly Thr Leu Val Thr Val Ser Ser Ala Ser Thr
```

```
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Ala Ala Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Ala Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly
465                 470


<210> SEQ ID NO 67
<211> LENGTH: 470
<212> TYPE: PRT
<213> ORGANISM: Artificial Sequence
<220> FEATURE:
<223> OTHER INFORMATION: anti-PD-L1 antibody heavy chain with L239A,
      L240A, H315A and K327A variants and signal peptide C

<400> SEQUENCE: 67

Met Met Ser Phe Val Ser Leu Leu Leu Val Gly Ile Leu Phe His Ala
1               5                   10                  15
```

```
Thr Gln Ala Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Thr Pro Gly Lys Gly Leu
    50                  55                  60

Glu Trp Val Ser Gly Ile Ser Trp Lys Ser Asn Ile Ile Gly Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Leu
            100                 105                 110

Tyr Tyr Cys Ala Arg Asp Ile Thr Gly Ser Gly Ser Tyr Gly Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Ala Ala Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu Ala Gln Asp
                325                 330                 335

Trp Leu Asn Gly Lys Glu Tyr Lys Cys Ala Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
```

```
        435                 440                 445

Cys Ser Val Met His Glu Ala Leu His Asn His Tyr Thr Gln Lys Ser
    450                 455                 460

Leu Ser Leu Ser Pro Gly
465                 470


<210> SEQ ID NO 68
<211> LENGTH: 470
<212> TYPE: PRT
<213> ORGANISM: Artificial Sequence
<220> FEATURE:
<223> OTHER INFORMATION: anti-PD-L1 antibody heavy chain with L239A,
      L240A, K327A and H440Q variants and signal peptide C

<400> SEQUENCE: 68

Met Met Ser Phe Val Ser Leu Leu Leu Val Gly Ile Leu Phe His Ala
1               5                   10                  15

Thr Gln Ala Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Thr Pro Gly Lys Gly Leu
    50                  55                  60

Glu Trp Val Ser Gly Ile Ser Trp Lys Ser Asn Ile Ile Gly Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Leu
            100                 105                 110

Tyr Tyr Cys Ala Arg Asp Ile Thr Gly Ser Gly Ser Tyr Gly Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Ala Ala Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320
```

```
Asn Ser Thr Tyr Arg Val Val Ser Val Leu Thr Val Leu His Gln Asp
                325                 330                 335

Trp Leu Asn Gly Lys Glu Tyr Lys Cys Ala Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn Gln Tyr Thr Gln Lys Ser
    450                 455                 460

Leu Ser Leu Ser Pro Gly
465                 470


<210> SEQ ID NO 69
<211> LENGTH: 470
<212> TYPE: PRT
<213> ORGANISM: Artificial Sequence
<220> FEATURE:
<223> OTHER INFORMATION: anti-PD-L1 antibody heavy chain with L239A,
      L240A, H315A, K327A and H440 variants and signal peptide C

<400> SEQUENCE: 69

Met Met Ser Phe Val Ser Leu Leu Leu Val Gly Ile Leu Phe His Ala
1               5                   10                  15

Thr Gln Ala Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Thr Pro Gly Lys Gly Leu
    50                  55                  60

Glu Trp Val Ser Gly Ile Ser Trp Lys Ser Asn Ile Ile Gly Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Leu
            100                 105                 110

Tyr Tyr Cys Ala Arg Asp Ile Thr Gly Ser Gly Ser Tyr Gly Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205
```

```
Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Ala Ala Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu Ala Gln Asp
                325                 330                 335

Trp Leu Asn Gly Lys Glu Tyr Lys Cys Ala Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn Gln Tyr Thr Gln Lys Ser
    450                 455                 460

Leu Ser Leu Ser Pro Gly
465                 470


<210> SEQ ID NO 70
<211> LENGTH: 470
<212> TYPE: PRT
<213> ORGANISM: Artificial Sequence
<220> FEATURE:
<223> OTHER INFORMATION: anti-PD-L1 antibody heavy chain with L239A,
      L240A and K327A variants and signal peptide LHC

<400> SEQUENCE: 70

Met Asp Trp Thr Trp Arg Ile Leu Phe Leu Val Ala Ala Ala Thr Gly
1               5                   10                  15

Ala His Ser Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Thr Pro Gly Lys Gly Leu
    50                  55                  60

Glu Trp Val Ser Gly Ile Ser Trp Lys Ser Asn Ile Ile Gly Tyr Ala
65                  70                  75                  80

Asp Ser Val Lys Gly Arg Phe Thr Ile Ser Arg Asp Asn Ala Lys Asn
```

```
                85                  90                  95

Ser Leu Tyr Leu Gln Met Asn Ser Leu Arg Ala Glu Asp Thr Ala Leu
            100                 105                 110

Tyr Tyr Cys Ala Arg Asp Ile Thr Gly Ser Gly Ser Tyr Gly Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Ala Ala Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Ala Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly
465                 470
```

<210> SEQ ID NO 71
<211> LENGTH: 470
<212> TYPE: PRT
<213> ORGANISM: Artificial Sequence

```
<220> FEATURE:
<223> OTHER INFORMATION: anti-PD-L1 antibody heavy chain with L239A,
      L240A, H315A and K327A variants and signal peptide LHC

<400> SEQUENCE: 71

Met Asp Trp Thr Trp Arg Ile Leu Phe Leu Val Ala Ala Ala Thr Gly
1               5                   10                  15

Ala His Ser Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Thr Pro Gly Lys Gly Leu
    50                  55                  60

Glu Trp Val Ser Gly Ile Ser Trp Lys Ser Asn Ile Ile Gly Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Leu
            100                 105                 110

Tyr Tyr Cys Ala Arg Asp Ile Thr Gly Ser Gly Ser Tyr Gly Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Ala Ala Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu Ala Gln Asp
                325                 330                 335

Trp Leu Asn Gly Lys Glu Tyr Lys Cys Ala Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
```

```
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly
465                 470


<210> SEQ ID NO 72
<211> LENGTH: 470
<212> TYPE: PRT
<213> ORGANISM: Artificial Sequence
<220> FEATURE:
<223> OTHER INFORMATION: anti-PD-L1 antibody heavy chain with L239A,
      L240A, K327A and H440Q variants and signal peptide LHC

<400> SEQUENCE: 72

Met Asp Trp Thr Trp Arg Ile Leu Phe Leu Val Ala Ala Ala Thr Gly
1               5                   10                  15

Ala His Ser Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Thr Pro Gly Lys Gly Leu
    50                  55                  60

Glu Trp Val Ser Gly Ile Ser Trp Lys Ser Asn Ile Ile Gly Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Leu
            100                 105                 110

Tyr Tyr Cys Ala Arg Asp Ile Thr Gly Ser Gly Ser Tyr Gly Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Ala Ala Gly Gly Pro Ser Val Phe Leu Phe Pro Pro Lys Pro Lys
            260                 265                 270
```

```
Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Ala Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn Gln Tyr Thr Gln Lys Ser
    450                 455                 460

Leu Ser Leu Ser Pro Gly
465                 470


<210> SEQ ID NO 73
<211> LENGTH: 470
<212> TYPE: PRT
<213> ORGANISM: Artificial Sequence
<220> FEATURE:
<223> OTHER INFORMATION: anti-PD-L1 antibody heavy chain with L239A,
      L240A, H315A, K327A and H440 variants and signal peptide LHC

<400> SEQUENCE: 73

Met Asp Trp Thr Trp Arg Ile Leu Phe Leu Val Ala Ala Ala Thr Gly
1               5                   10                  15

Ala His Ser Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Thr Pro Gly Lys Gly Leu
    50                  55                  60

Glu Trp Val Ser Gly Ile Ser Trp Lys Ser Asn Ile Ile Gly Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Leu
            100                 105                 110

Tyr Tyr Cys Ala Arg Asp Ile Thr Gly Ser Gly Ser Tyr Gly Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160
```

Gly Gly Thr Ala Ala Leu Gly Cys Leu Val Lys Asp Tyr Phe Pro Glu
165 170 175

Pro Val Thr Val Ser Trp Asn Ser Gly Ala Leu Thr Ser Gly Val His
180 185 190

Thr Phe Pro Ala Val Leu Gln Ser Ser Gly Leu Tyr Ser Leu Ser Ser
195 200 205

Val Val Thr Val Pro Ser Ser Ser Leu Gly Thr Gln Thr Tyr Ile Cys
210 215 220

Asn Val Asn His Lys Pro Ser Asn Thr Lys Val Asp Lys Arg Val Glu
225 230 235 240

Pro Lys Ser Cys Asp Lys Thr His Thr Cys Pro Pro Cys Pro Ala Pro
245 250 255

Glu Ala Ala Gly Gly Pro Ser Val Phe Leu Phe Pro Pro Lys Pro Lys
260 265 270

Asp Thr Leu Met Ile Ser Arg Thr Pro Glu Val Thr Cys Val Val Val
275 280 285

Asp Val Ser His Glu Asp Pro Glu Val Lys Phe Asn Trp Tyr Val Asp
290 295 300

Gly Val Glu Val His Asn Ala Lys Thr Lys Pro Arg Glu Glu Gln Tyr
305 310 315 320

Asn Ser Thr Tyr Arg Val Val Ser Val Leu Thr Val Leu Ala Gln Asp
325 330 335

Trp Leu Asn Gly Lys Glu Tyr Lys Cys Ala Val Ser Asn Lys Ala Leu
340 345 350

Pro Ala Pro Ile Glu Lys Thr Ile Ser Lys Ala Lys Gly Gln Pro Arg
355 360 365

Glu Pro Gln Val Tyr Thr Leu Pro Pro Ser Arg Glu Glu Met Thr Lys
370 375 380

Asn Gln Val Ser Leu Thr Cys Leu Val Lys Gly Phe Tyr Pro Ser Asp
385 390 395 400

Ile Ala Val Glu Trp Glu Ser Asn Gly Gln Pro Glu Asn Asn Tyr Lys
405 410 415

Thr Thr Pro Pro Val Leu Asp Ser Asp Gly Ser Phe Phe Leu Tyr Ser
420 425 430

Lys Leu Thr Val Asp Lys Ser Arg Trp Gln Gln Gly Asn Val Phe Ser
435 440 445

Cys Ser Val Met His Glu Ala Leu His Asn Gln Tyr Thr Gln Lys Ser
450 455 460

Leu Ser Leu Ser Pro Gly
465 470

<210> SEQ ID NO 74
<211> LENGTH: 1413
<212> TYPE: DNA
<213> ORGANISM: Artificial Sequence
<220> FEATURE:
<223> OTHER INFORMATION: Codon optimized nucleic acid sequence encoding anti-PD-L1 antibody heavy chain with L239A, L240A and K327A variants and signal peptide C

<400> SEQUENCE: 74
atgatgtcct ttgtctctct gctcctggtt ggcatcctat tccatgccac ccaggccgag 60
gtgcagctgg tggagtctgg gggaggcttg gtccagcctg ggaggtccct gagactctcc 120
tgtgcagcct ctggattcac ctttgatgat tatgccatgc actgggtccg ccagactcca 180

```
gggaagggcc tggagtgggt ctcaggaatt agttggaaaa gtaacatcat tggatacgcg    240

gactccgtga agggccgatt caccatctcc agagacaacg ccaagaactc cctgtatctt    300

caaatgaaca gcctgagagc cgaggacacg gctttgtatt actgtgcaag agatattacc    360

ggatccggct cttacggctg gttcgacccc tggggccagg gaaccctggt caccgtctcc    420

tcagcctcca ccaagggccc atcggtcttc cccctggcac cctctagcaa gagcacctct    480

gggggcacag cggccctggg ctgcctggtc aaggactact tccccgaacc ggtgacggtg    540

tcgtggaact caggcgccct gaccagcggc gtgcacacct tcccggctgt cctacagtcc    600

tcaggactct actccctcag cagcgtggtg accgtgccct ccagcagctt gggcacccag    660

acctacatct gcaacgtgaa tcacaagccc agcaacacca aggtggacaa gcgggttgag    720

cccaaatctt gtgacaaaac tcacacatgc ccaccgtgcc cagcacctga agccgccggg    780

ggaccgtcag tcttcctctt ccccccaaaa cccaaggaca ccctcatgat ctcccggacc    840

cctgaggtca catgcgtggt ggtggacgtg agccacgaag accctgaggt caagttcaac    900

tggtacgtgg acggcgtgga ggtgcataat gccaagacaa agccgagaga ggagcagtac    960

aacagcacgt accgtgtggt cagcgtcctc accgtcctgc accaggactg gctgaatggc   1020

aaggagtaca agtgcgccgt ctccaacaaa gccctcccag cccccatcga gaaaaccatc   1080

tccaaagcca aagggcagcc ccgagaacca caggtgtaca ccctgccccc atcccgggag   1140

gagatgacca agaaccaggt cagcctgacc tgcctggtca aaggcttcta tcccagcgac   1200

atcgccgtgg agtgggagag caatgggcag ccggagaaca actacaagac cacgcctccc   1260

gtgctggact ccgacggctc cttcttcctc tattctaagc tcaccgtgga caagagcagg   1320

tggcagcagg ggaacgtctt ctcatgctcc gtgatgcatg aggctctgca caaccactac   1380

acgcagaaga gcctctccct gtctcccggg tga                                1413
```

<210> SEQ ID NO 75
<211> LENGTH: 1413
<212> TYPE: DNA
<213> ORGANISM: Artificial Sequence
<220> FEATURE:
<223> OTHER INFORMATION: Codon optimized nucleic acid sequence encoding anti-PD-L1 antibody heavy chain with L239A, L240A, H315A and K327A variants and signal peptide C

<400> SEQUENCE: 75

```
atgatgtcct ttgtctctct gctcctggtt ggcatcctat tccatgccac ccaggccgag     60

gtgcagctgg tggagtctgg gggaggcttg gtccagcctg ggaggtccct gagactctcc    120

tgtgcagcct ctggattcac ctttgatgat tatgccatgc actgggtccg ccagactcca    180

gggaagggcc tggagtgggt ctcaggaatt agttggaaaa gtaacatcat tggatacgcg    240

gactccgtga agggccgatt caccatctcc agagacaacg ccaagaactc cctgtatctt    300

caaatgaaca gcctgagagc cgaggacacg gctttgtatt actgtgcaag agatattacc    360

ggatccggct cttacggctg gttcgacccc tggggccagg gaaccctggt caccgtctcc    420

tcagcctcca ccaagggccc atcggtcttc cccctggcac cctctagcaa gagcacctct    480

gggggcacag cggccctggg ctgcctggtc aaggactact tccccgaacc ggtgacggtg    540

tcgtggaact caggcgccct gaccagcggc gtgcacacct tcccggctgt cctacagtcc    600

tcaggactct actccctcag cagcgtggtg accgtgccct ccagcagctt gggcacccag    660

acctacatct gcaacgtgaa tcacaagccc agcaacacca aggtggacaa gcgggttgag    720

cccaaatctt gtgacaaaac tcacacatgc ccaccgtgcc cagcacctga agccgccggg    780
```

```
ggaccgtcag tcttcctctt ccccccaaaa cccaaggaca ccctcatgat ctcccggacc    840

cctgaggtca catgcgtggt ggtggacgtg agccacgaag accctgaggt caagttcaac    900

tggtacgtgg acggcgtgga ggtgcataat gccaagacaa agccgagaga ggagcagtac    960

aacagcacgt accgtgtggt cagcgtcctc accgtcctgg ctcaggactg gctgaatggc   1020

aaggagtaca agtgcgccgt ctccaacaaa gccctcccag cccccatcga gaaaaccatc   1080

tccaaagcca aagggcagcc ccgagaacca caggtgtaca ccctgccccc atcccgggag   1140

gagatgacca agaaccaggt cagcctgacc tgcctggtca aaggcttcta tcccagcgac   1200

atcgccgtgg agtgggagag caatgggcag ccggagaaca actacaagac cacgcctccc   1260

gtgctggact ccgacggctc cttcttcctc tattctaagc tcaccgtgga caagagcagg   1320

tggcagcagg ggaacgtctt ctcatgctcc gtgatgcatg aggctctgca caaccactac   1380

acgcagaaga gcctctccct gtctcccggg tga                                1413
```

```
<210> SEQ ID NO 76
<211> LENGTH: 1413
<212> TYPE: DNA
<213> ORGANISM: Artificial Sequence
<220> FEATURE:
<223> OTHER INFORMATION: Codon optimized nucleic acid sequence encoding
      anti-PD-L1 antibody heavy chain with L239A, L240A, K327A and H440Q
      variants and signal peptide C

<400> SEQUENCE: 76

atgatgtcct ttgtctctct gctcctggtt ggcatcctat tccatgccac ccaggccgag     60

gtgcagctgg tggagtctgg gggaggcttg gtccagcctg ggaggtccct gagactctcc    120

tgtgcagcct ctggattcac ctttgatgat tatgccatgc actgggtccg ccagactcca    180

gggaagggcc tggagtgggt ctcaggaatt agttggaaaa gtaacatcat tggatacgcg    240

gactccgtga agggccgatt caccatctcc agagacaacg ccaagaactc cctgtatctt    300

caaatgaaca gcctgagagc cgaggacacg gctttgtatt actgtgcaag agatattacc    360

ggatccggct cttacggctg gttcgacccc tggggccagg gaaccctggt caccgtctcc    420

tcagcctcca ccaagggccc atcggtcttc cccctggcac cctctagcaa gagcacctct    480

gggggcacag cggccctggg ctgcctggtc aaggactact tccccgaacc ggtgacggtg    540

tcgtggaact caggcgccct gaccagcggc gtgcacacct tcccggctgt cctacagtcc    600

tcaggactct actccctcag cagcgtggtg accgtgccct ccagcagctt gggcacccag    660

acctacatct gcaacgtgaa tcacaagccc agcaacacca aggtggacaa gcgggttgag    720

cccaaatctt gtgacaaaac tcacacatgc ccaccgtgcc cagcacctga agccgccggg    780

ggaccgtcag tcttcctctt ccccccaaaa cccaaggaca ccctcatgat ctcccggacc    840

cctgaggtca catgcgtggt ggtggacgtg agccacgaag accctgaggt caagttcaac    900

tggtacgtgg acggcgtgga ggtgcataat gccaagacaa agccgagaga ggagcagtac    960

aacagcacgt accgtgtggt cagcgtcctc accgtcctgc accaggactg gctgaatggc   1020

aaggagtaca agtgcgccgt ctccaacaaa gccctcccag cccccatcga gaaaaccatc   1080

tccaaagcca aagggcagcc ccgagaacca caggtgtaca ccctgccccc atcccgggag   1140

gagatgacca agaaccaggt cagcctgacc tgcctggtca aaggcttcta tcccagcgac   1200

atcgccgtgg agtgggagag caatgggcag ccggagaaca actacaagac cacgcctccc   1260

gtgctggact ccgacggctc cttcttcctc tattctaagc tcaccgtgga caagagcagg   1320
```

```
tggcagcagg ggaacgtctt ctcatgctcc gtgatgcatg aggctctgca caaccagtac   1380

acgcagaaga gcctctccct gtctcccggg tga                                1413
```

<210> SEQ ID NO 77
<211> LENGTH: 1413
<212> TYPE: DNA
<213> ORGANISM: Artificial Sequence
<220> FEATURE:
<223> OTHER INFORMATION: Codon optimized nucleic acid sequence encoding anti-PD-L1 antibody heavy chain with L239A, L240A, H315A, K327A and H440 variants and signal peptide C

<400> SEQUENCE: 77

```
atgatgtcct ttgtctctct gctcctggtt ggcatcctat tccatgccac ccaggccgag     60

gtgcagctgg tggagtctgg gggaggcttg gtccagcctg ggaggtccct gagactctcc    120

tgtgcagcct ctggattcac ctttgatgat tatgccatgc actgggtccg ccagactcca    180

gggaagggcc tggagtgggt ctcaggaatt agttggaaaa gtaacatcat tggatacgcg    240

gactccgtga agggccgatt caccatctcc agagacaacg ccaagaactc cctgtatctt    300

caaatgaaca gcctgagagc cgaggacacg gctttgtatt actgtgcaag agatattacc    360

ggatccggct cttacggctg gttcgacccc tggggccagg gaaccctggt caccgtctcc    420

tcagcctcca ccaagggccc atcggtcttc cccctggcac cctctagcaa gagcacctct    480

gggggcacag cggccctggg ctgcctggtc aaggactact tccccgaacc ggtgacggtg    540

tcgtggaact caggcgccct gaccagcggc gtgcacacct tcccggctgt cctacagtcc    600

tcaggactct actccctcag cagcgtggtg accgtgccct ccagcagctt gggcacccag    660

acctacatct gcaacgtgaa tcacaagccc agcaacacca aggtggacaa gcgggttgag    720

cccaaatctt gtgacaaaac tcacacatgc ccaccgtgcc cagcacctga agccgccggg    780

ggaccgtcag tcttcctctt ccccccaaaa cccaaggaca ccctcatgat ctcccggacc    840

cctgaggtca catgcgtggt ggtggacgtg agccacgaag accctgaggt caagttcaac    900

tggtacgtgg acggcgtgga ggtgcataat gccaagacaa agccgagaga ggagcagtac    960

aacagcacgt accgtgtggt cagcgtcctc accgtcctgg ctcaggactg gctgaatggc   1020

aaggagtaca agtgcgccgt ctccaacaaa gccctcccag cccccatcga gaaaaccatc   1080

tccaaagcca aagggcagcc ccgagaacca caggtgtaca ccctgccccc atcccgggag   1140

gagatgacca agaaccaggt cagcctgacc tgcctggtca aaggcttcta tcccagcgac   1200

atcgccgtgg agtgggagag caatgggcag ccggagaaca actacaagac cacgcctccc   1260

gtgctggact ccgacggctc cttcttcctc tattctaagc tcaccgtgga caagagcagg   1320

tggcagcagg ggaacgtctt ctcatgctcc gtgatgcatg aggctctgca caaccagtac   1380

acgcagaaga gcctctccct gtctcccggg tga                                1413
```

<210> SEQ ID NO 78
<211> LENGTH: 1413
<212> TYPE: DNA
<213> ORGANISM: Artificial Sequence
<220> FEATURE:
<223> OTHER INFORMATION: Codon optimized nucleic acid sequence encoding anti-PD-L1 antibody heavy chain with L239A, L240A and K327A variants and signal peptide LHC

<400> SEQUENCE: 78

```
atggactgga cttggagaat cctgttcctg gtggccgctg ctaccggcgc tcattctgaa     60

gtgcagctgg tggaatctgg cggcggattg gttcagcctg gcagatccct gagactgtct    120
```

```
tgtgccgcct ctggcttcac cttcgacgac tacgctatgc actgggtccg acagacccct    180
ggcaaaggac tggaatgggt gtccggcatc tcctggaagt ccaacatcat cggctacgcc    240
gactccgtga agggcagatt caccatctcc agagacaacg ccaagaactc cctgtacctg    300
cagatgaaca gcctgagagc cgaggacacc gctctgtact actgcgccag agacatcacc    360
ggctccggct cttacggatg gttcgatcct tggggccagg gcacactggt cacagtgtcc    420
tctgcttcca ccaagggacc cagcgttttc cctctggctc catcctccaa gtctacctct    480
ggcggaacag ctgctctggg ctgcctggtc aaggactact ttcctgagcc tgtgaccgtg    540
tcctggaact ctggcgctct gacatctggc gtgcacacct ttccagctgt gctgcagtcc    600
tccggcctgt actctctgtc ctctgtcgtg accgtgcctt ccagctctct gggaacccag    660
acctacatct gcaatgtgaa ccacaagcct tccaacacca aggtggacaa gagagtggaa    720
cccaagtcct gcgacaagac ccacacctgt cctccatgtc ctgctccaga agctgctggc    780
ggcccttccg tgtttctgtt ccctccaaag cctaaggaca ccctgatgat ctctcggacc    840
cctgaagtga cctgcgtggt ggtggatgtg tctcacgagg acccagaagt gaagttcaat    900
tggtacgtgg acggcgtgga agtgcacaat gccaagacca agcctagaga ggaacagtac    960
aactccacct atagagtggt gtccgtgctg accgtgctgc accaggattg gctgaacggc   1020
aaagagtaca agtgcgccgt gtccaacaag gccctgcctg ctcctatcga aaagaccatc   1080
agcaaggcca agggccagcc tagggaaccc caggtttaca ccctgcctcc aagccgggaa   1140
gagatgacca agaaccaggt gtccctgacc tgcctcgtga agggattcta cccctccgat   1200
atcgccgtgg aatgggagtc taatggccag ccagagaaca actacaagac aacccctcct   1260
gtgctggact ccgacggctc attcttcctg tactccaagc tgacagtgga caagtccaga   1320
tggcagcagg gcaacgtgtt ctcctgctcc gtgatgcacg aggccctgca caatcactac   1380
acacagaagt ccctgtctct gtcccctggc tga                                1413
```

<210> SEQ ID NO 79
<211> LENGTH: 1413
<212> TYPE: DNA
<213> ORGANISM: Artificial Sequence
<220> FEATURE:
<223> OTHER INFORMATION: Codon optimized nucleic acid sequence encoding anti-PD-L1 antibody heavy chain with L239A, L240A, H315A and K327A variants and signal peptide LHC

<400> SEQUENCE: 79

```
atggactgga cttggagaat cctgttcctg gtggccgctg ctaccggcgc tcattctgaa     60
gtgcagctgg tggaatctgg cggcggattg gttcagcctg gcagatccct gagactgtct    120
tgtgccgcct ctggcttcac cttcgacgac tacgctatgc actgggtccg acagacccct    180
ggcaaaggac tggaatgggt gtccggcatc tcctggaagt ccaacatcat cggctacgcc    240
gactccgtga agggcagatt caccatctcc agagacaacg ccaagaactc cctgtacctg    300
cagatgaaca gcctgagagc cgaggacacc gctctgtact actgcgccag agacatcacc    360
ggctccggct cttacggatg gttcgatcct tggggccagg gcacactggt cacagtgtcc    420
tctgcttcca ccaagggacc cagcgttttc cctctggctc catcctccaa gtctacctct    480
ggcggaacag ctgctctggg ctgcctggtc aaggactact ttcctgagcc tgtgaccgtg    540
tcctggaact ctggcgctct gacatctggc gtgcacacct ttccagctgt gctgcagtcc    600
tccggcctgt actctctgtc ctctgtcgtg accgtgcctt ccagctctct gggaacccag    660
```

```
acctacatct gcaatgtgaa ccacaagcct tccaacacca aggtggacaa gagagtggaa    720

cccaagtcct gcgacaagac ccacacctgt cctccatgtc ctgctccaga agctgctggc    780

ggcccttccg tgtttctgtt ccctccaaag cctaaggaca ccctgatgat ctctcggacc    840

cctgaagtga cctgcgtggt ggtggatgtg tctcacgagg acccagaagt gaagttcaat    900

tggtacgtgg acggcgtgga agtgcacaat gccaagacca agcctagaga ggaacagtac    960

aactccacct atagagtggt gtccgtgctg accgtgctgg cccaggattg gctgaacggc   1020

aaagagtaca agtgcgccgt gtccaacaag gccctgcctg ctcctatcga aaagaccatc   1080

agcaaggcca agggccagcc tagggaaccc caggtttaca ccctgcctcc aagccgggaa   1140

gagatgacca agaaccaggt gtccctgacc tgcctcgtga agggattcta cccctccgat   1200

atcgccgtgg aatgggagtc taatggccag ccagagaaca actacaagac aacccctcct   1260

gtgctggact ccgacggctc attcttcctg tactccaagc tgacagtgga caagtccaga   1320

tggcagcagg gcaacgtgtt ctcctgctcc gtgatgcacg aggccctgca caatcactac   1380

acacagaagt ccctgtctct gtcccctggc tga                                1413
```

<210> SEQ ID NO 80
<211> LENGTH: 1413
<212> TYPE: DNA
<213> ORGANISM: Artificial Sequence
<220> FEATURE:
<223> OTHER INFORMATION: Codon optimized nucleic acid sequence encoding anti-PD-L1 antibody heavy chain with L239A, L240A, K327A and H440Q variants and signal peptide LHC

<400> SEQUENCE: 80

```
atggactgga cttggagaat cctgttcctg gtggccgctg ctaccggcgc tcattctgaa     60

gtgcagctgg tggaatctgg cggcggattg gttcagcctg gcagatccct gagactgtct    120

tgtgccgcct ctggcttcac cttcgacgac tacgctatgc actgggtccg acagacccct    180

ggcaaaggac tggaatgggt gtccggcatc tcctggaagt ccaacatcat cggctacgcc    240

gactccgtga agggcagatt caccatctcc agagacaacg ccaagaactc cctgtacctg    300

cagatgaaca gcctgagagc cgaggacacc gctctgtact actgcgccag agacatcacc    360

ggctccggct cttacggatg gttcgatcct tggggccagg gcacactggt cacagtgtcc    420

tctgcttcca ccaagggacc cagcgttttc cctctggctc catcctccaa gtctacctct    480

ggcggaacag ctgctctggg ctgcctggtc aaggactact ttcctgagcc tgtgaccgtg    540

tcctggaact ctggcgctct gacatctggc gtgcacacct ttccagctgt gctgcagtcc    600

tccggcctgt actctctgtc ctctgtcgtg accgtgcctt ccagctctct gggaacccag    660

acctacatct gcaatgtgaa ccacaagcct tccaacacca aggtggacaa gagagtggaa    720

cccaagtcct gcgacaagac ccacacctgt cctccatgtc ctgctccaga agctgctggc    780

ggcccttccg tgtttctgtt ccctccaaag cctaaggaca ccctgatgat ctctcggacc    840

cctgaagtga cctgcgtggt ggtggatgtg tctcacgagg acccagaagt gaagttcaat    900

tggtacgtgg acggcgtgga agtgcacaat gccaagacca agcctagaga ggaacagtac    960

aactccacct atagagtggt gtccgtgctg accgtgctgc accaggattg gctgaacggc   1020

aaagagtaca agtgcgccgt gtccaacaag gccctgcctg ctcctatcga aaagaccatc   1080

agcaaggcca agggccagcc tagggaaccc caggtttaca ccctgcctcc aagccgggaa   1140

gagatgacca agaaccaggt gtccctgacc tgcctcgtga agggattcta cccctccgat   1200

atcgccgtgg aatgggagtc taatggccag ccagagaaca actacaagac aacccctcct   1260
```

```
gtgctggact ccgacggctc attcttcctg tactccaagc tgacagtgga caagtccaga   1320

tggcagcagg gcaacgtgtt ctcctgctcc gtgatgcacg aggccctgca caatcagtac   1380

acacagaagt ccctgtctct gtcccctggc tga                                1413


<210> SEQ ID NO 81
<211> LENGTH: 1413
<212> TYPE: DNA
<213> ORGANISM: Artificial Sequence
<220> FEATURE:
<223> OTHER INFORMATION: Codon optimized nucleic acid sequence encoding
      anti-PD-L1 antibody heavy chain with L239A, L240A, H315A, K327A
      and H440 variants and signal peptide LHC

<400> SEQUENCE: 81

atggactgga cttggagaat cctgttcctg gtggccgctg ctaccggcgc tcattctgaa     60

gtgcagctgg tggaatctgg cggcggattg gttcagcctg gcagatccct gagactgtct    120

tgtgccgcct ctggcttcac cttcgacgac tacgctatgc actgggtccg acagacccct    180

ggcaaaggac tggaatgggt gtccggcatc tcctggaagt ccaacatcat cggctacgcc    240

gactccgtga agggcagatt caccatctcc agagacaacg ccaagaactc cctgtacctg    300

cagatgaaca gcctgagagc cgaggacacc gctctgtact actgcgccag agacatcacc    360

ggctccggct cttacggatg gttcgatcct tggggccagg gcacactggt cacagtgtcc    420

tctgcttcca ccaagggacc cagcgttttc cctctggctc catcctccaa gtctacctct    480

ggcggaacag ctgctctggg ctgcctggtc aaggactact ttcctgagcc tgtgaccgtg    540

tcctggaact ctggcgctct gacatctggc gtgcacacct ttccagctgt gctgcagtcc    600

tccggcctgt actctctgtc ctctgtcgtg accgtgcctt ccagctctct gggaacccag    660

acctacatct gcaatgtgaa ccacaagcct tccaacacca aggtggacaa gagagtggaa    720

cccaagtcct gcgacaagac ccacacctgt cctccatgtc ctgctccaga agctgctggc    780

ggcccttccg tgtttctgtt ccctccaaag cctaaggaca ccctgatgat ctctcggacc    840

cctgaagtga cctgcgtggt ggtggatgtg tctcacgagg acccagaagt gaagttcaat    900

tggtacgtgg acggcgtgga agtgcacaat gccaagacca agcctagaga ggaacagtac    960

aactccacct atagagtggt gtccgtgctg accgtgctgg cccaggattg gctgaacggc   1020

aaagagtaca agtgcgccgt gtccaacaag gccctgcctg ctcctatcga aaagaccatc   1080

agcaaggcca agggccagcc tagggaaccc caggtttaca ccctgcctcc aagccgggaa   1140

gagatgacca agaaccaggt gtccctgacc tgcctcgtga agggattcta cccctccgat   1200

atcgccgtgg aatgggagtc taatggccag ccagagaaca actacaagac aacccctcct   1260

gtgctggact ccgacggctc attcttcctg tactccaagc tgacagtgga caagtccaga   1320

tggcagcagg gcaacgtgtt ctcctgctcc gtgatgcacg aggccctgca caatcagtac   1380

acacagaagt ccctgtctct gtcccctggc tga                                1413


<210> SEQ ID NO 82
<211> LENGTH: 645
<212> TYPE: DNA
<213> ORGANISM: Artificial Sequence
<220> FEATURE:
<223> OTHER INFORMATION: Codon optimized nucleic acid sequence encoding
      anti-PD-L1 antibody light chain

<400> SEQUENCE: 82

gacatccaga tgacccagtc tccatcctcc ctgtctgcat ctgtaggaga cagagtcacc     60
```

```
atcacttgcc gggcaagtca gagcattagc agctatttaa attggtatca gcagaaacca    120

gggaaagccc ctaagcctct gatctatgtc gcatccagtt tgcaaagtgg ggtcccatca    180

tctttcagtg gcagtggatc tgggacagat ttcactctca ccatcagcag tctgcaacct    240

gaagattttg caacttacta ctgtcaacag agttacagta accctatcac gttcggccaa    300

gggaccaggc tggaaatcaa acgaactgtg gctgcaccat ctgtcttcat cttcccgcca    360

tctgatgagc agcttaagtc cggaactgct agcgttgtgt gcctgctgaa taacttctat    420

cccagagagg ccaaagtaca gtggaaggtg gataacgccc tccaatcggg aaactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gttag                    645
```

<210> SEQ ID NO 83
<211> LENGTH: 645
<212> TYPE: DNA
<213> ORGANISM: Artificial Sequence
<220> FEATURE:
<223> OTHER INFORMATION: Codon optimized nucleic acid sequence encoding anti-PD-L1 antibody light chain

<400> SEQUENCE: 83

```
gacatccaga tgacccagtc tccatcctct ctgtccgcct ctgtgggcga cagagtgacc     60

atcacctgtc gggcctctca gtccatctcc tcctacctga actggtatca gcagaagccc    120

ggcaaggccc ctaagcctct gatctatgtg gcctccagtc tgcagtctgg cgtgccctct    180

tctttctccg gctctggctc tggcaccgac tttaccctga caatctccag cctgcagcct    240

gaggacttcg ccacctacta ctgccagcag tcctacagca accctatcac cttcggccag    300

ggcaccagac tggaaatcaa gagaaccgtg gccgctcctt ccgtgttcat cttcccacct    360

tccgacgagc agctgaagtc cggcacagct tctgtcgtgt gcctgctgaa caacttctac    420

cctcgggaag ccaaggtgca gtggaaggtg gacaatgctc tgcagtccgg caactcccaa    480

gagtccgtga ccgagcagga ctccaaggac tctacctaca gcctgtcctc cacactgacc    540

ctgtccaagg ccgactacga gaagcacaag gtgtacgcct gcgaagtgac ccatcagggc    600

ctgtctagcc ctgtgaccaa gtctttcaac cggggcgagt gctga                    645
```

<210> SEQ ID NO 84
<211> LENGTH: 233
<212> TYPE: PRT
<213> ORGANISM: Artificial Sequence
<220> FEATURE:
<223> OTHER INFORMATION: anti-PD-L1 antibody light chain with signal peptide C

<400> SEQUENCE: 84

```
Met Met Ser Phe Val Ser Leu Leu Leu Val Gly Ile Leu Phe His Ala
1               5                   10                  15

Thr Gln Ala Asp Ile Gln Met Thr Gln Ser Pro Ser Ser Leu Ser Ala
            20                  25                  30

Ser Val Gly Asp Arg Val Thr Ile Thr Cys Arg Ala Ser Gln Ser Ile
        35                  40                  45

Ser Ser Tyr Leu Asn Trp Tyr Gln Gln Lys Pro Gly Lys Ala Pro Lys
    50                  55                  60

Pro Leu Ile Tyr Val Ala Ser Ser Leu Gln Ser Gly Val Pro Ser Ser
65                  70                  75                  80
```

```
Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Ser Tyr Ser
            100                 105                 110

Asn Pro Ile Thr Phe Gly Gln Gly Thr Arg Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 85
<211> LENGTH: 236
<212> TYPE: PRT
<213> ORGANISM: Artificial Sequence
<220> FEATURE:
<223> OTHER INFORMATION: anti-PD-L1 antibody light chain with signal peptide LLC

<400> SEQUENCE: 85

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Ser Ile Ser Ser Tyr Leu Asn Trp Tyr Gln Gln Lys Pro Gly Lys
    50                  55                  60

Ala Pro Lys Pro Leu Ile Tyr Val Ala Ser Ser Leu Gln Ser Gly Val
65                  70                  75                  80

Pro Ser Ser Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ser Tyr Ser Asn Pro Ile Thr Phe Gly Gln Gly Thr Arg Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
```

```
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235


<210> SEQ ID NO 86
<211> LENGTH: 702
<212> TYPE: DNA
<213> ORGANISM: Artificial Sequence
<220> FEATURE:
<223> OTHER INFORMATION: Codon optimized nucleic acid sequence encoding
      anti-PD-L1 antibody light chain with signal peptide C

<400> SEQUENCE: 86

atgatgtcct ttgtctctct gctcctggtt ggcatcctat tccatgccac ccaggccgac      60

atccagatga cccagtctcc atcctccctg tctgcatctg taggagacag agtcaccatc     120

acttgccggg caagtcagag cattagcagc tatttaaatt ggtatcagca gaaaccaggg     180

aaagccccta agctcctgat ctatgtcgca tccagtttgc aaagtggggt cccatcatct     240

ttcagtggca gtggatctgg gacagatttc actctcacca tcagcagtct gcaacctgaa     300

gattttgcaa cttactactg tcaacagagt tacagtaacc ctatcacgtt cggccaaggg     360

accaggctgg aaatcaaacg aactgtggct gcaccatctg tcttcatctt cccgccatct     420

gatgagcagc ttaagtccgg aactgctagc gttgtgtgcc tgctgaataa cttctatccc     480

agagaggcca aagtacagtg gaaggtggat aacgccctcc aatcgggaaa ctcccaggag     540

agtgtcacag agcaggacag caaggacagc acctacagcc tcagcagcac cctgacgctg     600

agcaaagcag actacgagaa acacaaagtc tacgcctgcg aagtcaccca tcagggcctg     660

agctcgcccg tcacaaagag cttcaacagg ggagagtgtt ag                        702


<210> SEQ ID NO 87
<211> LENGTH: 711
<212> TYPE: DNA
<213> ORGANISM: Artificial Sequence
<220> FEATURE:
<223> OTHER INFORMATION: Codon optimized nucleic acid sequence encoding
      anti-PD-L1 antibody light chain with signal peptide LLC

<400> SEQUENCE: 87

atggacatga gagtgcctgc tcagctgctg ggactgctgc tgttgtggtt gagaggcgcc      60

agatgcgaca tccagatgac ccagtctcca tcctctctgt ccgcctctgt gggcgacaga     120

gtgaccatca cctgtcgggc ctctcagtcc atctcctcct acctgaactg gtatcagcag     180

aagcccggca aggcccctaa gctcctgatc tatgtggcct ccagtctgca gtctggcgtg     240

ccctcttctt tctccggctc tggctctggc accgacttta ccctgacaat ctccagcctg     300

cagcctgagg acttcgccac ctactactgc cagcagtcct acagcaaccc tatcaccttc     360

ggccagggca ccagactgga aatcaagaga accgtggccg ctccttccgt gttcatcttc     420

ccaccttccg acgagcagct gaagtccggc acagcttctg tcgtgtgcct gctgaacaac     480

ttctaccctc gggaagccaa ggtgcagtgg aaggtggaca atgctctgca gtccggcaac     540

tcccaagagt ccgtgaccga gcaggactcc aaggactcta cctacagcct gtcctccaca     600

ctgaccctgt ccaaggccga ctacgagaag cacaaggtgt acgcctgcga agtgacccat     660

cagggcctgt ctagccctgt gaccaagtct ttcaaccggg gcgagtgctg a              711
```

<210> SEQ ID NO 88
<211> LENGTH: 19
<212> TYPE: PRT
<213> ORGANISM: Artificial Sequence
<220> FEATURE:
<223> OTHER INFORMATION: Signal peptide C

<400> SEQUENCE: 88

Met Met Ser Phe Val Ser Leu Leu Leu Val Gly Ile Leu Phe His Ala
1 5 10 15

Thr Gln Ala

<210> SEQ ID NO 89
<211> LENGTH: 22
<212> TYPE: PRT
<213> ORGANISM: Artificial Sequence
<220> FEATURE:
<223> OTHER INFORMATION: Signal peptide LLC

<400> SEQUENCE: 89

Met Asp Met Arg Val Pro Ala Gln Leu Leu Gly Leu Leu Leu Leu Trp
1 5 10 15

Leu Arg Gly Ala Arg Cys
20

<210> SEQ ID NO 90
<211> LENGTH: 19
<212> TYPE: PRT
<213> ORGANISM: Artificial Sequence
<220> FEATURE:
<223> OTHER INFORMATION: Signal peptide LHC

<400> SEQUENCE: 90

Met Asp Trp Thr Trp Arg Ile Leu Phe Leu Val Ala Ala Ala Thr Gly
1 5 10 15

Ala His Ser

<210> SEQ ID NO 91
<211> LENGTH: 57
<212> TYPE: DNA
<213> ORGANISM: Artificial Sequence
<220> FEATURE:
<223> OTHER INFORMATION: Nucleic acid sequence encoding signal peptide C

<400> SEQUENCE: 91
atgatgtcct ttgtctctct gctcctggtt ggcatcctat tccatgccac ccaggcc 57

<210> SEQ ID NO 92
<211> LENGTH: 66
<212> TYPE: DNA
<213> ORGANISM: Artificial Sequence
<220> FEATURE:
<223> OTHER INFORMATION: Nucleic acid sequence encoding signal peptide LLC

<400> SEQUENCE: 92
atggacatga gagtgcctgc tcagctgctg ggactgctgc tgttgtggtt gagaggcgcc 60
agatgc 66

<210> SEQ ID NO 93
<211> LENGTH: 57
<212> TYPE: DNA
<213> ORGANISM: Artificial Sequence
<220> FEATURE:
<223> OTHER INFORMATION: Nucleic acid sequence encoding signal peptide

LHC

<400> SEQUENCE: 93
atggactgga cttggagaat cctgttcctg gtggccgctg ctaccggcgc tcattct 57

<210> SEQ ID NO 94
<211> LENGTH: 118
<212> TYPE: PRT
<213> ORGANISM: Homo sapiens

<400> SEQUENCE: 94

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115
```

<210> SEQ ID NO 95
<211> LENGTH: 107
<212> TYPE: PRT
<213> ORGANISM: Homo sapiens

<400> SEQUENCE: 95

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
            100                 105
```

<210> SEQ ID NO 96
<211> LENGTH: 107
<212> TYPE: PRT
<213> ORGANISM: Homo sapiens

<400> SEQUENCE: 96

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
```

```
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 97
<211> LENGTH: 214
<212> TYPE: PRT
<213> ORGANISM: Homo sapiens

<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 98
<211> LENGTH: 447
<212> TYPE: PRT
<213> ORGANISM: Homo sapiens

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
```

```
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445
```

<210> SEQ ID NO 99
<211> LENGTH: 329
<212> TYPE: PRT
<213> ORGANISM: Homo sapiens

<400> SEQUENCE: 99

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 100
<211> LENGTH: 447
<212> TYPE: PRT
<213> ORGANISM: Artificial Sequence
<220> FEATURE:
<223> OTHER INFORMATION: anti-PD-L1 atezolizumab antibody heavy chain with L235A, L236A, and K323A variants

<400> SEQUENCE: 100

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Ala Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

```
Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445


<210> SEQ ID NO 101
<211> LENGTH: 447
<212> TYPE: PRT
<213> ORGANISM: Artificial Sequence
<220> FEATURE:
<223> OTHER INFORMATION: anti-PD-L1 atezolizumab antibody heavy chain
      with L235A, L236A, L311A, and K323A variants

<400> SEQUENCE: 101

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu Ala Gln Asp Trp Leu Asn Gly Lys Glu Tyr
305                 310                 315                 320
```

```
Lys Cys Ala Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445


<210> SEQ ID NO 102
<211> LENGTH: 447
<212> TYPE: PRT
<213> ORGANISM: Artificial Sequence
<220> FEATURE:
<223> OTHER INFORMATION: anti-PD-L1 atezolizumab antibody heavy chain
      with L235A, L236A, K323A, and H436Q variants

<400> SEQUENCE: 102

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
```

```
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Ala Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn Gln Tyr Thr Gln Lys Ser Leu Ser Leu Ser Pro Gly
        435                 440                 445


<210> SEQ ID NO 103
<211> LENGTH: 447
<212> TYPE: PRT
<213> ORGANISM: Artificial Sequence
<220> FEATURE:
<223> OTHER INFORMATION: anti-PD-L1 atezolizumab antibody heavy chain
      with L235A, L236A, L311A, K323A, and H436Q variants

<400> SEQUENCE: 103

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140
```

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu Ala Gln Asp Trp Leu Asn Gly Lys Glu Tyr
305                 310                 315                 320

Lys Cys Ala Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn Gln Tyr Thr Gln Lys Ser Leu Ser Leu Ser Pro Gly
        435                 440                 445


<210> SEQ ID NO 104
<211> LENGTH: 329
<212> TYPE: PRT
<213> ORGANISM: Artificial Sequence
<220> FEATURE:
<223> OTHER INFORMATION: anti-PD-L1 atezolizumab antibody heavy chain
      constant region with L235A, L236A, and K323A variants

<400> SEQUENCE: 104

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325


<210> SEQ ID NO 105
<211> LENGTH: 329
<212> TYPE: PRT
<213> ORGANISM: Artificial Sequence
<220> FEATURE:
<223> OTHER INFORMATION: anti-PD-L1 atezolizumab antibody heavy chain
      constant region with L235A, L236A, L311A, and K323A variants

<400> SEQUENCE: 105

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
```

```
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

Ala Gln Asp Trp Leu Asn Gly Lys Glu Tyr Lys Cys Ala Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325


<210> SEQ ID NO 106
<211> LENGTH: 329
<212> TYPE: PRT
<213> ORGANISM: Artificial Sequence
<220> FEATURE:
<223> OTHER INFORMATION: anti-PD-L1 atezolizumab antibody heavy chain
      constant region with L235A, L236A, K323A, and H436Q variants

<400> SEQUENCE: 106

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110
```

```
Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn Gln Tyr Thr
305                 310                 315                 320

Gln Lys Ser Leu Ser Leu Ser Pro Gly
                325


<210> SEQ ID NO 107
<211> LENGTH: 329
<212> TYPE: PRT
<213> ORGANISM: Artificial Sequence
<220> FEATURE:
<223> OTHER INFORMATION: anti-PD-L1 atezolizumab antibody heavy chain
      constant region with L235A, L236A, L311A, K323A, and H436Q
      variants

<400> SEQUENCE: 107

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
```

```
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

Ala Gln Asp Trp Leu Asn Gly Lys Glu Tyr Lys Cys Ala Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn Gln Tyr Thr
305                 310                 315                 320

Gln Lys Ser Leu Ser Leu Ser Pro Gly
                325


<210> SEQ ID NO 108
<211> LENGTH: 329
<212> TYPE: PRT
<213> ORGANISM: Homo sapiens

<400> SEQUENCE: 108

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

-continued

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

MODIFIED ANTI-PD-L1 ANTIBODY AND METHODS AND USES FOR TREATING A NEURODEGENERATIVE DISEASE

This continuation application claims the benefit of priority and is entitled to the filing date pursuant to 35 U.S.C. § 120 of U.S. Non-Provisional patent application Ser. No. 16/852,508, filed Apr. 19, 2020, a 35 U.S.C. § 111 patent application which claims the benefit of priority and is entitled to the filing date pursuant to 35 U.S.C. § 119(e) of U.S. Provisional Patent Application Ser. No. 62/836,247, filed on Apr. 19, 2019 and U.S. Non-Provisional patent application Ser. No. 16/852,508 claims the benefit of priority and is entitled to the filing date pursuant to 35 U.S.C. 119(a) of European Patent Application Serial No. 19170438.6, filed on Apr. 19, 2019, the content of each of which is hereby incorporated by reference in its entirety.

Neurodegeneration is the progressive loss of structure or function of neurons, including death of neurons. Many neurodegenerative diseases occur as a result of neurodegenerative processes, resulting in progressive decline in behavioral, social, cognitive or motor functions. Currently, there are no effective treatments to cure, modify or halt the progression of neurodegenerative disorders, and the approved pharmacotherapies provide only modest and transient symptomatic relief.

Most neurodegenerative pathologies share a common neuroinflammatory component, which is part of disease progression, and contributes to disease escalation. Among these pathologies is Alzheimer's disease (AD) and age-related dementia, amyotrophic lateral sclerosis, Parkinson's disease, and Huntington's disease, debilitating neurodegenerative conditions characterized by progressive cognitive and/or functional decline. However, despite the chronic neuroinflammatory component in neurodegenerative disease pathology, clinical therapies with anti-inflammatory agents over the past decade have all proven unsuccessful or even deleterious to-date.

The present specification provides a unique insight into why targeting the inflammatory component of neurodegenerative pathologies using systemic anti-inflammatory drugs have fallen short. The present specification provides a therapeutic, methods and uses based on this understanding that overcomes the drawbacks of existing therapies of neurodegenerative pathologies.

SUMMARY

The present specification discloses a modified anti-Programmed Death-Ligand 1 (anti-PD-L1) antibody exhibiting high affinity and specificity for human PD-L1, enhanced clearance rate from the blood, abolished Fc-related effector functions, and improved safety profile relative to the unaltered antibody, while maintaining therapeutic efficacy for neurodegenerative disease modification. A disclosed modified anti-PD-L1 antibody comprises a heavy chain constant domain containing amino acid sequence variants that lack Fc-related effector function and promote clearance of the modified anti-PD-L1 antibody disclosed herein faster than an anti-PD-L1 antibody not containing the same amino acid sequence variants. For example, a disclosed modified anti-PD-L1 antibody comprises a heavy chain constant domain containing amino acid sequence variants in the lower hinge region and/or the N-terminal half of the CH2 domain that abolish Fc-related effector function and amino acid sequence variants in the CH2 domain and/or CH3 domain that promote clearance of the anti-PD-L1 antibody faster than an anti-PD-L1 antibody not containing the same amino acid variants located in the CH2 domain and/or CH3 domain. A disclosed modified human anti-PD-L1 antibody lacking Fc-related effector function lacks antibody dependent cellular cytotoxicity (ADCC), complement-dependent cytotoxic activity (CDC) and/or antibody dependent cellular phagocytosis (ADCP).

The present specification also discloses pharmaceutical compositions comprising a modified human anti-PD-L1 antibody disclosed herein as well as a medicament comprising a modified human anti-PD-L1 antibody disclosed herein.

The present specification also discloses pharmaceutical kits comprising modified human anti-PD-L1 antibody disclosed herein, a pharmaceutical composition disclosed herein, or a medicament disclosed herein.

The present specification also discloses methods of treatment and uses that employ an administration regime using the disclosed modified anti-PD-L1 antibody which ensures the antibodies are present for only a specific period of time and then is sufficiently cleared from the body to ensure treatment efficacy is maintained.

BRIEF DESCRIPTION OF DRAWINGS

FIG. 1B showing pre-test results of cognitive behavior in DM-hTAU and wild type animals; FIG. 1C showing results of cognitive behavior using the T-maze following treatment; FIG. 1D showing test results of cognitive behavior using the Y-maze following treatment; and FIG. 1E showing test results of cognitive behavior using Novel Object recognition following treatment (NOR).

FIG. 2B showing myeloid cells in the spleen; FIG. 2C showing levels of $CD4^+$ memory T cells in the blood; and FIG. 2D showing $CD4^+$ memory T cells in the spleen.

FIG. 3B showing the quantitative distribution of $CD45^{low}/CD11b^{high}$ myeloid cells in anti-PD-L1-treated mice and IgG-treated mice.

FIG. 4B showing the quantitative distribution of $CD45^{low}/CD11b^{high}$ myeloid cells in anti-PD-L1-treated mice and IgG-treated mice.

FIG. 5B showing representative projections of confocal z-axis stacks, indicating colocalization of $GFP^+$ cells (green), IBA-1 (blue), and IL-10 (red) in the brains of anti-PD-L1-treated DM-hTAU$^{GFP/+}$ mice (scale bar: 50 μm).

FIG. 6B showing RAWM performance one-month after treatment of FXFAD mice, each group treated with a different dose of anti-PD-L1 antibody along with wild-type littermates which served as controls (*P<0.05, P<0.01, *P<0.001); and FIG. 6C showing RAWM performance two-months after treatment of three groups of FXFAD mice, each group treated with a different dose of anti-PD-L1 antibody along with wild-type littermates which served as controls (*P<0.05, P<0.01, *P<0.001).

FIG. 7B showing mean fluorescence of detected GFAP$^+$ cells, corrected to the mean fluorescence of the whole dentate gyrus (CTCF)(P<0.01); and FIG. 7C showing the number of detected GFAP$^+$ cells exhibiting fluorescence greater than 1000 pixels (**P<0.01).

FIG. 8B showing T-maze performance one-month after treatment of DM-hTAU mice, each group treated with a different dose of anti-PD-L1 antibody along with wild-type littermates and anti-IgG2-treated mice, both of which served as controls (*P<0.05, P<0.01, *P<0.001).

FIG. 9B showing T-maze performance two-months after treatment of three groups of DM-hTAU mice, each group treated with a different dose of anti-PD-L1 antibody along with wild-type littermates and anti-IgG2-treated mice, both of which served as controls (*P<0.05, P<0.01, *P<0.001).

FIG. 11A-I show dose-dependent effect of anti-PD-L1 on inflammatory cytokine profile in DM-hTAU mice, with FIG. 11A shows representative image of IL-1β immunoreactivity in mice treated with anti-IgG antibody control; FIG. 11B shows representative image of IL-1β immunoreactivity in mice treated with anti-PD-L1 antibody; FIG. 11C shows representative orthogonal projection of confocal z-axis stacks, indicating colocalization of IL-1β (green) with GFAP+ astrocytes (red), but not with IBA-1$^+$ microglia/macrophages (white), in the dentate gyrus; cell nuclei stained with DAPI (blue) (scale bar, 100 μm); FIG. 11D shows quantitative measurement of hippocampal IL-1β protein levels, measured by FRET-based ELISA, in mice treated with anti-PD-L1 antibodies compared to untreated and anti-IgG antibody-treated wild-type littermates (data represented as mean±s.e.m; *P<0.05, P<0.01, *P<0.001); FIG. 11E shows linear regression analysis revealing a correlation between cognitive performance of DM-hTAU mice in a T-maze assay and IL-1β protein levels in their brains; FIG. 11F shows quantitative measurement of mRNA expression levels tested by RT-qPCR for the gene tnf-a; FIG. 11G shows quantitative measurement of mRNA expression levels tested by RT-qPCR for the gene il-6; FIG. 11H shows quantitative determination of mRNA expression levels tested by RT-qPCR for the gene il-12p40; and FIG. 11I shows quantitative measurement of mRNA expression levels measured by RT-qPCR for the gene il-1β.

FIG. 20B showing T-maze performance four weeks after treatment of DM-hTAU mice, each group treated with a different anti-PD-L1 antibody variant along with wild-type littermates and Variant 1-B12-treated mice, both of which served as controls (Error bars represent mean±s.e.m.; *P<0.05, P<0.01, *P<0.001); FIG. 20C showing Y-maze performance six-weeks after treatment of DM-hTAU mice, each group treated with a different anti-PD-L1 antibody variant along with wild-type littermates and Variant 1-B12-treated mice, both of which served as controls (Error bars represent mean±s.e.m.; *P<0.05, P<0.01, *P<0.001); and FIG. 20D showing T-maze performance eight-weeks after treatment of DM-hTAU mice, each group treated with a different anti-PD-L1 antibody variant along with wild-type littermates and anti-B12-treated mice, both of which served as controls (Error bars represent mean±s.e.m.; *P<0.05, P<0.01, *P<0.001).

FIG. 22B showing the results obtained from the Variant 3-ATZ (Fc effector null-H436Q) antibody (error bars represent mean±s.e.m.).

FIG. 23B showing the results obtained from the Variant 3-ATZ (Fc effector null-H436Q) antibody (error bars represent mean±s.e.m.).

FIG. 24B showing the results obtained with the Variant 3-ATZ (Fc effector null-H436Q) antibody (error bars represent mean±s.e.m.).

FIG. 26B showing same data as in FIG. 26A but comparing performance in T-maze between different treatment groups at 2-week post treatment; and FIG. 26C showing same data as in FIG. 26A but comparing performance in T-maze between different treatment groups at 4-week post treatment. One-way ANOVA and Fisher exact-test post hoc analysis. Data are represented as mean±s.e.m.

FIG. 28A-H show effect of Variant 2-ATZ (Fc effector null-H311A) antibody or isotype control Variant 2-B12 (an anti-B12 antibody containing the human IgG1 Fc effector null and H311A substitutions) on spatial learning and memory in DM-hTAU mice, with FIG. 28A illustrating the experimental design with black arrowheads indicating time points of treatment, red arrowheads indicating time points of blood withdrawn and tissue collection, and drawings indicate time points of cognitive scoring using a T-maze; FIG. 28B showing T-maze performance two weeks after the first treatment of DM-hTAU mice with the either the Variant 2-ATZ (Fc effector null-H311A) antibody or the isotype control antibody along with wild-type littermates (error bars represent mean±s.e.m.; n.s. not significant, *P<0.001); FIG. 28C showing T-maze performance four-weeks after the first treatment of DM-hTAU mice with the either the Variant 2-ATZ (Fc effector null-H311A) antibody or the isotype control antibody along with wild-type littermates (error bars represent mean±s.e.m.; *P<0.001); FIG. 28D showing T-maze performance four-weeks after the second treatment of DM-hTAU mice with the either the Variant 2-ATZ (Fc effector null-H311A) antibody or isotype control antibody along with wild-type littermates (error bars represent mean±s.e.m.; *P<0.001); FIG. 28E showing T-maze performance two-weeks after the third treatment of DM-hTAU mice with the either the Variant 2-ATZ (Fc effector null-H311A) antibody or isotype control antibody along with wild-type littermates (error bars represent mean±s.e.m.; *P<0.001); FIG. 28F showing T-maze performance four-weeks after the third treatment of DM-hTAU mice with the either the Variant 2-ATZ (Fc effector null-H311A) antibody or isotype control antibody along with wild-type littermates (error bars represent mean±s.e.m.; *P<0.001); FIG. 28G showing T-maze performance six-weeks after the third treatment of DM-hTAU mice with the either the Variant 2-ATZ (Fc effector null-H311A) antibody or the isotype control antibody along with wild-type littermates (error bars represent mean±s.e.m.; P<0.01, *P<0.001); and FIG. 28H showing T-maze performance eight-weeks after the third treatment of DM-hTAU mice with the either the Variant 2-ATZ (Fc effector null-H311A) antibody or the isotype control antibody along with wild-type littermates (error bars represent mean±s.e.m.; P<0.01, ***P<0.001).

FIG. 31B showing correlation between hippocampal tau aggregation of hippocampi excised 2 weeks after testing cognitive performance (week 4 of the study).

FIG. 33B showing the correlation between PD-L1 receptor occupancy and serum concentration of the Variant 2-G09 (Fc effector null-H315A) antibody; FIG. 33C showing the correlation between PD-L1 receptor occupancy and serum concentration of the Variant 3-G09 (Fc effector null-H440Q) antibody; and FIG. 33D showing the correlation between PD-L1 receptor occupancy and serum concentration of the Variant 4-G09 (Fc effector null-H315A+H440Q) antibody.

FIG. 35B showing effector memory (EM), central memory (CM) and naïve $CD4^-$ T cells. Data represented as mean±s.e.m.; *P<0.05, P<0.01, *P<0.001.

FIG. 36B showing a dose response ADCC assay of human IgG1, a negative control antibody, with CHO-K1/PD-L1 cells; FIG. 36C showing a dose response ADCC assay of Variant 2-G09 (Fc effector null-H315A), a modified anti-PD-L1 antibody variant disclosed herein, with CHO-K1/PD-L1 cells; FIG. 36D showing a dose response ADCC assay of Rituxan, a positive control antibody, with Raji/CD-20 cells; and FIG. 36E showing a dose response curve of a biosimilar of atezolizumab, a commercially available humanized anti-PD-L1 monoclonal antibody known to be deprived of ADCC Fc activity, with CHO-K1/PD-L1 cells.

FIG. 36B showing a dose response CDC assay of human IgG1, a negative control antibody, with CHO-K1/PD-L1 cells; FIG. 36C showing a dose response CDC assay of Variant 2-G09 (Fc effector null-H315A), a modified anti-PD-L1 antibody variant disclosed herein, with CHO-K1/PD-L1 cells; and FIG. 36D showing a dose response CDC assay of a biosimilar of atezolizumab, a commercially available humanized anti-PD-L1 monoclonal antibody known to be deprived of ADCC Fc activity, with CHO-K1/PD-L1 cells.

DETAILED DESCRIPTION

Figure 1A:
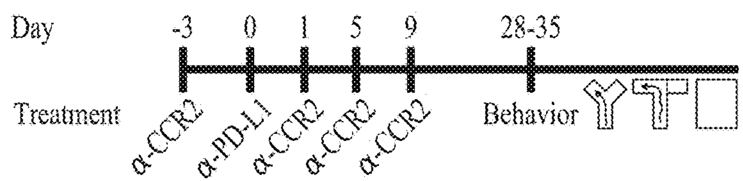
FIG. 1A-E show blocking CCR2 abrogates the beneficial effect of anti-PD-L1 antibody in DM-hTAU with FIG. 1A illustrating the experimental design.

Physiological entry of immune cells to CNS is orchestrated by the brain's choroid plexus (CP) epithelium. Trafficking through the CP is dependent on Interferon-gamma (IFN-γ) signaling that derives from T cells that reside in the periphery, including within the CP stroma. Under pathologic conditions, leukocyte trafficking through the CP is either insufficient or even impaired. One way to augment trafficking is by boosting levels of IFN-γ signaling at the CP.

Immune checkpoints are regulatory pathways for maintaining systemic immune homeostasis and tolerance. Without wishing to be limited to any theory, selective blockade of immune checkpoints reactivates a systemic IFN-γ-dependent cascade of immunological responses suppressed due to pathologic conditions. The increased IFN-γ signaling results in increased levels of leukocyte trafficking molecules expressed by the CP and in turn, migration of leukocyte across the choroid plexus epithelium into the CNS territory and recruitment of monocyte-derived macrophages and other immunoregulatory cells (T cells) to diseased sites within the brain. Importantly, this recruitment results in a comprehensive effect on brain function, including reduced of amyloid plaque burden, restored immunological balance within the brain parenchyma, reduced neuroinflammation, reduced gliosis, reduced synaptic loss, increased hippocampal neurogenesis, increased neuronal protection and enhanced neuronal survival, collectively leading to neuroprotection and/or mitigation of cognitive decline. Thus, blockade of immune checkpoints restores healthy brain-immune dialogue via increased IFN-γ signaling that enables brain maintenance and repair of a pathologic condition.

A systemic immune response is evoked by using neutralizing antibodies for immune checkpoints, such as, e.g., Programmed cell death protein 1 (PD-1), PD-L1 and T-cell immunoglobulin and mucin-domain containing-3 (TIM-3). When induced in animals with established neurodegenerative disease pathology, treatment with these neutralizing antibodies resulted in an immunological response that cleared cerebral amyloid-β (Aβ) plaques and improved cognitive performance. Thus, using neutralizing antibodies for immune checkpoint members resulted in an IFN-γ-dependent immune response that reversed the disease state.

In addition, this immune response was needed in order to mobilize immune cells to the CNS in a way that was shown to be IFN-γ-dependent. The present specification discloses experiments which demonstrate that systemic single administration of a blocking agent (e.g., antibody) of the immune checkpoint, under conditions of chronic neurodegenerative diseases, improves cognitive performance that was depended upon entry of peripheral monocyte-derived macrophages to the diseased brain (see Example 1). These experiments further indicate that monocyte-derived macrophages in the diseased brain parenchyma are needed for the resolution of the local inflammation, and promote local phagocytic activity, needed for the removal of cellular debris and for clearance of pathological conformations of misfolded and aggregated proteins (see Example 1).

Furthermore, the present specification discloses experiments which reveal that continuous exposure to neutralizing antibodies for immune checkpoint members was not only unnecessary to maintain a beneficial effect, expended exposure time to such antibodies was therapeutically less effective (see Example 3). These results indicate that greater treatment efficacy for a neurodegenerative disease is achieved when an immune checkpoint pathway is only transiently blocked. This finding is contrary to cancer treatments, where continuous exposure to neutralizing antibodies for an immune checkpoint is required for optimal therapeutic efficacy.

Not only does a transient blockade of an immune checkpoint pathway show greater efficacy in treating a neurodegenerative disease, such transient exposure should also help reduce the risk of developing immune-related adverse effects like autoimmune disease. The present specification reveals that in non-obese diabetic (NOD) mice that spontaneously develop diabetes in advanced age, exposure to neutralizing antibodies for an immune checkpoint member at young age accelerate the appearance of diabetes. The acceleration in diabetic appearance correlate with antibody exposure the shorter the antibody exposure time the lower rate of diabetic appearance at young age. (see Example 9).

The finding that recruitment of peripheral immune cells across the blood-cerebrospinal fluid barrier (BCSFB) into the brain and transient exposure to neutralizing antibodies are necessary and essential components in reversing the disease state of a brain, reveal that immune checkpoint antibodies required to achieve the safest and most efficacious outcome for a neurodegenerative disease need a particular set of characteristics that differ and even oppose to the immune checkpoint antibody characteristics needed for treating cancer.

For example, antibodies for an immune checkpoint with optimal therapeutic efficacy for a neurodegenerative disease should be an antibody that lacks cytotoxic activity. A typical full-length antibody includes the Fragment crystallizable (Fc) region. Among other things, the Fc region mediates the proper binding of the antibody to the appropriate Fc receptor which initiates several physiological effects including the lysing of target cells whose membrane-surface antigens are bound by the antibody. Referred to as antibody dependent cellular cytotoxicity (ADCC), complement-dependent cytotoxic activity (CDC) or antibody dependent cellular phagocytosis (ADCP), this lysing mechanism is part of the humoral immune response needed to limit and contain infection. However, since recruitment of peripheral immune cells are needed to initiate reactivation the systemic IFN-γ-dependent cascade of immunological responses, immune checkpoint antibodies having Fc effector activity are undesirable as such lysing activity will destroy the peripheral immune cells, depleting the population of cells needed for activation of the choroid plexus and also cells that are needed for recruitment to the brain. Thus, an antibody for an immune checkpoint member lacking Fc effector function would be an advantageous characteristic when used in a therapy for treating a neurogenerative disease. In the context of a cancer treatment, however, cytotoxic activity may be beneficial because the goal of a cancer immunotherapy is the eradication of the tumor cells, and as such, the lysing of target cancer cells is highly desirable.

As another example, antibodies for an immune checkpoint with optimal therapeutic efficacy for a neurodegenerative disease should be an antibody that can be quickly cleared from the body, i.e., an enhanced clearance rate. As discussed above, the present specification shows that a transient blockade of an immune checkpoint pathway show greater efficacy in treating a neurodegenerative disease when compared to continuous exposure of the antibody. In addition, continuous exposure of an antibody increases the risk of eliciting an autoimmune response. Thus, an antibody for an immune checkpoint member that can mediate an efficacious response but then be removed from the body in a manner that avoids the deleterious effects of continuous exposure to that antibody would be an advantageous characteristic when used in a therapy for treating a neurogenerative disease.

The present specification discloses a modified anti-PD-L1 monoclonal antibody that abolishes Fc-related effector function and enhances clearance rate of the modified anti-PD-L1 antibody while maintaining therapeutic efficacy for neurodegenerative disease modification (Examples 4-8). In addition, the present specification discloses methods of treatment and uses that employ an administration regime of the disclosed anti-PD-L1 antibody that ensures the antibody is present for only a specific period of time and then is sufficiently cleared from the body to ensure treatment efficacy is maintained (Examples 1-9).

Aspects of the present disclosure comprise, in part, a modified anti-PD-L1 antibody. A modified anti-PD-L1 antibody disclosed herein can be a typical full-length immunoglobulin molecule composed of two immunoglobulin (Ig) heavy chains and two Ig light chains. Such antibodies comprise an antigen-binding fragment (Fab) and a Fragment crystallizable (Fc) region. A preferred modified anti-PD-L1 antibody disclosed herein is a humanized anti-PD-L1 antibody or a human anti-PD-L1 antibody; a more preferred modified anti-PD-L1 antibody disclosed herein is a humanized IgG anti-PD-L1 antibody or a human IgG anti-PD-L1 antibody; an even more preferred modified anti-PD-L1 antibody disclosed herein is a humanized IgG1 anti-PD-L1 antibody or a human IgG1 anti-PD-L1 antibody. A modified anti-PD-L1 antibody disclosed here has antagonistic or inactivating activity, preferably neutralizing activity.

An anti-PD-L1 antibody disclosed herein can also be a variant of a full-length antibody so long as the variant exhibits the desired biological activity disclosed herein, i.e., abolishes Fc-related effector function and enhances clearance rate of the modified anti-PD-L1 antibody while maintaining therapeutic efficacy for neurodegenerative disease modification. For example, an anti-PD-L1 antibody fragment disclosed herein could comprise a light chain including the light chain variable region and light chain constant region and a heavy chain comprising only the CH2 and CH3 domains. Suitable anti-PD-L1 antibody fragments disclosed herein are described in, e.g., Holliger, P., and Hudson, P. J., Engineered antibody fragments and the rise of single domains. Nat. Biotechnol. 23: 1126-1136 (2005); Cuesta, A. M., Sainz-Pastor, N., Bonet, J., Oliva, B., and Alvarez-Vallina, L., Multivalent antibodies: when design surpasses evolution. Trends Biotechnol. 28: 355-362 (2010); and Nelson, A. L., Antibody fragments: hope and hype. MAbs 2, 77-83 (2010), each of which is hereby incorporated by reference in its entirety. For general disclosure on the structure of antibodies, and antigenic compound-binding fragments thereof, see, e.g., Pluckthun in The Pharmacology of Monoclonal Antibodies, vol. 113, Rosenburg and Moore eds., Springer-Verlag, New York, pp. 269-315 (1994); Borrabeck, Antibody Engineering, 2d ed. (Oxford University Press 1995), each of which is hereby incorporated by reference in its entirety. Examples of variants of a modified anti-PD-L1 antibody disclosed herein include without limitation, a fragment of a modified anti-PD-L1 antibody, a single-chain variant of a modified anti-PD-L1 antibody. An anti-PD-L1 antibody disclosed herein also includes molecularly engineered antibodies, such as, e.g., a dimer, a multimer, a multispecific antibody, a humanized antibody, a human antibody, a chimeric antibody, a bi-functional antibody, or a tri-functional antibody.

Full-length anti-PD-L1 antibodies are heterotetrameric glycoproteins of about 150,000 daltons, composed of two identical immunoglobulin heavy (H) chains and two identical immunoglobulin light (L) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. whereas each light chain has a variable domain at the amino-terminus followed by a single constant domain There are five types of mammalian immunoglobulin heavy chain: gamma (γ), delta (δ), alpha (α), mu (μ) and epsilon (ε), each defining a class of immunoglobulins: IgG, IgD, IgA, IgM and IgE, respectively. Heavy chains IgG and IgA have approximately 450 amino acids. Heavy chains IgM and IgE have approximately 550 amino acids. Each heavy chain comprises a constant region and a variable region. A constant region is the same for all immunoglobulins of the same class but differs between classes. Each heavy chain has a variable region comprising a variable domain (VH) at the amino-terminus followed by a constant region comprising a number of constant domains. Heavy chains IgG, IgD, and IgA have a constant region composed of three tandem immunoglobulin domains (CH1, CH2 and CH3) and have a hinge region for added flexibility. Heavy chains IgM and IgE have a constant region composed of four tandem immunoglobulin domains (CH1, CH2, CH3 and CH4). The variable region of the heavy chain differs between different B cells, but is the same for all immunoglobulins produced by the same B cell or B cell clone. The variable domain is composed of a single immunoglobulin domain.

There are two types of mammalian immunoglobulin light chains: the kappa (κ) chain and the lambda (λ) chain. The lambda class has four subtypes λ1, λ2, λ3, and λ4. Only one type of light chain is present in a typical antibody, thus the two light chains of an individual antibody are identical. The approximate length of a light chain is from 211 to 217 amino acids. Each light chain is composed of two tandem immunoglobulin domains, a variable domain (VL) at the amino-terminus followed by a constant domain. The variable domain is important for binding antigen and the constant domain determines the light chain type, i.e., kappa or lambda). The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The complete antigen-recognition and antigen-binding site is contained within the variable domains of the antibody. This site includes a dimer of one heavy chain variable domain (VH) and one light chain variable domain (VL) in tight, non-covalent association. Each domain comprises four framework regions (FR), which largely adopting a β-sheet configuration, connected by three hypervariable regions, which form loops connecting, and in some cases form part of, the β-sheet structure. Each hypervariable region comprises an amino acid sequence corresponding to a complementarity determining region (CDRs). Collectively, it the three-dimensional configuration of the six CDR regions that define an antigen-binding site on the surface of the VH-VL dimmer that confers antigen-binding specificity. See e.g., Cyrus Chothia, et al., Conformations of Immunoglobulin Hypervariable Regions, Nature 342(6252): 877-883 (1989); Elvin A. Kabat, et al Sequences of Proteins of Immunological Interest, 5th Ed. Public Health Service, National Institutes of Health, Bethesda, Md. (1991), each of which is incorporated by reference in its entirety. The constant domains of the antibody are not involved directly in binding an antibody to an antigen, but exhibit various effector functions, such as participation of the antibody in antibody dependent cellular cytotoxicity.

A target antigen generally has one or more binding sites, also called epitopes, which are recognized by the CDR-formed antigen-binding site. An "epitope" is synonymous with "antigenic determinant" and refers to the site on a target antigen, such as, e.g., a peptide, polysaccharide or lipid-containing molecule, capable of specific binding to an immunoglobulin or T-cell receptor or otherwise interacting with a molecule. Each antibody that specifically binds to a different epitope has a different structure. Thus, one antigen may be recognized by more than one antibody.

A modified anti-PD-L1 antibody disclosed herein can be a polyclonal antibody or a monoclonal antibody, Polyclonal antibodies refer to a heterogeneous population of antibody molecules that contain at least two species of antibody capable of binding to a particular antigen. By definition, a polyclonal antibody includes at least two different antibodies that bind to at least two different epitopes. Monoclonal antibodies refer to a substantially homogeneous population of antibody molecules that contain only one species of antibody capable of binding a particular antigen i.e., the individual antibodies comprising the population are identical except for possible naturally occurring mutations that may be present in minor amounts. By definition, a monoclonal antibody binds to a single epitope. Monoclonal antibodies are highly specific, being directed against a single antigenic site. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler et al (1975) Nature 256:495, or may be made by recombinant DNA methods (see for example: U.S. Pat. Nos. 4,816,567; 5,807,715). The monoclonal antibodies may also be isolated from phage antibody libraries using the techniques described in Clackson et al (1991) Nature, 352:624-628; Marks et al (1991) J. Mol. Biol., 222:581-597.

In an embodiment, a modified anti-PD-L1 antibody disclosed herein comprises a heavy chain variable domain ($V_H$) and/or a light chain variable domain ($V_L$) that selectively binds to an epitope present in PD-L1 or a fragment thereof. In aspects of this embodiment, a modified anti-PD-L1 antibody disclosed herein comprises a heavy chain variable domain ($V_H$) and/or a light chain variable domain ($V_L$) that selectively binds to an epitope present in the PD-L1 of SEQ ID NO: 1. In aspects of this embodiment, a modified anti-PD-L1 antibody disclosed herein specifically binds an epitope present in SEQ ID NO: 1. In aspects of this embodiment, a modified anti-PD-L1 antibody disclosed herein may comprise a heavy chain variable domain ($V_H$) and/or a light chain variable domain ($V_L$) that selectively binds to an epitope having an amino acid identity of, e.g., at least about 90%, at least about 91%, at least about 92%, at least about 93%, at least about 94%, at least about 95%, at least about 96%, at least about 97%, at least about 98%, or at least about 99%, relative to the PD-L1 of SEQ ID NO: 1. In other aspects of this embodiment, a modified anti-PD-L1 antibody disclosed herein may comprise a heavy chain variable domain ($V_H$) and/or a light chain variable domain ($V_L$) that selectively binds to an epitope having an amino acid identity in the range of, e.g., about 90% to about 100%, about 95% to about 100%, about 90% to about 99%, about 95% to about 99%, about 90% to about 97%, about 95% to about 97%, or about 97% to about 99%, relative to SEQ ID NO: 1. In yet other aspects of this embodiment, a modified anti-PD-L1 antibody disclosed herein may comprise a heavy chain variable domain ($V_H$) and/or a light chain variable domain ($V_L$) that selectively binds to an epitope having, e.g., at least 1, at least 2, at least 3, or at least 4, contiguous and/or non-contiguous amino acid deletions, additions, and/or substitutions relative to SEQ ID NO: 1; or at most 1, at most 2, at most 3, at most 4, contiguous and/or non-contiguous amino acid deletions, additions, and/or substitutions relative to the PD-L1 of SEQ ID NO: 1. In still other aspects of this embodiment, a modified anti-PD-L1 antibody disclosed herein may comprise a heavy chain variable domain ($V_H$) and/or a light chain variable domain ($V_L$) that selectively binds to an epitope having, e.g., about 1 to about 2, about 1 to about 3, about 1 to about 4, about 2 to about 3, about 2 to about 4, or about 3 to about 4 contiguous and/or non-contiguous amino acid deletions, additions, and/or substitutions relative to the PD-L1 of SEQ ID NO: 1.

In aspects of this embodiment, a modified anti-PD-L1 antibody disclosed herein comprises a heavy chain variable domain ($V_H$) comprising SEQ ID NO: 2. In other aspects of this embodiment, a modified anti-PD-L1 antibody disclosed herein comprises a heavy chain variable domain ($V_H$) that may comprise a sequence having an amino acid identity of, e.g., at least about 90%, at least about 91%, at least about 92%, at least about 93%, at least about 94%, at least about 95%, at least about 96%, at least about 97%, at least about 98%, or at least about 99%, relative to SEQ ID NO: 2 and is a functional antibody that selectively binds to an epitope present in PD-L1, such as PD-L1 of SEQ ID NO: 1. In yet other aspects of this embodiment, a modified anti-PD-L1 antibody disclosed herein comprises a heavy chain variable domain ($V_H$) that may comprise a sequence having an amino acid identity in the range of, e.g., about 90% to about 100%, about 95% to about 100%, about 90% to about 99%, about 95% to about 99%, about 90% to about 97%, about 95% to about 97%, or about 97% to about 99%, relative to SEQ ID NO: 2 and is a functional antibody that selectively binds to an epitope present in PD-L1, such as PD-L1 of SEQ ID NO: 1.

In aspects of this embodiment, a modified anti-PD-L1 antibody disclosed herein comprises a heavy chain variable domain ($V_H$) that may comprise a sequence having, e.g., at least 1, at least 2, at least 3, at least 4, at least 5, at least 6, at least 7, at least 8, at least 9, at least 10, at least 11, or at least 12 contiguous amino acid deletions, additions, and/or substitutions relative to SEQ ID NO: 2 and is a functional antibody that selectively binds to an epitope present in PD-L1, such as PD-L1 of SEQ ID NO: 1; or at most 1, at most 2, at most 3, at most 4, at most 5, at most 6, at most 7, at most 8, at most 9, at most 10, at most 11, or at most 12 contiguous amino acid deletions, additions, and/or substitutions relative to SEQ ID NO: 2 and is a functional antibody that selectively binds to an epitope present in PD-L1, such as PD-L1 of SEQ ID NO: 1. In other aspects of this embodiment, a modified anti-PD-L1 antibody disclosed herein comprises a heavy chain variable domain ($V_H$) that may comprise a sequence having, e.g., 1 to 2, 1 to 3, 1 to 4, 1 to 5, 1 to 6, 1 to 7, 1 to 8, 1 to 9, 1 to 10, 1 to 11, 1 to 12, 2 to 3, 2 to 4, 2 to 5, 2 to 6, 2 to 7, 2 to 8, 2 to 9, 2 to 10, 2 to 11, 2 to 12, 3 to 4, 3 to 5, 3 to 6, 3 to 7, 3 to 8, 3 to 9, 3 to 10, 3 to 11, 3 to 12, 4 to 5, 4 to 6, 4 to 7, 4 to 8, 4 to 9, 4 to 10, 4 to 11, 4 to 12, 5 to 6, 5 to 7, 5 to 8, 5 to 9, 5 to 10, 5 to 11, 5 to 12, 6 to 7, 6 to 8, 6 to 9, 6 to 10, 6 to 11, 6 to 12, 7 to 8, 7 to 9, 7 to 10, 7 to 11, 7 to 12, 8 to 9, 8 to 10, 8 to 11, 8 to 12, 9 to 10, 9 to 11, 9 to 12, 10 to 11, 10 to 12, or 11 to 12 contiguous amino acid deletions, additions, and/or substitutions relative to SEQ ID NO: 2 and is a functional antibody that selectively binds to an epitope present in PD-L1, such as PD-L1 of SEQ ID NO: 1.

In aspects of this embodiment, a modified anti-PD-L1 antibody disclosed herein comprises a heavy chain variable domain ($V_H$) that may comprise a sequence having, e.g., at least 1, at least 2, at least 3, at least 4, at least 5, at least 6, at least 7, at least 8, at least 9, at least 10, at least 11, or at least 12 non-contiguous amino acid deletions, additions, and/or substitutions relative to SEQ ID NO: 2 and is a functional antibody that selectively binds to an epitope present in PD-L1, such as PD-L1 of SEQ ID NO: 1; or at most 1, at most 2, at most 3, at most 4, at most 5, at most 6, at most 7, at most 8, at most 9, at most 10, at most 11, or at most 12 non-contiguous amino acid deletions, additions, and/or substitutions relative to SEQ ID NO: 2 and is a functional antibody that selectively binds to an epitope present in PD-L1, such as PD-L1 of SEQ ID NO: 1. In other aspects of this embodiment, a modified anti-PD-L1 antibody disclosed herein comprises a heavy chain variable domain ($V_H$) that may comprise a sequence having, e.g., 1 to 2, 1 to 3, 1 to 4, 1 to 5, 1 to 6, 1 to 7, 1 to 8, 1 to 9, 1 to 10, 1 to 11, 1 to 12, 2 to 3, 2 to 4, 2 to 5, 2 to 6, 2 to 7, 2 to 8, 2 to 9, 2 to 10, 2 to 11, 2 to 12, 3 to 4, 3 to 5, 3 to 6, 3 to 7, 3 to 8, 3 to 9, 3 to 10, 3 to 11, 3 to 12, 4 to 5, 4 to 6, 4 to 7, 4 to 8, 4 to 9, 4 to 10, 4 to 11, 4 to 12, 5 to 6, 5 to 7, 5 to 8, 5 to 9, 5 to 10, 5 to 11, 5 to 12, 6 to 7, 6 to 8, 6 to 9, 6 to 10, 6 to 11, 6 to 12, 7 to 8, 7 to 9, 7 to 10, 7 to 11, 7 to 12, 8 to 9, 8 to 10, 8 to 11, 8 to 12, 9 to 10, 9 to 11, 9 to 12, 10 to 11, 10 to 12, or 11 to 12 non-contiguous amino acid deletions, additions, and/or substitutions relative to SEQ ID NO: 2 and is a functional antibody that selectively binds to an epitope present in PD-L1, such as PD-L1 of SEQ ID NO: 1.

In another embodiment, a modified anti-PD-L1 antibody disclosed herein comprises a heavy chain variable domain ($V_H$) comprising a heavy chain variable domain ($V_H$) CDR1 region, a CDR2 region, and a CDR3 region that selectively binds to an epitope present in PD-L1. In aspects of this embodiment, a modified anti-PD-L1 antibody disclosed herein comprises a heavy chain variable domain ($V_H$) comprising a heavy chain variable domain ($V_H$) CDR1 region, a CDR2 region, and a CDR3 region that selectively binds to an epitope present in the PD-L1 of SEQ ID NO: 1. In aspects of this embodiment, a modified anti-PD-L1 antibody disclosed herein comprises a heavy chain variable domain ($V_H$) comprising a heavy chain variable domain ($V_H$) CDR1 region, a CDR2 region, and a CDR3 region that may selectively binds to an epitope present in sequence having an amino acid identity of, e.g., at least about 90%, at least about 91%, at least about 92%, at least about 93%, at least about 94%, at least about 95%, at least about 96%, at least about 97%, at least about 98%, or at least about 99%, relative to the PD-L1 of SEQ ID NO: 1. In other aspects of this embodiment, a modified anti-PD-L1 antibody disclosed herein comprises a heavy chain variable domain ($V_H$) comprising a heavy chain variable domain ($V_H$) CDR1 region, a CDR2 region, and a CDR3 region that may selectively binds to an epitope present in sequence having an amino acid identity in the range of, e.g., about 90% to about 100%, about 95% to about 100%, about 90% to about 99%, about 95% to about 99%, about 90% to about 97%, about 95% to about 97%, or about 97% to about 99%, relative to the PD-L1 of SEQ ID NO: 1. In yet other aspects of this embodiment, a modified anti-PD-L1 antibody disclosed herein comprises a heavy chain variable domain ($V_H$) comprising a heavy chain variable domain ($V_H$) CDR1 region, a CDR2 region, and a CDR3 region that may selectively binds to an epitope present in sequence having, e.g., at least 1, at least 2, at least 3, or at least 4, contiguous and/or non-contiguous amino acid deletions, additions, and/or substitutions relative to the PD-L1 of SEQ ID NO: 1; or at most 1, at most 2, at most 3, at most 4, contiguous and/or non-contiguous amino acid deletions, additions, and/or substitutions relative to the PD-L1 of SEQ ID NO: 1. In still other aspects of this embodiment, a modified anti-PD-L1 antibody disclosed herein comprises a heavy chain variable domain ($V_H$) comprising a heavy chain variable domain ($V_H$) CDR1 region, a CDR2 region, and a CDR3 region that may selectively binds to an epitope present in sequence having, e.g., about 1 to about 2, about 1 to about 3, about 1 to about 4, about 2 to about 3, about 2 to about 4, or about 3 to about 4 contiguous and/or non-contiguous amino acid deletions, additions, and/or substitutions relative to the PD-L1 of SEQ ID NO: 1.

In an aspect of this embodiment, a modified anti-PD-L1 antibody disclosed herein comprises a heavy chain variable domain ($V_H$) comprising a heavy chain variable domain ($V_H$) CDR1 region comprising SEQ ID NO: 3 (IMGT) or SEQ ID NO: 4 (Kabat). In aspects of this embodiment, a modified anti-PD-L1 antibody disclosed herein comprises a heavy chain variable domain ($V_H$) that may comprise a heavy chain variable domain ($V_H$) CDR1 region having one amino acid deletion, addition, and/or substitution relative to SEQ ID NO: 3 (IMGT) or SEQ ID NO: 4 (Kabat).

In another aspect of this embodiment, a modified anti-PD-L1 antibody disclosed herein comprises a heavy chain variable domain ($V_H$) comprises a heavy chain variable domain ($V_H$) CDR2 region comprising SEQ ID NO: 5 (IMGT) or SEQ ID NO: 6 (Kabat). In aspects of this embodiment, a modified anti-PD-L1 antibody disclosed herein comprises a heavy chain variable domain ($V_H$) that may comprise a heavy chain variable domain ($V_H$) CDR2 region disclosed herein having 1 or 2 amino acid deletions, additions, and/or substitutions relative to SEQ ID NO: 5 (IMGT) or SEQ ID NO: 6 (Kabat).

In an aspect of this embodiment, a modified anti-PD-L1 antibody disclosed herein comprises a heavy chain variable domain ($V_H$) comprising a heavy chain variable domain ($V_H$) CDR3 region comprising SEQ ID NO: 7 (IMGT) or SEQ ID NO: 8 (Kabat). In aspects of this embodiment, a modified anti-PD-L1 antibody disclosed herein comprises a heavy chain variable domain ($V_H$) that may comprise a heavy chain variable domain ($V_H$) CDR3 region having one amino acid deletion, addition, and/or substitution relative to SEQ ID NO: 7 (IMGT) or SEQ ID NO: 8 (Kabat).

In an aspect of this embodiment, a modified anti-PD-L1 antibody disclosed herein comprises a heavy chain variable domain ($V_H$) comprising a heavy chain variable domain ($V_H$) CDR1 region comprising SEQ ID NO: 3 (IMGT) or SEQ ID NO: 4 (Kabat), a heavy chain variable domain ($V_H$) CDR2 region comprising SEQ ID NO: 5 (IMGT) or SEQ ID NO: 6 (Kabat), and a heavy chain variable domain ($V_H$) CDR3 region comprising SEQ ID NO: 7 (IMGT) or SEQ ID NO: 8 (Kabat). In aspects of this embodiment, a modified anti-PD-L1 antibody disclosed herein comprises a heavy chain variable domain ($V_H$) that may comprise a heavy chain variable domain ($V_H$) CDR1 region having one amino acid deletion, addition, and/or substitution relative to SEQ ID NO: 3 (IMGT) or SEQ ID NO: 4 (Kabat), a heavy chain variable domain ($V_H$) CDR2 region having 1 or 2 amino acid deletions, additions, and/or substitutions relative to SEQ ID NO: 5 (IMGT) or SEQ ID NO: 6 (Kabat), and a heavy chain variable domain ($V_H$) CDR3 region having one amino acid deletion, addition, and/or substitution relative to SEQ ID NO: 7 (IMGT) or SEQ ID NO: 8 (Kabat).

In another embodiment, a modified anti-PD-L1 antibody disclosed herein comprises a light chain variable domain ($V_L$) CDR1 region, a CDR2 region, and a CDR3 region that selectively binds an epitope disclosed herein. In aspects of this embodiment, a modified anti-PD-L1 antibody disclosed herein comprises a light chain variable domain ($V_L$) CDR1 region, a CDR2 region, and a CDR3 region that selectively binds an epitope present in the PD-L1 of SEQ ID NO: 1.

In other aspects of this embodiment, a modified anti-PD-L1 antibody disclosed herein comprises a light chain variable domain ($V_L$) comprising SEQ ID NO: 9. In yet other aspects of this embodiment, a modified anti-PD-L1 antibody disclosed herein comprises a light chain variable domain ($V_L$) comprising a sequence having an amino acid identity of, e.g., at least about 90%, at least about 91%, at least about 92%, at least about 93%, at least about 94%, at least about 95%, at least about 96%, at least about 97%, at least about 98%, or at least about 99%, relative to of SEQ ID NO: 9 and is a functional antibody that selectively binds to an epitope present in PD-L1, such as PD-L1 of SEQ ID NO: 1. In still other aspects of this embodiment, a modified anti-PD-L1 antibody disclosed herein comprises a light chain variable domain ($V_L$) comprising a sequence having an amino acid identity in the range of, e.g., about 90% to about 100%, about 95% to about 100%, about 90% to about 99%, about 95% to about 99%, about 90% to about 97%, about 95% to about 97%, or about 97% to about 99%, relative to of SEQ ID NO: 9 and is a functional antibody that selectively binds to an epitope present in PD-L1, such as PD-L1 of SEQ ID NO: 1.

In other aspects of this embodiment, a modified anti-PD-L1 antibody disclosed herein comprises a light chain variable domain ($V_L$) that may comprise a sequence having, e.g., at least 1, at least 2, at least 3, at least 4, at least 5, at least 6, at least 7, at least 8, at least 9, or at least 10 contiguous amino acid deletions, additions, and/or substitutions relative to SEQ ID NO: 9 and is a functional antibody that selectively binds to an epitope present in PD-L1, such as PD-L1 of SEQ ID NO: 1; or at most 1, at most 2, at most 3, at most 4, at most 5, at most 6, at most 7, at most 8, at most 9, or at most 10 contiguous amino acid deletions, additions, and/or substitutions relative to SEQ ID NO: 9 and is a functional antibody that selectively binds to an epitope present in PD-L1, such as PD-L1 of SEQ ID NO: 1. In yet other aspects of this embodiment, a modified anti-PD-L1 antibody disclosed herein comprises a light chain variable domain ($V_L$) that may comprise a sequence having, e.g., 1 to 2, 1 to 3, 1 to 4, 1 to 5, 1 to 6, 1 to 7, 1 to 8, 1 to 9, 1 to 10, 2 to 3, 2 to 4, 2 to 5, 2 to 6, 2 to 7, 2 to 8, 2 to 9, 2 to 10, 3 to 4, 3 to 5, 3 to 6, 3 to 7, 3 to 8, 3 to 9, 3 to 10, 4 to 5, 4 to 6, 4 to 7, 4 to 8, 4 to 9, 4 to 10, 5 to 6, 5 to 7, 5 to 8, 5 to 9, 5 to 10, 6 to 7, 6 to 8, 6 to 9, 6 to 10, 7 to 8, 7 to 9, 7 to 10, 8 to 9, 8 to 10, or 9 to 10 contiguous amino acid deletions, additions, and/or substitutions relative to SEQ ID NO: 9. and is a functional antibody that selectively binds to an epitope present in PD-L1, such as PD-L1 of SEQ ID NO: 1.

In other aspects of this embodiment, a modified anti-PD-L1 antibody disclosed herein comprises a light chain variable domain ($V_L$) that may comprise a sequence having, e.g., at least 1, at least 2, at least 3, at least 4, at least 5, at least 6, at least 7, at least 8, at least 9, or at least 10 non-contiguous amino acid deletions, additions, and/or substitutions relative to SEQ ID NO: 9 and is a functional antibody that selectively binds to an epitope present in PD-L1, such as PD-L1 of SEQ ID NO: 1; or at most 1, at most 2, at most 3, at most 4, at most 5, at most 6, at most 7, at most 8, at most 9, or at most 10 contiguous amino acid deletions, additions, and/or substitutions relative to SEQ ID NO: 9 and is a functional antibody that selectively binds to an epitope present in PD-L1, such as PD-L1 of SEQ ID NO: 1. In yet other aspects of this embodiment, a modified anti-PD-L1 antibody disclosed herein comprises a light chain variable domain ($V_L$) that may comprise a sequence having, e.g., 1 to 2, 1 to 3, 1 to 4, 1 to 5, 1 to 6, 1 to 7, 1 to 8, 1 to 9, 1 to 10, 2 to 3, 2 to 4, 2 to 5, 2 to 6, 2 to 7, 2 to 8, 2 to 9, 2 to 10, 3 to 4, 3 to 5, 3 to 6, 3 to 7, 3 to 8, 3 to 9, 3 to 10, 4 to 5, 4 to 6, 4 to 7, 4 to 8, 4 to 9, 4 to 10, 5 to 6, 5 to 7, 5 to 8, 5 to 9, 5 to 10, 6 to 7, 6 to 8, 6 to 9, 6 to 10, 7 to 8, 7 to 9, 7 to 10, 8 to 9, 8 to 10, or 9 to 10 non-contiguous amino acid deletions, additions, and/or substitutions relative to SEQ ID NO: 9 and is a functional antibody that selectively binds to an epitope present in PD-L1, such as PD-L1 of SEQ ID NO: 1.

In another embodiment, a modified anti-PD-L1 antibody disclosed herein comprises a light chain variable domain ($V_L$) comprising a light chain variable domain ($V_L$) CDR1 region, a CDR2 region, and a CDR3 region that selectively binds to an epitope present in PD-L1. In aspects of this embodiment, a modified anti-PD-L1 antibody disclosed herein comprises a light chain variable domain ($V_L$) comprising a light chain variable domain ($V_L$) CDR1 region, a CDR2 region, and a CDR3 region that selectively binds to an epitope present in the PD-L1 of SEQ ID NO: 1. In aspects of this embodiment, a modified anti-PD-L1 antibody disclosed herein comprises a light chain variable domain ($V_L$) comprising a light chain variable domain ($V_L$) CDR1 region, a CDR2 region, and a CDR3 region that selectively binds to an epitope present in sequence having an amino acid identity of, e.g., at least about 90%, at least about 91%, at least about 92%, at least about 93%, at least about 94%, at least about 95%, at least about 96%, at least about 97%, at least about 98%, or at least about 99%, relative to the PD-L1 of SEQ ID NO: 1. In other aspects of this embodiment, a modified anti-PD-L1 antibody disclosed herein comprises a light chain variable domain ($V_L$) comprising a light chain variable domain ($V_L$) CDR1 region, a CDR2 region, and a CDR3 region that selectively binds to an epitope present in sequence having an amino acid identity in the range of, e.g., about 90% to about 100%, about 95% to about 100%, about 90% to about 99%, about 95% to about 99%, about 90% to about 97%, about 95% to about 97%, or about 97% to about 99%, relative to the PD-L1 of SEQ ID NO: 1. In yet other aspects of this embodiment, a modified anti-PD-L1 antibody disclosed herein comprises a light chain variable domain ($V_L$) comprising a light chain variable domain ($V_L$) CDR1 region, a CDR2 region, and a CDR3 region that selectively binds to an epitope present in sequence having, e.g., at least 1, at least 2, at least 3, or at least 4, contiguous and/or non-contiguous amino acid deletions, additions, and/or substitutions relative to the PD-L1 of SEQ ID NO: 1; or at most 1, at most 2, at most 3, at most 4, contiguous and/or non-contiguous amino acid deletions, additions, and/or substitutions relative to the PD-L1 of SEQ ID NO: 1. In still other aspects of this embodiment, a modified anti-PD-L1 antibody disclosed herein comprises a light chain variable domain ($V_L$) comprising a light chain variable domain ($V_L$) CDR1 region, a CDR2 region, and a CDR3 region that selectively binds to an epitope present in sequence having, e.g., about 1 to about 2, about 1 to about 3, about 1 to about 4, about 2 to about 3, about 2 to about 4, or about 3 to about 4 contiguous and/or non-contiguous amino acid deletions, additions, and/or substitutions relative to the PD-L1 of SEQ ID NO: 1.

In an aspect of this embodiment, a modified anti-PD-L1 antibody disclosed herein comprises a light chain variable domain ($V_L$) comprising a light chain variable domain ($V_L$) CDR1 region comprising SEQ ID NO: 10 (IMGT) or SEQ ID NO: 11 (Kabat). In aspects of this embodiment, a modified anti-PD-L1 antibody disclosed herein comprises a light chain variable domain ($V_H$) that may comprise a light chain variable domain ($V_H$) CDR3 region having one amino acid deletion, addition, and/or substitution relative to SEQ ID NO: 10 (IMGT) or SEQ ID NO: 11 (Kabat).

In an aspect of this embodiment, a modified anti-PD-L1 antibody disclosed herein comprises a light chain variable domain ($V_L$) comprising a light chain variable domain ($V_L$) CDR2 region comprising SEQ ID NO: 12 (IMGT) or SEQ ID NO: 13 (Kabat). In aspects of this embodiment, a modified anti-PD-L1 antibody disclosed herein comprises a light chain variable domain ($V_H$) that may comprise a light chain variable domain ($V_H$) CDR3 region having one amino acid deletion, addition, and/or substitution relative to SEQ ID NO: 13 (Kabat).

In an aspect of this embodiment, a modified anti-PD-L1 antibody disclosed herein comprises a light chain variable domain ($V_L$) comprising a light chain variable domain ($V_L$) CDR3 region comprising SEQ ID NO: 14 (IMGT) or SEQ ID NO: 15 (Kabat). In aspects of this embodiment, a modified anti-PD-L1 antibody disclosed herein comprises a light chain variable domain ($V_H$) that may comprise a light chain variable domain ($V_H$) CDR3 region having one amino acid deletion, addition, and/or substitution relative to SEQ ID NO: 14 (IMGT) or SEQ ID NO: 15 (Kabat).

In an aspect of this embodiment, a modified anti-PD-L1 antibody disclosed herein comprises a light chain variable domain ($V_L$) comprising a light chain variable domain ($V_L$) CDR1 region comprising SEQ ID NO: 10 (IMGT) or SEQ ID NO: 11 (Kabat), a light chain variable domain ($V_L$) CDR2 region comprising SEQ ID NO: 12 (IMGT) or SEQ ID NO: 13 (Kabat), and a light chain variable domain ($V_L$) CDR3 region comprising SEQ ID NO: 14 (IMGT) or SEQ ID NO: 15 (Kabat). In aspects of this embodiment, a modified anti-PD-L1 antibody disclosed herein comprises a light chain variable domain ($V_H$) that may comprise a light chain variable domain ($V_H$) CDR3 region having one amino acid deletion, addition, and/or substitution relative to SEQ ID NO: 10 (IMGT) or SEQ ID NO: 11 (Kabat), a light chain variable domain ($V_H$) CDR3 region having one amino acid deletion, addition, and/or substitution relative to SEQ ID NO: 13 (Kabat), and a light chain variable domain ($V_H$) CDR3 region having one amino acid deletion, addition, and/or substitution relative to SEQ ID NO: 14 (IMGT) or SEQ ID NO: 15 (Kabat).

In aspects of this embodiment, a modified anti-PD-L1 antibody disclosed herein comprises a heavy chain variable domain ($V_H$) comprising SEQ ID NO: 2 and a light chain variable domain ($V_L$) comprising SEQ ID NO: 9. In other aspects of this embodiment, a modified anti-PD-L1 antibody disclosed herein comprises a heavy chain variable domain ($V_H$) that may comprise a sequence having an amino acid identity of, e.g., at least about 90%, at least about 91%, at least about 92%, at least about 93%, at least about 94%, at least about 95%, at least about 96%, at least about 97%, at least about 98%, or at least about 99%, relative to SEQ ID NO: 2 and a light chain variable domain ($V_L$) that may comprise a sequence having an amino acid identity of, e.g., at least about 90%, at least about 91%, at least about 92%, at least about 93%, at least about 94%, at least about 95%, at least about 96%, at least about 97%, at least about 98%, or at least about 99%, relative to SEQ ID NO: 9. In yet other aspects of this embodiment, a modified anti-PD-L1 antibody disclosed herein comprises a heavy chain variable domain ($V_H$) that may comprise a sequence having an amino acid identity in the range of, e.g., about 90% to about 100%, about 95% to about 100%, about 90% to about 99%, about 95% to about 99%, about 90% to about 97%, about 95% to about 97%, or about 97% to about 99%, relative to SEQ ID NO: 2 and a light chain variable domain ($V_L$) that may comprise a sequence having an amino acid identity in the range of, e.g., about 90% to about 100%, about 95% to about 100%, about 90% to about 99%, about 95% to about 99%, about 90% to about 97%, about 95% to about 97%, or about 97% to about 99%, relative to SEQ ID NO: 9.

In aspects of this embodiment, a modified anti-PD-L1 antibody disclosed herein comprises a heavy chain variable domain ($V_H$) that may comprise a sequence having, e.g., at least 1, at least 2, at least 3, at least 4, at least 5, at least 6, at least 7, at least 8, at least 9, at least 10, at least 11, or at least 12 contiguous amino acid deletions, additions, and/or substitutions relative to SEQ ID NO: 2; or at most 1, at most 2, at most 3, at most 4, at most 5, at most 6, at most 7, at most 8, at most 9, at most 10, at most 11, or at most 12 contiguous amino acid deletions, additions, and/or substitutions relative to SEQ ID NO: 2, and a light chain variable domain ($V_L$) that may comprise a sequence having, e.g., at least 1, at least 2, at least 3, at least 4, at least 5, at least 6, at least 7, at least 8, at least 9, or at least 10 contiguous amino acid deletions, additions, and/or substitutions relative to SEQ ID NO: 9; or at most 1, at most 2, at most 3, at most 4, at most 5, at most 6, at most 7, at most 8, at most 9, or at most 10 contiguous amino acid deletions, additions, and/or substitutions relative to SEQ ID NO: 9. In other aspects of this embodiment, a modified anti-PD-L1 antibody disclosed herein comprises a heavy chain variable domain ($V_H$) that may comprise a sequence having, e.g., 1 to 2, 1 to 3, 1 to 4, 1 to 5, 1 to 6, 1 to 7, 1 to 8, 1 to 9, 1 to 10, 1 to 11, 1 to 12, 2 to 3, 2 to 4, 2 to 5, 2 to 6, 2 to 7, 2 to 8, 2 to 9, 2 to 10, 2 to 11, 2 to 12, 3 to 4, 3 to 5, 3 to 6, 3 to 7, 3 to 8, 3 to 9, 3 to 10, 3 to 11, 3 to 12, 4 to 5, 4 to 6, 4 to 7, 4 to 8, 4 to 9, 4 to 10, 4 to 11, 4 to 12, 5 to 6, 5 to 7, 5 to 8, 5 to 9, 5 to 10, 5 to 11, 5 to 12, 6 to 7, 6 to 8, 6 to 9, 6 to 10, 6 to 11, 6 to 12, 7 to 8, 7 to 9, 7 to 10, 7 to 11, 7 to 12, 8 to 9, 8 to 10, 8 to 11, 8 to 12, 9 to 10, 9 to 11, 9 to 12, 10 to 11, 10 to 12, or 11 to 12 contiguous amino acid deletions, additions, and/or substitutions relative to SEQ ID NO: 2 and a light chain variable domain ($V_L$) that may comprise a sequence having, e.g., 1 to 2, 1 to 3, 1 to 4, 1 to 5, 1 to 6, 1 to 7, 1 to 8, 1 to 9, 1 to 10, 2 to 3, 2 to 4, 2 to 5, 2 to 6, 2 to 7, 2 to 8, 2 to 9, 2 to 10, 3 to 4, 3 to 5, 3 to 6, 3 to 7, 3 to 8, 3 to 9, 3 to 10, 4 to 5, 4 to 6, 4 to 7, 4 to 8, 4 to 9, 4 to 10, 5 to 6, 5 to 7, 5 to 8, 5 to 9, 5 to 10, 6 to 7, 6 to 8, 6 to 9, 6 to 10, 7 to 8, 7 to 9, 7 to 10, 8 to 9, 8 to 10, or 9 to 10 contiguous amino acid deletions, additions, and/or substitutions relative to SEQ ID NO: 9.

In aspects of this embodiment, a modified anti-PD-L1 antibody disclosed herein comprises a heavy chain variable domain ($V_H$) that may comprise a sequence having, e.g., at least 1, at least 2, at least 3, at least 4, at least 5, at least 6, at least 7, at least 8, at least 9, at least 10, at least 11, or at least 12 non-contiguous amino acid deletions, additions, and/or substitutions relative to SEQ ID NO: 2; or at most 1, at most 2, at most 3, at most 4, at most 5, at most 6, at most 7, at most 8, at most 9, at most 10, at most 11, or at most 12 non-contiguous amino acid deletions, additions, and/or substitutions relative to SEQ ID NO: 2, and a light chain variable domain ($V_L$) that may comprise a sequence having, e.g., at least 1, at least 2, at least 3, at least 4, at least 5, at least 6, at least 7, at least 8, at least 9, or at least 10 non-contiguous amino acid deletions, additions, and/or substitutions relative to SEQ ID NO: 9; or at most 1, at most 2, at most 3, at most 4, at most 5, at most 6, at most 7, at most 8, at most 9, or at most 10 non-contiguous amino acid deletions, additions, and/or substitutions relative to SEQ ID NO: 9. In other aspects of this embodiment, a modified anti-PD-L1 antibody disclosed herein comprises a heavy chain variable domain ($V_H$) that may comprise a sequence having, e.g., 1 to 2, 1 to 3, 1 to 4, 1 to 5, 1 to 6, 1 to 7, 1 to 8, 1 to 9, 1 to 10, 1 to 11, 1 to 12, 2 to 3, 2 to 4, 2 to 5, 2 to 6, 2 to 7, 2 to 8, 2 to 9, 2 to 10, 2 to 11, 2 to 12, 3 to 4, 3 to 5, 3 to 6, 3 to 7, 3 to 8, 3 to 9, 3 to 10, 3 to 11, 3 to 12, 4 to 5, 4 to 6, 4 to 7, 4 to 8, 4 to 9, 4 to 10, 4 to 11, 4 to 12, 5 to 6, 5 to 7, 5 to 8, 5 to 9, 5 to 10, 5 to 11, 5 to 12, 6 to 7, 6 to 8, 6 to 9, 6 to 10, 6 to 11, 6 to 12, 7 to 8, 7 to 9, 7 to 10, 7 to 11, 7 to 12, 8 to 9, 8 to 10, 8 to 11, 8 to 12, 9 to 10, 9 to 11, 9 to 12, 10 to 11, 10 to 12, or 11 to 12 non-contiguous amino acid deletions, additions, and/or substitutions relative to SEQ ID NO: 2 and a light chain variable domain ($V_L$) that may comprise a sequence having, e.g., 1 to 2, 1 to 3, 1 to 4, 1 to 5, 1 to 6, 1 to 7, 1 to 8, 1 to 9, 1 to 10, 2 to 3, 2 to 4, 2 to 5, 2 to 6, 2 to 7, 2 to 8, 2 to 9, 2 to 10, 3 to 4, 3 to 5, 3 to 6, 3 to 7, 3 to 8, 3 to 9, 3 to 10, 4 to 5, 4 to 6, 4 to 7, 4 to 8, 4 to 9, 4 to 10, 5 to 6, 5 to 7, 5 to 8, 5 to 9, 5 to 10, 6 to 7, 6 to 8, 6 to 9, 6 to 10, 7 to 8, 7 to 9, 7 to 10, 8 to 9, 8 to 10, or 9 to 10 non-contiguous amino acid deletions, additions, and/or substitutions relative to SEQ ID NO: 9.

In another embodiment, a modified anti-PD-L1 antibody disclosed herein comprises a heavy chain variable domain ($V_H$) comprising a heavy chain variable domain ($V_H$) CDR1 region, a CDR2 region, and a CDR3 region and a light chain variable domain ($V_L$) comprising a light chain variable domain ($V_L$) CDR1 region, a CDR2 region, and a CDR3 region that selectively binds to an epitope present in PD-L1. In aspects of this embodiment, a modified anti-PD-L1 antibody disclosed herein comprises a heavy chain variable domain ($V_H$) comprising a heavy chain variable domain ($V_H$) CDR1 region, a CDR2 region, and a CDR3 region and a light chain variable domain ($V_L$) comprising a light chain variable domain ($V_L$) CDR1 region, a CDR2 region, and a CDR3 region that selectively binds to an epitope present in the PD-L1 of SEQ ID NO: 1. In aspects of this embodiment, a modified anti-PD-L1 antibody disclosed herein comprises a heavy chain variable domain ($V_H$) comprising a heavy chain variable domain ($V_H$) CDR1 region, a CDR2 region, and a CDR3 region and a light chain variable domain ($V_L$) comprising a light chain variable domain ($V_L$) CDR1 region, a CDR2 region, and a CDR3 region that may selectively binds to an epitope present in sequence having an amino acid identity of, e.g., at least about 90%, at least about 91%, at least about 92%, at least about 93%, at least about 94%, at least about 95%, at least about 96%, at least about 97%, at least about 98%, or at least about 99%, relative to the PD-L1 of SEQ ID NO: 1. In other aspects of this embodiment, a modified anti-PD-L1 antibody disclosed herein comprises a heavy chain variable domain ($V_H$) comprising a heavy chain variable domain ($V_H$) CDR1 region, a CDR2 region, and a CDR3 region and a light chain variable domain ($V_L$) comprising a light chain variable domain ($V_L$) CDR1 region, a CDR2 region, and a CDR3 region that may selectively binds to an epitope present in sequence having an amino acid identity in the range of, e.g., about 90% to about 100%, about 95% to about 100%, about 90% to about 99%, about 95% to about 99%, about 90% to about 97%, about 95% to about 97%, or about 97% to about 99%, relative to the PD-L1 of SEQ ID NO: 1. In yet other aspects of this embodiment, a modified anti-PD-L1 antibody disclosed herein comprises a heavy chain variable domain ($V_H$) comprising a heavy chain variable domain ($V_H$) CDR1 region, a CDR2 region, and a CDR3 region and a light chain variable domain ($V_L$) comprising a light chain variable domain ($V_L$) CDR1 region, a CDR2 region, and a CDR3 region that may selectively binds to an epitope present in sequence having, e.g., at least 1, at least 2, at least 3, or at least 4, contiguous and/or non-contiguous amino acid deletions, additions, and/or substitutions relative to the PD-L1 of SEQ ID NO: 1; or at most 1, at most 2, at most 3, at most 4, contiguous and/or non-contiguous amino acid deletions, additions, and/or substitutions relative to the PD-L1 of SEQ ID NO: 1. In still other aspects of this embodiment, a modified anti-PD-L1 antibody disclosed herein comprises a heavy chain variable domain ($V_H$) comprising a heavy chain variable domain ($V_H$) CDR1 region, a CDR2 region, and a CDR3 region and a light chain variable domain ($V_L$) comprising a light chain variable domain ($V_L$) CDR1 region, a CDR2 region, and a CDR3 region that may selectively binds to an epitope present in sequence having, e.g., about 1 to about 2, about 1 to about 3, about 1 to about 4, about 2 to about 3, about 2 to about 4, or about 3 to about 4 contiguous and/or non-contiguous amino acid deletions, additions, and/or substitutions relative to the PD-L1 of SEQ ID NO: 1.

In an aspect of this embodiment, a modified anti-PD-L1 antibody disclosed herein comprises a heavy chain variable domain ($V_H$) comprising a heavy chain variable domain ($V_H$) CDR1 region comprising SEQ ID NO: 3 (IMGT) or SEQ ID NO: 4 (Kabat), a heavy chain variable domain ($V_H$) CDR2 region comprising SEQ ID NO: 5 (IMGT) or SEQ ID NO: 6 (Kabat), and a heavy chain variable domain ($V_H$) CDR3 region comprising SEQ ID NO: 7 (IMGT) or SEQ ID NO: 8 (Kabat) and a light chain variable domain ($V_L$) comprising a light chain variable domain ($V_L$) CDR1 region comprising SEQ ID NO: 10 (IMGT) or SEQ ID NO: 11 (Kabat), a light chain variable domain ($V_L$) CDR2 region comprising SEQ ID NO: 12 (IMGT) or SEQ ID NO: 13 (Kabat), and a light chain variable domain ($V_L$) CDR3 region comprising SEQ ID NO: 14 (IMGT) or SEQ ID NO: 15 (Kabat). In aspects of this embodiment, a modified anti-PD-L1 antibody disclosed herein comprises a heavy chain variable domain ($V_H$) that may comprise a heavy chain variable domain ($V_H$) CDR1 region having one amino acid deletion, addition, and/or substitution relative to SEQ ID NO: 3 (IMGT) or SEQ ID NO: 4 (Kabat), a heavy chain variable domain ($V_H$) CDR2 region having 1 or 2 amino acid deletions, additions, and/or substitutions relative to SEQ ID NO: 5 (IMGT) or SEQ ID NO: 6 (Kabat), and a heavy chain variable domain ($V_H$) CDR3 region having one amino acid deletion, addition, and/or substitution relative to SEQ ID NO: 7 (IMGT) or SEQ ID NO: 8 (Kabat) and a light chain variable domain ($V_H$) that may comprise a light chain variable domain ($V_H$) CDR3 region having one amino acid deletion, addition, and/or substitution relative to SEQ ID NO: 10 (IMGT) or SEQ ID NO: 11 (Kabat), a light chain variable domain ($V_H$) CDR3 region having one amino acid deletion, addition, and/or substitution relative to SEQ ID NO: 13 (Kabat), and a light chain variable domain ($V_H$) CDR3 region having one amino acid deletion, addition, and/or substitution relative to SEQ ID NO: 14 (IMGT) or SEQ ID NO: 15 (Kabat).

In another embodiment, a modified anti-PD-L1 antibody disclosed herein comprises a light chain comprising a light chain variable region disclosed herein and a light chain constant region. In an aspect of this embodiment, a modified anti-PD-L1 antibody disclosed herein comprises a kappa light chain comprising a light chain variable region disclosed herein and a light chain constant region. In aspects of this embodiment, a modified anti-PD-L1 antibody disclosed herein comprises a kappa light chain comprising a light chain variable region disclosed herein and a light chain constant region of SEQ ID NO: 16, SEQ ID NO: 17, SEQ ID NO: 18, SEQ ID NO: 19, or SEQ ID NO: 20. In aspects of this embodiment, a modified anti-PD-L1 antibody disclosed herein comprises a kappa light chain of SEQ ID NO: 21, SEQ ID NO: 22, SEQ ID NO: 23, SEQ ID NO: 24, or SEQ ID NO: 25.

In another aspect of this embodiment, a modified anti-PD-L1 antibody disclosed herein comprises a lambda light chain comprising a light chain variable region disclosed herein and a light chain constant region. In aspects of this embodiment, a modified anti-PD-L1 antibody disclosed herein comprises a lambda light chain comprising a light chain variable region disclosed herein and a light chain constant region of SEQ ID NO: 26, SEQ ID NO: 27, SEQ ID NO: 28, SEQ ID NO: 29, SEQ ID NO: 30, or SEQ ID NO: 31. In aspects of this embodiment, a modified anti-PD-L1 antibody disclosed herein comprises a lambda light chain of SEQ ID NO: 32, SEQ ID NO: 33, SEQ ID NO: 34, SEQ ID NO: 35, SEQ ID NO: 36, or SEQ ID NO: 37.

In an embodiment, an anti-PD-L1 antibody disclosed herein comprises a heavy chain constant domain ($C_H$) that lack Fc effector function. In another embodiment, an anti-PD-L1 antibody disclosed herein comprises a heavy chain constant domain ($C_H$) which lacks cytotoxicity. In aspects of this embodiment, an anti-PD-L1 antibody disclosed herein comprises a heavy chain constant domain ($C_H$) which lacks antibody dependent cellular cytotoxicity (ADCC), complement-dependent cytotoxic activity (CDC) and/or antibody dependent cellular phagocytosis (ADCP). In aspects of this embodiment, a heavy chain constant domain ($C_H$) lacking Fc effector function is an IgG immunoglobulin. In other aspects of this embodiment, a heavy chain constant domain ($C_H$) lacking Fc effector function that is an IgG immunoglobulin is an IgG1 immunoglobulin, an IgG2 immunoglobulin, an IgG3 immunoglobulin, or an IgG4 immunoglobulin.

In an embodiment, a modified anti-PD-L1 antibody disclosed herein comprises an IgG1 immunoglobulin heavy chain constant domain ($C_H$) lacking cytotoxicity which comprises 1, 2, 3, 4 or 5 amino acid deletions, additions or substitutions located in the lower hinge region and/or the N-terminal half of the $C_H2$ domain. In aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which can comprise 1, 2, 3, 4 or 5 amino acid deletions, additions or substitutions located in the lower hinge region and/or the N-terminal half of the $C_H2$ domain that reduces or eliminates cytotoxicity. In other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which can comprise an amino acid deletion, addition or substitution at position L239, L240, K327, or any combination thereof that reduces or eliminates cytotoxicity. In yet other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which can comprise an amino acid substitution of A, C, D, E, G, H, K, N, P, Q, R, S, T, W, or Y at position L239, an amino acid substitution of A, C, D, E, G, H, K, N, P, Q, R, S, T, W, or Y at position L240, an amino acid substitution of A, C, D, F, G, H, I, L, M, N, P, S, T, V, W, or Y at position K327, or any combination thereof that reduces or eliminates cytotoxicity. In yet other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which can comprise an amino acid substitution of A, C, W, or Y at position L239, an amino acid substitution of A, C, W, or Y at position L240, an amino acid substitution of A, D, G, H, M, N, P, S, or T at position K327, or any combination thereof that reduces or eliminates cytotoxicity. In further aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which comprises an amino acid substitution of A at position L239 (L239A), an amino acid substitution of A at position L240 (L240A), an amino acid substitution of A at position K327 (K327A), or any combination thereof that reduces or eliminates cytotoxicity. In other aspects of this embodiment, a modified anti-PD-L1 antibody disclosed herein comprises an IgG1 immunoglobulin heavy chain constant domain ($C_H$) that lacks, or has reduced cytotoxicity is SEQ ID NO: 41, SEQ ID NO: 42, SEQ ID NO: 43, or SEQ ID NO: 44.

In an embodiment, a modified anti-PD-L1 antibody disclosed herein may comprise an IgG2 immunoglobulin heavy chain constant domain ($C_H$) lacking cytotoxicity which can comprise 1, 2, 3, 4 or 5 amino acid deletions, additions or substitutions located in the lower hinge region and/or the N-terminal half of the $C_H2$ domain. In aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise 1, 2, 3, 4 or 5 amino acid deletions, additions or substitutions located in the lower hinge region and/or the N-terminal half of the $C_H2$ domain that reduces or eliminates cytotoxicity. In other aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise an amino acid deletion, addition or substitution at position V236, A237, K323, or any combination thereof that reduces or eliminates cytotoxicity. In yet other aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise an amino acid substitution of A, C, D, E, F, G, H, K, N, P, Q, R, S, T, W, or Y at position V236, an amino acid substitution of C, D, E, F, H, I, K, M, N, L, P, Q, R, V, Y, or W at position A237, an amino acid substitution of A, C, D, F, G, H, I, L, M, N, P, S, T, V, W, or Y at position K323, or any combination thereof that reduces or eliminates cytotoxicity. In yet other aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise an amino acid substitution of A, C, F, T, or Y at position V236, an amino acid substitution of C, E, I, K, M, L, P, Q, R, or V at position A237, an amino acid substitution of A, D, G, H, M, N, P, S, or T at position K323, or any combination thereof that reduces or eliminates cytotoxicity. In further aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise an amino acid substitution of A at position V236 (V236A), an amino acid substitution of L at position A237 (A237L), an amino acid substitution of A at position K323 (K323A), or any combination thereof that reduces or eliminates cytotoxicity. In other aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise an amino acid substitution of A at position V236 (V236A), an amino acid substitution of A at position K323 (K323A), or any combination thereof that reduces or eliminates cytotoxicity.

In an embodiment, a modified anti-PD-L1 antibody disclosed herein may comprise an IgG4 immunoglobulin heavy chain constant domain ($C_H$) lacking cytotoxicity which can comprise 1, 2, 3, 4 or 5 amino acid deletions, additions or substitutions located in the lower hinge region and/or the N-terminal half of the $C_H2$ domain. In aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise 1, 2, 3, 4 or 5 amino acid deletions, additions or substitutions located in the lower hinge region and/or the N-terminal half of the $C_H2$ domain that reduces or eliminates cytotoxicity. In other aspects of this embodiment, a modified anti-PD-L1 antibody disclosed herein can comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise an amino acid deletion, addition or substitution at position F/V236, L/A/E237, K324, or any combination thereof that reduces or eliminates cytotoxicity. In yet other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise an amino acid substitution of A, C, D, E, F, G, H, K, N, P, Q, R, S, T, W, or Y at position V236, an amino acid substitution of A, C, D, E, G, H, I, K, N, P, Q, R, S, T, or V at position F236, an amino acid substitution of A, C, D, E, G, H, K, N, P, Q, R, S, T, W, or Y at position L237, an amino acid substitution of C, D, E, F, H, I, K, M, N, L, P, Q, R, V, Y, or W at position A237, an amino acid substitution of A, C, F, G, H, I, L, M, N, P, R, S, T, V, W, or Y at position E237, an amino acid substitution of A, C, D, F, G, H, I, L, M, N, P, S, T, V, W, or Y at position K324, or any combination thereof that reduces or eliminates cytotoxicity. In yet other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise an amino acid substitution of A, C, F, T, or Y at position V236, an amino acid substitution of C, I, or Vat position F236, an amino acid substitution of A, C, W, or Y at position L237, an amino acid substitution of C, E, I, K, M, L, P, Q, R, or V at position A237, an amino acid substitution of A, H, N, P, R, S, or T at position E237, an amino acid substitution of A, D, G, H, M, N, P, S, or T at position K324, or any combination thereof that reduces or eliminates cytotoxicity. In further aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise an amino acid substitution of A at position V236 (V236A), an amino acid substitution of I at position F236 (F2361), an amino acid substitution of A at position L237 (L237A), an amino acid substitution of L at position A237 (A237L), an amino acid substitution of A at position E237 (E237A), an amino acid substitution of A at position K324 (K324A), or any combination thereof that reduces or eliminates cytotoxicity.

In an embodiment, a modified anti-PD-L1 antibody disclosed herein comprises a heavy chain constant domain ($C_H$) containing amino acid sequence variants that promote clearance of a modified anti-PD-L1 antibody faster than an anti-PD-L1 antibody not containing the same amino acid sequence variants (the unmodified anti-PD-L1 referenced antibody). In relation to all embodiments, faster clearance refers to either or both of (i) clearance of an increased amount of a modified anti-PD-L1 antibody disclosed herein over the same, given time period relative to the unmodified anti-PD-L1 referenced antibody; and (ii) clearance of substantially the entire amount of a modified anti-PD-L1 antibody disclosed herein over a reduced time period relative to the unmodified anti-PD-L1 referenced antibody. Suitably, for a given time period, clearance rate (amount of antibody cleared for the given time period) is increased at least 25%, at least 50%, at least 75%, at least 100%, at least 125%, at least 150%, at least 175%, at least 200%, at least 250%, at least 300%, at least 350%, at least 400%, at least 450%, at least 500% relative to an unmodified anti-PD-L1 reference antibody. Further suitably, the given time period commences at or shortly after antibody administration, and may have a duration of 30 hours, 36 hours or 42 hours. A modified anti-PD-L1 antibody disclosed herein can be substantially all cleared over a time period that is reduced compared to that needed for substantially all of the unmodified anti-PD-L1 reference antibody to be cleared, suitably reduced at least 25%, at least 50%, at least 75%, at least 100%, at least 125%, at least 150%, at least 175%, at least 200%, at least 250%, at least 300%, at least 350%, at least 400%, at least 450%, at least 500% relative to an unmodified anti-PD-L1 reference antibody. In aspects of this embodiment, a heavy chain constant domain ($C_H$) containing amino acid sequence variants that promote clearance of the modified anti-PD-L1 antibody faster than an anti-PD-L1 antibody not containing the same amino acid sequence variants is an IgG immunoglobulin over the same period of time. In other aspects of this embodiment, an IgG immunoglobulin heavy chain constant domain ($C_H$) containing amino acid sequence variants that promote clearance of the modified anti-PD-L1 antibody faster than an anti-PD-L1 antibody not containing the same amino acid sequence variants is an IgG1 immunoglobulin, an IgG2 immunoglobulin, an IgG3 immunoglobulin, or an IgG4 immunoglobulin over the same period of time.

In aspects of this embodiment, a modified anti-PD-L1 antibody disclosed herein comprises an IgG1 immunoglobulin heavy chain constant domain ($C_H$) containing amino acid sequence variants in the $C_H2$ domain and/or $C_H3$ domain that promote clearance of the modified anti-PD-L1 antibody faster than an anti-PD-L1 antibody not containing the same amino acid variants located in the $C_H2$ domain and/or $C_H3$ domain over the same period of time. In other aspects of this embodiment, a modified anti-PD-L1 antibody disclosed herein comprises an IgG1 immunoglobulin heavy chain constant domain ($C_H$) comprising 1, 2, 3, 4 or 5 amino acid deletions, additions or substitutions located in the $C_H2$ domain and/or $C_H3$ domain that promote clearance of the modified anti-PD-L1 antibody faster than an anti-PD-L1 antibody not containing the same amino acid deletions, additions or substitutions located in the $C_H2$ domain and/or $C_H3$ domain over the same period of time.

In aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which can comprise 1, 2, 3, 4 or 5 amino acid deletions, additions or substitutions located in the $C_H2$ domain and/or $C_H3$ domain that promote clearance of the modified anti-PD-L1 antibody faster than an anti-PD-L1 antibody not containing the same amino acid deletions, additions or substitutions located in the $C_H2$ domain and/or $C_H3$ domain. In other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which can comprise an amino acid deletion, addition or substitution at position H315, H440, or both positions that promote clearance of the modified anti-PD-L1 antibody faster than an anti-PD-L1 antibody not containing the same H315 and H440 amino acid deletions, additions or substitutions. In other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which can comprise an amino acid substitution of A, C, D, E, F, G, I, K, L, M, P. Q, R, S, T, V, or W at position H315, an amino acid substitution of A, C, D, E, F, G, I, K, L, M, P. Q, R, S, T, V, or W at position H440, or any combination thereof that promote clearance of the modified anti-PD-L1 antibody faster than an anti-PD-L1 antibody not containing the same H315 and H440 amino acid substitutions. In yet other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which can comprise an amino acid substitution of C, D, E, K, Q, R, S, T, or W at position H315, an amino acid substitution of C, D, E, K, Q, R, S, T, or W at position H440, or any combination thereof that promote clearance of the modified anti-PD-L1 antibody faster than an anti-PD-L1 antibody not containing the same H315 and H440 amino acid substitutions. In yet other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which comprises an amino acid substitution of A at position H315 (H315A), an amino acid substitution of Q at position H440 (H440Q), or any combination thereof that promote clearance of the modified anti-PD-L1 antibody faster than an anti-PD-L1 antibody not containing the same H315 and H440 amino acid substitutions over the same period of time.

In other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which comprises a H315A variant, a H440Q variant, or any combination thereof that promote faster clearance of the modified anti-PD-L1 antibody by, e.g., at least 25%, at least 50%, at least 75%, at least 100%, at least 125%, at least 150%, at least 175%, at least 200%, at least 250%, at least 300%, at least 350%, at least 400%, at least 450%, at least 500% relative to an anti-PD-L1 antibody not comprising a H315A variant and a H440Q variant over the same period of time. In yet other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which comprises a H315A variant, a H440Q variant, or any combination thereof that promote faster clearance of the modified anti-PD-L1 antibody by, e.g., at most 10%, at most 25%, at most 50%, at most 75%, at most 100%, at most 125%, at most 150%, at most 175%, at most 200%, at most 250%, at most 300%, at most 350%, at most 400%, at most 450%, at most 500% relative to an anti-PD-L1 antibody not comprising a H315A variant and a H440Q variant over the same period of time. In still other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which comprises a H315A variant, a H440Q variant, or any combination thereof that promote faster clearance of the modified anti-PD-L1 antibody by, e.g., about 25% to about 50%, about 25% to about 100%, about 25% to about 150%, about 25% to about 200%, about 25% to about 250%, about 25% to about 300%, about 25% to about 350%, about 25% to about 400%, about 25% to about 450%, about 25% to about 500%, about 50% to about 100%, about 50% to about 150%, about 50% to about 200%, about 50% to about 250%, about 50% to about 300%, about 50% to about 350%, about 50% to about 400%, about 50% to about 450%, about 50% to about 500%, about 100% to about 150%, about 100% to about 200%, about 100% to about 250%, about 100% to about 300%, about 100% to about 350%, about 100% to about 400%, about 100% to about 450%, about 100% to about 500%, about 150% to about 200%, about 150% to about 250%, about 150% to about 300%, about 150% to about 350%, about 150% to about 400%, about 150% to about 450%, about 150% to about 500%, about 200% to about 250%, about 200% to about 300%, about 200% to about 350%, about 200% to about 400%, about 200% to about 450%, about 200% to about 500%, about 250% to about 300%, about 250% to about 350%, about 250% to about 400%, about 250% to about 450%, or about 250% to about 500%, relative to an anti-PD-L1 antibody not comprising a H315A variant and a H440Q variant over the same period of time.

In other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which comprises a H315A variant, a H440Q variant, or any combination thereof that promotes clearance of the modified anti-PD-L1 antibody in, e.g., about 1 day, about 2 days, about 3 days, about 4 days, about 5 days, about 6 days, or about 7 days. In yet other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which comprises a H315A variant, a H440Q variant, or any combination thereof that promotes clearance of the modified anti-PD-L1 antibody in, e.g., at least 1 day, at least 2 days, at least 3 days, at least 4 days, at least 5 days, at least 6 days, or at least 7 days. In still other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which comprises a H315A variant, a H440Q variant, or any combination thereof that promotes clearance of the modified anti-PD-L1 antibody in, e.g., at most 1 day, at most 2 days, at most 3 days, at most 4 days, at most 5 days, at most 6 days, or at most 7 days. In other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which comprises a H315A variant, a H440Q variant, or any combination thereof that promotes clearance of the modified anti-PD-L1 antibody in, e.g., about 1 day to about 2 days, about 1 day to about 3 days, about 1 day to about 4 days, about 1 day to about 5 days, about 1 day to about 6 days, about 1 day to about 7 days, about 2 days to about 3 days, about 2 days to about 4 days, about 2 days to about 5 days, about 2 days to about 6 days, about 2 days to about 7 days, about 3 days to about 4 days, about 3 days to about 5 days, about 3 days to about 6 days, about 3 days to about 7 days, about 4 days to about 5 days, about 4 days to about 6 days, about 4 days to about 7 days, about 5 days to about 6 days, about 5 days to about 7 days, or about 6 days to about 7 days.

In aspects of this embodiment, a modified anti-PD-L1 antibody disclosed herein may comprise an IgG2 immunoglobulin heavy chain constant domain ($C_H$) containing amino acid sequence variants in the $C_H2$ domain and/or $C_H3$ domain that promote clearance of the modified anti-PD-L1 antibody faster than an anti-PD-L1 antibody not containing the same amino acid variants located in the $C_H2$ domain and/or $C_H3$ domain over the same period of time. In other aspects of this embodiment, a modified anti-PD-L1 antibody disclosed herein may comprise an IgG2 immunoglobulin heavy chain constant domain ($C_H$) comprising 1, 2, 3, 4 or 5 amino acid deletions, additions or substitutions located in the $C_H2$ domain and/or $C_H3$ domain that promote clearance of the modified anti-PD-L1 antibody faster than an anti-PD-L1 antibody not containing the same amino acid deletions, additions or substitutions located in the $C_H2$ domain and/or $C_H3$ domain over the same period of time.

In aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise 1, 2, 3, 4 or 5 amino acid deletions, additions or substitutions located in the $C_H2$ domain and/or $C_H3$ domain that promote clearance of the modified anti-PD-L1 antibody faster than an anti-PD-L1 antibody not containing the same amino acid deletions, additions or substitutions located in the $C_H2$ domain and/or $C_H3$ domain over the same period of time. In other aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise an amino acid deletion, addition or substitution at position H315, H440, or both positions that promote clearance of the modified anti-PD-L1 antibody faster than an anti-PD-L1 antibody not containing the same H315 and H440 amino acid deletions, additions or substitutions over the same period of time. In other aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise an amino acid substitution of A, C, D, E, F, G, I, K, L, M, P. Q, R, S, T, V, or W at position H315, an amino acid substitution of A, C, D, E, F, G, I, K, L, M, P. Q, R, S, T, V, or W at position H440, or any combination thereof that promote clearance of the modified anti-PD-L1 antibody faster than an anti-PD-L1 antibody not containing the same H315 and H440 amino acid substitutions over the same period of time. In yet other aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise an amino acid substitution of C, D, E, K, Q, R, S, T, or W at position H315, an amino acid substitution of C, D, E, K, Q, R, S, T, or W at position H440, or any combination thereof that promote clearance of the modified anti-PD-L1 antibody faster than an anti-PD-L1 antibody not containing the same H315 and H440 amino acid substitutions over the same period of time. In yet other aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise an amino acid substitution of A at position H315 (H315A), an amino acid substitution of Q at position H440 (H440Q), or any combination thereof that promote clearance of the modified anti-PD-L1 antibody faster than an anti-PD-L1 antibody not containing the same H315 and H440 amino acid substitutions over the same period of time.

In other aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise a H315A variant, a H440Q variant, or any combination thereof that promote faster clearance of the modified anti-PD-L1 antibody by, e.g., at least 25%, at least 50%, at least 75%, at least 100%, at least 125%, at least 150%, at least 175%, at least 200%, at least 250%, at least 300%, at least 350%, at least 400%, at least 450%, at least 500% relative to an anti-PD-L1 antibody not comprising a H315A variant and a H440Q variant over the same period of time. In yet other aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise a H315A variant, a H440Q variant, or any combination thereof that promote faster clearance of the modified anti-PD-L1 antibody by, e.g., at most 25%, at most 50%, at most 75%, at most 100%, at most 125%, at most 150%, at most 175%, at most 200%, at most 250%, at most 300%, at most 350%, at most 400%, at most 450%, at most 500% relative to an anti-PD-L1 antibody not comprising a H315A variant and a H440Q variant over the same period of time. In still other aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise a H315A variant, a H440Q variant, or any combination thereof that promote faster clearance of the modified anti-PD-L1 antibody by, e.g., about 25% to about 50%, about 25% to about 100%, about 25% to about 150%, about 25% to about 200%, about 25% to about 250%, about 25% to about 300%, about 25% to about 350%, about 25% to about 400%, about 25% to about 450%, about 25% to about 500%, about 50% to about 100%, about 50% to about 150%, about 50% to about 200%, about 50% to about 250%, about 50% to about 300%, about 50% to about 350%, about 50% to about 400%, about 50% to about 450%, about 50% to about 500%, about 100% to about 150%, about 100% to about 200%, about 100% to about 250%, about 100% to about 300%, about 100% to about 350%, about 100% to about 400%, about 100% to about 450%, about 100% to about 500%, about 150% to about 200%, about 150% to about 250%, about 150% to about 300%, about 150% to about 350%, about 150% to about 400%, about 150% to about 450%, about 150% to about 500%, about 200% to about 250%, about 200% to about 300%, about 200% to about 350%, about 200% to about 400%, about 200% to about 450%, about 200% to about 500%, about 250% to about 300%, about 250% to about 350%, about 250% to about 400%, about 250% to about 450%, or about 250% to about 500%, relative to an anti-PD-L1 antibody not comprising a H315A variant and a H440Q variant over the same period of time.

In other aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise a H315A variant, a H440Q variant, or any combination thereof that promotes clearance of the modified anti-PD-L1 antibody in, e.g., about 1 day, about 2 days, about 3 days, about 4 days, about 5 days, about 6 days, or about 7 days. In yet other aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise a H315A variant, a H440Q variant, or any combination thereof that promotes clearance of the modified anti-PD-L1 antibody in, e.g., at least 1 day, at least 2 days, at least 3 days, at least 4 days, at least 5 days, at least 6 days, or at least 7 days. In still other aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise a H315A variant, a H440Q variant, or any combination thereof that promotes clearance of the modified anti-PD-L1 antibody in, e.g., at most 1 day, at most 2 days, at most 3 days, at most 4 days, at most 5 days, at most 6 days, or at most 7 days. In other aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise a H315A variant, a H440Q variant, or any combination thereof that promotes clearance of the modified anti-PD-L1 antibody in, e.g., about 1 day to about 2 days, about 1 day to about 3 days, about 1 day to about 4 days, about 1 day to about 5 days, about 1 day to about 6 days, about 1 day to about 7 days, about 2 days to about 3 days, about 2 days to about 4 days, about 2 days to about 5 days, about 2 days to about 6 days, about 2 days to about 7 days, about 3 days to about 4 days, about 3 days to about 5 days, about 3 days to about 6 days, about 3 days to about 7 days, about 4 days to about 5 days, about 4 days to about 6 days, about 4 days to about 7 days, about 5 days to about 6 days, about 5 days to about 7 days, or about 6 days to about 7 days.

In aspects of this embodiment, a modified anti-PD-L1 antibody disclosed herein may comprise an IgG4 immunoglobulin heavy chain constant domain ($C_H$) containing amino acid sequence variants in the $C_H2$ domain and/or $C_H3$ domain that promote clearance of the modified anti-PD-L1 antibody faster than an anti-PD-L1 antibody not containing the same amino acid variants located in the $C_H2$ domain and/or $C_H3$ domain over the same period of time. In other aspects of this embodiment, a modified anti-PD-L1 antibody disclosed herein may comprise an IgG4 immunoglobulin heavy chain constant domain ($C_H$) comprising 1, 2, 3, 4 or 5 amino acid deletions, additions or substitutions located in the $C_H2$ domain and/or $C_H3$ domain that promote clearance of the modified anti-PD-L1 antibody faster than an anti-PD-L1 antibody not containing the same amino acid deletions, additions or substitutions located in the $C_H2$ domain and/or $C_H3$ domain over the same period of time.

In aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise 1, 2, 3, 4 or 5 amino acid deletions, additions or substitutions located in the $C_H2$ domain and/or $C_H3$ domain that promote clearance of the modified anti-PD-L1 antibody faster than an anti-PD-L1 antibody not containing the same amino acid deletions, additions or substitutions located in the $C_H2$ domain and/or $C_H3$ domain over the same period of time. In other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise an amino acid deletion, addition or substitution at position H312, H437, or both positions that promote clearance of the modified anti-PD-L1 antibody faster than an anti-PD-L1 antibody not containing the same H312 and H437 amino acid deletions, additions or substitutions over the same period of time. In other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise an amino acid substitution of A, C, D, E, F, G, I, K, L, M, P. Q, R, S, T, V, or W at position H312, an amino acid substitution of A, C, D, E, F, G, I, K, L, M, P. Q, R, S, T, V, or W at position H437, or any combination thereof that promote clearance of the modified anti-PD-L1 antibody faster than an anti-PD-L1 antibody not containing the same H312 and H437 amino acid substitutions over the same period of time. In yet other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise an amino acid substitution of C, D, E, K, Q, R, S, T, or W at position H312, an amino acid substitution of C, D, E, K, Q, R, S, T, or W at position H437, or any combination thereof that promote clearance of the modified anti-PD-L1 antibody faster than an anti-PD-L1 antibody not containing the same H312 and H437 amino acid substitutions over the same period of time. In yet other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise an amino acid substitution of A at position H312 (H312A), an amino acid substitution of Q at position H437 (H437Q), or any combination thereof that promote clearance of the modified anti-PD-L1 antibody faster than an anti-PD-L1 antibody not containing the same H312 and H437 amino acid substitutions over the same period of time.

In other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise a H312A variant, a H437Q variant, or any combination thereof that promote faster clearance of the modified anti-PD-L1 antibody by, e.g., at least 25%, at least 50%, at least 75%, at least 100%, at least 125%, at least 150%, at least 175%, at least 200%, at least 250%, at least 300%, at least 350%, at least 400%, at least 450%, at least 500% relative to an anti-PD-L1 antibody not comprising a H312A variant and a H437Q variant over the same period of time. In yet other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise a H312A variant, a H437Q variant, or any combination thereof that promote faster clearance of the modified anti-PD-L1 antibody by, e.g., at most 25%, at most 50%, at most 75%, at most 100%, at most 125%, at most 150%, at most 175%, at most 200%, at most 250%, at most 300%, at most 350%, at most 400%, at most 450%, at most 500% relative to an anti-PD-L1 antibody not comprising a H312A variant and a H437Q variant over the same period of time. In still other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise a H312A variant, a H437Q variant, or any combination thereof that promote faster clearance of the modified anti-PD-L1 antibody by, e.g., about 25% to about 50%, about 25% to about 100%, about 25% to about 150%, about 25% to about 200%, about 25% to about 250%, about 25% to about 300%, about 25% to about 350%, about 25% to about 400%, about 25% to about 450%, about 25% to about 500%, about 50% to about 100%, about 50% to about 150%, about 50% to about 200%, about 50% to about 250%, about 50% to about 300%, about 50% to about 350%, about 50% to about 400%, about 50% to about 450%, about 50% to about 500%, about 100% to about 150%, about 100% to about 200%, about 100% to about 250%, about 100% to about 300%, about 100% to about 350%, about 100% to about 400%, about 100% to about 450%, about 100% to about 500%, about 150% to about 200%, about 150% to about 250%, about 150% to about 300%, about 150% to about 350%, about 150% to about 400%, about 150% to about 450%, about 150% to about 500%, about 200% to about 250%, about 200% to about 300%, about 200% to about 350%, about 200% to about 400%, about 200% to about 450%, about 200% to about 500%, about 250% to about 300%, about 250% to about 350%, about 250% to about 400%, about 250% to about 450%, or about 250% to about 500%, relative to an anti-PD-L1 antibody not comprising a H312A variant and a H437Q variant over the same period of time.

In other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise a H312A variant, a H437Q variant, or any combination thereof that promotes clearance of the modified anti-PD-L1 antibody by, e.g., about 1 day, about 2 days, about 3 days, about 4 days, about 5 days, about 6 days, or about 7 days. In yet other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise a H312A variant, a H437Q variant, or any combination thereof that promotes clearance of the modified anti-PD-L1 antibody by, e.g., at least 1 day, at least 2 days, at least 3 days, at least 4 days, at least 5 days, at least 6 days, or at least 7 days. In still other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise a H312A variant, a H437Q variant, or any combination thereof that promotes clearance of the modified anti-PD-L1 antibody by, e.g., at most 1 day, at most 2 days, at most 3 days, at most 4 days, at most 5 days, at most 6 days, or at most 7 days. In other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise a H312A variant, a H437Q variant, or any combination thereof that promotes clearance of the modified anti-PD-L1 antibody by, e.g., about 1 day to about 2 days, about 1 day to about 3 days, about 1 day to about 4 days, about 1 day to about 5 days, about 1 day to about 6 days, about 1 day to about 7 days, about 2 days to about 3 days, about 2 days to about 4 days, about 2 days to about 5 days, about 2 days to about 6 days, about 2 days to about 7 days, about 3 days to about 4 days, about 3 days to about 5 days, about 3 days to about 6 days, about 3 days to about 7 days, about 4 days to about 5 days, about 4 days to about 6 days, about 4 days to about 7 days, about 5 days to about 6 days, about 5 days to about 7 days, or about 6 days to about 7 days.

In an embodiment, a modified anti-PD-L1 antibody disclosed herein comprises a heavy chain constant domain ($C_H$) containing amino acid sequence variants that reduce the half-life of the modified anti-PD-L1 antibody more than an anti-PD-L1 antibody not containing the same amino acid sequence variants. In aspects of this embodiment, a heavy chain constant domain ($C_H$) containing amino acid sequence variants that reduce the half-life of the modified anti-PD-L1 antibody more than an anti-PD-L1 antibody not containing the same amino acid sequence variants is an IgG immunoglobulin. In other aspects of this embodiment, an IgG immunoglobulin heavy chain constant domain ($C_H$) containing amino acid sequence variants that reduce the half-life of the modified anti-PD-L1 antibody more than an anti-PD-L1 antibody not containing the same amino acid sequence variants is an IgG1 immunoglobulin, an IgG2 immunoglobulin, an IgG3 immunoglobulin, or an IgG4 immunoglobulin.

In aspects of this embodiment, a modified anti-PD-L1 antibody disclosed herein comprises an IgG1 immunoglobulin heavy chain constant domain ($C_H$) containing amino acid sequence variants in the CH2 domain and/or CH3 domain that reduce the half-life of the modified anti-PD-L1 antibody more than an anti-PD-L1 antibody not containing the same amino acid variants located in the CH2 domain and/or CH3 domain. In other aspects of this embodiment, a modified anti-PD-L1 antibody disclosed herein comprises an IgG1 immunoglobulin heavy chain constant domain ($C_H$) comprising 1, 2, 3, 4 or 5 amino acid deletions, additions or substitutions located in the CH2 domain and/or CH3 domain that reduce the half-life of the modified anti-PD-L1 antibody more than an anti-PD-L1 antibody not containing the same amino acid deletions, additions or substitutions located in the CH2 domain and/or CH3 domain.

In aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which can comprise 1, 2, 3, 4 or 5 amino acid deletions, additions or substitutions located in the CH2 domain and/or CH3 domain that reduce the half-life of the modified anti-PD-L1 antibody more than an anti-PD-L1 antibody not containing the same amino acid deletions, additions or substitutions located in the CH2 domain and/or CH3 domain. In other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which can comprise an amino acid deletion, addition or substitution at position H315, H440, or both positions that reduce the half-life of the modified anti-PD-L1 antibody more than an anti-PD-L1 antibody not containing the same H315 and H440 amino acid deletions, additions or substitutions. In other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which can comprise an amino acid substitution of A, C, D, E, F, G, I, K, L, M, P. Q, R, S, T, V, or W at position H315, an amino acid substitution of A, C, D, E, F, G, I, K, L, M, P. Q, R, S, T, V, or W at position H440, or any combination thereof that reduce the half-life of the modified anti-PD-L1 antibody more than an anti-PD-L1 antibody not containing the same H315 and H440 amino acid substitutions. In yet other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which can comprise an amino acid substitution of C, D, E, K, Q, R, S, T, or W at position H315, an amino acid substitution of C, D, E, K, Q, R, S, T, or W at position H440, or any combination thereof that reduce the half-life of the modified anti-PD-L1 antibody more than an anti-PD-L1 antibody not containing the same H315 and H440 amino acid substitutions. In yet other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which comprises an amino acid substitution of A at position H315 (H315A), an amino acid substitution of Q at position H440 (H440Q), or any combination thereof that reduce the half-life of the modified anti-PD-L1 antibody more than an anti-PD-L1 antibody not containing the same H315 and H440 amino acid substitutions.

In other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which comprises a H315A variant, a H440Q variant, or any combination thereof that reduce the half-life of the modified anti-PD-L1 antibody by, e.g., at least 25%, at least 50%, at least 75%, at least 100%, at least 125%, at least 150%, at least 175%, at least 200%, at least 250%, at least 300%, at least 350%, at least 400%, at least 450%, at least 500% relative to an anti-PD-L1 antibody not comprising a H315A variant and a H440Q variant. In yet other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which comprises a H315A variant, a H440Q variant, or any combination thereof that reduce the half-life of the modified anti-PD-L1 antibody by, e.g., at most 25%, at most 50%, at most 75%, at most 100%, at most 125%, at most 150%, at most 175%, at most 200%, at most 250%, at most 300%, at most 350%, at most 400%, at most 450%, at most 500% relative to an anti-PD-L1 antibody not comprising a H315A variant and a H440Q variant. In still other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which comprises a H315A variant, a H440Q variant, or any combination thereof that reduce the half-life of the modified anti-PD-L1 antibody by, e.g., about 25% to about 50%, about 25% to about 100%, about 25% to about 150%, about 25% to about 200%, about 25% to about 250%, about 25% to about 300%, about 25% to about 350%, about 25% to about 400%, about 25% to about 450%, about 25% to about 500%, about 50% to about 100%, about 50% to about 150%, about 50% to about 200%, about 50% to about 250%, about 50% to about 300%, about 50% to about 350%, about 50% to about 400%, about 50% to about 450%, about 50% to about 500%, about 100% to about 150%, about 100% to about 200%, about 100% to about 250%, about 100% to about 300%, about 100% to about 350%, about 100% to about 400%, about 100% to about 450%, about 100% to about 500%, about 150% to about 200%, about 150% to about 250%, about 150% to about 300%, about 150% to about 350%, about 150% to about 400%, about 150% to about 450%, about 150% to about 500%, about 200% to about 250%, about 200% to about 300%, about 200% to about 350%, about 200% to about 400%, about 200% to about 450%, about 200% to about 500%, about 250% to about 300%, about 250% to about 350%, about 250% to about 400%, about 250% to about 450%, or about 250% to about 500%, relative to an anti-PD-L1 antibody not comprising a H315A variant and a H440Q variant.

In other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which comprises a H315A variant, a H440Q variant, or any combination thereof that has a half-life of, e.g., about 1 day, about 2 days, about 3 days, about 4 days, about 5 days, about 6 days, or about 7 days. In yet other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which comprises a H315A variant, a H440Q variant, or any combination thereof that has a half-life of, e.g., at least 1 day, at least 2 days, at least 3 days, at least 4 days, at least 5 days, at least 6 days, or at least 7 days. In still other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which comprises a H315A variant, a H440Q variant, or any combination thereof that has a half-life of, e.g., at most 1 day, at most 2 days, at most 3 days, at most 4 days, at most 5 days, at most 6 days, or at most 7 days. In other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which comprises a H315A variant, a H440Q variant, or any combination thereof that has a half-life of, e.g., about 1 day to about 2 days, about 1 day to about 3 days, about 1 day to about 4 days, about 1 day to about 5 days, about 1 day to about 6 days, about 1 day to about 7 days, about 2 days to about 3 days, about 2 days to about 4 days, about 2 days to about 5 days, about 2 days to about 6 days, about 2 days to about 7 days, about 3 days to about 4 days, about 3 days to about 5 days, about 3 days to about 6 days, about 3 days to about 7 days, about 4 days to about 5 days, about 4 days to about 6 days, about 4 days to about 7 days, about 5 days to about 6 days, about 5 days to about 7 days, or about 6 days to about 7 days.

In other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which comprises a H315A variant, a H440Q variant, or any combination thereof that has a half-life of, e.g., about 30 hours, about 32 hours, about 34 hours, about 36 hours, about 38 hours, about 40 hours, about 42 hours, about 44 hours, about 46 hours, or about 48 hours. In yet other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which comprises a H315A variant, a H440Q variant, or any combination thereof that has a half-life of, e.g., at least 30 hours, at least 32 hours, at least 34 hours, at least 36 hours, at least 38 hours, at least 40 hours, at least 42 hours, at least 44 hours, at least 46 hours, or at least 48 hours. In still other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which comprises a H315A variant, a H440Q variant, or any combination thereof that has a half-life of, e.g., at most 30 hours, at most 32 hours, at most 34 hours, at most 36 hours, at most 38 hours, at most 40 hours, at most 42 hours, at most 44 hours, at most 46 hours, or at most 48 hours. In other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which comprises a H315A variant, a H440Q variant, or any combination thereof that has a half-life of, e.g., about 30 hours to about 36 hours, about 30 hours to about 42 hours, about 30 hours to about 48 hours, about 32 hours to about 36 hours, about 32 hours to about 42 hours, about 32 hours to about 48 hours, about 34 hours to about 36 hours, about 34 hours to about 42 hours, about 34 hours to about 48 hours, about 36 hours to about 42 hours, about 36 hours to about 48 hours, or about 42 hours to about 48 hours.

In aspects of this embodiment, a modified anti-PD-L1 antibody disclosed herein may comprise an IgG2 immunoglobulin heavy chain constant domain ($C_H$) containing amino acid sequence variants in the CH2 domain and/or CH3 domain that reduce the half-life of the modified anti-PD-L1 antibody more than an anti-PD-L1 antibody not containing the same amino acid variants located in the CH2 domain and/or CH3 domain. In other aspects of this embodiment, a modified anti-PD-L1 antibody disclosed herein may comprises an IgG2 immunoglobulin heavy chain constant domain ($C_H$) that can comprise 1, 2, 3, 4 or 5 amino acid deletions, additions or substitutions located in the CH2 domain and/or CH3 domain that reduce the half-life of the modified anti-PD-L1 antibody more than an anti-PD-L1 antibody not containing the same amino acid deletions, additions or substitutions located in the CH2 domain and/or CH3 domain.

In aspects of this embodiment, a modified anti-PD-L1 antibody disclosed herein may comprises an IgG2 immunoglobulin heavy chain constant domain ($C_H$) of SEQ ID NO: 45, SEQ ID NO: 46, SEQ ID NO: 47 or SEQ ID NO: 48 which can comprise 1, 2, 3, 4 or 5 amino acid deletions, additions or substitutions located in the CH2 domain and/or CH3 domain that reduce the half-life of the modified anti-PD-L1 antibody more than an anti-PD-L1 antibody not containing the same amino acid deletions, additions or substitutions located in the CH2 domain and/or CH3 domain. In other aspects of this embodiment, a modified anti-PD-L1 antibody disclosed herein may comprises an IgG2 immunoglobulin heavy chain constant domain ($C_H$) of SEQ ID NO: 45, SEQ ID NO: 46, SEQ ID NO: 47 or SEQ ID NO: 48 which can comprise an amino acid deletion, addition or substitution at position H311, H436, or both positions that reduce the half-life of the modified anti-PD-L1 antibody more than an anti-PD-L1 antibody not containing the same H311 and H436 amino acid deletions, additions or substitutions. In other aspects of this embodiment, a modified anti-PD-L1 antibody disclosed herein may comprises an IgG2 immunoglobulin heavy chain constant domain ($C_H$) of SEQ ID NO: 45, SEQ ID NO: 46, SEQ ID NO: 47 or SEQ ID NO: 48 which can comprise an amino acid substitution of A, C, D, E, F, G, I, K, L, M, P. Q, R, S, T, V, or W at position H311, an amino acid substitution of A, C, D, E, F, G, I, K, L, M, P. Q, R, S, T, V, or W at position H436, or any combination thereof that reduce the half-life of the modified anti-PD-L1 antibody more than an anti-PD-L1 antibody not containing the same H311 and H436 amino acid substitutions. In yet other aspects of this embodiment, a modified anti-PD-L1 antibody disclosed herein may comprises an IgG2 immunoglobulin heavy chain constant domain ($C_H$) of SEQ ID NO: 45, SEQ ID NO: 46, SEQ ID NO: 47 or SEQ ID NO: 48 which can comprise an amino acid substitution of C, D, E, K, Q, R, S, T, or W at position H311, an amino acid substitution of C, D, E, K, Q, R, S, T, or W at position H436, or any combination thereof that reduce the half-life of the modified anti-PD-L1 antibody more than an anti-PD-L1 antibody not containing the same H311 and H436 amino acid substitutions. In yet other aspects of this embodiment, a modified anti-PD-L1 antibody disclosed herein may comprises an IgG2 immunoglobulin heavy chain constant domain ($C_H$) of SEQ ID NO: 45, SEQ ID NO: 46, SEQ ID NO: 47 or SEQ ID NO: 48 which can comprise an amino acid substitution of A at position H311 (H311A), an amino acid substitution of Q at position H436 (H436Q), or any combination thereof that reduce the half-life of the modified anti-PD-L1 antibody more than an anti-PD-L1 antibody not containing the same H311 and H436 amino acid substitutions.

In other aspects of this embodiment, a modified anti-PD-L1 antibody disclosed herein may comprises an IgG2 immunoglobulin heavy chain constant domain ($C_H$) of SEQ ID NO: 45, SEQ ID NO: 46, SEQ ID NO: 47 or SEQ ID NO: 48 which can comprise a H311A variant, a H436Q variant, or any combination thereof that reduce the half-life of the modified anti-PD-L1 antibody by, e.g., at least 25%, at least 50%, at least 75%, at least 100%, at least 125%, at least 150%, at least 175%, at least 200%, at least 250%, at least 300%, at least 350%, at least 400%, at least 450%, at least 500% relative to an anti-PD-L1 antibody not comprising a H311A variant and a H436Q variant. In yet other aspects of this embodiment, a modified anti-PD-L1 antibody disclosed herein may comprises an IgG2 immunoglobulin heavy chain constant domain ($C_H$) of SEQ ID NO: 45, SEQ ID NO: 46, SEQ ID NO: 47 or SEQ ID NO: 48 which can comprise a H311A variant, a H436Q variant, or any combination thereof that reduce the half-life of the modified anti-PD-L1 antibody by, e.g., at most 25%, at most 50%, at most 75%, at most 100%, at most 125%, at most 150%, at most 175%, at most 200%, at most 250%, at most 300%, at most 350%, at most 400%, at most 450%, at most 500% relative to an anti-PD-L1 antibody not comprising a H311A variant and a H436Q variant. In still other aspects of this embodiment, a modified anti-PD-L1 antibody disclosed herein may comprises an IgG2 immunoglobulin heavy chain constant domain ($C_H$) of SEQ ID NO: 45, SEQ ID NO: 46, SEQ ID NO: 47 or SEQ ID NO: 48 which can comprise a H311A variant, a H436Q variant, or any combination thereof that reduce the half-life of the modified anti-PD-L1 antibody by, e.g., about 25% to about 50%, about 25% to about 100%, about 25% to about 150%, about 25% to about 200%, about 25% to about 250%, about 25% to about 300%, about 25% to about 350%, about 25% to about 400%, about 25% to about 450%, about 25% to about 500%, about 50% to about 100%, about 50% to about 150%, about 50% to about 200%, about 50% to about 250%, about 50% to about 300%, about 50% to about 350%, about 50% to about 400%, about 50% to about 450%, about 50% to about 500%, about 100% to about 150%, about 100% to about 200%, about 100% to about 250%, about 100% to about 300%, about 100% to about 350%, about 100% to about 400%, about 100% to about 450%, about 100% to about 500%, about 150% to about 200%, about 150% to about 250%, about 150% to about 300%, about 150% to about 350%, about 150% to about 400%, about 150% to about 450%, about 150% to about 500%, about 200% to about 250%, about 200% to about 300%, about 200% to about 350%, about 200% to about 400%, about 200% to about 450%, about 200% to about 500%, about 250% to about 300%, about 250% to about 350%, about 250% to about 400%, about 250% to about 450%, or about 250% to about 500%, relative to an anti-PD-L1 antibody not comprising a H311A variant and a H436Q variant.

In other aspects of this embodiment, a modified anti-PD-L1 antibody disclosed herein may comprises an IgG2 immunoglobulin heavy chain constant domain ($C_H$) of SEQ ID NO: 45, SEQ ID NO: 46, SEQ ID NO: 47 or SEQ ID NO: 48 which can comprise a H311A variant, a H436Q variant, or any combination thereof that has a half-life of, e.g., about 1 day, about 2 days, about 3 days, about 4 days, about 5 days, about 6 days, or about 7 days. In yet other aspects of this embodiment, a modified anti-PD-L1 antibody disclosed herein may comprises an IgG2 immunoglobulin heavy chain constant domain ($C_H$) of SEQ ID NO: 45, SEQ ID NO: 46, SEQ ID NO: 47 or SEQ ID NO: 48 which can comprise a H311A variant, a H436Q variant, or any combination thereof that has a half-life of, e.g., at least 1 day, at least 2 days, at least 3 days, at least 4 days, at least 5 days, at least 6 days, or at least 7 days. In still other aspects of this embodiment, a modified anti-PD-L1 antibody disclosed herein may comprises an IgG2 immunoglobulin heavy chain constant domain ($C_H$) of SEQ ID NO: 45, SEQ ID NO: 46, SEQ ID NO: 47 or SEQ ID NO: 48 which can comprise a H311A variant, a H436Q variant, or any combination thereof that has a half-life of, e.g., at most 1 day, at most 2 days, at most 3 days, at most 4 days, at most 5 days, at most 6 days, or at most 7 days. In other aspects of this embodiment, a modified anti-PD-L1 antibody disclosed herein may comprises an IgG2 immunoglobulin heavy chain constant domain ($C_H$) of SEQ ID NO: 45, SEQ ID NO: 46, SEQ ID NO: 47 or SEQ ID NO: 48 which can comprise a H311A variant, a H436Q variant, or any combination thereof that has a half-life of, e.g., about 1 day to about 2 days, about 1 day to about 3 days, about 1 day to about 4 days, about 1 day to about 5 days, about 1 day to about 6 days, about 1 day to about 7 days, about 2 days to about 3 days, about 2 days to about 4 days, about 2 days to about 5 days, about 2 days to about 6 days, about 2 days to about 7 days, about 3 days to about 4 days, about 3 days to about 5 days, about 3 days to about 6 days, about 3 days to about 7 days, about 4 days to about 5 days, about 4 days to about 6 days, about 4 days to about 7 days, about 5 days to about 6 days, about 5 days to about 7 days, or about 6 days to about 7 days.

In other aspects of this embodiment, a modified anti-PD-L1 antibody disclosed herein may comprises an IgG2 immunoglobulin heavy chain constant domain ($C_H$) of SEQ ID NO: 45, SEQ ID NO: 46, SEQ ID NO: 47 or SEQ ID NO: 48 which can comprise a H311A variant, a H436Q variant, or any combination thereof that has a half-life of, e.g., about 30 hours, about 32 hours, about 34 hours, about 36 hours, about 38 hours, about 40 hours, about 42 hours, about 44 hours, about 46 hours, or about 48 hours. In yet other aspects of this embodiment, a modified anti-PD-L1 antibody disclosed herein may comprises an IgG2 immunoglobulin heavy chain constant domain ($C_H$) of SEQ ID NO: 45, SEQ ID NO: 46, SEQ ID NO: 47 or SEQ ID NO: 48 which can comprise a H311A variant, a H436Q variant, or any combination thereof that has a half-life of, e.g., at least 30 hours, at least 32 hours, at least 34 hours, at least 36 hours, at least 38 hours, at least 40 hours, at least 42 hours, at least 44 hours, at least 46 hours, or at least 48 hours. In still other aspects of this embodiment, a modified anti-PD-L1 antibody disclosed herein may comprises an IgG2 immunoglobulin heavy chain constant domain ($C_H$) of SEQ ID NO: 45, SEQ ID NO: 46, SEQ ID NO: 47 or SEQ ID NO: 48 which can comprise a H311A variant, a H436Q variant, or any combination thereof that has a half-life of, e.g., at most 30 hours, at most 32 hours, at most 34 hours, at most 36 hours, at most 38 hours, at most 40 hours, at most 42 hours, at most 44 hours, at most 46 hours, or at most 48 hours. In other aspects of this embodiment, a modified anti-PD-L1 antibody disclosed herein may comprises an IgG2 immunoglobulin heavy chain constant domain ($C_H$) of SEQ ID NO: 45, SEQ ID NO: 46, SEQ ID NO: 47 or SEQ ID NO: 48 which can comprise a H311A variant, a H436Q variant, or any combination thereof that has a half-life of, e.g., about 30 hours to about 36 hours, about 30 hours to about 42 hours, about 30 hours to about 48 hours, about 32 hours to about 36 hours, about 32 hours to about 42 hours, about 32 hours to about 48 hours, about 34 hours to about 36 hours, about 34 hours to about 42 hours, about 34 hours to about 48 hours, about 36 hours to about 42 hours, about 36 hours to about 48 hours, or about 42 hours to about 48 hours.

In aspects of this embodiment, a modified anti-PD-L1 antibody disclosed herein may comprise an IgG4 immunoglobulin heavy chain constant domain ($C_H$) containing amino acid sequence variants in the CH2 domain and/or CH3 domain that reduce the half-life of the modified anti-PD-L1 antibody more than an anti-PD-L1 antibody not containing the same amino acid variants located in the CH2 domain and/or CH3 domain. In other aspects of this embodiment, a modified anti-PD-L1 antibody disclosed herein may comprise an IgG4 immunoglobulin heavy chain constant domain ($C_H$) that can comprise 1, 2, 3, 4 or 5 amino acid deletions, additions or substitutions located in the CH2 domain and/or CH3 domain that reduce the half-life of the modified anti-PD-L1 antibody more than an anti-PD-L1 antibody not containing the same amino acid deletions, additions or substitutions located in the CH2 domain and/or CH3 domain.

In aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise 1, 2, 3, 4 or 5 amino acid deletions, additions or substitutions located in the CH2 domain and/or CH3 domain that reduce the half-life of an anti-PD-L1 antibody disclosed herein more than an anti-PD-L1 antibody not containing the same amino acid deletions, additions or substitutions located in the CH2 domain and/or CH3 domain. In other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise an amino acid deletion, addition or substitution at position H312, H437, or both positions that reduce the half-life of the modified anti-PD-L1 antibody more than an anti-PD-L1 antibody not containing the same H312 and H437 amino acid deletions, additions or substitutions. In other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise an amino acid substitution of A, C, D, E, F, G, I, K, L, M, P. Q, R, S, T, V, or W at position H312, an amino acid substitution of A, C, D, E, F, G, I, K, L, M, P. Q, R, S, T, V, or W at position H437, or any combination thereof that reduce the half-life of the modified anti-PD-L1 antibody more than an anti-PD-L1 antibody not containing the same H312 and H437 amino acid substitutions. In yet other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise an amino acid substitution of C, D, E, K, Q, R, S, T, or W at position H312, an amino acid substitution of C, D, E, K, Q, R, S, T, or W at position H437, or any combination thereof that reduce the half-life of the modified anti-PD-L1 antibody more than an anti-PD-L1 antibody not containing the same H312 and H437 amino acid substitutions. In yet other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise an amino acid substitution of A at position H312 (H312A), an amino acid substitution of Q at position H437 (H437Q), or any combination thereof that reduce the half-life of the modified anti-PD-L1 antibody more than an anti-PD-L1 antibody not containing the same H312 and H437 amino acid substitutions.

In other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise a H312A variant, a H437Q variant, or any combination thereof that reduce the half-life of the modified anti-PD-L1 antibody by, e.g., at least 25%, at least 50%, at least 75%, at least 100%, at least 125%, at least 150%, at least 175%, at least 200%, at least 250%, at least 300%, at least 350%, at least 400%, at least 450%, at least 500% relative to an anti-PD-L1 antibody not comprising a H312A variant and a H437Q variant. In yet other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise a H312A variant, a H437Q variant, or any combination thereof that reduce the half-life of the modified anti-PD-L1 antibody by, e.g., at most 25%, at most 50%, at most 75%, at most 100%, at most 125%, at most 150%, at most 175%, at most 200%, at most 250%, at most 300%, at most 350%, at most 400%, at most 450%, at most 500% relative to an anti-PD-L1 antibody not comprising a H312A variant and a H437Q variant. In still other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise a H312A variant, a H437Q variant, or any combination thereof that reduce the half-life of the modified anti-PD-L1 antibody by, e.g., about 25% to about 50%, about 25% to about 100%, about 25% to about 150%, about 25% to about 200%, about 25% to about 250%, about 25% to about 300%, about 25% to about 350%, about 25% to about 400%, about 25% to about 450%, about 25% to about 500%, about 50% to about 100%, about 50% to about 150%, about 50% to about 200%, about 50% to about 250%, about 50% to about 300%, about 50% to about 350%, about 50% to about 400%, about 50% to about 450%, about 50% to about 500%, about 100% to about 150%, about 100% to about 200%, about 100% to about 250%, about 100% to about 300%, about 100% to about 350%, about 100% to about 400%, about 100% to about 450%, about 100% to about 500%, about 150% to about 200%, about 150% to about 250%, about 150% to about 300%, about 150% to about 350%, about 150% to about 400%, about 150% to about 450%, about 150% to about 500%, about 200% to about 250%, about 200% to about 300%, about 200% to about 350%, about 200% to about 400%, about 200% to about 450%, about 200% to about 500%, about 250% to about 300%, about 250% to about 350%, about 250% to about 400%, about 250% to about 450%, or about 250% to about 500%, relative to an anti-PD-L1 antibody not comprising a H312A variant and a H437Q variant.

In other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise a H312A variant, a H437Q variant, or any combination thereof that has a half-life of, e.g., about 1 day, about 2 days, about 3 days, about 4 days, about 5 days, about 6 days, or about 7 days. In yet other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise a H312A variant, a H437Q variant, or any combination thereof that has a half-life of, e.g., at least 1 day, at least 2 days, at least 3 days, at least 4 days, at least 5 days, at least 6 days, or at least 7 days. In still other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise a H312A variant, a H437Q variant, or any combination thereof that has a half-life of, e.g., at most 1 day, at most 2 days, at most 3 days, at most 4 days, at most 5 days, at most 6 days, or at most 7 days. In other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise a H312A variant, a H437Q variant, or any combination thereof that has a half-life of, e.g., about 1 day to about 2 days, about 1 day to about 3 days, about 1 day to about 4 days, about 1 day to about 5 days, about 1 day to about 6 days, about 1 day to about 7 days, about 2 days to about 3 days, about 2 days to about 4 days, about 2 days to about 5 days, about 2 days to about 6 days, about 2 days to about 7 days, about 3 days to about 4 days, about 3 days to about 5 days, about 3 days to about 6 days, about 3 days to about 7 days, about 4 days to about 5 days, about 4 days to about 6 days, about 4 days to about 7 days, about 5 days to about 6 days, about 5 days to about 7 days, or about 6 days to about 7 days.

In other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise a H312A variant, a H437Q variant, or any combination thereof that has a half-life of, e.g., about 30 hours, about 32 hours, about 34 hours, about 36 hours, about 38 hours, about 40 hours, about 42 hours, about 44 hours, about 46 hours, or about 48 hours. In yet other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise a H312A variant, a H437Q variant, or any combination thereof that has a half-life of, e.g., at least 30 hours, at least 32 hours, at least 34 hours, at least 36 hours, at least 38 hours, at least 40 hours, at least 42 hours, at least 44 hours, at least 46 hours, or at least 48 hours. In still other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise a H312A variant, a H437Q variant, or any combination thereof that has a half-life of, e.g., at most 30 hours, at most 32 hours, at most 34 hours, at most 36 hours, at most 38 hours, at most 40 hours, at most 42 hours, at most 44 hours, at most 46 hours, or at most 48 hours. In other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise a H312A variant, a H437Q variant, or any combination thereof that has a half-life of, e.g., about 30 hours to about 36 hours, about 30 hours to about 42 hours, about 30 hours to about 48 hours, about 32 hours to about 36 hours, about 32 hours to about 42 hours, about 32 hours to about 48 hours, about 34 hours to about 36 hours, about 34 hours to about 42 hours, about 34 hours to about 48 hours, about 36 hours to about 42 hours, about 36 hours to about 48 hours, or about 42 hours to about 48 hours.

In an embodiment, a modified anti-PD-L1 antibody disclosed herein can comprise a heavy chain constant domain ($C_H$) containing amino acid sequence variants that reduce interaction of the modified anti-PD-L1 antibody with its cognate FcRn receptor more than an anti-PD-L1 antibody not containing the same amino acid sequence variants. In aspects of this embodiment, a heavy chain constant domain ($C_H$) containing amino acid sequence variants that reduce interaction of the modified anti-PD-L1 antibody with its cognate FcRn receptor more than an anti-PD-L1 antibody not containing the same amino acid sequence variants is an IgG immunoglobulin. In other aspects of this embodiment, an IgG immunoglobulin heavy chain constant domain ($C_H$) containing amino acid sequence variants that reduce interaction of the modified anti-PD-L1 antibody with its cognate FcRn receptor more than an anti-PD-L1 antibody not containing the same amino acid sequence variants is an IgG1 immunoglobulin, an IgG2 immunoglobulin, an IgG3 immunoglobulin, or an IgG4 immunoglobulin.

In aspects of this embodiment, a modified anti-PD-L1 antibody disclosed herein may comprise an IgG1 immunoglobulin heavy chain constant domain ($C_H$) containing amino acid sequence variants in the CH2 domain and/or CH3 domain that reduce interaction of the modified anti-PD-L1 antibody with its cognate FcRn receptor more than an anti-PD-L1 antibody not containing the same amino acid variants located in the CH2 domain and/or CH3 domain. In other aspects of this embodiment, a modified anti-PD-L1 antibody disclosed herein may comprise an IgG1 immunoglobulin heavy chain constant domain ($C_H$) that can comprise 1, 2, 3, 4 or 5 amino acid deletions, additions or substitutions located in the CH2 domain and/or CH3 domain that reduce interaction of the modified anti-PD-L1 antibody with its cognate FcRn receptor more than an anti-PD-L1 antibody not containing the same amino acid deletions, additions or substitutions located in the CH2 domain and/or CH3 domain.

In aspects of this embodiment, a modified anti-PD-L1 antibody disclosed herein may comprise an IgG1 immunoglobulin heavy chain constant domain ($C_H$) of SEQ ID NO: 38, SEQ ID NO: 39 or SEQ ID NO: 40 which can comprise 1, 2, 3, 4 or 5 amino acid deletions, additions or substitutions located in the CH2 domain and/or CH3 domain that reduce interaction of the modified anti-PD-L1 antibody with its cognate FcRn receptor more than an anti-PD-L1 antibody not containing the same amino acid deletions, additions or substitutions located in the CH2 domain and/or CH3 domain. In other aspects of this embodiment, a modified anti-PD-L1 antibody disclosed herein may comprise an IgG1 immunoglobulin heavy chain constant domain ($C_H$) of SEQ ID NO: 38, SEQ ID NO: 39 or SEQ ID NO: 40 which can comprise an amino acid deletion, addition or substitution at position H315, H440, or both positions that reduce interaction of the modified anti-PD-L1 antibody with its cognate FcRn receptor more than an anti-PD-L1 antibody not containing the same H315 and H440 amino acid deletions, additions or substitutions. In other aspects of this embodiment, a modified anti-PD-L1 antibody disclosed herein may comprise an IgG1 immunoglobulin heavy chain constant domain ($C_H$) of SEQ ID NO: 38, SEQ ID NO: 39 or SEQ ID NO: 40 which can comprise an amino acid substitution of A, C, D, E, F, G, I, K, L, M, P. Q, R, S, T, V, or W at position H315, an amino acid substitution of A, C, D, E, F, G, I, K, L, M, P. Q, R, S, T, V, or W at position H440, or any combination thereof that reduce interaction of the modified anti-PD-L1 antibody with its cognate FcRn receptor more than an anti-PD-L1 antibody not containing the same H315 and H440 amino acid substitutions. In yet other aspects of this embodiment, a modified anti-PD-L1 antibody disclosed herein may comprise an IgG1 immunoglobulin heavy chain constant domain ($C_H$) of SEQ ID NO: 38, SEQ ID NO: 39 or SEQ ID NO: 40 which can comprise an amino acid substitution of C, D, E, K, Q, R, S, T, or W at position H315, an amino acid substitution of C, D, E, K, Q, R, S, T, or W at position H440, or any combination thereof that reduce interaction of the modified anti-PD-L1 antibody with its cognate FcRn receptor more than an anti-PD-L1 antibody not containing the same H315 and H440 amino acid substitutions. In yet other aspects of this embodiment, a modified anti-PD-L1 antibody disclosed herein comprises an IgG1 immunoglobulin heavy chain constant domain ($C_H$) of SEQ ID NO: 38, SEQ ID NO: 39 or SEQ ID NO: 40 which comprises an amino acid substitution of A at position H315 (H315A), an amino acid substitution of Q at position H440 (H440Q), or any combination thereof that reduce interaction of the modified anti-PD-L1 antibody with its cognate FcRn receptor more than an anti-PD-L1 antibody not containing the same H315 and H440 amino acid substitutions.

In other aspects of this embodiment, a modified anti-PD-L1 antibody disclosed herein may comprise an IgG1 immunoglobulin heavy chain constant domain ($C_H$) of SEQ ID NO: 38, SEQ ID NO: 39 or SEQ ID NO: 40 which comprises a H315A variant, a H440Q variant, or any combination thereof that reduce interaction of the modified anti-PD-L1 antibody with the FcRn receptor by, e.g., at least 10%, at least 20%, at least 30%, at least 40%, at least 50%, at least 60%, at least 70%, at least 80%, or at least 90% relative to an anti-PD-L1 antibody not comprising a H315A variant and a H440Q variant. In yet other aspects of this embodiment, a modified anti-PD-L1 antibody disclosed herein may comprise an IgG1 immunoglobulin heavy chain constant domain ($C_H$) of SEQ ID NO: 38, SEQ ID NO: 39 or SEQ ID NO: 40 which comprises a H315A variant, a H440Q variant, or any combination thereof that reduce interaction of the modified anti-PD-L1 antibody with the FcRn receptor by, e.g., at most 10%, at most 20%, at most 30%, at most 40%, at most 50%, at most 60%, at most 70%, at most 80%, or at most 90% relative to an anti-PD-L1 antibody not comprising a H315A variant and a H440Q variant. In still other aspects of this embodiment, a modified anti-PD-L1 antibody disclosed herein may comprise an IgG1 immunoglobulin heavy chain constant domain ($C_H$) of SEQ ID NO: 38, SEQ ID NO: 39 or SEQ ID NO: 40 which comprises a H315A variant, a H440Q variant, or any combination thereof that reduce interaction of the modified anti-PD-L1 antibody with the FcRn receptor by, e.g., about 10% to about 20%, about 10% to about 30%, about 10% to about 40%, about 10% to about 50%, about 10% to about 60%, about 10% to about 70%, about 10% to about 80%, about 10% to about 90%, about 20% to about 30%, about 20% to about 40%, about 20% to about 50%, about 20% to about 60%, about 20% to about 70%, about 20% to about 80%, about 20% to about 90%, about 30% to about 40%, about 30% to about 50%, about 30% to about 60%, about 30% to about 70%, about 30% to about 80%, about 30% to about 90%, about 40% to about 50%, about 40% to about 60%, about 40% to about 70%, about 40% to about 80%, about 40% to about 90%, about 50% to about 60%, about 50% to about 70%, about 50% to about 80%, about 50% to about 90%, about 60% to about 70%, about 60% to about 80%, about 60% to about 90%, about 70% to about 80%, about 70% to about 90%, or about 80% to about 90%, relative to an anti-PD-L1 antibody not comprising a H315A variant and a H440Q variant.

In other aspects of this embodiment, a modified anti-PD-L1 antibody disclosed herein may comprise an IgG1 immunoglobulin heavy chain constant domain ($C_H$) of SEQ ID NO: 38, SEQ ID NO: 39 or SEQ ID NO: 40 which comprises a H315A variant, a H440Q variant, or any combination thereof that reduce interaction of the modified anti-PD-L1 antibody with the FcRn receptor by, e.g., at least 100%, at least 125%, at least 150%, at least 175%, at least 200%, at least 250%, at least 300%, at least 350%, at least 400%, at least 450%, at least 500% relative to an anti-PD-L1 antibody not comprising a H315A variant and a H440Q variant. In yet other aspects of this embodiment, a modified anti-PD-L1 antibody disclosed herein may comprise an IgG1 immunoglobulin heavy chain constant domain ($C_H$) of SEQ ID NO: 38, SEQ ID NO: 39 or SEQ ID NO: 40 which comprises a H315A variant, a H440Q variant, or any combination thereof that reduce interaction of the modified anti-PD-L1 antibody with the FcRn receptor by, e.g., at most 100%, at most 125%, at most 150%, at most 175%, at most 200%, at most 250%, at most 300%, at most 350%, at most 400%, at most 450%, at most 500% relative to an anti-PD-L1 antibody not comprising a H315A variant and a H440Q variant. In still other aspects of this embodiment, a modified anti-PD-L1 antibody disclosed herein may comprise an IgG1 immunoglobulin heavy chain constant domain ($C_H$) of SEQ ID NO: 38, SEQ ID NO: 39 or SEQ ID NO: 40 which comprises a H315A variant, a H440Q variant, or any combination thereof that reduce interaction of the modified anti-PD-L1 antibody with the FcRn receptor by, e.g., about 100% to about 150%, about 100% to about 200%, about 100% to about 250%, about 100% to about 300%, about 100% to about 350%, about 100% to about 400%, about 100% to about 450%, about 100% to about 500%, about 150% to about 200%, about 150% to about 250%, about 150% to about 300%, about 150% to about 350%, about 150% to about 400%, about 150% to about 450%, about 150% to about 500%, about 200% to about 250%, about 200% to about 300%, about 200% to about 350%, about 200% to about 400%, about 200% to about 450%, about 200% to about 500%, about 250% to about 300%, about 250% to about 350%, about 250% to about 400%, about 250% to about 450%, or about 250% to about 500%, relative to an anti-PD-L1 antibody not comprising a H315A variant and a H440Q variant.

In aspects of this embodiment, a modified anti-PD-L1 antibody disclosed herein may comprise an IgG2 immunoglobulin heavy chain constant domain ($C_H$) containing amino acid sequence variants in the CH2 domain and/or CH3 domain that reduce interaction of the modified anti-PD-L1 antibody with its cognate FcRn receptor more than an anti-PD-L1 antibody not containing the same amino acid variants located in the CH2 domain and/or CH3 domain. In other aspects of this embodiment, a modified anti-PD-L1 antibody disclosed herein may comprise an IgG2 immunoglobulin heavy chain constant domain ($C_H$) that can comprise 1, 2, 3, 4 or 5 amino acid deletions, additions or substitutions located in the CH2 domain and/or CH3 domain that reduce interaction of the modified anti-PD-L1 antibody with its cognate FcRn receptor more than an anti-PD-L1 antibody not containing the same amino acid deletions, additions or substitutions located in the CH2 domain and/or CH3 domain.

In aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise 1, 2, 3, 4 or 5 amino acid deletions, additions or substitutions located in the CH2 domain and/or CH3 domain that reduce interaction of the modified anti-PD-L1 antibody with its cognate FcRn receptor more than an anti-PD-L1 antibody not containing the same amino acid deletions, additions or substitutions located in the CH2 domain and/or CH3 domain. In other aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise an amino acid deletion, addition or substitution at position H311, H436, or both positions that reduce interaction of the modified anti-PD-L1 antibody with its cognate FcRn receptor more than an anti-PD-L1 antibody not containing the same H311 and H436 amino acid deletions, additions or substitutions. In other aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise an amino acid substitution of A, C, D, E, F, G, I, K, L, M, P. Q, R, S, T, V, or W at position H311, an amino acid substitution of A, C, D, E, F, G, I, K, L, M, P. Q, R, S, T, V, or W at position H436, or any combination thereof that reduce interaction of the modified anti-PD-L1 antibody with its cognate FcRn receptor more than an anti-PD-L1 antibody not containing the same H311 and H436 amino acid substitutions. In yet other aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise an amino acid substitution of C, D, E, K, Q, R, S, T, or W at position H311, an amino acid substitution of C, D, E, K, Q, R, S, T, or W at position H436, or any combination thereof that reduce interaction of the modified anti-PD-L1 antibody with its cognate FcRn receptor more than an anti-PD-L1 antibody not containing the same H311 and H436 amino acid substitutions. In yet other aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise an amino acid substitution of A at position H311 (H311A), an amino acid substitution of Q at position H436 (H436Q), or any combination thereof that reduce interaction of the modified anti-PD-L1 antibody with its cognate FcRn receptor more than an anti-PD-L1 antibody not containing the same H311 and H436 amino acid substitutions.

In other aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise a H311A variant, a H436Q variant, or any combination thereof that reduce interaction of the modified anti-PD-L1 antibody with the FcRn receptor by, e.g., at least 10%, at least 20%, at least 30%, at least 40%, at least 50%, at least 60%, at least 70%, at least 80%, or at least 90% relative to an anti-PD-L1 antibody not comprising a H311A variant and a H436Q variant. In yet other aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise a H311A variant, a H436Q variant, or any combination thereof that reduce interaction of the modified anti-PD-L1 antibody with the FcRn receptor by, e.g., at most 10%, at most 20%, at most 30%, at most 40%, at most 50%, at most 60%, at most 70%, at most 80%, or at most 90% relative to an anti-PD-L1 antibody not comprising a H311A variant and a H436Q variant. In still other aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise a H311A variant, a H436Q variant, or any combination thereof that reduce interaction of the modified anti-PD-L1 antibody with the FcRn receptor by, e.g., about 10% to about 20%, about 10% to about 30%, about 10% to about 40%, about 10% to about 50%, about 10% to about 60%, about 10% to about 70%, about 10% to about 80%, about 10% to about 90%, about 20% to about 30%, about 20% to about 40%, about 20% to about 50%, about 20% to about 60%, about 20% to about 70%, about 20% to about 80%, about 20% to about 90%, about 30% to about 40%, about 30% to about 50%, about 30% to about 60%, about 30% to about 70%, about 30% to about 80%, about 30% to about 90%, about 40% to about 50%, about 40% to about 60%, about 40% to about 70%, about 40% to about 80%, about 40% to about 90%, about 50% to about 60%, about 50% to about 70%, about 50% to about 80%, about 50% to about 90%, about 60% to about 70%, about 60% to about 80%, about 60% to about 90%, about 70% to about 80%, about 70% to about 90%, or about 80% to about 90%, relative to an anti-PD-L1 antibody not comprising a H311A variant and a H436Q variant.

In other aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise a H311A variant, a H436Q variant, or any combination thereof that reduce interaction of the modified anti-PD-L1 antibody with the FcRn receptor by, e.g., at least 100%, at least 125%, at least 150%, at least 175%, at least 200%, at least 250%, at least 300%, at least 350%, at least 400%, at least 450%, at least 500 relative to an anti-PD-L1 antibody not comprising a H311A variant and a H436Q variant. In yet other aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise a H311A variant, a H436Q variant, or any combination thereof that reduce interaction of the modified anti-PD-L1 antibody with the FcRn receptor by, e.g., at most 100%, at most 125%, at most 150%, at most 175%, at most 200%, at most 250%, at most 300%, at most 350%, at most 400%, at most 450%, at most 500% relative to an anti-PD-L1 antibody not comprising a H311A variant and a H436Q variant. In still other aspects of this embodiment, a modified anti-PD-L1 antibody disclosed herein may comprise an IgG2 immunoglobulin heavy chain constant domain ($C_H$) of SEQ ID NO: 45, SEQ ID NO: 46, SEQ ID NO: 47 or SEQ ID NO: 48 which can comprise a H311A variant, a H436Q variant, or any combination thereof that reduce interaction of the modified anti-PD-L1 antibody with the FcRn receptor by, e.g., about 100% to about 150%, about 100% to about 200%, about 100% to about 250%, about 100% to about 300%, about 100% to about 350%, about 100% to about 400%, about 100% to about 450%, about 100% to about 500%, about 150% to about 200%, about 150% to about 250%, about 150% to about 300%, about 150% to about 350%, about 150% to about 400%, about 150% to about 450%, about 150% to about 500%, about 200% to about 250%, about 200% to about 300%, about 200% to about 350%, about 200% to about 400%, about 200% to about 450%, about 200% to about 500%, about 250% to about 300%, about 250% to about 350%, about 250% to about 400%, about 250% to about 450%, or about 250% to about 500%, relative to an anti-PD-L1 antibody not comprising a H311A variant and a H436Q variant.

In aspects of this embodiment, a modified anti-PD-L1 antibody disclosed herein may comprise an IgG4 immunoglobulin heavy chain constant domain ($C_H$) containing amino acid sequence variants in the CH2 domain and/or CH3 domain that reduce interaction of the modified anti-PD-L1 antibody with its cognate FcRn receptor more than an anti-PD-L1 antibody not containing the same amino acid variants located in the CH2 domain and/or CH3 domain. In other aspects of this embodiment, a modified anti-PD-L1 antibody disclosed herein may comprise an IgG4 immunoglobulin heavy chain constant domain ($C_H$) can comprise 1, 2, 3, 4 or 5 amino acid deletions, additions or substitutions located in the CH2 domain and/or CH3 domain that reduce interaction of the modified anti-PD-L1 antibody with its cognate FcRn receptor more than an anti-PD-L1 antibody not containing the same amino acid deletions, additions or substitutions located in the CH2 domain and/or CH3 domain.

In aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise 1, 2, 3, 4 or 5 amino acid deletions, additions or substitutions located in the CH2 domain and/or CH3 domain that reduce interaction of the modified anti-PD-L1 antibody with its cognate FcRn receptor more than an anti-PD-L1 antibody not containing the same amino acid deletions, additions or substitutions located in the CH2 domain and/or CH3 domain. In other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise an amino acid deletion, addition or substitution at position H312, H437, or both positions that reduce interaction of the modified anti-PD-L1 antibody with its cognate FcRn receptor more than an anti-PD-L1 antibody not containing the same H312 and H437 amino acid deletions, additions or substitutions. In other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise an amino acid substitution of A, C, D, E, F, G, I, K, L, M, P. Q, R, S, T, V, or W at position H312, an amino acid substitution of A, C, D, E, F, G, I, K, L, M, P. Q, R, S, T, V, or W at position H437, or any combination thereof that reduce interaction of the modified anti-PD-L1 antibody with its cognate FcRn receptor more than an anti-PD-L1 antibody not containing the same H312 and H437 amino acid substitutions. In yet other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise an amino acid substitution of C, D, E, K, Q, R, S, T, or W at position H312, an amino acid substitution of C, D, E, K, Q, R, S, T, or W at position H437, or any combination thereof that reduce interaction of the modified anti-PD-L1 antibody with its cognate FcRn receptor more than an anti-PD-L1 antibody not containing the same H312 and H437 amino acid substitutions. In yet other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise an amino acid substitution of A at position H312 (H312A), an amino acid substitution of Q at position H437 (H437Q), or any combination thereof that reduce interaction of the modified anti-PD-L1 antibody with its cognate FcRn receptor more than an anti-PD-L1 antibody not containing the same H312 and H437 amino acid substitutions.

In other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise a H312A variant, a H437Q variant, or any combination thereof that reduce interaction of the modified anti-PD-L1 antibody with the FcRn receptor by, e.g., at least 10%, at least 20%, at least 30%, at least 40%, at least 50%, at least 60%, at least 70%, at least 80%, or at least 90% relative to an anti-PD-L1 antibody not comprising a H312A variant and a H437Q variant. In yet other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise a H312A variant, a H437Q variant, or any combination thereof that reduce interaction of the modified anti-PD-L1 antibody with the FcRn receptor by, e.g., at most 10%, at most 20%, at most 30%, at most 40%, at most 50%, at most 60%, at most 70%, at most 80%, or at most 90% relative to an anti-PD-L1 antibody not comprising a H312A variant and a H437Q variant. In still other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise a H312A variant, a H437Q variant, or any combination thereof that reduce interaction of the modified anti-PD-L1 antibody with the FcRn receptor by, e.g., about 10% to about 20%, about 10% to about 30%, about 10% to about 40%, about 10% to about 50%, about 10% to about 60%, about 10% to about 70%, about 10% to about 80%, about 10% to about 90%, about 20% to about 30%, about 20% to about 40%, about 20% to about 50%, about 20% to about 60%, about 20% to about 70%, about 20% to about 80%, about 20% to about 90%, about 30% to about 40%, about 30% to about 50%, about 30% to about 60%, about 30% to about 70%, about 30% to about 80%, about 30% to about 90%, about 40% to about 50%, about 40% to about 60%, about 40% to about 70%, about 40% to about 80%, about 40% to about 90%, about 50% to about 60%, about 50% to about 70%, about 50% to about 80%, about 50% to about 90%, about 60% to about 70%, about 60% to about 80%, about 60% to about 90%, about 70% to about 80%, about 70% to about 90%, or about 80% to about 90%, relative to an anti-PD-L1 antibody not comprising a H312A variant and a H437Q variant.

In other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise a H312A variant, a H437Q variant, or any combination thereof that reduce interaction of the modified anti-PD-L1 antibody with the FcRn receptor by, e.g., at least 100%, at least 125%, at least 150%, at least 175%, at least 200%, at least 250%, at least 300%, at least 350%, at least 400%, at least 450%, at least 500% relative to an anti-PD-L1 antibody not comprising a H312A variant and a H437Q variant. In yet other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise a H312A variant, a H437Q variant, or any combination thereof that reduce interaction of the modified anti-PD-L1 antibody with the FcRn receptor by, e.g., at most 100%, at most 125%, at most 150%, at most 175%, at most 200%, at most 250%, at most 300%, at most 350%, at most 400%, at most 450%, at most 500% relative to an anti-PD-L1 antibody not comprising a H312A variant and a H437Q variant. In still other aspects of this embodiment, a modified anti-PD-L1 antibody disclosed herein may comprise an IgG4 immunoglobulin heavy chain constant domain ($C_H$) of SEQ ID NO: 49, SEQ ID NO: 50, SEQ ID NO: 51, SEQ ID NO: 52 or SEQ ID NO: 53 which can comprise a H312A variant, a H437Q variant, or any combination thereof that reduce interaction of the modified anti-PD-L1 antibody with the FcRn receptor by, e.g., about 100% to about 150%, about 100% to about 200%, about 100% to about 250%, about 100% to about 300%, about 100% to about 350%, about 100% to about 400%, about 100% to about 450%, about 100% to about 500%, about 150% to about 200%, about 150% to about 250%, about 150% to about 300%, about 150% to about 350%, about 150% to about 400%, about 150% to about 450%, about 150% to about 500%, about 200% to about 250%, about 200% to about 300%, about 200% to about 350%, about 200% to about 400%, about 200% to about 450%, about 200% to about 500%, about 250% to about 300%, about 250% to about 350%, about 250% to about 400%, about 250% to about 450%, or about 250% to about 500%, relative to an anti-PD-L1 antibody not comprising a H312A variant and a H437Q variant.

In aspects of this embodiment, a modified anti-PD-L1 antibody disclosed herein has a half-life of, e.g., about 1 day, about 2 days, about 3 days, about 4 days, about 5 days, about 6 days, or about 7 days. In other aspects of this embodiment, an anti-PD-L1 antibody disclosed herein has a half-life of, e.g., at least 1 day, at least 2 days, at least 3 days, at least 4 days, at least 5 days, at least 6 days, or at least 7 days. In yet other aspects of this embodiment, a modified anti-PD-L1 antibody disclosed herein has a half-life of, e.g., at most 1 day, at most 2 days, at most 3 days, at most 4 days, at most 5 days, at most 6 days, or at most 7 days. In still other aspects of this embodiment, an anti-PD-L1 antibody disclosed herein has a half-life of, e.g., about 1 day to about 2 days, about 1 day to about 3 days, about 1 day to about 4 days, about 1 day to about 5 days, about 1 day to about 6 days, about 1 day to about 7 days, about 2 days to about 3 days, about 2 days to about 4 days, about 2 days to about 5 days, about 2 days to about 6 days, about 2 days to about 7 days, about 3 days to about 4 days, about 3 days to about 5 days, about 3 days to about 6 days, about 3 days to about 7 days, about 4 days to about 5 days, about 4 days to about 6 days, about 4 days to about 7 days, about 5 days to about 6 days, about 5 days to about 7 days, or about 6 days to about 7 days.

In an embodiment, a modified anti-PD-L1 antibody disclosed herein comprises an IgG1 immunoglobulin heavy chain of SEQ ID NO: 41, SEQ ID NO: 42, SEQ ID NO: 43, or SEQ ID NO: 44 and a light chain of SEQ ID NO: 21, SEQ ID NO: 22, SEQ ID NO: 23, SEQ ID NO: 24, SEQ ID NO: 25, SEQ ID NO: 32, SEQ ID NO: 33, SEQ ID NO: 34, SEQ ID NO: 35, SEQ ID NO: 36, or SEQ ID NO: 37. In aspects of this embodiment, a modified anti-PD-L1 antibody disclosed herein comprises an IgG1 immunoglobulin heavy chain of SEQ ID NO: 41, SEQ ID NO: 42, SEQ ID NO: 43, or SEQ ID NO: 44 and a kappa light chain of SEQ ID NO: 21, SEQ ID NO: 22, SEQ ID NO: 23, SEQ ID NO: 24, or SEQ ID NO: 25. In an aspect of this embodiment, a modified anti-PD-L1 antibody disclosed herein comprises an IgG1 immunoglobulin heavy chain of SEQ ID NO: 44 and a kappa light chain of SEQ ID NO: 21. In other aspects of this embodiment, a modified anti-PD-L1 antibody disclosed herein comprises an IgG1 immunoglobulin heavy chain of SEQ ID NO: 41, SEQ ID NO: 42, SEQ ID NO: 43, or SEQ ID NO: 44 and a lambda light chain of SEQ ID NO: 32, SEQ ID NO: 33, SEQ ID NO: 34, SEQ ID NO: 35, SEQ ID NO: 36, or SEQ ID NO: 37.

In an embodiment, a modified anti-PD-L1 antibody disclosed herein comprises an IgG1 immunoglobulin heavy chain of SEQ ID NO: 41, SEQ ID NO: 42, SEQ ID NO: 43, or SEQ ID NO: 44 and a light chain comprising a light chain variable region of SEQ ID NO: 9. In aspects of this embodiment, a modified anti-PD-L1 antibody disclosed herein comprises an IgG1 immunoglobulin heavy chain of SEQ ID NO: 41, SEQ ID NO: 42, SEQ ID NO: 43, or SEQ ID NO: 44 and a light chain comprising a light chain variable region of SEQ ID NO: 9 and a light chain constant region of SEQ ID NO: 16, SEQ ID NO: 17, SEQ ID NO: 18, SEQ ID NO: 19, SEQ ID NO: 20, SEQ ID NO: 26, SEQ ID NO: 27, SEQ ID NO: 28, SEQ ID NO: 29, SEQ ID NO: 30, or SEQ ID NO: 31. In other aspects of this embodiment, a modified anti-PD-L1 antibody disclosed herein comprises an IgG1 immunoglobulin heavy chain of SEQ ID NO: 41, SEQ ID NO: 42, SEQ ID NO: 43, or SEQ ID NO: 44 and a light chain comprising a light chain variable region of SEQ ID NO: 9 and a kappa light chain constant region of SEQ ID NO: 16, SEQ ID NO: 17, SEQ ID NO: 18, SEQ ID NO: 19, or SEQ ID NO: 20. In yet other aspects of this embodiment, a modified anti-PD-L1 antibody disclosed herein comprises an IgG1 immunoglobulin heavy chain of SEQ ID NO: 41, SEQ ID NO: 42, SEQ ID NO: 43, or SEQ ID NO: 44 and a light chain comprising a light chain variable region of SEQ ID NO: 9 and a lambda light chain constant region of SEQ ID NO: 26, SEQ ID NO: 27, SEQ ID NO: 28, SEQ ID NO: 29, SEQ ID NO: 30, or SEQ ID NO: 31.

In an embodiment, a modified anti-PD-L1 antibody disclosed herein comprises an IgG1 immunoglobulin heavy chain of SEQ ID NO: 44 and a light chain comprising a light chain variable region of SEQ ID NO: 9. In aspects of this embodiment, a modified anti-PD-L1 antibody disclosed herein comprises an IgG1 immunoglobulin heavy chain of SEQ ID NO: 44 and a light chain comprising a light chain variable region of SEQ ID NO: 9 and a light chain constant region of SEQ ID NO: 16, SEQ ID NO: 17, SEQ ID NO: 18, SEQ ID NO: 19, SEQ ID NO: 20, SEQ ID NO: 26, SEQ ID NO: 27, SEQ ID NO: 28, SEQ ID NO: 29, SEQ ID NO: 30, or SEQ ID NO: 31. In other aspects of this embodiment, a modified anti-PD-L1 antibody disclosed herein comprises an IgG1 immunoglobulin heavy chain of SEQ ID NO: 44 and a light chain comprising a light chain variable region of SEQ ID NO: 9 and a kappa light chain constant region of SEQ ID NO: 16, SEQ ID NO: 17, SEQ ID NO: 18, SEQ ID NO: 19, or SEQ ID NO: 20. In yet other aspects of this embodiment, a modified anti-PD-L1 antibody disclosed herein comprises an IgG1 immunoglobulin heavy chain of SEQ ID NO: 44 and a light chain comprising a light chain variable region of SEQ ID NO: 9 and a kappa light chain constant region of SEQ ID NO: 16. In still other aspects of this embodiment, a modified anti-PD-L1 antibody disclosed herein comprises an IgG1 immunoglobulin heavy chain of SEQ ID NO: 44 and a light chain comprising a light chain variable region of SEQ ID NO: 9 and a lambda light chain constant region of SEQ ID NO: 26, SEQ ID NO: 27, SEQ ID NO: 28, SEQ ID NO: 29, SEQ ID NO: 30, or SEQ ID NO: 31.

In an embodiment, a modified anti-PD-L1 antibody disclosed herein comprises an IgG1 immunoglobulin heavy chain of SEQ ID NO: 41, SEQ ID NO: 42, SEQ ID NO: 43, or SEQ ID NO: 44 and a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15. In aspects of this embodiment, a modified anti-PD-L1 antibody disclosed herein comprises an IgG1 immunoglobulin heavy chain of SEQ ID NO: 41, SEQ ID NO: 42, SEQ ID NO: 43, or SEQ ID NO: 44 and a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15 and a light chain constant region of SEQ ID NO: 16, SEQ ID NO: 17, SEQ ID NO: 18, SEQ ID NO: 19, SEQ ID NO: 20, SEQ ID NO: 26, SEQ ID NO: 27, SEQ ID NO: 28, SEQ ID NO: 29, SEQ ID NO: 30, or SEQ ID NO: 31. In aspects of this embodiment, a modified anti-PD-L1 antibody disclosed herein comprises an IgG1 immunoglobulin heavy chain of SEQ ID NO: 41, SEQ ID NO: 42, SEQ ID NO: 43, or SEQ ID NO: 44 and a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15 and a kappa light chain constant region of SEQ ID NO: 16, SEQ ID NO: 17, SEQ ID NO: 18, SEQ ID NO: 19, or SEQ ID NO: 20. In an aspect of this embodiment, a modified anti-PD-L1 antibody disclosed herein comprises an IgG1 immunoglobulin heavy chain of SEQ ID NO: 41, SEQ ID NO: 42, SEQ ID NO: 43, or SEQ ID NO: 44 and a light chain comprising a light chain variable region including CDR1 of SEQ ID NO: 10 or SEQ ID NO: 11, a CDR2 of SEQ ID NO: 12 or SEQ ID NO: 13 or a CDR3 of SEQ ID NO: 14 or SEQ ID NO 15 and a kappa light chain constant region of SEQ ID NO: 16. In aspects of this embodiment, a modified anti-PD-L1 antibody disclosed herein comprises an IgG1 immunoglobulin heavy chain of SEQ ID NO: 41, SEQ ID NO: 42, SEQ ID NO: 43, or SEQ ID NO: 44 and a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15 and a lambda light chain constant region of SEQ ID NO: 26, SEQ ID NO: 27, SEQ ID NO: 28, SEQ ID NO: 29, SEQ ID NO: 30, or SEQ ID NO: 31.

In an embodiment, a modified anti-PD-L1 antibody disclosed herein comprises an IgG1 immunoglobulin heavy chain of SEQ ID NO: 44 and a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15. In aspects of this embodiment, a modified anti-PD-L1 antibody disclosed herein comprises an IgG1 immunoglobulin heavy chain of SEQ ID NO: 44 and a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15 and a light chain constant region of SEQ ID NO: 16, SEQ ID NO: 17, SEQ ID NO: 18, SEQ ID NO: 19, SEQ ID NO: 20, SEQ ID NO: 26, SEQ ID NO: 27, SEQ ID NO: 28, SEQ ID NO: 29, SEQ ID NO: 30, or SEQ ID NO: 31. In aspects of this embodiment, a modified anti-PD-L1 antibody disclosed herein comprises an IgG1 immunoglobulin heavy chain of SEQ ID NO: 44 and a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15 and a kappa light chain constant region of SEQ ID NO: 16, SEQ ID NO: 17, SEQ ID NO: 18, SEQ ID NO: 19, or SEQ ID NO: 20. In an aspect of this embodiment, a modified anti-PD-L1 antibody disclosed herein comprises an IgG1 immunoglobulin heavy chain of SEQ ID NO: 44 and a light chain comprising a light chain variable region including CDR1 of SEQ ID NO: 10 or SEQ ID NO: 11, a CDR2 of SEQ ID NO: 12 or SEQ ID NO: 13 or a CDR3 of SEQ ID NO: 14 or SEQ ID NO 15 and a kappa light chain constant region of SEQ ID NO: 16. In aspects of this embodiment, a modified anti-PD-L1 antibody disclosed herein comprises an IgG1 immunoglobulin heavy chain of SEQ ID NO: 44 and a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15 and a lambda light chain constant region of SEQ ID NO: 26, SEQ ID NO: 27, SEQ ID NO: 28, SEQ ID NO: 29, SEQ ID NO: 30, or SEQ ID NO: 31.

In an embodiment, a modified anti-PD-L1 antibody disclosed herein comprises an IgG1 immunoglobulin heavy chain comprising a heavy chain variable region of SEQ ID NO: 2, a heavy chain constant region of SEQ ID NO: 54, SEQ ID NO: 55, SEQ ID NO: 56, or SEQ ID NO: 57 and a light chain of SEQ ID NO: 21, SEQ ID NO: 22, SEQ ID NO: 23, SEQ ID NO: 24, SEQ ID NO: 25, SEQ ID NO: 32, SEQ ID NO: 33, SEQ ID NO: 34, SEQ ID NO: 35, SEQ ID NO: 36, or SEQ ID NO: 37. In aspects of this embodiment, a modified anti-PD-L1 antibody disclosed herein comprises an IgG1 immunoglobulin heavy chain comprising a heavy chain variable region of SEQ ID NO: 2, a heavy chain constant region of SEQ ID NO: 54, SEQ ID NO: 55, SEQ ID NO: 56, or SEQ ID NO: 57 and a kappa light chain of SEQ ID NO: 21, SEQ ID NO: 22, SEQ ID NO: 23, SEQ ID NO: 24, or SEQ ID NO: 25. In an aspect of this embodiment, a modified anti-PD-L1 antibody disclosed herein comprises an IgG1 immunoglobulin heavy chain comprising a heavy chain variable region of SEQ ID NO: 2, a heavy chain constant region of SEQ ID NO: 57 and a kappa light chain of SEQ ID NO: 21. In other aspects of this embodiment, a modified anti-PD-L1 antibody disclosed herein comprises an IgG1 immunoglobulin heavy chain comprising a heavy chain variable region of SEQ ID NO: 2, a heavy chain constant region of SEQ ID NO: 54, SEQ ID NO: 55, SEQ ID NO: 56, or SEQ ID NO: 57 and a lambda light chain of SEQ ID NO: 32, SEQ ID NO: 33, SEQ ID NO: 34, SEQ ID NO: 35, SEQ ID NO: 36, or SEQ ID NO: 37.

In an embodiment, a modified anti-PD-L1 antibody disclosed herein comprises an IgG1 immunoglobulin heavy chain comprising a heavy chain variable region of SEQ ID NO: 2, a heavy chain constant region of SEQ ID NO: 54, SEQ ID NO: 55, SEQ ID NO: 56, or SEQ ID NO: 57 and a light chain comprising a light chain variable region of SEQ ID NO: 9. In aspects of this embodiment, a modified anti-PD-L1 antibody disclosed herein comprises an IgG1 immunoglobulin heavy chain comprising a heavy chain variable region of SEQ ID NO: 2, a heavy chain constant region of SEQ ID NO: 54, SEQ ID NO: 55, SEQ ID NO: 56, or SEQ ID NO: 57, a light chain comprising a light chain variable region of SEQ ID NO: 9 and a light chain constant region of SEQ ID NO: 16, SEQ ID NO: 17, SEQ ID NO: 18, SEQ ID NO: 19, SEQ ID NO: 20, SEQ ID NO: 26, SEQ ID NO: 27, SEQ ID NO: 28, SEQ ID NO: 29, SEQ ID NO: 30, or SEQ ID NO: 31. In other aspects of this embodiment, a modified anti-PD-L1 antibody disclosed herein comprises an IgG1 immunoglobulin heavy chain comprising a heavy chain variable region of SEQ ID NO: 2, a heavy chain constant region of SEQ ID NO: 54, SEQ ID NO: 55, SEQ ID NO: 56, or SEQ ID NO: 57, a light chain comprising a light chain variable region of SEQ ID NO: 9 and a kappa light chain constant region of SEQ ID NO: 16, SEQ ID NO: 17, SEQ ID NO: 18, SEQ ID NO: 19, or SEQ ID NO: 20. In yet other aspects of this embodiment, a modified anti-PD-L1 antibody disclosed herein comprises an IgG1 immunoglobulin heavy chain comprising a heavy chain variable region of SEQ ID NO: 2, a heavy chain constant region of SEQ ID NO: 54, SEQ ID NO: 55, SEQ ID NO: 56, or SEQ ID NO: 57, a light chain comprising a light chain variable region of SEQ ID NO: 9 and a lambda light chain constant region of SEQ ID NO: 26, SEQ ID NO: 27, SEQ ID NO: 28, SEQ ID NO: 29, SEQ ID NO: 30, or SEQ ID NO: 31.

In an embodiment, a modified anti-PD-L1 antibody disclosed herein comprises an IgG1 immunoglobulin heavy chain comprising a heavy chain variable region of SEQ ID NO: 2, a heavy chain constant region of SEQ ID NO: 57, and a light chain comprising a light chain variable region of SEQ ID NO: 9. In aspects of this embodiment, a modified anti-PD-L1 antibody disclosed herein comprises an IgG1 immunoglobulin heavy chain comprising a heavy chain variable region of SEQ ID NO: 2, a heavy chain constant region of SEQ ID NO: 57, a light chain comprising a light chain variable region of SEQ ID NO: 9 and a light chain constant region of SEQ ID NO: 16, SEQ ID NO: 17, SEQ ID NO: 18, SEQ ID NO: 19, SEQ ID NO: 20, SEQ ID NO: 26, SEQ ID NO: 27, SEQ ID NO: 28, SEQ ID NO: 29, SEQ ID NO: 30, or SEQ ID NO: 31. In other aspects of this embodiment, a modified anti-PD-L1 antibody disclosed herein comprises an IgG1 immunoglobulin heavy chain comprising a heavy chain variable region of SEQ ID NO: 2, a heavy chain constant region of SEQ ID NO: 57, a light chain comprising a light chain variable region of SEQ ID NO: 9 and a kappa light chain constant region of SEQ ID NO: 16, SEQ ID NO: 17, SEQ ID NO: 18, SEQ ID NO: 19, or SEQ ID NO: 20. In yet other aspects of this embodiment, a modified anti-PD-L1 antibody disclosed herein comprises an IgG1 immunoglobulin heavy chain comprising a heavy chain variable region of SEQ ID NO: 2, a heavy chain constant region of SEQ ID NO: 57, a light chain comprising a light chain variable region of SEQ ID NO: 9 and a lambda light chain constant region of SEQ ID NO: 26, SEQ ID NO: 27, SEQ ID NO: 28, SEQ ID NO: 29, SEQ ID NO: 30, or SEQ ID NO: 31.

In an embodiment, a modified anti-PD-L1 antibody disclosed herein comprises an IgG1 immunoglobulin heavy chain comprising a heavy chain variable region of SEQ ID NO: 2, a heavy chain constant region of SEQ ID NO: 54, SEQ ID NO: 55, SEQ ID NO: 56, or SEQ ID NO: 57, and a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15. In aspects of this embodiment, a modified anti-PD-L1 antibody disclosed herein comprises an IgG1 immunoglobulin heavy chain comprising a heavy chain variable region of SEQ ID NO: 2, a heavy chain constant region of SEQ ID NO: 54, SEQ ID NO: 55, SEQ ID NO: 56, or SEQ ID NO: 57, a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15 and a light chain constant region of SEQ ID NO: 16, SEQ ID NO: 17, SEQ ID NO: 18, SEQ ID NO: 19, SEQ ID NO: 20, SEQ ID NO: 26, SEQ ID NO: 27, SEQ ID NO: 28, SEQ ID NO: 29, SEQ ID NO: 30, or SEQ ID NO: 31. In aspects of this embodiment, a modified anti-PD-L1 antibody disclosed herein comprises an IgG1 immunoglobulin heavy chain comprising a heavy chain variable region of SEQ ID NO: 2, a heavy chain constant region of SEQ ID NO: 54, SEQ ID NO: 55, SEQ ID NO: 56, or SEQ ID NO: 57, a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15 and a kappa light chain constant region of SEQ ID NO: 16, SEQ ID NO: 17, SEQ ID NO: 18, SEQ ID NO: 19, or SEQ ID NO: 20. In an aspect of this embodiment, a modified anti-PD-L1 antibody disclosed herein comprises an IgG1 immunoglobulin heavy chain comprising a heavy chain variable region of SEQ ID NO: 2, a heavy chain constant region of SEQ ID NO: 54, SEQ ID NO: 55, SEQ ID NO: 56, or SEQ ID NO: 57, a light chain comprising a light chain variable region including CDR1 of SEQ ID NO: 10 or SEQ ID NO: 11, a CDR2 of SEQ ID NO: 12 or SEQ ID NO: 13 or a CDR3 of SEQ ID NO: 14 or SEQ ID NO 15 and a kappa light chain constant region of SEQ ID NO: 16. In aspects of this embodiment, a modified anti-PD-L1 antibody disclosed herein comprises an IgG1 immunoglobulin heavy chain comprising a heavy chain variable region of SEQ ID NO: 2, a heavy chain constant region of SEQ ID NO: 54, SEQ ID NO: 55, SEQ ID NO: 56, or SEQ ID NO: 57, a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15 and a lambda light chain constant region of SEQ ID NO: 26, SEQ ID NO: 27, SEQ ID NO: 28, SEQ ID NO: 29, SEQ ID NO: 30, or SEQ ID NO: 31.

In an embodiment, a modified anti-PD-L1 antibody disclosed herein comprises an IgG1 immunoglobulin heavy chain comprising a heavy chain variable region of SEQ ID NO: 2, a heavy chain constant region of SEQ ID NO: 57, and a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15. In aspects of this embodiment, a modified anti-PD-L1 antibody disclosed herein comprises an IgG1 immunoglobulin heavy chain comprising a heavy chain variable region of SEQ ID NO: 2, a heavy chain constant region of SEQ ID NO: 57, a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15 and a light chain constant region of SEQ ID NO: 16, SEQ ID NO: 17, SEQ ID NO: 18, SEQ ID NO: 19, SEQ ID NO: 20, SEQ ID NO: 26, SEQ ID NO: 27, SEQ ID NO: 28, SEQ ID NO: 29, SEQ ID NO: 30, or SEQ ID NO: 31. In aspects of this embodiment, a modified anti-PD-L1 antibody disclosed herein comprises an IgG1 immunoglobulin heavy chain comprising a heavy chain variable region of SEQ ID NO: 2, a heavy chain constant region of SEQ ID NO: 57, a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15 and a kappa light chain constant region of SEQ ID NO: 16, SEQ ID NO: 17, SEQ ID NO: 18, SEQ ID NO: 19, or SEQ ID NO: 20. In an aspect of this embodiment, a modified anti-PD-L1 antibody disclosed herein comprises an IgG1 immunoglobulin heavy chain comprising a heavy chain variable region of SEQ ID NO: 2, a heavy chain constant region of SEQ ID NO: 57, a light chain comprising a light chain variable region including CDR1 of SEQ ID NO: 10 or SEQ ID NO: 11, a CDR2 of SEQ ID NO: 12 or SEQ ID NO: 13 or a CDR3 of SEQ ID NO: 14 or SEQ ID NO 15 and a kappa light chain constant region of SEQ ID NO: 16. In aspects of this embodiment, a modified anti-PD-L1 antibody disclosed herein comprises an IgG1 immunoglobulin heavy chain comprising a heavy chain variable region of SEQ ID NO: 2, a heavy chain constant region of SEQ ID NO: 57, a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15 and a lambda light chain constant region of SEQ ID NO: 26, SEQ ID NO: 27, SEQ ID NO: 28, SEQ ID NO: 29, SEQ ID NO: 30, or SEQ ID NO: 31.

In an embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 54, SEQ ID NO: 55, SEQ ID NO: 56, or SEQ ID NO: 57 and a light chain of SEQ ID NO: 21, SEQ ID NO: 22, SEQ ID NO: 23, SEQ ID NO: 24, SEQ ID NO: 25, SEQ ID NO: 32, SEQ ID NO: 33, SEQ ID NO: 34, SEQ ID NO: 35, SEQ ID NO: 36, or SEQ ID NO: 37. In aspects of this embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 54, SEQ ID NO: 55, SEQ ID NO: 56, or SEQ ID NO: 57 and a kappa light chain of SEQ ID NO: 21, SEQ ID NO: 22, SEQ ID NO: 23, SEQ ID NO: 24, or SEQ ID NO: 25. In an aspect of this embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 or SEQ ID NO: 5 or SEQ ID NO: 6, and a CDR3 of SEQ ID NO: 7 or SEQ ID NO: 8, a heavy chain constant region of SEQ ID NO: 57 and a kappa light chain of SEQ ID NO: 21. In other aspects of this embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 54, SEQ ID NO: 55, SEQ ID NO: 56, or SEQ ID NO: 57 and a lambda light chain of SEQ ID NO: 32, SEQ ID NO: 33, SEQ ID NO: 34, SEQ ID NO: 35, SEQ ID NO: 36, or SEQ ID NO: 37.

In an embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 54, SEQ ID NO: 55, SEQ ID NO: 56, or SEQ ID NO: 57 and a light chain comprising a light chain variable region of SEQ ID NO: 9. In aspects of this embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 54, SEQ ID NO: 55, SEQ ID NO: 56, or SEQ ID NO: 57, a light chain comprising a light chain variable region of SEQ ID NO: 9 and a light chain constant region of SEQ ID NO: 16, SEQ ID NO: 17, SEQ ID NO: 18, SEQ ID NO: 19, SEQ ID NO: 20, SEQ ID NO: 26, SEQ ID NO: 27, SEQ ID NO: 28, SEQ ID NO: 29, SEQ ID NO: 30, or SEQ ID NO: 31. In other aspects of this embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 54, SEQ ID NO: 55, SEQ ID NO: 56, or SEQ ID NO: 57, a light chain comprising a light chain variable region of SEQ ID NO: 9 and a kappa light chain constant region of SEQ ID NO: 16, SEQ ID NO: 17, SEQ ID NO: 18, SEQ ID NO: 19, or SEQ ID NO: 20. In yet other aspects of this embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 54, SEQ ID NO: 55, SEQ ID NO: 56, or SEQ ID NO: 57, a light chain comprising a light chain variable region of SEQ ID NO: 9 and a lambda light chain constant region of SEQ ID NO: 26, SEQ ID NO: 27, SEQ ID NO: 28, SEQ ID NO: 29, SEQ ID NO: 30, or SEQ ID NO: 31.

In an embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 57, and a light chain comprising a light chain variable region of SEQ ID NO: 9. In aspects of this embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 57, a light chain comprising a light chain variable region of SEQ ID NO: 9 and a light chain constant region of SEQ ID NO: 16, SEQ ID NO: 17, SEQ ID NO: 18, SEQ ID NO: 19, SEQ ID NO: 20, SEQ ID NO: 26, SEQ ID NO: 27, SEQ ID NO: 28, SEQ ID NO: 29, SEQ ID NO: 30, or SEQ ID NO: 31. In other aspects of this embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 57, a light chain comprising a light chain variable region of SEQ ID NO: 9 and a kappa light chain constant region of SEQ ID NO: 16, SEQ ID NO: 17, SEQ ID NO: 18, SEQ ID NO: 19, or SEQ ID NO: 20. In yet other aspects of this embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 57, a light chain comprising a light chain variable region of SEQ ID NO: 9 and a lambda light chain constant region of SEQ ID NO: 26, SEQ ID NO: 27, SEQ ID NO: 28, SEQ ID NO: 29, SEQ ID NO: 30, or SEQ ID NO: 31.

In an embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 54, SEQ ID NO: 55, SEQ ID NO: 56, or SEQ ID NO: 57, and a light chain comprising a light chain variable region including CDR1 of SEQ ID NO: 10 or SEQ ID NO: 11, a CDR2 of SEQ ID NO: 12 or SEQ ID NO: 13 or a CDR3 of SEQ ID NO: 14 or SEQ ID NO 15. In aspects of this embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 54, SEQ ID NO: 55, SEQ ID NO: 56, or SEQ ID NO: 57, a light chain comprising a light chain variable region including CDR1 of SEQ ID NO: 10 or SEQ ID NO: 11, a CDR2 of SEQ ID NO: 12 or SEQ ID NO: 13 or a CDR3 of SEQ ID NO: 14 or SEQ ID NO 15 and a light chain constant region of SEQ ID NO: 16, SEQ ID NO: 17, SEQ ID NO: 18, SEQ ID NO: 19, SEQ ID NO: 20, SEQ ID NO: 26, SEQ ID NO: 27, SEQ ID NO: 28, SEQ ID NO: 29, SEQ ID NO: 30, or SEQ ID NO: 31. In aspects of this embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 54, SEQ ID NO: 55, SEQ ID NO: 56, or SEQ ID NO: 57, a light chain comprising a light chain variable region including CDR1 of SEQ ID NO: 10 or SEQ ID NO: 11, a CDR2 of SEQ ID NO: 12 or SEQ ID NO: 13 or a CDR3 of SEQ ID NO: 14 or SEQ ID NO 15 and a kappa light chain constant region of SEQ ID NO: 16, SEQ ID NO: 17, SEQ ID NO: 18, SEQ ID NO: 19, or SEQ ID NO: 20. In an aspect of this embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 54, SEQ ID NO: 55, SEQ ID NO: 56, or SEQ ID NO: 57, a light chain comprising a light chain variable region including CDR1 of SEQ ID NO: 10 or SEQ ID NO: 11, a CDR2 of SEQ ID NO: 12 or SEQ ID NO: 13 or a CDR3 of SEQ ID NO: 14 or SEQ ID NO 15 and a kappa light chain constant region of SEQ ID NO: 16. In aspects of this embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 54, SEQ ID NO: 55, SEQ ID NO: 56, or SEQ ID NO: 57, a light chain comprising a light chain variable region including CDR1 of SEQ ID NO: 10 or SEQ ID NO: 11, a CDR2 of SEQ ID NO: 12 or SEQ ID NO: 13 or a CDR3 of SEQ ID NO: 14 or SEQ ID NO 15 and a lambda light chain constant region of SEQ ID NO: 26, SEQ ID NO: 27, SEQ ID NO: 28, SEQ ID NO: 29, SEQ ID NO: 30, or SEQ ID NO: 31.

In an embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 57, and a light chain comprising a light chain variable region including CDR1 of SEQ ID NO: 10 or SEQ ID NO: 11, a CDR2 of SEQ ID NO: 12 or SEQ ID NO: 13 or a CDR3 of SEQ ID NO: 14 or SEQ ID NO 15. In aspects of this embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 57, a light chain comprising a light chain variable region including CDR1 of SEQ ID NO: 10 or SEQ ID NO: 11, a CDR2 of SEQ ID NO: 12 or SEQ ID NO: 13 or a CDR3 of SEQ ID NO: 14 or SEQ ID NO 15 and a light chain constant region of SEQ ID NO: 16, SEQ ID NO: 17, SEQ ID NO: 18, SEQ ID NO: 19, SEQ ID NO: 20, SEQ ID NO: 26, SEQ ID NO: 27, SEQ ID NO: 28, SEQ ID NO: 29, SEQ ID NO: 30, or SEQ ID NO: 31. In aspects of this embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 57, a light chain comprising a light chain variable region including CDR1 of SEQ ID NO: 10 or SEQ ID NO: 11, a CDR2 of SEQ ID NO: 12 or SEQ ID NO: 13 or a CDR3 of SEQ ID NO: 14 or SEQ ID NO 15 and a kappa light chain constant region of SEQ ID NO: 16, SEQ ID NO: 17, SEQ ID NO: 18, SEQ ID NO: 19, or SEQ ID NO: 20. In an aspect of this embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 57, a light chain comprising a light chain variable region including CDR1 of SEQ ID NO: 10 or SEQ ID NO: 11, a CDR2 of SEQ ID NO: 12 or SEQ ID NO: 13 or a CDR3 of SEQ ID NO: 14 or SEQ ID NO 15 and a kappa light chain constant region of SEQ ID NO: 16. In aspects of this embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 57, a light chain comprising a light chain variable region including CDR1 of SEQ ID NO: 10 or SEQ ID NO: 11, a CDR2 of SEQ ID NO: 12 or SEQ ID NO: 13 or a CDR3 of SEQ ID NO: 14 or SEQ ID NO 15 and a lambda light chain constant region of SEQ ID NO: 26, SEQ ID NO: 27, SEQ ID NO: 28, SEQ ID NO: 29, SEQ ID NO: 30, or SEQ ID NO: 31.

In an embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 54, SEQ ID NO: 55, SEQ ID NO: 56, or SEQ ID NO: 57, and a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15. In aspects of this embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 54, SEQ ID NO: 55, SEQ ID NO: 56, or SEQ ID NO: 57, a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15 and a light chain constant region of SEQ ID NO: 16, SEQ ID NO: 17, SEQ ID NO: 18, SEQ ID NO: 19, SEQ ID NO: 20, SEQ ID NO: 26, SEQ ID NO: 27, SEQ ID NO: 28, SEQ ID NO: 29, SEQ ID NO: 30, or SEQ ID NO: 31. In aspects of this embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 54, SEQ ID NO: 55, SEQ ID NO: 56, or SEQ ID NO: 57, a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15 and a kappa light chain constant region of SEQ ID NO: 16, SEQ ID NO: 17, SEQ ID NO: 18, SEQ ID NO: 19, or SEQ ID NO: 20. In an aspect of this embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 54, SEQ ID NO: 55, SEQ ID NO: 56, or SEQ ID NO: 57, a light chain comprising a light chain variable region including CDR1 of SEQ ID NO: 10 or SEQ ID NO: 11, a CDR2 of SEQ ID NO: 12 or SEQ ID NO: 13 or a CDR3 of SEQ ID NO: 14 or SEQ ID NO 15 and a kappa light chain constant region of SEQ ID NO: 16. In aspects of this embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 54, SEQ ID NO: 55, SEQ ID NO: 56, or SEQ ID NO: 57, a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15 and a lambda light chain constant region of SEQ ID NO: 26, SEQ ID NO: 27, SEQ ID NO: 28, SEQ ID NO: 29, SEQ ID NO: 30, or SEQ ID NO: 31.

In an embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 57, and a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15. In aspects of this embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 57, a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15 and a light chain constant region of SEQ ID NO: 16, SEQ ID NO: 17, SEQ ID NO: 18, SEQ ID NO: 19, SEQ ID NO: 20, SEQ ID NO: 26, SEQ ID NO: 27, SEQ ID NO: 28, SEQ ID NO: 29, SEQ ID NO: 30, or SEQ ID NO: 31. In aspects of this embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 57, a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15 and a kappa light chain constant region of SEQ ID NO: 16, SEQ ID NO: 17, SEQ ID NO: 18, SEQ ID NO: 19, or SEQ ID NO: 20. In an aspect of this embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 57, a light chain comprising a light chain variable region including CDR1 of SEQ ID NO: 10 or SEQ ID NO: 11, a CDR2 of SEQ ID NO: 12 or SEQ ID NO: 13 or a CDR3 of SEQ ID NO: 14 or SEQ ID NO 15 and a kappa light chain constant region of SEQ ID NO: 16. In aspects of this embodiment, a modified anti-PD-L1 antibody disclosed herein comprises an IgG1 immunoglobulin heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, a heavy chain constant region of SEQ ID NO: 57, a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15 and a lambda light chain constant region of SEQ ID NO: 26, SEQ ID NO: 27, SEQ ID NO: 28, SEQ ID NO: 29, SEQ ID NO: 30, or SEQ ID NO: 31.

Whether two sequences have high sequence identity (or homology) is routinely calculated using a percentage similarity or identity, terms that are well known in the art. Sequences for a PD-L1 antigen may be compared to SEQ ID NO: 1. Sequences for an anti-PD-L1 antibody may be compared to SEQ ID NOs: 2-15. The term "percent (%) amino acid sequence identity" with respect to any of SEQ ID NOs: 1-15 is defined as the percentage of amino acid residues in a candidate sequence that are identical with the amino acid residues in any of SEQ ID NOS: 1-15 amino acid sequence, after aligning the sequences and introducing gaps, if necessary, to achieve the maximum percent sequence identity, and not considering any conservative substitutions as part of the sequence identity. Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art and from the teaching herein.

Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., *CLUSTAL W Improving the Sensitivity of Progressive Multiple Sequence Alignment Through Sequence Weighting, Position-Specific Gap Penalties and Weight Matrix Choice,* 22(22) Nucleic Acids Research 4673-4680 (1994); and iterative refinement, see, e.g., Osamu Gotoh, *Significant Improvement in Accuracy of Multiple Protein Sequence Alignments by Iterative Refinement as Assessed by Reference to Structural Alignments,* 264(4) J. Mol. Biol. 823-838 (1996).

Local methods align sequences by identifying one or more conserved motifs shared by all of the input sequences. Non-limiting methods include, e.g., Match-box, see, e.g., Eric Depiereux and Ernest Feytmans, *Match-Box: A Fundamentally New Algorithm for the Simultaneous Alignment of Several Protein Sequences,* 8(5) CABIOS 501-509 (1992); Gibbs sampling, see, e.g., C. E. Lawrence et al., *Detecting Subtle Sequence Signals: A Gibbs Sampling Strategy for Multiple Alignment,* 262(5131) Science 208-214 (1993); Align-M, see, e.g., Ivo Van Walle et al., *Align-M—A New Algorithm for Multiple Alignment of Highly Divergent Sequences,* 20(9) Bioinformatics: 1428-1435 (2004).

Hybrid methods combine functional aspects of both global and local alignment methods. Non-limiting methods include, e.g., segment-to-segment comparison, see, e.g., Burkhard Morgenstern et al., *Multiple DNA and Protein Sequence Alignment Based On Segment-To-Segment Comparison,* 93(22) Proc. Natl. Acad. Sci. U.S.A. 12098-12103 (1996); T-Coffee, see, e.g., Cédric Notredame et al., *T-Coffee: A Novel Algorithm for Multiple Sequence Alignment,* 302(1) J. Mol. Biol. 205-217 (2000); MUSCLE, see, e.g., Robert C. Edgar, *MUSCLE: Multiple Sequence Alignment With High Score Accuracy and High Throughput,* 32(5) Nucleic Acids Res. 1792-1797 (2004); and DIALIGN-T, see, e.g., Amarendran R Subramanian et al., *DIALIGN-T: An Improved Algorithm for Segment-Based Multiple Sequence Alignment,* 6(1) BMC Bioinformatics 66 (2005).

The present specification describes various polypeptide variants where one amino acid is substituted for another, such as, e.g., a PD-L1 antigen, a heavy chain variable domain ($V_H$), a light chain variable domain ($V_L$), and a CDR 1, CDR2, and CDR3 regions. A substitution can be assessed by a variety of factors, such as, e.g., the physic properties of the amino acid being substituted (Table 1) or how the original amino acid would tolerate a substitution (Table 2). The selections of which amino acid can be substituted for another amino acid in a polypeptide are known to a person of ordinary skill in the art.

TABLE 1

| Amino Acid Properties | |
|---|---|
| Property | Amino Acids |
| Aliphatic | G, A, I, L, M, P, V |
| Aromatic | F, H, W, Y |
| C-beta branched | I, V, T |
| Hydrophobic | C, F, I, L, M, V, W |
| Small polar | D, N, P |
| Small non-polar | A, C, G, S, T |
| Large polar | E, H, K, Q, R, W, Y |
| Large non-polar | F, I, L, M, V |
| Charged | D, E, H, K, R |
| Uncharged | C, S, T |
| Negative | D, E |
| Positive | H, K, R |
| Acidic | D, E |
| Basic | K, R |
| Amide | N, Q |

TABLE 2

| Amino Acid Substitutions | | | |
|---|---|---|---|
| Amino Acid | Favored Substitution | Neutral Substitutions | Disfavored substitution |
| A | G, S, T | C, E, I, K, M, L, P, Q, R, V | D, F, H, N, Y, W |
| C | F, S, Y, W | A, H, I, M, L, T, V | D, E, G, K, N, P, Q, R |
| D | E, N | G, H, K, P, Q, R, S, T | A, C, I, L, |
| E | D, K, Q | A, H, N, P, R, S, T | C, F, G, I, L, M, V, W, Y |
| F | M, L, W, Y | C, I, V | A, D, E, G, H, K, N, P, Q, R, S, T |
| G | A, S | D, K, N, P, Q, R | C, E, F, H, I, L, M,T, V, W, Y |
| H | N, Y | C, D, E, K, Q, R, S, T, W | A, F, G, I, L, M, P, V |
| I | V, L, M | A, C, T, F, Y | D, E, G, H, K, N, P, Q, R, S, W |
| K | Q, E, R | A, D, G, H, M, N, P, S, T | C, F, I, L, V, W, Y |
| L | F, I, M, V | A, C, W, Y | D, E, G, H, K, N, P, Q, R, S, T |
| M | F, I, L, V | A, C, R, Q, K, T, W, Y | D, E, G, H, N, P, S |
| N | D, H, S | E, G, K, Q, R, T | A, C, F, I, L, M, P, V, W, Y |
| P | — | A, D, E, G, K, Q, R, S, T | C, F, H, I, L, M, N, V, W, Y |
| Q | E, K, R | A, D, G, H, M, N, P, S, T | C, F, I, L, V, W, Y |
| R | K, Q | A, D, E, G, H, M, N, P, S, T | C, F, I, L, V, W, Y |
| S | A, N, T | C, D, E, G, H, K, P, Q, R, T | F, I, L, M, V, W, Y |
| T | S | A, C, D, E, H, I, K, M, N, P, Q, R, V | F, G, L, W, Y |
| V | I, L, M | A, C, F, T, Y | D, E, G, H, K, N, P, Q, R, S, W |
| W | F, Y | H, L, M | A, C, D, E, G, I, K, N, P, Q, R, S, T, V |
| Y | F, H, W | C, I, L, M, V | A, D, E, G, K, N, P, Q, R, S, T |

Matthew J. Betts and Robert, B. Russell, Amino Acid Properties and Consequences of Substitutions, pp. 289-316, In Bioinformatics for Geneticists, (eds Michael R. Barnes, Ian C. Gray, Wiley, 2003).

In aspects of this embodiment, a hydrophic amino acid at one particular position in an insulin-like protein disclosed herein can be substituted with another hydrophic amino acid. Examples of hydrophic amino acids include, e.g., C, F, I, L, M, V and W. In another aspect of this embodiment, an aliphatic amino acid at one particular position in an insulin-like protein disclosed herein can be substituted with another aliphatic amino acid. Examples of aliphatic amino acids include, e.g., A, I, L, P, and V. In yet another aspect of this embodiment, an aromatic amino acid at one particular position in an insulin-like protein disclosed herein can be substituted with another aromatic amino acid. Examples of aromatic amino acids include, e.g., F, H, W and Y. In still another aspect of this embodiment, a stacking amino acid at one particular position in an insulin-like protein disclosed herein can be substituted with another stacking amino acid. Examples of stacking amino acids include, e.g., F, H, Wand Y. In a further aspect of this embodiment, a polar amino acid at one particular position in an insulin-like protein disclosed herein can be substituted with another polar amino acid. Examples of polar amino acids include, e.g., D, E, K, N, Q, and R. In a further aspect of this embodiment, a less polar or indifferent amino acid at one particular position in an insulin-like protein disclosed herein can be substituted with another less polar or indifferent amino acid. Examples of less polar or indifferent amino acids include, e.g., A, H, G, P, S, T, and Y. In a yet further aspect of this embodiment, a positive charged amino acid at one particular position in an insulin-like protein disclosed herein can be substituted with another positive charged amino acid. Examples of positive charged amino acids include, e.g., K, R, and H. In a still further aspect of this embodiment, a negative charged amino acid at one particular position in an insulin-like protein disclosed herein can be substituted with another negative charged amino acid. Examples of negative charged amino acids include, e.g., D and E. In another aspect of this embodiment, a small amino acid at one particular position in an insulin-like protein disclosed herein can be substituted with another small amino acid. Examples of small amino acids include, e.g., A, D, G, N, P, S, and T. In yet another aspect of this embodiment, a C-beta branching amino acid at one particular position in an insulin-like protein disclosed herein can be substituted with another C-beta branching amino acid. Examples of C-beta branching amino acids include, e.g., I, T and V.

In an embodiment, a modified anti-PD-L1 antibody disclosed herein specifically binds an epitope disclosed herein. In aspects of this embodiment, a modified anti-PD-L1 antibody disclosed herein specifically binds an epitope present in the PD-L1 of SEQ ID NO: 1. In aspects of this embodiment, a modified anti-PD-L1 antibody disclosed herein specifically binds an epitope having an amino acid identity of, e.g., at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, relative to the PD-L1 of SEQ ID NO: 1. In other aspects of this embodiment, a modified anti-PD-L1 antibody disclosed herein specifically binds an epitope having an amino acid identity in the range of, e.g., about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, about 95% to about 97%, or about 97% to about 99%, relative to the PD-L1 of SEQ ID NO: 1. In yet other aspects of this embodiment, a modified anti-PD-L1 antibody disclosed herein specifically binds an epitope having, e.g., at least 1, at least 2, at least 3, or at least 4, contiguous and/or non-contiguous amino acid deletions, additions, and/or substitutions relative to the PD-L1 of SEQ ID NO: 1; or at most 1, at most 2, at most 3, at most 4, contiguous and/or non-contiguous amino acid deletions, additions, and/or substitutions relative to the PD-L1 of SEQ ID NO: 1. In still other aspects of this embodiment, a modified anti-PD-L1 antibody disclosed herein specifically binds an epitope having, e.g., about 1 to about 2, about 1 to about 3, about 1 to about 4, about 2 to about 3, about 2 to about 4, or about 3 to about 4 contiguous and/or non-contiguous amino acid deletions, additions, and/or substitutions relative to the PD-L1 of SEQ ID NO: 1.

As used herein, the term "selectively binds" or "selective binding", when made in reference to an antibody, refers to the discriminatory binding of the antibody to the indicated target epitope such that the antibody does not substantially cross react with non-target epitopes. The minimal size of a peptide epitope, as defined herein, is about five amino acids, and a peptide epitope typically comprises at least 5, at least 6, at least 7, at least 8, at least 9, at least 10, at least 11, at least 12, at least 13, at least 14, at least 15, or at least 20 amino acids. A peptide epitope may be discontinuous, i.e., it comprises amino acid residues that are not adjacent in the primary structure of the peptide but are brought together into an epitope by way of the secondary, tertiary, or quaternary structure of the peptide. Furthermore, it is also noted that an epitope might comprise a portion of a molecule other than an amino acid sequence, such as, e.g., a carbohydrate moiety, a lipid moiety like lipoproteins or glycolipids, or a chemically-modified amino acid moiety like a phosphorylated amino acid.

In an embodiment, a modified anti-PD-L1 antibody disclosed herein may selectively bind an epitope present on a PD-L1. In aspects of this embodiment, a modified anti-PD-L1 antibody disclosed herein selectively binds an epitope present in the PD-L1 of SEQ ID NO: 1. In aspects of this embodiment, a modified anti-PD-L1 antibody disclosed herein selectively binds an epitope having an amino acid identity of, e.g., at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, relative to the PD-L1 of SEQ ID NO: 1. In other aspects of this embodiment, a modified anti-PD-L1 antibody disclosed herein selectively binds an epitope having an amino acid identity in the range of, e.g., about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, about 95% to about 97%, or about 97% to about 99%, relative to the PD-L1 of SEQ ID NO: 1. In yet other aspects of this embodiment, a modified anti-PD-L1 antibody disclosed herein selectively binds an epitope having, e.g., at least 1, at least 2, at least 3, or at least 4, contiguous and/or non-contiguous amino acid deletions, additions, and/or substitutions relative to the PD-L1 of SEQ ID NO: 1; or at most 1, at most 2, at most 3, at most 4, contiguous and/or non-contiguous amino acid deletions, additions, and/or substitutions relative to the PD-L1 of SEQ ID NO: 1. In still other aspects of this embodiment, a modified anti-PD-L1 antibody disclosed herein selectively binds an epitope having, e.g., about 1 to about 2, about 1 to about 3, about 1 to about 4, about 2 to about 3, about 2 to about 4, or about 3 to about 4 contiguous and/or non-contiguous amino acid deletions, additions, and/or substitutions relative to the PD-L1 of SEQ ID NO: 1.

In aspects of this embodiment, a modified anti-PD-L1 antibody disclosed herein binds to an epitope present in PD-L1 comprising, e.g., at least 5, at least 6, at least 7, at least 8, at least 9, at least 10, at least 11, at least 12, at least 13, at least 14, at least 15, or at least 20 amino acids. In other aspects of this embodiment, a modified anti-PD-L1 antibody disclosed herein binds to an epitope comprising, e.g., at most 5, at most 6, at most 7, at most 8, at most 9, at most 10, at most 11, at most 12, at most 13, at most 14, at most 15, or at most 20 amino acids. In other aspects of this embodiment, a modified anti-PD-L1 antibody disclosed herein binds to an epitope present in PD-L1 comprising, e.g., about 5 to about 7, about 5 to about 8, about 7 to about 9, about 5 to about 10, about 5 to about 12, about 5 to about 15, about 5 to about 18, about 5 to about 20, about 6 to about 7, about 6 to about 8, about 6 to about 9, about 6 to about 10, about 6 to about 12, about 6 to about 15, about 6 to about 18, about 6 to about 20, about 7 to about 8, about 7 to about 9, about 7 to about 10, about 7 to about 12, about 7 to about 15, about 7 to about 18, about 7 to about 20, about 8 to about 9, about 8 to about 10, about 8 to about 12, about 8 to about 15, about 8 to about 18, about 8 to about 20, about 9 to about 10, about 9 to about 12, about 9 to about 15, about 9 to about 18, about 9 to about 20, about 10 to about 12, about 10 to about 15, about 10 to about 18, or about 10 to about 20.

In other aspects of this embodiment, a modified anti-PD-L1 antibody disclosed herein binds to an epitope comprising, e.g., at least 5, at least 6, at least 7, at least 8, at least 9, at least 10, at least 11, at least 12, at least 13, at least 14, at least 15, or at least 20 amino acids from the PD-L1 of SEQ ID NO: 1. In other aspects of this embodiment, a modified anti-PD-L1 antibody disclosed herein binds to an epitope comprising, e.g., at most 5, at most 6, at most 7, at most 8, at most 9, at most 10, at most 11, at most 12, at most 13, at most 14, at most 15, or at most 20 amino acids from the PD-L1 of SEQ ID NO: 1. In other aspects of this embodiment, a modified anti-PD-L1 antibody disclosed herein binds to an epitope comprising, e.g., about 5 to about 7, about 5 to about 8, about 7 to about 9, about 5 to about 10, about 5 to about 12, about 5 to about 15, about 5 to about 18, about 5 to about 20, about 6 to about 7, about 6 to about 8, about 6 to about 9, about 6 to about 10, about 6 to about 12, about 6 to about 15, about 6 to about 18, about 6 to about 20, about 7 to about 8, about 7 to about 9, about 7 to about 10, about 7 to about 12, about 7 to about 15, about 7 to about 18, about 7 to about 20, about 8 to about 9, about 8 to about 10, about 8 to about 12, about 8 to about 15, about 8 to about 18, about 8 to about 20, about 9 to about 10, about 9 to about 12, about 9 to about 15, about 9 to about 18, about 9 to about 20, about 10 to about 12, about 10 to about 15, about 10 to about 18, or about 10 to about 20 from the PD-L1 of SEQ ID NO: 1.

Selective binding includes binding properties such as, e.g., binding affinity, binding specificity, and binding avidity. Binding affinity refers to the length of time the antibody resides at its epitope binding site, and can be viewed as the strength with which an antibody binds its epitope. Binding affinity can be described an antibody's equilibrium dissociation constant (KD), which is defined as the ratio Kd/Ka at equilibrium. Where Ka is the antibody's association rate constant and kd is the antibody's dissociation rate constant. Binding affinity is determined by both the association and the dissociation and alone neither high association or low dissociation can ensure high affinity. The association rate constant (Ka), or on-rate constant (Kon), measures the number of binding events per unit time, or the propensity of the antibody and the antigen to associate reversibly into its antibody-antigen complex. The association rate constant is expressed in M-1 s-1, and is symbolized as follows: [Ab]×[Ag]×Kon. The larger the association rate constant, the more rapidly the antibody binds to its antigen, or the higher the binding affinity between antibody and antigen. The dissociation rate constant (Kd), or off-rate constant (Koff), measures the number of dissociation events per unit time propensity of an antibody-antigen complex to separate (dissociate) reversibly into its component molecules, namely the antibody and the antigen. The dissociation rate constant is expressed in s-1, and is symbolized as follows: [Ab+Ag]×Koff. The smaller the dissociation rate constant, the more tightly bound the antibody is to its antigen, or the higher the binding affinity between antibody and antigen. The equilibrium dissociation constant (KD) measures the rate at which new antibody-antigen complexes formed equals the rate at which antibody-antigen complexes dissociate at equilibrium. The equilibrium dissociation constant is expressed in M, and is defined as Koff/Kon=[Ab]×[Ag]/[Ab+Ag], where [Ab] is the molar concentration of the antibody, [Ag] is the molar concentration of the antigen, and [Ab+Ag] is the of molar concentration of the antibody-antigen complex, where all concentrations are of such components when the system is at equilibrium. The smaller the equilibrium dissociation constant, the more tightly bound the antibody is to its antigen, or the higher the binding affinity between antibody and antigen.

Thus, in an embodiment, the binding affinity of a modified anti-PD-L1 antibody disclosed herein may have an association rate constant for an epitope present in a PD-L1 of, e.g., less than $1\times10^5$ $M^{-1}$ $s^{-1}$, less than $1\times10^6$ $M^{-1}$ $s^{-1}$, less than $1\times10^7$ $M^{-1}$ $s^{-1}$, or less than $1\times10^8$ $M^{-1}$ $s^{-1}$. In another embodiment, the binding affinity of a modified anti-PD-L1 antibody disclosed herein may have an association rate constant for an epitope present in a PD-L1 of, e.g., more than $1\times10^5$ $M^{-1}$ $s^{-1}$, more than $1\times10^6$ $M^{-1}$ $s^{-1}$, more than $1\times10^7$ $M^{-1}$ $s^{-1}$, or more than $1\times10^8$ $M^{-1}$ $s^{-1}$. In other aspects, the binding affinity of a modified anti-PD-L1 antibody disclosed herein may have an association rate constant for an epitope present in a PD-L1 of between $1\times10^5$ $M^{-1}$ $s^{-1}$ to $1\times10^8$ $M^{-1}$ $s^{-1}$, $1\times10^6$ $M^{-1}$ $s^{-1}$ to $1\times10^8$ $M^{-1}$ $s^{-1}$, $1\times10^5$ $M^{-1}$ $s^{-1}$ to $1\times10^7$ $M^{-1}$ $s^{-1}$, or $1\times10^6$ $M^{-1}$ $s^{-1}$ to $1\times10^7$ $M^{-1}$ $s^{-1}$.

In another embodiment, the binding affinity of a modified anti-PD-L1 antibody disclosed herein may have an association rate constant for an epitope other than an epitope present on a PD-L1 of, e.g., less than $1\times10^0$ $M^{-1}$ $s^{-1}$, less than $1\times10^1$ $M^{-1}$ $s^{-1}$, less than $1\times10^2$ $M^{-1}$ $s^{-1}$, less than $1\times10^3$ $M^{-1}$ $s^{-1}$, or less than $1\times10^4$ $M^{-1}$ $s^{-1}$. In another embodiment, the binding affinity of a modified anti-PD-L1 antibody disclosed herein may have an association rate constant for an epitope other than an epitope present on a PD-L1 of, e.g., at most $1\times10^0$ $M^{-1}$ $s^{-1}$, at most $1\times10^1$ $M^{-1}$ $s^{-1}$, at most $1\times10^2$ $M^{-1}$ $s^{-1}$, at most $1\times10^3$ $M^{-1}$ $s^{-1}$, or at most $1\times10^4$ $M^{-1}$ $s^{-1}$.

In another embodiment, the binding affinity of a modified anti-PD-L1 antibody disclosed herein may have a disassociation rate constant for an epitope present in a PD-L1 of, e.g., less than $1\times10^{-3}$ $s^{-1}$, less than $1\times10^{-4}$ $s^{-1}$, or less than $1\times10^{-5}$ $s^{-1}$. In other aspects of this embodiment, the binding affinity of a modified anti-PD-L1 antibody disclosed herein may have a disassociation rate constant for an epitope present in a PD-L1 of, e.g., less than $1.0\times10^{-4}$ $s^{-1}$, less than $2.0\times10^{-4}$ $s^{-1}$, less than $3.0\times10^{-4}$ $s^{-1}$, less than $4.0\times10^{-4}$ $s^{-1}$, less than $5.0\times10^{-4}$ $s^{-1}$, less than $6.0\times10^{-4}$ $s^{-1}$, less than $7.0\times10^{-4}$ $s^{-1}$, less than $8.0\times10^{-4}$ $s^{-1}$, or less than $9.0\times10^{-4}$ $s^{-1}$. In another embodiment, the binding affinity of a modified anti-PD-L1 antibody disclosed herein may have a disassociation rate constant for an epitope present in a PD-L1 of, e.g., more than $1\times10^{-3}$ $s^{-1}$, more than $1\times10^{-4}$ $s^{-1}$, or more than $1\times10^{-5}$ $s^{-1}$. In other aspects of this embodiment, the binding affinity of a modified anti-PD-L1 antibody disclosed herein may have a disassociation rate constant for an epitope present in a PD-L1 of, e.g., more than $1.0\times10^{-4}$ $s^{-1}$, more than $2.0\times10^{-4}$ $s^{-1}$, more than $3.0\times10^{-4}$ $s^{-1}$, more than $4.0\times10^{-4}$ $s^{-1}$, more than $5.0\times10^{-4}$ $s^{-1}$, more than $6.0\times10^{-4}$ $s^{-1}$, more than $7.0\times10^{-4}$ $s^{-1}$, more than $8.0\times10^{-4}$ $s^{-1}$, or more than $9.0\times10^{-4}$ $s^{-1}$. In other aspects, the binding affinity of a modified anti-PD-L1 antibody disclosed herein may have a disassociation rate constant for an epitope present in a PD-L1 of between, e.g., $1\times10^{-3}$ $s^{-1}$ to $1\times10^{-5}$ $s^{-1}$, $1\times10^{-3}$ $s^{-1}$ to $1\times10^{-4}$ $s^{-1}$, or $1\times10^{-4}$ $s^{-1}$ to $1\times10^{-5}$ $s^{-1}$.

In another embodiment, the binding affinity of a modified anti-PD-L1 antibody disclosed herein may have an equilibrium disassociation constant for an epitope present in a PD-L1 of less than 0.500 nM. In aspects of this embodiment, the binding affinity of a modified anti-PD-L1 antibody disclosed herein disclosed may have an equilibrium disassociation constant for an epitope present in a PD-L1 of, e.g., less than 0.500 nM, less than 0.450 nM, less than 0.400 nM, less than 0.350 nM, less than 0.300 nM, less than 0.250 nM, less than 0.200 nM, less than 0.150 nM, less than 0.100 nM, or less than 0.050 nM. In another embodiment, the binding affinity of a modified anti-PD-L1 antibody disclosed herein may have an equilibrium disassociation constant for an epitope present in a PD-L1 of more than 0.500 nM. In aspects of this embodiment, the binding affinity of a modified anti-PD-L1 antibody disclosed herein may have an equilibrium disassociation constant for an epitope present in a PD-L1 of, e.g., more than 0.500 nM, more than 0.450 nM, more than 0.400 nM, more than 0.350 nM, more than 0.300 nM, more than 0.250 nM, more than 0.200 nM, more than 0.150 nM, more than 0.100 nM, or more than 0.050 nM.

Binding specificity is the ability of an antibody to discriminate between a molecule containing its epitope and a molecule that does not contain that epitope. One way to measure binding specificity is to compare the Kon association rate of the antibody for a molecule containing its epitope relative to the Kon association rate of the antibody for a molecule that does not contain that epitope. For example, comparing the association rate constant (Ka) of a modified anti-PD-L1 antibody disclosed herein that selectively binds to an epitope present in a PD-L1 to an epitope not present in a PD-L1. In aspects of this embodiment, a modified anti-PD-L1 antibody disclosed herein may have an association rate constant (Ka) for an epitope not present in a PD-L1 of, e.g., less than $1\times10^0$ $M^{-1}$ $s^{-1}$, less than $1\times10^1$ $M^{-1}$ $s^{-1}$, less than $1\times10^2$ $M^{-1}$ $s^{-1}$, less than $1\times10^3$ $M^{-1}$ $s^{-1}$, or less than $1\times10^4$ $M^{-1}$ $s^{-1}$. In other aspects of this embodiment, a modified anti-PD-L1 antibody disclosed herein may have an association rate constant (Ka) for an epitope not present in a PD-L1 of, e.g., at most $1\times10^0$ $M^{-1}$ $s^{-1}$, at most $1\times10^1$ $M^{-1}$ $s^{-1}$, at most $1\times10^2$ $M^{-1}$ $s^{-1}$, at most $1\times10^3$ $M^{-1}$ $s^{-1}$, or at most $1\times10^4$ $M^{-1}$ $s^{-1}$.

In other aspects of this embodiment, a modified anti-PD-L1 antibody disclosed herein may have an association rate constant (Ka) for its epitope relative to an epitope not present in a PD-L1 of, e.g., at least 2-fold more, at least 3-fold more, at least 4-fold more, at least 5-fold more, at least 6-fold more, at least 7-fold more, at least 8-fold more, or at least 9-fold more. In yet other aspects of this embodiment, a modified anti-PD-L1 antibody disclosed herein may have an association rate constant (Ka) for its epitope relative to an epitope not present in a PD-L1 of, e.g., at least 10-fold more, at least 100-fold more, at least 1,000-fold more or at least 10,000-fold more.

In other aspects of this embodiment, a modified anti-PD-L1 antibody disclosed herein may have an association rate constant (Ka) for its epitope relative to an epitope not present in a PD-L1 of, e.g., at most 1-fold more, at most 2-fold more, at most 3-fold more, at most 4-fold more, at most 5-fold more, at most 6-fold more, at most 7-fold more, at most 8-fold more, or at most 9-fold more. In yet other aspects of this embodiment, anti-PD-L1 antibody disclosed herein may have an association rate constant (Ka) for its epitope relative to an epitope not present in a PD-L1 of, e.g., at most 10-fold more, at most 100-fold more, at most 1,000-fold more or at most 10,000-fold more.

The binding specificity of a modified anti-PD-L1 antibody disclosed herein may also be characterized as a ratio that such a modified anti-PD-L1 antibody disclosed herein can discriminate its epitope relative to an epitope not present in a PD-L1. In aspects of this embodiment, a modified anti-PD-L1 antibody disclosed herein may have a binding specificity ratio for its epitope relative to an epitope not present in a PD-L1 of, e.g., at least 2:1, at least 3:1, at least 4:1, at least 5:1, at least 64:1, at least 7:1, at least 8:1, at least 9:1, at least 10:1, at least 15:1, at least 20:1, at least 25:1, at least 30:1, at least 35:1, or at least 40:1.

Binding avidity, also known as functional affinity, refers to the sum total of the functional binding strength between a multivalent antibody and its antigen. Antibody molecules can have more than one binding site (e.g., 2 for IgG), and many antigens contain more than one antigenic site. While binding avidity of an antibody depends on the binding affinities of the individual antibody binding sites, binding avidity is greater than the binding affinity as all the antibody-antigen interactions must be broken simultaneously for the antibody to dissociate completely. It is envisioned that a modified anti-PD-L1 antibody disclosed herein may selectively bind to any and all epitopes for that antibody.

Aspects of the present specification disclose, in part, a therapeutic composition. A therapeutic composition disclosed herein may comprise one or more anti-PD-L1 antibodies disclosed herein and optionally may further comprise one or more pharmaceutical acceptable carriers. As used herein "pharmaceutically acceptable" refers to any molecular entity or composition that does not produce an adverse, allergic or other untoward or unwanted reaction when administered to an individual. As used herein, the term "therapeutic composition" is synonymous with "pharmaceutically acceptable therapeutic composition" and refers to a therapeutically effective concentration of an active ingredient, such as, e.g., a modified anti-PD-L1 antibody disclosed herein. A therapeutic composition comprising a modified anti-PD-L1 antibody disclosed herein is useful for medical and veterinary applications. A therapeutic composition may be administered to an individual alone, or in combination with other supplementary active ingredients, agents, drugs or hormones. The therapeutic compositions may be manufactured using any of a variety of processes, including, without limitation, conventional mixing, dissolving, granulating, dragee-making, levigating, emulsifying, encapsulating, entrapping, and lyophilizing. The therapeutic composition can take any of a variety of forms including, without limitation, a sterile solution, suspension, emulsion, lyophilizate, tablet, pill, pellet, capsule, powder, syrup, elixir or any other dosage form suitable for administration.

The amount of a modified anti-PD-L1 antibody disclosed herein included in a therapeutic composition is an amount sufficient to elicit an appropriate therapeutic response in the individual. Typically, this amount is also one that does not cause significant adverse side effects. Thus, an amount of a modified anti-PD-L1 antibody disclosed herein included in a therapeutic composition is an effective and safe amount of a modified anti-PD-L1 antibody disclosed herein. Such amount will vary depending on which specific anti-PD-L1 antibody or antibodies are employed. An optimal amount for a particular therapeutic composition can be ascertained by a person skilled in the art using standard and routine studies involving observation of antibody titers and other responses in individuals.

A therapeutic composition disclosed herein can optionally include one or more pharmaceutically acceptable carriers that facilitate processing of an active ingredient into therapeutic compositions. As used herein, the term "pharmacologically acceptable carriers" is synonymous with "pharmacological carriers" and means any compound that has substantially no long term or permanent detrimental effect when administered and encompasses terms such as "pharmacologically acceptable vehicle, stabilizer, diluent, additive, auxiliary or excipient." Such a carrier generally is mixed with an active compound, or permitted to dilute or enclose the active compound and can be a solid, semi-solid, or liquid agent. It is understood that the active ingredients can be soluble or can be delivered as a suspension in the desired carriers. Any of a variety of pharmaceutically acceptable carrier can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in PHARMACEUTICAL DOSAGE FORMS AND DRUG DELIVERY SYSTEMS (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); GOODMAN & GILMAN'S THE PHARMACOLOGICAL BASIS OF THERAPEUTICS (Joel G. Hardman et al., eds., McGraw-Hill Professional, 10th ed. 2001); and HANDBOOK OF PHARMACEUTICAL EXCIPIENTS (Raymond C. Rowe et al., APhA Publications, 4th edition 2003). These protocols are routine procedures and any modifications are well within the scope of one skilled in the art and from the teaching herein.

A therapeutic composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a therapeutic composition disclosed herein, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. An active ingredient, such as, e.g., a modified anti-PD-L1 antibody disclosed herein, may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a therapeutic composition.

Aspects of the present specification disclose, in part, a pharmaceutical kit. A kit disclosed herein can comprise one or more containers including a modified anti-PD-L1 antibody or a therapeutic composition disclosed herein. A kit disclosed herein can further include a label or instructions providing useful information including, without limitation, details on a modified anti-PD-L1 antibody or a therapeutic composition disclosed herein, a description on how to prepare and use a modified anti-PD-L1 antibody or a therapeutic composition disclosed herein to treat and/or prevent a neurodegenerative disease disclosed herein, a description on how to detect a blood serum level of a modified anti-PD-L1 antibody disclosed herein in an individual after administration of a modified anti-PD-L1 antibody or a therapeutic composition disclosed herein, and/or a marketing authorization number (e.g. an FDA or EMA authorization number). A kit disclosed herein can further include a delivery system useful for administering a modified anti-PD-L1 antibody or a therapeutic composition disclosed herein, such as, e.g., an injection device. A kit disclosed herein can further include one or more containers including another pharmaceutical composition used as an adjunct therapy with a modified anti-PD-L1 antibody or a therapeutic composition disclosed herein. The contents of the kit can be enclosed in an outer casing. The outer casing can be a box, a sealed bag, a foil pouch, etc. In certain embodiments, the contents of a kit disclosed herein are enclosed in a box.

Aspects of the present specification discloses, in part, a method of treating a neurodegenerative disease. In another aspect, the present specification discloses, in part, a method for reducing Aβ-plaque burden in an individual diagnosed with Alzheimer's disease. In another aspect, the present specification discloses, in part, a method for reducing hippocampal gliosis in a patient diagnosed with Alzheimer's disease.

Such methods include therapeutic (following disease onset) and prophylactic (prior to disease onset or pathology). For example, therapeutic and prophylactic methods of treating an individual for a neurodegenerative disease include treatment of an individual having or at risk of having a neurodegenerative disease or pathology, treating an individual with a neurodegenerative disease, and methods of protecting an individual from a neurodegenerative disease, to decrease or reduce the probability of a neurodegenerative disease in an individual, to decrease or reduce susceptibility of an individual to a neurodegenerative disease, or to inhibit or prevent a neurodegenerative disease in an individual. Such methods include administering an immunogenic composition disclosed herein to therapeutically or prophylactically treat an individual having or at risk of having a neurodegenerative disease or pathology. Accordingly, methods can treat the neurodegenerative disease or pathology, or provide the individual with protection from a neurodegenerative disease (e.g., prophylactic protection).

In one embodiment, a method of treating a neurodegenerative disease comprises administering to an individual in need thereof a modified anti-PD-L1 antibody disclosed herein or therapeutic composition disclosed herein in an amount sufficient to reduce one or more physiological conditions or symptom associated with a neurodegenerative disease or pathology, thereby treating the neurodegenerative disease. In aspects of this embodiment, a therapeutic composition comprises one or more anti-PD-L1 antibodies disclosed herein.

In one embodiment, a modified anti-PD-L1 antibody disclosed herein or therapeutic composition disclosed herein is used to treat a neurodegenerative disease. Use of a modified anti-PD-L1 antibody disclosed herein or therapeutic composition disclosed herein treats a neurodegenerative disease by reducing one or more physiological conditions or symptom associated with a neurodegenerative or pathology. In aspects of this embodiment, administration of an anti-PD-L1 or therapeutic composition disclosed herein is in an amount sufficient to reduce one or more physiological conditions or symptom associated with a neurodegenerative or pathology, thereby treating the neurodegenerative disease.

A neurodegenerative disease refers to any condition, disease or disorder where a pathophysiology effect is due to the progressive loss of structure or function of neurons, including death of neurons. A neurodegenerative disease includes, without limitation, aged-related dementia, Alzheimer's disease, amyotrophic lateral sclerosis, dementia, Parkinson's disease Huntington's disease, primary progressive multiple sclerosis; secondary progressive multiple sclerosis, corticobasal degeneration, Rett syndrome, a tauopathy, a retinal degeneration disorder; anterior ischemic optic neuropathy; glaucoma; uveitis; depression; trauma-associated stress or post-traumatic stress disorder, frontotemporal dementia, Lewy body dementias, mild cognitive impairments, posterior cortical atrophy, primary progressive aphasia, progressive supranuclear palsy or an injury of the CNS.

Tauopathies are a clinically, morphologically and biochemically heterogeneous class of neurodegenerative diseases characterized by a pathological aggregation of tau protein in neurofibrillary or gliofibrillary tangles in the human brain. Tau is a microtubule-associated protein (MAP) that binds to microtubules and promotes their polymerization. It plays an important role in maintaining axonal transport and neuronal integrity but has a physiological role in dendrites, and it is expressed at low levels in glial cells. In a tauopathy, tangles are formed by hyperphosphorylation of tau causing it to aggregate in an insoluble form. Non-limiting examples of tauopathies include Alzheimer's disease, argyrophilic grain disease, chronic traumatic encephalopathy, corticobasal degeneration, dementia pugilistica, frontotemporal dementia, frontotemporal lobar degeneration, Hallervorden-Spatz disease, Huntington's disease, ganglioglioma, gangliocytoma, globular glial tauopathy, lead encephalopathy, lipofuscinosis, Lytico-Bodig disease (Parkinson-dementia complex of Guam), meningioangiomatosis, Parkinsonism disease linked to chromosome 17, Pick's disease, primary age-related tauopathy (PART), formerly known as neurofibrillary tangle-only dementia (NFT-dementia), postencephalitic parkinsonism, progressive supranuclear palsy, subacute sclerosing panencephalitis and tuberous sclerosis.

Retinal degeneration disorders are ones that result in the deterioration of the retina due to the death of photoreceptor cells. There are several causes for retinal degeneration, including artery or vein occlusion, diabetic retinopathy, retrolental fibroplasia/retinopathy of prematurity, or disease (usually hereditary). Symptoms include, without limitation, impaired vision, night blindness, retinal detachment, light sensitivity, glare sensitivity, tunnel vision, loss of depth perception, loss of contrast, night blindness, loss of central vision, loss of peripheral vision and total loss of vision. Retinal degeneration disorders include, without limitation, Age-Related Macular Degeneration (wet and dry), Retinitis Pigmentosa, Choroideremia, Cone-Rod Retinal Dystrophy, Gyrate Atrophy, Juvenile Retinoschisis, Vitelliform Macular Dystrophy (Best's Disease), Abetalipoproteinemia (Bassen-Kornzweig Disease), Bardet-Biedl Syndrome, Blue Cone Monochromatism Disease, Dominant Drusen, Goldman-Favre Vitreoretinal Dystrophy (Enhanced S-cone Syndrome), Kearns-Sayre Syndrome, Laurence-Moon Syndrome, Leber's Congenital Amaurosis, Leber's Refsum disease, Oguchi Disease, Peripapillary (pericentral) Choroidal Dystrophy, Pigment Pattern Dystrophy, Sorsby Macular Dystrophy, Stargardt's Disease, Stickler's Syndrome, Usher Syndrome and Wagner's Vitreoretinal Dystrophy.

An injury of the CNS includes, without limitation, a spinal cord injury, a closed head injury, a blunt trauma, a penetrating trauma, a hemorrhagic stroke, an ischemic stroke, a cerebral ischemia, an optic nerve injury, a myocardial infarction, an organophosphate poisoning and an injury caused by tumor excision.

Aspects of the present specification provide, in part, an individual. An individual comprises any mammal including a human, and a human can be a patient.

A method disclosed herein comprises a treatment for a neurodegenerative disease. A treatment comprises any therapeutic or beneficial effect, including any objective or individually measurable or detectable improvement or benefit provided to a particular individual. A therapeutic or beneficial effect can but need not be complete ablation of all or any particular adverse condition, symptom, disorder, illness, disease or complication caused by or associated with a neurodegenerative disease or pathology. Thus, a satisfactory clinical endpoint is achieved when there is an incremental improvement or a partial reduction in an adverse condition, symptom, disorder, illness, disease or complication caused by or associated with a neurodegenerative disease or pathology, or an inhibition, decrease, reduction, suppression, prevention, limit or control of worsening or progression of one or more conditions, adverse symptoms, disorders, illnesses, diseases or complications caused by or associated with a neurodegenerative disease or pathology over a short or long duration.

In aspects of this embodiment, a method of treatment or use disclosed herein may reduce, decrease, inhibited, limit, delay or prevent a neurodegenerative disease or pathology. In other aspects of this embodiment, a method of treatment or use disclosed herein may decrease, reduce, inhibit, suppresses, prevent, control or limit one or more adverse conditions, symptoms, disorders, illnesses, diseases or complications caused by or associated with a neurodegenerative disease or pathology. In yet other aspects of this embodiment, a method of treatment or use disclosed herein may improve, accelerate, facilitate, enhance, augment, or hasten recovery of an individual from a neurodegenerative disease or pathology, or one or more adverse symptoms, disorders, illnesses, diseases or complications caused by or associated with a neurodegenerative disease or pathology.

In other aspects of this embodiment, a method of treatment or use disclosed herein may stabilize a neurodegenerative disease, pathology, or an adverse condition, symptom, disorder, illness, disease or complication caused by or associated with a neurodegenerative disease or pathology. In yet other aspects of this embodiment, a method of treatment or use disclosed herein may reduce or eliminate the need, dosage frequency or amount of a concurrent or subsequent treatment such as another drug or other agent used for treating an individual having or at risk of having a neurodegenerative disease or pathology. For example, reducing an amount of an adjunct therapy, for example, a reduction or decrease of a treatment for a neurodegenerative disease or pathology.

One or more physiological conditions or symptom associated with a neurodegenerative disease or pathology will respond to a method of treatment disclosed herein. The symptoms of a neurodegenerative disease or pathology vary depending on the phase of disease, but include, without limitation improved CNS function, cognition, learning, memory, plasticity.

The term "CNS function" as used herein refers, inter alia, to receiving and processing sensory information, thinking, learning, memorizing, perceiving, producing and understanding language, controlling motor function and auditory and visual responses, maintaining balance and equilibrium, movement coordination, the conduction of sensory information and controlling such autonomic functions as breathing, heart rate, and digestion.

The terms "cognition", "cognitive function" and "cognitive performance" are used herein interchangeably and are related to any mental process or state that involves but is not limited to learning, memory, creation of imagery, thinking, awareness, reasoning, spatial ability, speech and language skills, language acquisition and capacity for judgment attention. Cognition is formed in multiple areas of the brain such as hippocampus, cortex and other brain structures. However, it is assumed that long term memories are stored at least in part in the cortex and it is known that sensory information is acquired, consolidated and retrieved by a specific cortical structure, the gustatory cortex, which resides within the insular cortex.

In humans, cognitive function may be measured by any know method, for example and without limitation, by the clinical global impression of change scale (CIBIC-plus scale); the Mini Mental State Exam (MMSE); the Neuropsychiatric Inventory (NPI); the Clinical Dementia Rating Scale (CDR); the Cambridge Neuropsychological Test Automated Battery (CANTAB) or the Sandoz Clinical Assessment-Geriatric (SCAG). Cognitive function may also be measured indirectly using imaging techniques such as Positron Emission Tomography (PET), functional magnetic resonance imaging (fMRI), Single Photon Emission Computed Tomography (SPECT), or any other imaging technique that allows one to measure brain function.

An improvement of one or more of the processes affecting the cognition in a patient will signify an improvement of the cognitive function in said patient, thus in certain embodiments improving cognition comprises improving learning, plasticity, and/or long-term memory. The terms "improving" and "enhancing" may be used interchangeably. The term "learning" relates to acquiring or gaining new, or modifying and reinforcing, existing knowledge, behaviors, skills, values, or preferences. The term "memory" relates to the process in which information is encoded, stored, and retrieved. Memory has three distinguishable categories: sensory memory, short-term memory, and long-term memory.

The term "long term memory" is the ability to keep information for a long or unlimited period of time. Long term memory comprises two major divisions: explicit memory (declarative memory) and implicit memory (non-declarative memory). Long term memory is achieved by memory consolidation which is a category of processes that stabilize a memory trace after its initial acquisition. Consolidation is distinguished into two specific processes, synaptic consolidation, which occurs within the first few hours after learning, and system consolidation, where hippocampus-dependent memories become independent of the hippocampus over a period of weeks to years.

The term "plasticity" relates to synaptic plasticity, brain plasticity or neuroplasticity associated with the ability of the brain to change with learning, and to change the already acquired memory. One measurable parameter reflecting plasticity is memory extinction.

Aspects of the present specification provide, in part, administering a modified anti-PD-L1 antibody disclosed herein or therapeutic composition disclosed herein. As used herein, the term "administering" refers to any delivery mechanism that provides an immunogenic composition or therapeutic composition disclosed herein to an individual that potentially results in a clinically, therapeutically, or experimentally beneficial result. The actual delivery mechanism used to administer a composition disclosed herein to an individual can be determined by a person of ordinary skill in the art by taking into account factors, including, without limitation, the type of neurodegenerative disease, the location of the neurodegenerative disease, the cause of the neurodegenerative disease, the severity of the neurodegenerative disease, the degree of relief desired for neurodegenerative disease, the duration of relief desired for neurodegenerative disease, the particular anti-PD-L1 antibody and/or therapeutic composition used, the rate of excretion of the particular anti-PD-L1 antibody and/or therapeutic composition used, the pharmacodynamics of the particular anti-PD-L1 antibody and/or therapeutic composition used, the nature of the other compounds to be included in the therapeutic composition, the particular route of administration, the particular characteristics, history and risk factors of the individual, such as, e.g., age, weight, general health and the like, or any combination thereof.

A composition disclosed herein can be administered to an individual using a cellular uptake approach. Administration of a composition disclosed herein using a cellular uptake approach comprise a variety of enteral or parenteral approaches including, without limitation, oral administration in any acceptable form, such as, e.g., tablet, liquid, capsule, powder, or the like; topical administration in any acceptable form, such as, e.g., drops, spray, creams, gels or ointments; intravascular administration in any acceptable form, such as, e.g., intravenous injection, intravenous infusion, intra-arterial injection, intra-arterial infusion and catheter instillation into the vasculature; perk and intra-tissue administration in any acceptable form, such as, e.g., intraperitoneal injection, intramuscular injection, subcutaneous injection, subcutaneous infusion, intraocular injection, retinal injection, or sub-retinal injection or epidural injection; intravesicular administration in any acceptable form, such as, e.g., catheter instillation; and by placement device, such as, e.g., an implant, a patch, a pellet, a catheter, an osmotic pump, a suppository, a bioerodible delivery system, a non-bioerodible delivery system or another implanted extended or slow release system. An exemplary list of biodegradable polymers and methods of use are described in, e.g., *Handbook of Biodegradable Polymers* (Abraham J. Domb et al., eds., Overseas Publishers Association, 1997).

A modified anti-PD-L1 antibody disclosed herein and/or therapeutic composition disclosed herein is administered in an amount sufficient to treat a neurodegenerative disease. In aspects of this embodiment, the amount of anti-PD-L1 antibody and/or therapeutic composition administered is an amount sufficient to reduce one or more physiological conditions or symptom associated with a neurodegenerative disease or pathology or an amount sufficient to protect the individual against a neurodegenerative disease or pathology. As used herein, the term "amount sufficient" includes "effective amount", "effective dose", "therapeutically effective amount" or "therapeutically effective dose" and refers to the minimum amount of a modified anti-PD-L1 antibody disclosed herein and/or therapeutic composition necessary to achieve the desired therapeutic effect and includes an amount sufficient to reduce or inhibit one or more physiological conditions or symptom associated with a neurodegenerative disease or pathology.

In aspects of this embodiment, an effective amount of a modified anti-PD-L1 antibody disclosed herein and/or therapeutic composition disclosed herein reduces or inhibits one or more physiological conditions or symptom associated with a neurodegenerative disease or pathology by, e.g., at least 10%, at least 20%, at least 30%, at least 40%, at least 50%, at least 60%, at least 70%, at least 80%, at least 90% or at least 100%. In other aspects of this embodiment, an effective amount of a modified anti-PD-L1 antibody disclosed herein and/or therapeutic composition disclosed herein reduces or inhibits one or more physiological conditions or symptom associated with a neurodegenerative disease or pathology by, e.g., at most 10%, at most 20%, at most 30%, at most 40%, at most 50%, at most 60%, at most 70%, at most 80%, at most 90% or at most 100%. In yet other aspects of this embodiment, an effective amount of a modified anti-PD-L1 antibody disclosed herein and/or therapeutic composition disclosed herein reduces or inhibits one or more physiological conditions or symptom associated with a neurodegenerative disease or pathology by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%. In still other aspects of this embodiment, an effective amount of a modified anti-PD-L1 antibody and/or therapeutic composition disclosed herein reduces or inhibits one or more physiological conditions or symptom associated with a neurodegenerative disease or pathology for, e.g., at least one week, at least one month, at least two months, at least three months, at least four months, at least five months, at least six months, at least seven months, at least eight months, at least nine months, at least ten months, at least eleven months, or at least twelve months.

The actual effective amount of a modified anti-PD-L1 antibody disclosed herein and/or therapeutic composition disclosed herein to be administered to an individual can be determined by a person of ordinary skill in the art by taking into account factors, including, without limitation, the type of neurodegenerative disease, the location of the neurodegenerative disease, the cause of the neurodegenerative disease, the severity of the neurodegenerative disease, the degree of relief desired for neurodegenerative disease, the duration of relief desired for neurodegenerative disease, the particular anti-PD-L1 antibody and/or therapeutic composition used, the rate of excretion of the particular anti-PD-L1 antibody and/or therapeutic composition used, the pharmacodynamics of the particular anti-PD-L1 antibody and/or therapeutic composition used, the nature of the other compounds to be included in the immunogenic or therapeutic composition, the particular route of administration used, the particular characteristics, history and risk factors of the individual, such as, e.g., age, weight, general health and the like, or any combination thereof. Additionally, where repeated administration of a modified anti-PD-L1 antibody disclosed herein and/or therapeutic composition disclosed herein is used, the actual therapeutically effective amount will further depend upon factors, including, without limitation, the frequency of administration, the half-life of a modified anti-PD-L1 antibody disclosed herein and/or therapeutic composition disclosed herein, or any combination thereof. It is known by a person of ordinary skill in the art that an effective amount of a modified anti-PD-L1 antibody disclosed herein and/or therapeutic composition disclosed herein can be extrapolated from in vitro assays and in vivo administration studies using animal models prior to administration to humans. Wide variations in the necessary effective amount are to be expected in view of the differing efficiencies of the various routes of administration. For instance, oral administration generally would be expected to require higher dosage levels than administration by intravenous or intravitreal injection. Variations in these dosage levels can be adjusted using standard empirical routines of optimization, which are well-known to a person of ordinary skill in the art. The precise therapeutically effective dosage levels and patterns are preferably determined by the attending physician in consideration of the above-identified factors.

In other aspects of this embodiment, an effective amount of a modified anti-PD-L1 antibody disclosed herein and/or therapeutic composition disclosed herein generally is in the range of about 0.001 mg/kg/day to about 100 mg/kg/day. In aspects of this embodiment, an effective amount of a modified anti-PD-L1 antibody disclosed herein and/or therapeutic composition disclosed herein may be, e.g., at least 0.001 mg/kg/day, at least 0.01 mg/kg/day, at least 0.1 mg/kg/day, at least 1.0 mg/kg/day, or at least 5.0 mg/kg/day. In other aspects of this embodiment, an effective amount of a modified anti-PD-L1 antibody disclosed herein and/or therapeutic composition disclosed herein may be in the range of, e.g., about 0.001 mg/kg/day to about 0.01 mg/kg/day, about 0.001 mg/kg/day to about 0.1 mg/kg/day, about 0.001 mg/kg/day to about 1.0 mg/kg/day, about 0.001 mg/kg/day to about 5.0 mg/kg/day, about 0.01 mg/kg/day to about 0.1 mg/kg/day, about 0.01 mg/kg/day to about 1.0 mg/kg/day, about 0.01 mg/kg/day to about 5.0 mg/kg/day, about 0.1 mg/kg/day to about 1.0 mg/kg/day, about 0.1 mg/kg/day to about 5.0 mg/kg/day, or about 1.0 mg/kg/day to about 5.0 mg/kg/day.

In other aspects of this embodiment, an effective amount of a modified anti-PD-L1 antibody disclosed herein and/or therapeutic composition disclosed herein generally is in the range of about 0.001 mg/day to about 100 mg/day. In aspects of this embodiment, an effective amount of a modified anti-PD-L1 antibody disclosed herein and/or therapeutic composition disclosed herein may be, e.g., at least 0.001 mg/day, at least 0.01 mg/day, at least 0.1 mg/day, at least 1.0 mg/day, at least 5.0 mg/day, at least 10 mg/day, at least 15 mg/day, at least 20 mg/day, at least 25 mg/day, at least 30 mg/day, at least 35 mg/day, at least 40 mg/day, at least 45 mg/day, or at least 50 mg/day.

In other aspects of this embodiment, an effective amount of a modified anti-PD-L1 antibody disclosed herein and/or therapeutic composition disclosed herein may be in the range of, e.g., about 0.001 mg/day to about 10 mg/day, about 0.001 mg/day to about 15 mg/day, about 0.001 mg/day to about 20 mg/day, about 0.001 mg/day to about 25 mg/day, about 0.001 mg/day to about 30 mg/day, about 0.001 mg/day to about 35 mg/day, about 0.001 mg/day to about 40 mg/day, about 0.001 mg/day to about 45 mg/day, about 0.001 mg/day to about 50 mg/day, about 0.001 mg/day to about 75 mg/day, or about 0.001 mg/day to about 100 mg/day. In yet other aspects of this embodiment, an effective amount of a modified anti-PD-L1 antibody disclosed herein and/or therapeutic composition disclosed herein may be in the range of, e.g., about 0.01 mg/day to about 10 mg/day, about 0.01 mg/day to about 15 mg/day, about 0.01 mg/day to about 20 mg/day, about 0.01 mg/day to about 25 mg/day, about 0.01 mg/day to about 30 mg/day, about 0.01 mg/day to about 35 mg/day, about 0.01 mg/day to about 40 mg/day, about 0.01 mg/day to about 45 mg/day, about 0.01 mg/day to about 50 mg/day, about 0.01 mg/day to about 75 mg/day, or about 0.01 mg/day to about 100 mg/day. In still other aspects of this embodiment, an effective amount of a modified anti-PD-L1 antibody disclosed herein and/or therapeutic composition disclosed herein may be in the range of, e.g., about 0.1 mg/day to about 10 mg/day, about 0.1 mg/day to about 15 mg/day, about 0.1 mg/day to about 20 mg/day, about 0.1 mg/day to about 25 mg/day, about 0.1 mg/day to about 30 mg/day, about 0.1 mg/day to about 35 mg/day, about 0.1 mg/day to about 40 mg/day, about 0.1 mg/day to about 45 mg/day, about 0.1 mg/day to about 50 mg/day, about 0.1 mg/day to about 75 mg/day, or about 0.1 mg/day to about 100 mg/day.

In other aspects of this embodiment, an effective amount of a modified anti-PD-L1 antibody disclosed herein and/or therapeutic composition disclosed herein may be in the range of, e.g., about 1 mg/day to about 10 mg/day, about 1 mg/day to about 15 mg/day, about 1 mg/day to about 20 mg/day, about 1 mg/day to about 25 mg/day, about 1 mg/day to about 30 mg/day, about 1 mg/day to about 35 mg/day, about 1 mg/day to about 40 mg/day, about 1 mg/day to about 45 mg/day, about 1 mg/day to about 50 mg/day, about 1 mg/day to about 75 mg/day, or about 1 mg/day to about 100 mg/day. In yet other aspects of this embodiment, an effective amount of a modified anti-PD-L1 antibody disclosed herein and/or therapeutic composition disclosed herein may be in the range of, e.g., about 5 mg/day to about 10 mg/day, about 5 mg/day to about 15 mg/day, about 5 mg/day to about 20 mg/day, about 5 mg/day to about 25 mg/day, about 5 mg/day to about 30 mg/day, about 5 mg/day to about 35 mg/day, about 5 mg/day to about 40 mg/day, about 5 mg/day to about 45 mg/day, about 5 mg/day to about 50 mg/day, about 5 mg/day to about 75 mg/day, or about 5 mg/day to about 100 mg/day.

Dosing can be single dosage or cumulative (serial dosing), and can be readily determined by one skilled in the art. For instance, treatment of a neurodegenerative disease may comprise a one-time administration of an effective amount of a modified anti-PD-L1 antibody disclosed herein and/or therapeutic composition disclosed herein. As a non-limiting example, an effective amount of a modified anti-PD-L1 antibody disclosed herein and/or therapeutic composition disclosed herein can be administered once to an individual, e.g., as a single injection or deposition. Alternatively, treatment of a neurodegenerative disease may comprise multiple administrations of an effective amount of a modified anti-PD-L1 antibody disclosed herein and/or therapeutic composition disclosed herein carried out over a range of time periods, such as, e.g., daily, once every few days, weekly, monthly or yearly. As a non-limiting example, a modified anti-PD-L1 antibody disclosed herein and/or therapeutic composition disclosed herein can be administered one, two, three, four, five or six times yearly to an individual. The timing of administration can vary from individual to individual, depending upon such factors as the severity of an individual's symptoms. For example, an effective amount of a modified anti-PD-L1 antibody disclosed herein and/or therapeutic composition disclosed herein can be administered to an individual once every three months for an indefinite period of time, or until the individual no longer requires therapy. A person of ordinary skill in the art will recognize that the condition of the individual can be monitored throughout the course of treatment and that the effective amount of a modified anti-PD-L1 antibody disclosed herein and/or therapeutic composition disclosed herein that is administered can be adjusted accordingly.

A composition comprising a modified anti-PD-L1 antibody disclosed herein and/or therapeutic composition disclosed herein can also be administered to an individual in combination with other therapeutic compounds to increase the overall therapeutic effect of the treatment. The use of multiple compounds to treat an indication can increase the beneficial effects while reducing the presence of side effects.

In one embodiment, a method or use of treating a neurodegenerative disease comprises a dosage regimen comprising at least two courses of therapy, each course of therapy comprising in sequence a treatment session followed by an interval session of non-treatment. The disclose method or use comprises administering to an individual in need thereof a modified anti-PD-L1 antibody disclosed herein and/or therapeutic composition disclosed herein, wherein the anti-PD-L1 antibody and/or the therapeutic composition disclosed herein is administered by a dosage regime comprising at least two courses of therapy, each course of therapy comprising in sequence a treatment session followed by an interval session of non-treatment.

The term "treatment session" is used interchangeably herein with the terms "treatment period" or "period of treatment" and refers to a session during which a modified anti-PD-L1 antibody disclosed herein and/or therapeutic composition disclosed herein is administered to the individual being treated. A treatment session does not result in a therapeutically effective amount of a modified anti-PD-L1 antibody disclosed herein and/or therapeutic composition disclosed herein to be consistently maintained throughout the treatment session. As discussed in more detail below, sub-therapeutic levels of a modified anti-PD-L1 antibody disclosed herein and/or therapeutic composition disclosed herein occurs during the treatment session. A treatment session can be a single dosing event, or can be a multiple dosing regimen that occurs over a period of time.

The term "non-treatment session" is used interchangeably herein with the terms "non-treatment period", "period of no treatment", "interval session" or "interval session of non-treatment" and refers to a period of time during which a modified anti-PD-L1 antibody disclosed herein and/or therapeutic composition disclosed herein is not administered to the individual being treated. During the non-treatment session the level of a modified anti-PD-L1 antibody disclosed herein and/or therapeutic composition disclosed herein is at sub-therapeutic levels in the individual being treated. As disclosed herein, a "non-treatment session" is not the same event as a period of time that intervenes between a dosing event making up a multiple dosing regimen that occurs over a period of time during a treatment session. If administration of a modified anti-PD-L1 antibody disclosed herein and/or therapeutic composition disclosed herein during a treatment session is a repeated administration, the non-treatment session is longer than the intervening period between these repeated administrations during the treatment session.

The dosage regime may be determined in a number of ways. For example, the level of immunosuppression may be calibrated to a desired level for each patient who is being treated (personalized medicine), by monitoring the level or activity of IFN-γ-producing leukocytes or proliferation rate of leukocytes in response to stimulation individually, and adjusting the treatment session, the frequency of administration and the interval session empirically and personally as determined from the results of the monitoring.

In certain embodiments, the treatment session comprises administering a modified anti-PD-L1 antibody disclosed herein and/or therapeutic composition disclosed herein to the individual to achieve a half maximal effective concentration ($EC_{50}$) and this $EC_{50}$ is maintain during the treatment session for a specified period of time, at which point the administration is then stopped to reduce the level of a modified anti-PD-L1 antibody disclosed herein and/or therapeutic composition disclosed herein to below sub-therapeutic levels. A non-treatment period is maintained for a specified period of time and/or as long as a beneficial effect on cognition is maintained above the level before treatment commencement or above the cognition level before the last treatment session. In aspects of this embodiment, a beneficial effect on cognition is maintained is one that shows an improvement of, e.g. at least 10%, at least 20%, at least 30%, at least 40%, at least 50%, at least 60%, at least 70%, at least 80%, at least 90%, above the cognition level before treatment commencement or above the cognition level before the last treatment session.

In certain embodiments, the treatment session comprises administering a modified anti-PD-L1 antibody disclosed herein and/or therapeutic composition disclosed herein to the individual to achieve a minimal effective concentration (MEC) or more and this MEC is maintain during the treatment session for a specified period of time, at which point the administration is then stopped to reduce the level of a modified anti-PD-L1 antibody disclosed herein and/or therapeutic composition disclosed herein to below sub-therapeutic levels. A non-treatment period is maintained for a specified period of time and/or as long as a beneficial effect on cognition is maintained above the level before treatment commencement or above the cognition level before the last treatment session. In aspects of this embodiment, a beneficial effect on cognition is maintained is one that shows an improvement of, e.g. at least 10%, at least 20%, at least 30%, at least 40%, at least 50%, at least 60%, at least 70%, at least 80%, at least 90%, above the cognition level before treatment commencement or above the cognition level before the last treatment session.

In certain embodiments, the treatment session comprises administering a modified anti-PD-L1 antibody disclosed herein and/or therapeutic composition disclosed herein to the individual to achieve a half maximal inhibitory concentration ($IC_{50}$) and this $IC_{50}$ is maintain during the treatment session for a specified period of time, at which point the administration is then stopped to reduce the level of a modified anti-PD-L1 antibody disclosed herein and/or therapeutic composition disclosed herein to below sub-therapeutic levels. A non-treatment period is maintained for a specified period of time and/or as long as a beneficial effect on cognition is maintained above the level before treatment commencement or above the cognition level before the last treatment session. In aspects of this embodiment, a beneficial effect on cognition is maintained is one that shows an improvement of, e.g. at least 10%, at least 20%, at least 30%, at least 40%, at least 50%, at least 60%, at least 70%, at least 80%, at least 90%, above the cognition level before treatment commencement or above the cognition level before the last treatment session.

In certain embodiments, the treatment session comprises administering a modified anti-PD-L1 antibody disclosed herein and/or therapeutic composition disclosed herein to the individual to achieve a target occupancy of 50% or more and this target occupancy is maintained during the treatment session for a specified period of time, at which point the administration is then stopped to reduce the target occupancy of a modified anti-PD-L1 antibody disclosed herein and/or therapeutic composition disclosed herein to below sub-therapeutic levels. A non-treatment period is maintained for a specified period of time and/or as long as a beneficial effect on cognition is maintained above the level before treatment commencement or above the cognition level before the last treatment session. In aspects of this embodiment, a beneficial effect on cognition is maintained is one that shows an improvement of, e.g. at least 10%, at least 20%, at least 30%, at least 40%, at least 50%, at least 60%, at least 70%, at least 80%, at least 90%, above the cognition level before treatment commencement or above the cognition level before the last treatment session.

In certain embodiments, the treatment session comprises administering a modified anti-PD-L1 antibody disclosed herein and/or therapeutic composition disclosed herein to the individual to achieve a serum concentration of $1\times10^{-9}$ M or more and this serum concentration is maintain during the treatment session for a specified period of time, at which point the administration is then stopped to reduce the serum concentration of a modified anti-PD-L1 antibody disclosed herein and/or therapeutic composition disclosed herein to below sub-therapeutic levels. A non-treatment period is maintained for a specified period of time and/or as long as a beneficial effect on cognition is maintained above the level before treatment commencement or above the cognition level before the last treatment session. In aspects of this embodiment, a beneficial effect on cognition is maintained is one that shows an improvement of, e.g. at least 10%, at least 20%, at least 30%, at least 40%, at least 50%, at least 60%, at least 70%, at least 80%, at least 90%, above the cognition level before treatment commencement or above the cognition level before the last treatment session.

In certain embodiments, the treatment session comprises administering a modified anti-PD-L1 antibody disclosed herein and/or therapeutic composition disclosed herein to the individual to achieve a serum concentration of 0.15 μg/mL or more and this serum concentration is maintain during the treatment session for a specified period of time, at which point the administration is then stopped to reduce the serum concentration of a modified anti-PD-L1 antibody disclosed herein and/or therapeutic composition disclosed herein to below sub-therapeutic levels. A non-treatment period is maintained for a specified period of time and/or as long as a beneficial effect on cognition is maintained above the level before treatment commencement or above the cognition level before the last treatment session. In aspects of this embodiment, a beneficial effect on cognition is maintained is one that shows an improvement of, e.g. at least 10%, at least 20%, at least 30%, at least 40%, at least 50%, at least 60%, at least 70%, at least 80%, at least 90%, above the cognition level before treatment commencement or above the cognition level before the last treatment session.

In certain embodiments, the treatment session may be a single administration or it may comprise multiple administrations given during a prescribed period of time. In aspects of this embodiment, a treatment session may be multiple administrations given in the course of between, e.g., 1 day to one week, 1 day to two weeks, 2 days to two weeks, 3 days to two weeks, 4 days to two weeks, 5 days to two weeks, 6 days to two weeks, one week and two weeks, 10 days and two weeks. For example, the treatment session may comprise two administrations both given within one week, such as, e.g., the second administration given 1, 2, 3, 4, 5 or 6 days after the first administration. As another example, the treatment session may comprise three administrations all given within one week such as, e.g., given 1, 2 or 3 days after the preceding administration. As another example, the treatment session may comprise three administrations all given within two week such as, e.g., given 1, 2, 3, 4 or 5 days after the preceding administration. As another example, the treatment session may comprise four administrations all given within two week such as, e.g., given 1, 2, 3 or 4 days after the preceding administration.

In certain embodiments, the interval session of non-treatment may be between one week and six months, for example between 2 weeks to 4 weeks, 3 weeks to 4 weeks, 2 weeks to 5 weeks, 3 weeks to 5 weeks, 4 weeks to 5 weeks, 2 weeks to 6 weeks, 3 weeks to 6 weeks, 4 weeks to 6 weeks, 5 weeks to 6 weeks, 2 weeks to 2 months, 3 weeks to 2 months, 4 weeks to 2 months, 5 weeks to 2 months, 6 weeks to 2 months, 7 weeks to 2 months, 2 months to 3 months, 2 months to 4 months, 3 months to 4 months, 3 months to 5 months, 3 months to 5 months, 4 months to 5 months, 1 week to 6 months, 2 weeks to 6 months, 3 weeks to 6 months, 4 weeks to 6 months, 6 weeks to 6 months, 2 months to 6 months, 3 months to 6 months, 4 months to 6 months or 5 months to 6 months. In certain embodiments, the interval session of non-treatment may be 1 to 2 months in length, 1 to 3 months in length or 2 to 3 months in length.

In the treatment session, the administration of a modified anti-PD-L1 antibody disclosed herein and/or therapeutic composition disclosed herein may be a single administration or repeated administration, for example a modified anti-PD-L1 antibody disclosed herein and/or therapeutic composition disclosed herein may be administered only once and then immediately followed by an non-treatment session, or it may be administered daily, or once every two, three, four, five or six days, or once weekly for two weeks. These frequencies may be based on commonly used practices in the art, and may finally be determined by physicians in clinical trials. Alternatively, the frequency of the repeated administration in the treatment session could be adapted according to the nature of a modified anti-PD-L1 antibody disclosed herein and/or therapeutic composition disclosed herein. It should be understood that when a modified anti-PD-L1 antibody disclosed herein and/or therapeutic composition disclosed herein is administered during a treatment session at a relatively low frequency, for example once per week for two weeks, this treatment session is followed by a non-treatment interval session, the length of which is longer than the period between the repeated administrations during the treatment session (i.e. longer than one week in this example). The pause of one week between administrations during the treatment session in this example is not considered an interval session.

If the treatment session consists of a single administration of a modified anti-PD-L1 antibody disclosed herein and/or therapeutic composition disclosed herein, the dosage regimen is determined by the length of the non-treatment interval, so that a single administration of a modified anti-PD-L1 antibody disclosed herein and/or therapeutic composition disclosed herein is followed by a non-treatment interval of 7, 8, 9, 10, 12, 14, 18, 21, 24, 28 or 30 days or longer before the next single-administration treatment session. In particular, the dosage regimen consists of single administrations interspersed with non-treatment intervals of non-treatment of 2, 3 or 4 weeks. In addition, the dosage regimen may consist of a single administration of a modified anti-PD-L1 antibody disclosed herein and/or therapeutic composition disclosed herein interspersed with non-treatment intervals of non-treatment of 2 to 4 weeks, 2 to 3 weeks or 3 to 4 weeks.

If the treatment session consists of multiple administrations, the dosage regimen is determined by the length of the non-treatment interval, so that multiple administrations of a modified anti-PD-L1 antibody disclosed herein and/or therapeutic composition disclosed herein given within one week is followed by a non-treatment interval of 7, 10, 12, 14, 18, 21, 24, 28 or 30 days or longer before the next multiple-administration treatment session. In particular, the dosage regimen may consist of multiple administrations of a modified anti-PD-L1 antibody disclosed herein and/or therapeutic composition disclosed herein given within one week interspersed with non-treatment intervals of non-treatment of 2 or 3 or 4 weeks. In addition, the dosage regimen may consist of multiple administrations of a modified anti-PD-L1 antibody disclosed herein and/or therapeutic composition disclosed herein given within one week interspersed with intervals of non-treatment of 2 to 4 weeks, 2 to 3 weeks or 3 to 4 weeks.

As another example, the dosage regimen may comprise a treatment session including multiple administrations of a modified anti-PD-L1 antibody disclosed herein and/or therapeutic composition disclosed herein given within two weeks followed by a non-treatment interval of 2 weeks, 3 weeks or 1, 2, 3 or 4 months or longer before the next multiple-administration treatment session. In particular, the dosage regimen may comprise a treatment session including multiple administrations of a modified anti-PD-L1 antibody disclosed herein and/or therapeutic composition disclosed herein given within two weeks interspersed with intervals of non-treatment of 1, 2, 3 or 4 months. In addition, the dosage regimen may comprise a treatment session including multiple administrations of a modified anti-PD-L1 antibody disclosed herein and/or therapeutic composition disclosed herein given within two weeks interspersed with intervals of non-treatment of 1 to 2 months, 1 to 3 months, 1 to 4 months, 2 to 3 months, 2 to 4 months or 3 to 4 months.

As another example, the dosage regimen may comprise a treatment session including a single administration of a modified anti-PD-L1 antibody disclosed herein and/or therapeutic composition disclosed herein to achieve a serum concentration of $1\times10^{-9}$ M or more of the anti-PD-L1 antibody and this serum concentration is maintained during the treatment session for about 4 to about 7 days, about 5 to about 10 days, about 7 to about 10 days, or about 7 to about 14 days at which point the level of the anti-PD-L1 antibody is sub-therapeutic. This treatment session is followed by a non-treatment session where the serum concentration of a modified anti-PD-L1 antibody disclosed herein is at sub-therapeutic level and a non-treatment period is maintained for about 10 to about 30 days before the next treatment session is conducted. The reduction of the serum concentration of a modified anti-PD-L1 antibody disclosed herein during the treatment session can be achieved actively or passively.

As another example, the dosage regimen may comprise a treatment session including a single administration of a modified anti-PD-L1 antibody disclosed herein and/or therapeutic composition disclosed herein to achieve a serum concentration of 0.15 μg/mL or more of the anti-PD-L1 antibody and this serum concentration is maintained during the treatment session for about 4 to about 7 days, about 5 to about 10 days, about 7 to about 10 days, or about 7 to about 14 days at which point the level of the anti-PD-L1 antibody is sub-therapeutic. This treatment session is followed by a non-treatment session where the serum concentration of a modified anti-PD-L1 antibody disclosed herein is at sub-therapeutic level and a non-treatment period is maintained for about 10 to about 30 days before the next treatment session is conducted. The reduction of the serum concentration of a modified anti-PD-L1 antibody disclosed herein can be achieved actively or passively.

As another example, the dosage regimen may comprise a treatment session including a single administration of a modified anti-PD-L1 antibody disclosed herein and/or therapeutic composition disclosed herein to achieve an $EC_{50}$, a MEC or an $IC_{50}$ for a period of about 4 to about 7 days, about 5 to about 10 days, about 7 to about 10 days, or about 7 to about 14 days at which point the level of the anti-PD-L1 antibody is sub-therapeutic. This treatment session is followed by a non-treatment session where the level of a modified anti-PD-L1 antibody disclosed herein is at sub-therapeutic level for a period of about 10 to about 30 days before the next treatment session is conducted. The reduction of a modified anti-PD-L1 antibody disclosed herein can be achieved actively or passively.

As another example, the dosage regimen may comprise a treatment session including a single administration of a modified anti-PD-L1 antibody disclosed herein and/or therapeutic composition disclosed herein to achieve target occupancy of 50% or more for the anti-PD-L1 antibody for a period of about 4 to about 7 days, about 5 to about 10 days, about 7 to about 10 days, or about 7 to about 14 days at which point the level of the anti-PD-L1 antibody is sub-therapeutic. This treatment session is followed by a non-treatment session where target occupancy of a modified anti-PD-L1 antibody disclosed herein is at sub-therapeutic level for a period of about 10 to about 30 days before the next treatment session is conducted. The reduction of target occupancy of a modified anti-PD-L1 antibody disclosed herein can be achieved actively or passively.

As another example, the dosage regimen may comprise a treatment session including a single administration of a modified anti-PD-L1 antibody disclosed herein and/or therapeutic composition disclosed herein to increase serum concentration of an IFN-γ to 1-fold or more above basal level and this IFN-γ serum concentration is maintained during the treatment session for about 4 to about 7 days, about 5 to about 10 days, about 7 to about 10 days, or about 7 to about 14 days at which point the serum concentration of the IFN-γ is sub-therapeutic. This treatment session is followed by a non-treatment session where the serum concentration of the IFN-γ is at a sub-therapeutic level and a non-treatment period is maintained for about 10 to about 30 days before the next treatment session is conducted. The reduction of the IFN-γ serum concentration can be achieved actively or passively.

As another example, the dosage regimen may comprise a treatment session including a single administration of a modified anti-PD-L1 antibody disclosed herein and/or therapeutic composition disclosed herein to increase serum concentration of an CXCL10 to 1-fold or more above basal level and this CXCL10 serum concentration is maintained during the treatment session for about 4 to about 7 days, about 5 to about 10 days, about 7 to about 10 days, or about 7 to about 14 days at which point the serum concentration of the CXCL10 is sub-therapeutic. This treatment session is followed by a non-treatment session where the serum concentration of the CXCL10 is at a sub-therapeutic level and a non-treatment period is maintained for about 10 to about 30 days before the next treatment session is conducted. The reduction of the CXCL10 serum concentration can be achieved actively or passively.

As another example, the dosage regimen may comprise a treatment session including a single administration of a modified anti-PD-L1 antibody disclosed herein and/or therapeutic composition disclosed herein to increase a memory T cell population of 50% or more above basal level and this memory T cell population level is maintained during the treatment session for about 4 to about 7 days, about 5 to about 10 days, about 7 to about 10 days, or about 7 to about 14 days at which point the memory T cell population level is sub-therapeutic. This treatment session is followed by a non-treatment session where the memory T cell population level is at a sub-therapeutic level and a non-treatment period is maintained for about 10 to about 30 days before the next treatment session is conducted. The reduction of the memory T cell population level can be achieved actively or passively.

As another example, the dosage regimen may comprise a treatment session including multiple administrations of a modified anti-PD-L1 antibody disclosed herein and/or therapeutic composition disclosed herein to achieve a serum concentration of $1\times10^{-9}$ M or more of anti-PD-L1 antibody and this serum concentration is maintained during the treatment session for about 4 to about 7 days, about 5 to about 10 days, about 7 to about 10 days, or about 7 to about 14 days at which point the level of the anti-PD-L1 antibody is sub-therapeutic. This treatment session is followed by a non-treatment session where the serum concentration of a modified anti-PD-L1 antibody disclosed herein is at a sub-therapeutic level and a non-treatment period is maintained for about 10 to about 30 days before the next treatment session is conducted. The reduction of the serum concentration of a modified anti-PD-L1 antibody disclosed herein can be achieved actively or passively.

As another example, the dosage regimen may comprise a treatment session including multiple administrations of a modified anti-PD-L1 antibody disclosed herein and/or therapeutic composition disclosed herein to achieve a serum concentration of 0.15 μg/mL or more of anti-PD-L1 antibody and this serum concentration is maintained during the treatment session for about 4 to about 7 days, about 5 to about 10 days, about 7 to about 10 days, or about 7 to about 14 days at which point the level of the anti-PD-L1 antibody is sub-therapeutic. This treatment session is followed by a non-treatment session where the serum concentration of a modified anti-PD-L1 antibody disclosed herein is at a sub-therapeutic level and a non-treatment period is maintained for about 10 to about 30 days before the next treatment session is conducted. The reduction of the serum concentration of a modified anti-PD-L1 antibody disclosed herein can be achieved actively or passively.

As another example, the dosage regimen may comprise a treatment session including multiple administrations of a modified anti-PD-L1 antibody disclosed herein and/or therapeutic composition disclosed herein to achieve an $EC_{50}$, a MEC or an $IC_{50}$ for a period of about 4 to about 7 days, about 5 to about 10 days, about 7 to about 10 days, or about 7 to about 14 days at which point the level of the anti-PD-L1 antibody is sub-therapeutic. This treatment session is followed by a non-treatment session where the level of the anti-PD-L1 antibody is at sub-therapeutic level for a period of about 10 to about 30 days before the next treatment session is conducted. The reduction of a modified anti-PD-L1 antibody disclosed herein can be achieved actively or passively.

As another example, the dosage regimen may comprise a treatment session including multiple administrations of a modified anti-PD-L1 antibody disclosed herein and/or therapeutic composition disclosed herein to achieve target occupancy of 50% or more for the anti-PD-L1 antibody for a period of about 4 to about 7 days, about 5 to about 10 days, about 7 to about 10 days, or about 7 to about 14 days at which point the level of the anti-PD-L1 antibody is sub-therapeutic. This treatment session is followed by a non-treatment session where target occupancy of a modified anti-PD-L1 antibody disclosed herein is at a sub-therapeutic level for a period of about 10 to about 30 days before the next treatment session is conducted. The reduction of target occupancy of a modified anti-PD-L1 antibody disclosed herein can be achieved actively or passively.

As another example, the dosage regimen may comprise a treatment session including multiple administrations of a modified anti-PD-L1 antibody disclosed herein and/or therapeutic composition disclosed herein to increase serum concentration of an IFN-γ to 1-fold or more above basal level and this IFN-γ serum concentration is maintained during the treatment session for about 4 to about 7 days, about 5 to about 10 days, about 7 to about 10 days, or about 7 to about 14 days at which point the serum concentration of the IFN-γ is sub-therapeutic. This treatment session is followed by a non-treatment session where the serum concentration of the IFN-γ is at a sub-therapeutic level and a non-treatment period is maintained for about 10 to about 30 days before the next treatment session is conducted. The reduction of the IFN-γ serum concentration can be achieved actively or passively.

As another example, the dosage regimen may comprise a treatment session including multiple administrations of a modified anti-PD-L1 antibody disclosed herein and/or therapeutic composition disclosed herein to increase serum concentration of an CXCL10 to 1-fold or more above basal level and this CXCL10 serum concentration is maintained during the treatment session for about 4 to about 7 days, about 5 to about 10 days, about 7 to about 10 days, or about 7 to about 14 days at which point the serum concentration of the CXCL10 is sub-therapeutic. This treatment session is followed by a non-treatment session where the serum concentration of the CXCL10 is at a sub-therapeutic level and a non-treatment period is maintained for about 10 to about 30 days before the next treatment session is conducted. The reduction of the CXCL10 serum concentration can be achieved actively or passively.

As another example, the dosage regimen may comprise a treatment session including multiple administrations of a modified anti-PD-L1 antibody disclosed herein and/or therapeutic composition disclosed herein to increase a memory T cell population of 50% or more above basal level and this memory T cell population level is maintained during the treatment session for about 4 to about 7 days, about 5 to about 10 days, about 7 to about 10 days, or about 7 to about 14 days at which point the memory T cell population level is sub-therapeutic. This treatment session is followed by a non-treatment session where the memory T cell population level is at a sub-therapeutic level and a non-treatment period is maintained for about 10 to about 30 days before the next treatment session is conducted. The reduction of the memory T cell population level can be achieved actively or passively.

Aspects of the present specification disclose, in part, a polynucleotide comprising a nucleic acid sequence encoding a modified anti-PD-L1 antibody disclosed herein. In one embodiment, a polynucleotide comprises a nucleic acid sequence encodes a heavy chain of a modified anti-PD-L1 antibody disclosed herein. A polynucleotide comprising a nucleic acid sequence encoding a heavy chain of a modified anti-PD-L1 antibody disclosed herein can be codon-optimized. In addition, a polynucleotide comprising a nucleic acid sequence encoding a heavy chain of a modified anti-PD-L1 antibody disclosed herein can further include a polynucleotide encoding a signal peptide useful to effectively process the encoded polypeptide when expressed in a cell-cased expression system. In aspects of this embodiment, polynucleotide comprising a nucleic acid sequence encoding a heavy chain of a modified anti-PD-L1 antibody disclosed herein comprises SEQ ID NO: 58, SEQ ID NO: 59, SEQ ID NO: 60, SEQ ID NO: 61, SEQ ID NO: 62, SEQ ID NO: 63, SEQ ID NO: 64, or SEQ ID NO: 65. In other aspects of this embodiment, polynucleotide comprising a nucleic acid sequence encoding a heavy chain of a modified anti-PD-L1 antibody disclosed herein comprises SEQ ID NO: 74, SEQ ID NO: 75, SEQ ID NO: 76, SEQ ID NO: 77, SEQ ID NO: 78, SEQ ID NO: 79, SEQ ID NO: 80, or SEQ ID NO: 81.

In one embodiment, a polynucleotide comprises a nucleic acid sequence encodes a light chain of a modified anti-PD-L1 antibody disclosed herein. A polynucleotide comprising a nucleic acid sequence encoding a light chain of a modified anti-PD-L1 antibody disclosed herein can be codon-optimized. In addition, a polynucleotide comprising a nucleic acid sequence encoding a light chain of a modified anti-PD-L1 antibody disclosed herein can further include a polynucleotide encoding a signal peptide useful to effectively process the encoded polypeptide when expressed in a cell-cased expression system. In aspects of this embodiment, polynucleotide comprising a nucleic acid sequence encoding a light chain of a modified anti-PD-L1 antibody disclosed herein comprises SEQ ID NO: 82, or SEQ ID NO: 83. In other aspects of this embodiment, polynucleotide encoding a light chain of a modified anti-PD-L1 antibody disclosed herein comprises SEQ ID NO: 86, or SEQ ID NO: 87.

Aspects of the present specification disclose, in part, an expression construct. An expression construct comprises a polynucleotide disclosed herein operably-linked to an expression vector useful for expressing the polypeptide encoded by a nucleic acid sequence disclosed herein in a cell or cell-free extract. A wide variety of expression vectors can be employed for expressing a polynucleotide molecule encoding a modified Clostridial toxin, including, without limitation, a viral expression vector; a prokaryotic expression vector; eukaryotic expression vectors, such as, e.g., a yeast expression vector, an insect expression vector and a mammalian expression vector; and a cell-free extract expression vector. It is further understood that expression vectors can include control elements such as, e.g., a constitutive, tissue-specific, cell-specific or inducible promoter element, enhancer element or both.

Typically, a polynucleotide disclosed herein is subcloned into an expression vector to create an expression construct. In some embodiments, separate expression constructs are produced, with one expression construct encoding a polynucleotide encoding a heavy chain of a modified anti-PD-L1 antibody disclosed herein and another expression construct encoding a polynucleotide encoding a light chain of a modified anti-PD-L1 antibody disclosed herein. In some embodiments, a single expression construct encodes both a heavy chain of a modified anti-PD-L1 antibody disclosed herein and a light chain of a modified anti-PD-L1 antibody disclosed herein. Such single expression constructs can comprise an internal ribosome entry site (IRES) between the nucleic acid sequence encoding for the heavy chain of a modified anti-PD-L1 antibody disclosed herein and the nucleic acid sequence encoding for the light chain of a modified anti-PD-L1 antibody disclosed herein. In certain embodiments, the nucleotide sequence per se or of the vector's nucleic acid molecule comprises a viral self-cleaving 2A peptide between the nucleotide sequence encoding for the heavy chain and the nucleotide sequence encoding for the light chain. In particular the viral self-cleaving 2A peptide may be selected from the group consisting of T2A from Thosea asigna virus (TaV), F2A from Foot-and-mouth disease virus (FMDV), E2A from Equine rhinitis A virus (ERAV) and P2A from Porcine teschovirus-1 (PTV1).

An expression construct disclosed herein can be transiently or stably introduced into and maintained in appropriate host cells by, e.g., transfection or transduction, for expression and proper assembly of a modified anti-PD-L1 antibody disclosed herein. Stably-maintained expression constructs may be extra-chromosomal and replicate autonomously, or they may be integrated into the chromosomal material of the cell and replicate non-autonomously. The subsequently expressed modified anti-PD-L1 antibody can then be purified, isolated and examined for activity. Procedures and method for the recombinant production of antibodies as well as methods of screening for activity are well known to a person of ordinary skill in the art.

Aspects of the present specification can also be described as follows:

1. A modified anti-Programmed Death Ligand 1 (PD-L1) antibody which specifically binds to a human PD-L1, wherein the modified anti-PD-L1 antibody has one or more amino acid modifications to enhance a clearance rate of the modified anti-PD-L1 antibody from the blood relative to an anti-PD-L1 antibody without the one or more amino acid modifications.
2. The modified anti-PD-L1 antibody according to embodiment 1, wherein the modified anti-PD-L1 antibody further comprises one or more amino acid modifications to abolish Fc-related effector function.
3. A modified anti-Programmed Death Ligand 1 (PD-L1) antibody which specifically binds to a human PD-L1, wherein the modified anti-PD-L1 antibody has one or more amino acid modifications to enhanced a clearance rate of the modified anti-PD-L1 antibody from the blood relative to an anti-PD-L1 antibody without the one or more amino acid modifications and wherein the modified anti-PD-L1 antibody further comprises one or more amino acid modifications to abolish Fc-related effector function.
4. The modified anti-PD-L1 antibody according to any one of embodiments 1 or 3, comprising a heavy chain of SEQ ID NO: 38, wherein the one or more amino acid modifications to enhance a clearance rate of the modified anti-PD-L1 antibody is located at H315 and H440.

5. The modified anti-PD-L1 antibody according to any one of embodiments 2-4, further comprising a heavy chain of SEQ ID NO: 38, wherein the one or more amino acid modifications to abolish Fc-related effector function are located at L239, L240, and K327.
6. The modified anti-PD-L1 antibody according to embodiment 5, wherein the heavy chain is SEQ ID NO: 41, SEQ ID NO: 42, SEQ ID NO: 43, or SEQ ID NO: 44.
7. The modified anti-PD-L1 antibody according to any one of embodiments 1-6, further comprising a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15.
8. The modified anti-PD-L1 antibody according to embodiment 7, wherein the light chain variable region is SEQ ID NO: 9.
9. The modified anti-PD-L1 antibody according to embodiment 7 or 8, wherein the light chain further comprises a light chain constant region.
10. The modified anti-PD-L1 antibody according to any one of embodiments 1 or 3, comprising a heavy chain constant domain of SEQ ID NO: 108, wherein the one or more amino acid modifications to enhance a clearance rate of the modified anti-PD-L1 antibody is located at H315 and H440.
11. The modified anti-PD-L1 antibody according to any one of embodiments 2-4, further comprising a heavy chain constant domain of SEQ ID NO: 108, wherein the one or more amino acid modifications to abolish Fc-related effector function are located at L239, L240, and K327.
12. The modified anti-PD-L1 antibody according to embodiment 11, wherein the heavy chain constant domain is SEQ ID NO: 54, SEQ ID NO: 55, SEQ ID NO: 56, or SEQ ID NO: 57.
13. The modified anti-PD-L1 antibody according to any one of embodiments 10-12 further comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8; and a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15.
14. The modified anti-PD-L1 antibody according to embodiment 13, wherein the heavy chain variable region is SEQ ID NO: 2.
15. The modified anti-PD-L1 antibody according to embodiment 13 or 14, wherein the light chain variable region is SEQ ID NO: 9.
16. The modified anti-PD-L1 antibody according to embodiment 15, wherein the light chain further comprises a light chain constant region.
17. A modified anti-Programmed Death Ligand 1 (PD-L1) antibody which specifically binds to a human PD-L1, the modified anti-PD-L1 antibody comprising a heavy chain and a light chain, wherein the modified anti-PD-L1 antibody has one or more amino acid modifications in the heavy chain to enhance a clearance rate of the modified anti-PD-L1 antibody from the blood relative to an anti-PD-L1 antibody without the one or more amino acid modifications.
18. The modified anti-PD-L1 antibody according to embodiment 17, wherein the modified anti-PD-L1 antibody further comprises one or more amino acid modifications in the heavy chain to abolish Fc-related effector function.
19. A modified anti-Programmed Death Ligand 1 (PD-L1) antibody which specifically binds to a human PD-L1, the modified anti-PD-L1 antibody comprising a heavy chain and a light chain, wherein the modified anti-PD-L1 antibody has one or more amino acid modifications in the heavy chain to enhance a clearance rate of the modified anti-PD-L1 antibody from the blood relative to an anti-PD-L1 antibody without the one or more amino acid modifications and wherein the modified anti-PD-L1 antibody further comprises one or more amino acid modifications in the heavy chain to abolish Fc-related effector function.
20. The modified anti-PD-L1 antibody according to any one of embodiments 17 or 19, wherein the heavy chain is SEQ ID NO: 38, and wherein the one or more amino acid modifications to enhance a clearance rate of the modified anti-PD-L1 antibody is located at H315 and H440.
21. The modified anti-PD-L1 antibody according to any one of embodiments 18-20, wherein the heavy chain is SEQ ID NO: 38, and wherein the one or more amino acid modifications to abolish Fc-related effector function are located at L239, L240, and K327.
22. The modified anti-PD-L1 antibody according to embodiment 21, wherein the heavy chain is SEQ ID NO: 41, SEQ ID NO: 42, SEQ ID NO: 43, or SEQ ID NO: 44.
23. The modified anti-PD-L1 antibody according to any one of embodiments 17-22, wherein the light chain comprises a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15.
24. The modified anti-PD-L1 antibody according to embodiment 23, wherein the light chain variable region is SEQ ID NO: 9.
25. The modified anti-PD-L1 antibody according to embodiment 23 or 24, wherein the light chain further comprises a light chain constant region.
26. The modified anti-PD-L1 antibody according to any one of embodiments 17 or 19, wherein the heavy chain comprises a heavy chain constant domain of SEQ ID NO: 108, and wherein the one or more amino acid modifications to enhance a clearance rate of the modified anti-PD-L1 antibody is located at H315 and H440.
27. The modified anti-PD-L1 antibody according to any one of embodiments 18-20, wherein the heavy chain comprises a heavy chain constant domain of SEQ ID NO: 108, and wherein the one or more amino acid modifications to abolish Fc-related effector function are located at L239, L240, and K327.
28. The modified anti-PD-L1 antibody according to embodiment 27, wherein the heavy chain constant domain is SEQ ID NO: 54, SEQ ID NO: 55, SEQ ID NO: 56, or SEQ ID NO: 57.
29. The modified anti-PD-L1 antibody according to any one of embodiments 26-28 further comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8; and a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15.
30. The modified anti-PD-L1 antibody according to embodiment 29, wherein the heavy chain variable region is SEQ ID NO: 2.

31. The modified anti-PD-L1 antibody according to embodiment 29 or 30, wherein the light chain variable region is SEQ ID NO: 9.
32. The modified anti-PD-L1 antibody according to embodiment 31, wherein the light chain further comprises a light chain constant region.
33. A modified anti-Programmed Death Ligand 1 (PD-L1) antibody which specifically binds to a human PD-L1, the modified anti-PD-L1 antibody comprising a heavy chain including a heavy chain variable domain and a heavy chain constant domain and a light chain including a light chain variable domain and a light chain constant domain, wherein the modified anti-PD-L1 antibody has one or more amino acid modifications in the heavy chain constant domain to enhance a clearance rate of the modified anti-PD-L1 antibody from the blood relative to an anti-PD-L1 antibody without the one or more amino acid modifications.
34. The modified anti-PD-L1 antibody according to embodiment 7, wherein the modified anti-PD-L1 antibody further comprises one or more amino acid modifications in the heavy chain constant domain to abolish Fc-related effector function.
35. A modified anti-Programmed Death Ligand 1 (PD-L1) antibody which specifically binds to a human PD-L1, the modified anti-PD-L1 antibody comprising a heavy chain including a heavy chain variable domain and a heavy chain constant domain and a light chain including a light chain variable domain and a light chain constant domain, wherein the modified anti-PD-L1 antibody has one or more amino acid modifications in the heavy chain constant domain to enhance a clearance rate of the modified anti-PD-L1 antibody from the blood relative to an anti-PD-L1 antibody without the one or more amino acid modifications, and wherein the modified anti-PD-L1 antibody having one or more amino acid modifications in the heavy chain constant domain to abolish Fc-related effector function.
36. The modified anti-PD-L1 antibody according to any one of embodiments 33 or 35, wherein the heavy chain is SEQ ID NO: 38, and wherein the one or more amino acid modifications to enhance a clearance rate of the modified anti-PD-L1 antibody is located at H315 and H440.
37. The modified anti-PD-L1 antibody according to any one of embodiments 34-36, wherein the heavy chain is SEQ ID NO: 38, and wherein the one or more amino acid modifications to abolish Fc-related effector function are located at L239, L240, and K327.
38. The modified anti-PD-L1 antibody according to embodiment 37, wherein the heavy chain is SEQ ID NO: 41, SEQ ID NO: 42, SEQ ID NO: 43, or SEQ ID NO: 44.
39. The modified anti-PD-L1 antibody according to any one of embodiments 33-38, wherein the light chain variable region includes a CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15.
40. The modified anti-PD-L1 antibody according to embodiment 39, wherein the light chain variable region is SEQ ID NO: 9.
41. The modified anti-PD-L1 antibody according to any one of embodiments 33 or 35, wherein the heavy chain constant domain of SEQ ID NO: 108, and wherein the one or more amino acid modifications to enhance a clearance rate of the modified anti-PD-L1 antibody is located at H315 and H440.
42. The modified anti-PD-L1 antibody according to any one of embodiments 34-36, wherein the heavy chain constant domain of SEQ ID NO: 108, and wherein the one or more amino acid modifications to abolish Fc-related effector function are located at L239, L240, and K327.
43. The modified anti-PD-L1 antibody according to embodiment 42, wherein the heavy chain constant domain is SEQ ID NO: 54, SEQ ID NO: 55, SEQ ID NO: 56, or SEQ ID NO: 57.
44. The modified anti-PD-L1 antibody according to any one of embodiments 41-43, wherein the heavy chain variable region includes a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8; and the light chain variable region includes a CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15.
45. The modified anti-PD-L1 antibody according to embodiment 44, wherein the heavy chain variable region is SEQ ID NO: 2.
46. The modified anti-PD-L1 antibody according to embodiment 44 or 45, wherein the light chain variable region is SEQ ID NO: 9.
47. A modified anti-Programmed Death Ligand 1 (PD-L1) antibody which specifically binds to a human PD-L1, the modified anti-PD-L1 antibody comprising a heavy chain including a heavy chain variable domain and a heavy chain constant domain comprising a lower hinge region, a CH2 domain and a CH3 domain and a light chain including a light chain variable domain and a light chain constant domain, wherein the modified anti-PD-L1 antibody has one or more amino acid modifications in the CH2 domain and/or the CH3 domain to enhance a clearance rate of the modified anti-PD-L1 antibody from the blood relative to an anti-PD-L1 antibody without the one or more amino acid modifications.
48. The modified anti-PD-L1 antibody according to embodiment 47, wherein the modified anti-PD-L1 antibody further comprises one or more amino acid modifications in the lower hinge region and/or the CH2 domain to abolish Fc-related effector function.
49. A modified anti-Programmed Death Ligand 1 (PD-L1) antibody which specifically binds to a human PD-L1, the modified anti-PD-L1 antibody comprising a heavy chain including a heavy chain variable domain and a heavy chain constant domain comprising a lower hinge region, a CH2 domain and a CH3 domain and a light chain including a light chain variable domain and a light chain constant domain, wherein the modified anti-PD-L1 antibody has one or more amino acid modifications in the CH2 domain and/or the CH3 domain to enhanced a clearance rate of the modified anti-PD-L1 antibody from the blood relative to an anti-PD-L1 antibody without the one or more amino acid modifications, and wherein the modified anti-PD-L1 antibody having one or more amino acid modifications in the lower hinge region and/or the CH2 domain to abolished Fc-related effector function.
50. The modified anti-PD-L1 antibody according to any one of embodiments 47 or 49, wherein the heavy chain is SEQ ID NO: 38, and wherein the one or more amino acid modifications to enhance a clearance rate of the modified anti-PD-L1 antibody is located at H315 and H440.
51. The modified anti-PD-L1 antibody according to any one of embodiments 48-50, wherein the heavy chain is SEQ ID NO: 38, and wherein the one or more amino acid modifications to abolish Fc-related effector function are located at L239, L240, and K327.

52. The modified anti-PD-L1 antibody according to embodiment 51, wherein the heavy chain is SEQ ID NO: 41, SEQ ID NO: 42, SEQ ID NO: 43, or SEQ ID NO: 44.

53. The modified anti-PD-L1 antibody according to any one of embodiments 47-52, wherein the light chain variable region includes a CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15.

54. The modified anti-PD-L1 antibody according to embodiment 53, wherein the light chain variable region is SEQ ID NO: 9.

55. The modified anti-PD-L1 antibody according to any one of embodiments 47 or 49, wherein the heavy chain constant domain of SEQ ID NO: 108, and wherein the one or more amino acid modifications to enhance a clearance rate of the modified anti-PD-L1 antibody is located at H315 and H440.

56. The modified anti-PD-L1 antibody according to any one of embodiments 48-50, wherein the heavy chain constant domain of SEQ ID NO: 108, and wherein the one or more amino acid modifications to abolish Fc-related effector function are located at L239, L240, and K327.

57. The modified anti-PD-L1 antibody according to embodiment 56, wherein the heavy chain constant domain is SEQ ID NO: 54, SEQ ID NO: 55, SEQ ID NO: 56, or SEQ ID NO: 57.

58. The modified anti-PD-L1 antibody according to any one of embodiments 55-57, wherein the heavy chain variable region includes a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8; and the light chain variable region includes a CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15.

59. The modified anti-PD-L1 antibody according to embodiment 58, wherein the heavy chain variable region is SEQ ID NO: 2.

60. The modified anti-PD-L1 antibody according to embodiment 58 or 59, wherein the light chain variable region is SEQ ID NO: 9.

61. A modified anti-Programmed Death Ligand 1 (PD-L1) antibody, comprising a heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, and a heavy chain constant region of SEQ ID NO: 54, SEQ ID NO: 55, SEQ ID NO: 56, or SEQ ID NO: 57; and a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15, wherein the modified anti-PD-L1 antibody has a clearance rate from the blood that is enhanced relative to an unmodified anti-PD-L1 antibody; and wherein the modified anti-PD-L1 antibody lacks Fc-related effector function.

62. The modified anti-PD-L1 antibody according to embodiment 61, wherein the heavy chain variable region is SEQ ID NO: 2.

63. The modified anti-PD-L1 antibody according to embodiment 61 or 62, wherein the heavy chain constant region of SEQ ID NO: 54.

64. The modified anti-PD-L1 antibody according to embodiment 63, wherein the heavy chain is SEQ ID NO: 41.

65. The modified anti-PD-L1 antibody according to embodiment 61 or 62, wherein the heavy chain constant region is SEQ ID NO: 55.

66. The modified anti-PD-L1 antibody according to embodiment 65, wherein the heavy chain is SEQ ID NO: 42.

67. The modified anti-PD-L1 antibody according to embodiment 61 or 62, wherein the heavy chain constant region is SEQ ID NO: 56.

68. The modified anti-PD-L1 antibody according to embodiment 67, wherein the heavy chain is SEQ ID NO: 43.

69. The modified anti-PD-L1 antibody according to embodiment 61 or 62, wherein the heavy chain constant region is SEQ ID NO: 57.

70. The modified anti-PD-L1 antibody according to embodiment 69, wherein the heavy chain is SEQ ID NO: 44.

71. The modified anti-PD-L1 antibody according to any one of embodiments 61-70, wherein the light chain further comprises a light chain constant region.

72. The anti-PD-L1 antibody according to embodiment 71, wherein the light chain constant region is a kappa light chain constant region or a lambda light chain constant region.

73. The modified anti-PD-L1 antibody according to embodiment 72, wherein the kappa light chain constant region is SEQ ID NO: 16, SEQ ID NO: 17, SEQ ID NO: 18, SEQ ID NO: 19, or SEQ ID NO: 20.

74. The modified anti-PD-L1 antibody according to embodiment 72, wherein the lambda light chain constant region is SEQ ID NO: 26, SEQ ID NO: 27, SEQ ID NO: 28, SEQ ID NO: 29, SEQ ID NO: 30, or SEQ ID NO: 31.

75. The modified anti-PD-L1 antibody according to any one of embodiments 61-74, wherein the light chain variable region is SEQ ID NO: 9.

76. The modified anti-PD-L1 antibody according to any one of embodiments 61-75, wherein the light chain is SEQ ID NO: 21, SEQ ID NO: 22, SEQ ID NO: 23, SEQ ID NO: 24, SEQ ID NO: 25, SEQ ID NO: 32, SEQ ID NO: 33, SEQ ID NO: 34, SEQ ID NO: 35, SEQ ID NO: 36, or SEQ ID NO: 37.

77. A modified anti-Programmed Death Ligand 1 (PD-L1) antibody comprising a heavy chain of SEQ ID NO: 42, SEQ ID NO: 43 or SEQ ID NO: 44; and a light chain of SEQ ID NO 21.

78. A modified anti-Programmed Death Ligand 1 (PD-L1) antibody comprising a heavy chain of SEQ ID NO: 42; and a light chain of SEQ ID NO 21.

79. A modified anti-Programmed Death Ligand 1 (PD-L1) antibody comprising a heavy chain comprising a heavy chain variable region of SEQ ID NO: 2 and a heavy chain constant region of SEQ ID NO: 55, SEQ ID NO: 56, or SEQ ID NO: 57; and a light chain comprising a light chain variable region of SEQ ID NO 9 and a light chain constant region of SEQ ID NO: 16, SEQ ID NO: 17, SEQ ID NO: 18, SEQ ID NO: 19, or SEQ ID NO: 20.

80. A modified anti-Programmed Death Ligand 1 (PD-L1) antibody comprising a heavy chain comprising a heavy chain variable region of SEQ ID NO: 2 and a heavy chain constant region of SEQ ID NO: 55; and a light chain comprising a light chain variable region of SEQ ID NO 9 and a light chain constant region of SEQ ID NO: 16.

81. The modified anti-PD-L1 antibody according to any one of embodiments 1-80, having a half-life of about 30 hours to about 36 hours, about 30 hours to about 42 hours, about 30 hours to about 48 hours, about 32 hours to about 36 hours, about 32 hours to about 42 hours, about 32 hours to about 48 hours, about 34 hours to about 36 hours, about 34 hours to about 42 hours, about 34 hours to about 48 hours, about 36 hours to about 42 hours, about 36 hours to about 48 hours, about 42 hours to about 48 hours, about 1 day to about 2 days, about 1 day to about 3 days, about 1 day to about 4 days, about 1 day to about 5 days, about 1 day to about 6 days, about 1 day to about 7 days, about 2 days to about 3 days, about 2 days to about 4 days, about 2 days to about 5 days, about 2 days to about 6 days, about 2 days to about 7 days, about 3 days to about 4 days, about 3 days to about 5 days, about 3 days to about 6 days, about 3 days to about 7 days, about 4 days to about 5 days, about 4 days to about 6 days, about 4 days to about 7 days, about 5 days to about 6 days, about 5 days to about 7 days, or about 6 days to about 7 days.

82. The modified anti-PD-L1 antibody according to any one of embodiments 1-81, the modified anti-PD-L1 antibody is cleared from the blood in about 30 hours to about 36 hours, about 30 hours to about 42 hours, about 30 hours to about 48 hours, about 32 hours to about 36 hours, about 32 hours to about 42 hours, about 32 hours to about 48 hours, about 34 hours to about 36 hours, about 34 hours to about 42 hours, about 34 hours to about 48 hours, about 36 hours to about 42 hours, about 36 hours to about 48 hours, about 42 hours to about 48 hours, about 1 day to about 2 days, about 1 day to about 3 days, about 1 day to about 4 days, about 1 day to about 5 days, about 1 day to about 6 days, about 1 day to about 7 days, about 2 days to about 3 days, about 2 days to about 4 days, about 2 days to about 5 days, about 2 days to about 6 days, about 2 days to about 7 days, about 3 days to about 4 days, about 3 days to about 5 days, about 3 days to about 6 days, about 3 days to about 7 days, about 4 days to about 5 days, about 4 days to about 6 days, about 4 days to about 7 days, about 5 days to about 6 days, about 5 days to about 7 days, or about 6 days to about 7 days.

83. The modified anti-PD-L1 antibody according to any one of embodiments 1-82, the modified anti-PD-L1 antibody occupies its cognate PD-1 receptor for about 30 hours to about 36 hours, about 30 hours to about 42 hours, about 30 hours to about 48 hours, about 32 hours to about 36 hours, about 32 hours to about 42 hours, about 32 hours to about 48 hours, about 34 hours to about 36 hours, about 34 hours to about 42 hours, about 34 hours to about 48 hours, about 36 hours to about 42 hours, about 36 hours to about 48 hours, about 42 hours to about 48 hours, about 1 day to about 2 days, about 1 day to about 3 days, about 1 day to about 4 days, about 1 day to about 5 days, about 1 day to about 6 days, about 1 day to about 7 days, about 2 days to about 3 days, about 2 days to about 4 days, about 2 days to about 5 days, about 2 days to about 6 days, about 2 days to about 7 days, about 3 days to about 4 days, about 3 days to about 5 days, about 3 days to about 6 days, about 3 days to about 7 days, about 4 days to about 5 days, about 4 days to about 6 days, about 4 days to about 7 days, about 5 days to about 6 days, about 5 days to about 7 days, or about 6 days to about 7 days.

84. A pharmaceutical composition comprising a modified anti-PD-L1 antibody as defined in any one of embodiments 1-83.

85. Use of a modified anti-PD-L1 antibody as defined in any one of embodiments 1-83 for the manufacture of a medicament in treating a neurodegenerative disease.

86. Use according to embodiment 85, wherein the neurodegenerative disease includes aged-related dementia, Alzheimer's disease, amyotrophic lateral sclerosis, dementia, Parkinson's disease Huntington's disease, primary progressive multiple sclerosis; secondary progressive multiple sclerosis, corticobasal degeneration, Rett syndrome, a tauopathy, a retinal degeneration disorder; anterior ischemic optic neuropathy; glaucoma; uveitis; depression; trauma-associated stress or post-traumatic stress disorder, frontotemporal dementia, Lewy body dementias, mild cognitive impairments, posterior cortical atrophy, primary progressive aphasia, progressive supranuclear palsy or an injury of the CNS.

87. Use of a modified anti-PD-L1 antibody as defined in any one of embodiments 1-83 for the manufacture of a medicament in treating an Alzheimer's Disease.

88. A pharmaceutical kit comprising a modified anti-PD-L1 antibody as defined in any one of embodiments 1-83.

89. A pharmaceutical kit comprising a pharmaceutical composition as defined in embodiment 84.

90. A pharmaceutical kit comprising a medicament as defined in embodiment 85.

91. A method of treating a neurodegenerative disease, the method comprising administering to an individual in need thereof a modified anti-PD-L1 antibody as defined in any one of embodiments 1-83.

92. A method of treating a neurodegenerative disease, the method comprising administering to an individual in need thereof a pharmaceutical composition as defined in embodiment 84.

93. A method of treating a neurodegenerative disease, the method comprising administering to an individual in need thereof a medicament as defined in embodiment 85.

94. The method according to any one of embodiments 91-93, wherein the neurodegenerative disease includes aged-related dementia, Alzheimer's disease, amyotrophic lateral sclerosis, dementia, Parkinson's disease Huntington's disease, primary progressive multiple sclerosis; secondary progressive multiple sclerosis, corticobasal degeneration, Rett syndrome, a tauopathy, a retinal degeneration disorder; anterior ischemic optic neuropathy; glaucoma; uveitis; depression; trauma-associated stress or post-traumatic stress disorder, frontotemporal dementia, Lewy body dementias, mild cognitive impairments, posterior cortical atrophy, primary progressive aphasia, progressive supranuclear palsy or an injury of the CNS.

95. A modified anti-PD-L1 antibody as defined in any one of embodiments 1-83 for use in treating a neurodegenerative disease.

96. The modified anti-PD-L1 antibody according to embodiment 95, wherein the neurodegenerative disease includes aged-related dementia, Alzheimer's disease, amyotrophic lateral sclerosis, dementia, Parkinson's disease Huntington's disease, primary progressive multiple sclerosis; secondary progressive multiple sclerosis, corticobasal degeneration, Rett syndrome, a tauopathy, a retinal degeneration disorder; anterior ischemic optic neuropathy; glaucoma; uveitis; depression; trauma-associated stress or post-traumatic stress disorder, frontotemporal dementia, Lewy body dementias, mild cognitive impairments, posterior cortical atrophy, primary progressive aphasia, progressive supranuclear palsy or an injury of the CNS.

97. A method of treating an Alzheimer's Disease, the method comprising administering to an individual in need thereof a modified anti-PD-L1 antibody as defined in any one of embodiments 1-83.

98. A method of treating an Alzheimer's Disease, the method comprising administering to an individual in need thereof a pharmaceutical composition as defined in embodiment 84.

99. A method of treating an Alzheimer's Disease, the method comprising administering to an individual in need thereof a medicament as defined in embodiment 85.

100. A modified anti-PD-L1 antibody as defined in any one of embodiments 1-83 for use in treating an Alzheimer's Disease.

101. A polynucleotide comprising a nucleic acid sequence encoding a heavy chain from a modified anti-PD-L1 antibody as defined in any one of embodiments 1-83 or a nucleic acid sequence encoding a light chain from a modified anti-PD-L1 antibody as defined in any one of embodiments 1-83.

102. The polynucleotide according to embodiment 101, wherein the nucleic acid sequence encoding the heavy chain is SEQ ID NO: 58, SEQ ID NO: 59, SEQ ID NO: 60, SEQ ID NO: 61, SEQ ID NO: 62, SEQ ID NO: 63, SEQ ID NO: 64, or SEQ ID NO: 65.

103. The polynucleotide according to embodiment 101, wherein the nucleic acid sequence encoding the light chain is SEQ ID NO: 82 or SEQ ID NO: 83.

104. A polynucleotide of SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 86, or SEQ ID NO: 87.

105. An expression construct comprising a nucleic acid sequence encoding a heavy chain from a modified anti-PD-L1 antibody as defined in any one of embodiments 1-83.

106. The expression construct according to embodiment 105, wherein the nucleic acid sequence encoding the heavy chain is SEQ ID NO: 58, SEQ ID NO: 59, SEQ ID NO: 60, SEQ ID NO: 61, SEQ ID NO: 62, SEQ ID NO: 63, SEQ ID NO: 64, or SEQ ID NO: 65.

107. An expression construct comprising a nucleic acid sequence encoding a light chain from a modified anti-PD-L1 antibody as defined in any one of embodiments 1-83.

108. The expression construct according to embodiment 107, wherein the nucleic acid sequence encoding the light chain is SEQ ID NO: 82 or SEQ ID NO: 83.

109. An expression construct comprising SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 86, or SEQ ID NO: 87.

110. A method of making a modified anti-PD-L1 antibody comprising expressing in a host cell a first and a second expression construct, wherein the first expression construct is defined by embodiment 105 or 106, and the second expression construct is defined by embodiment 107 or 108.

111. A method of making a modified anti-PD-L1 antibody comprising expressing in a host cell a first and a second expression construct, wherein the first expression construct comprises SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 74, SEQ ID NO: 75, SEQ ID NO: 76, SEQ ID NO: 77, SEQ ID NO: 78, SEQ ID NO: 79, SEQ ID NO: 80, or SEQ ID NO: 81, and the second expression construct comprises SEQ ID NO: 82, SEQ ID NO: 83, SEQ ID NO: 86, or SEQ ID NO: 87.

112. The method according to embodiment 110 or 111, further comprising purifying the modified anti-PD-L1 antibody.

113. The method according to embodiments 110-112, wherein the modified anti-PD-L1 antibody produced is defined by any one of embodiments 1-83.

114. A modified anti-Programmed Death Ligand 1 (PD-L1) antibody, comprising a heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, and a heavy chain constant region of SEQ ID NO: 55; SEQ ID NO: 56 or SEQ ID NO: 57 and a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15.

115. The modified anti-PD-L1 antibody according to embodiment 114, wherein the heavy chain variable region is SEQ ID NO: 2.

116. The modified anti-PD-L1 antibody according to embodiment 115, wherein the heavy chain is SEQ ID NO: 42, SEQ ID NO: 43 or SEQ ID NO: 44.

117. The modified anti-PD-L1 antibody according to any one of embodiments 114-116, wherein the light chain variable region is SEQ ID NO: 9.

118. The modified anti-PD-L1 antibody according to any one of embodiments 114-117, wherein the light chain further comprises a kappa light chain constant region.

118. The modified anti-PD-L1 antibody according to embodiment 118, wherein the kappa light chain constant region is SEQ ID NO: 16.

120. The modified anti-PD-L1 antibody according to any one of embodiments 114-119, wherein the light chain is SEQ ID NO: 21.

121. A modified anti-Programmed Death Ligand 1 (PD-L1) antibody comprising a heavy chain comprising a heavy chain variable region of SEQ ID NO: 2 and a heavy chain constant region of SEQ ID NO: 55, SEQ ID NO: 56, or SEQ ID NO: 57; and a light chain comprising a light chain variable region of SEQ ID NO: 9 and a light chain constant region of SEQ ID NO: 16.

122. A pharmaceutical composition comprising a modified anti-PD-L1 antibody as defined in any one of embodiments 114-121.

123. A pharmaceutical kit comprising a modified anti-PD-L1 antibody as defined in any one of embodiments 114-121 or a pharmaceutical composition as defined in embodiment 122.

124. A modified anti-PD-L1 antibody as defined in any one of embodiments 114-121, a pharmaceutical composition as defined in embodiment 122, or a pharmaceutical kit as defined in embodiment 123 for treating an Alzheimer's Disease.

125. Use of a modified anti-PD-L1 antibody as defined in any one of embodiments 114-121 or a pharmaceutical composition as defined in embodiment 122 in the manufacture of a medicament in treating an Alzheimer's Disease.

126. Use of a modified anti-PD-L1 antibody as defined in any one of embodiments 114-121, a pharmaceutical composition as defined in embodiment 122, or a pharmaceutical kit as defined in embodiment 123 for treating an Alzheimer's Disease.

127. A method of treating an Alzheimer's Disease, the method comprising administering to an individual in need thereof a modified anti-PD-L1 antibody as defined in any one of embodiments 114-121, a pharmaceutical composition as defined in embodiment 122, a pharmaceutical kit as defined in embodiment 123, or a medicament as defined in embodiment 125.

128. A polynucleotide comprising a nucleic acid sequence encoding a heavy chain from a modified anti-PD-L1 antibody as defined in any one of embodiments 114-121 or a nucleic acid sequence encoding a light chain from a modified anti-PD-L1 antibody as defined in any one of embodiments 114-121.

129. The polynucleotide according to embodiment 128, wherein the nucleic acid sequence encoding the heavy chain comprises SEQ ID NO: 58, SEQ ID NO: 59, SEQ ID NO: 60, SEQ ID NO: 61, SEQ ID NO: 62, SEQ ID NO: 63, SEQ ID NO: 64, or SEQ ID NO: 65.

130. The polynucleotide according to embodiment 128 or 129, wherein the nucleic acid sequence encoding the light chain comprises SEQ ID NO: 82 or SEQ ID NO: 83.

131. An expression construct comprising a nucleic acid sequence encoding a heavy chain from a modified anti-PD-L1 antibody as defined in embodiment 128 or 129.

132. An expression construct comprising a nucleic acid sequence encoding a light chain from a modified anti-PD-L1 antibody as defined in embodiment 128 or 130.

133. A method of making a modified anti-PD-L1 antibody comprising expressing in a host cell a first and a second expression construct, wherein the first expression construct is defined by claim 131, and the second expression construct is defined by embodiment 132.

134. The method according to embodiment 133, wherein the modified anti-PD-L1 antibody produced is defined by any one of embodiments 114-121.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the antibodies, therapeutic compositions, or methods and uses disclosed herein.

In all the studies described herein two different animal models were employed, a 5×FAD mouse model for Alzheimer Disease (AD) and a DM-hTAU mouse model for dementia. The 5×FAD transgenic mice express mutant human APP(695) with the Swedish (K670N, M671L), Florida (I716V), and London (V7171) Familial Alzheimer's Disease (FAD) mutations along with human PS1 harboring two FAD mutations: M146L and L286V. 5×FAD mice recapitulate major features of Alzheimer's disease, i.e. amyloid pathology, brain inflammation and neuronal loss (Oakley et al, 2006). In 5×FAD mice, reduced hippocampal-dependent spatial learning/memory performance relative to age-matched wild-type (WT) mice can be detected starting from 5 to 6 months of age using a radial arm water maze (RAWM) (Puzzo et al, 2014), The DM-hTAU model is a transgenic mouse expressing the human-tau (htau) gene with two mutations, K257T/P301S (double mutant, DM), that are associated with severe phenotypes of frontotemporal-dementia in humans. These mice develop neurofibrillary-tangles (NFT), characteristic of a wide-range of tauopathies, including Alzheimer's-disease and other neurodegenerative diseases. Pathological features in these mice include cognitive deficits, neuroinflammation, glial cell activation, and phosphorylation of tau proteins, and accumulation of aggregated tau within the brain (Rosenmann et al, 2008). In DM-hTAU mice reduced learning skills are measured by testing behavioral performance using the T-maze spontaneous alteration test. A decline in learning skills is typically detected starting from 7 to 8 months of age. The assay includes habituation of the animal in a T-maze with 3 arms of which one arm is closed (novel). Healthy mice prefer to visit an unfamiliar space, therefore, upon opening of the closed arm, the wild-type (WT) animals prefer to go into the novel arm, and thus spend more than 60% of the total time (an average of 80 out of 120 seconds) in the novel arm. In contrast, the DM-hTAU mice showed no preference to the novel arm (around 30% of the total time per each arm).

Example 1

Anti-PD-L1 Antibody Activity Facilitates Monocyte-Derived Macrophage Entry into Diseased Brain Parenchyma to Resolve Neurogenic Pathologies Monocytes are recruited to tissues under pathological conditions, where they differentiate into macrophages or dendritic cells (DC). They have been shown to be indispensable in the immunological defense against pathogens, tumor cells, and as shown over the last decade, in resolving neurodegenerative diseases. To test if the beneficial effect of anti-PD-L1 treatment is dependent on monocyte homing into the brain, we took advantage of the fact that monocyte trafficking to tissues, including to the brain, is dependent on CC-chemokine ligand 2 (CCL2; also known as MCP1), which facilitates the emigration of Ly6Chi monocytes from the bone marrow to tissues. It is known that neutralizing antibodies to CCR2 impaired monocyte-derived macrophage homing to the CNS, and repair following spinal cord injury.

Figure 1B:
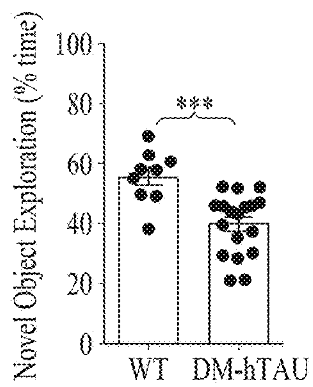
Figure 1C:
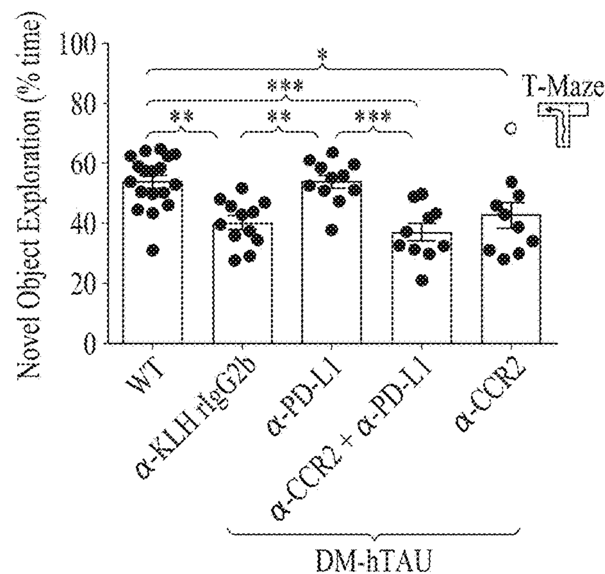
Figure 1D:
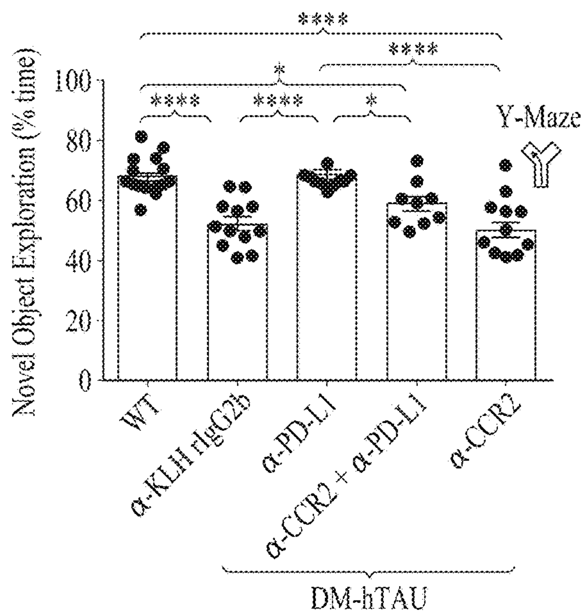
Figure 1E:
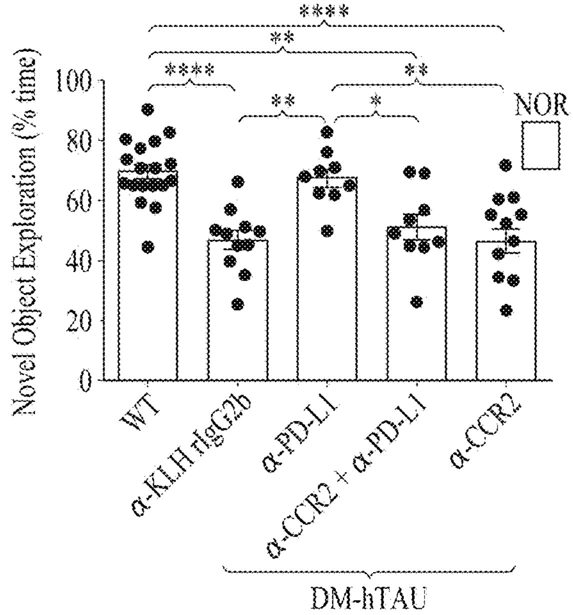
Figure 2A:
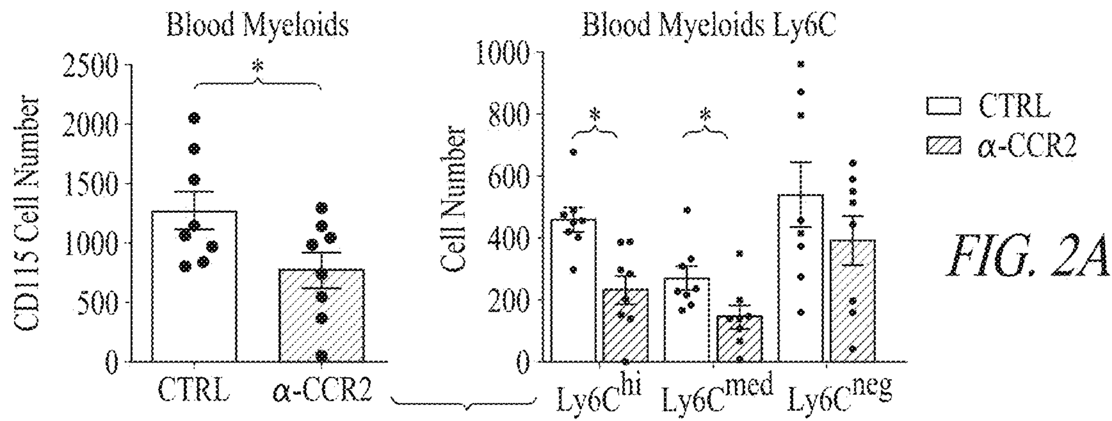
FIG. 2A-D show blocking CCR2 selectively affects only monocyte levels in the circulation without affecting T cell levels with FIG. 2A showing levels of myeloid cells in the blood.
Figure 2B:
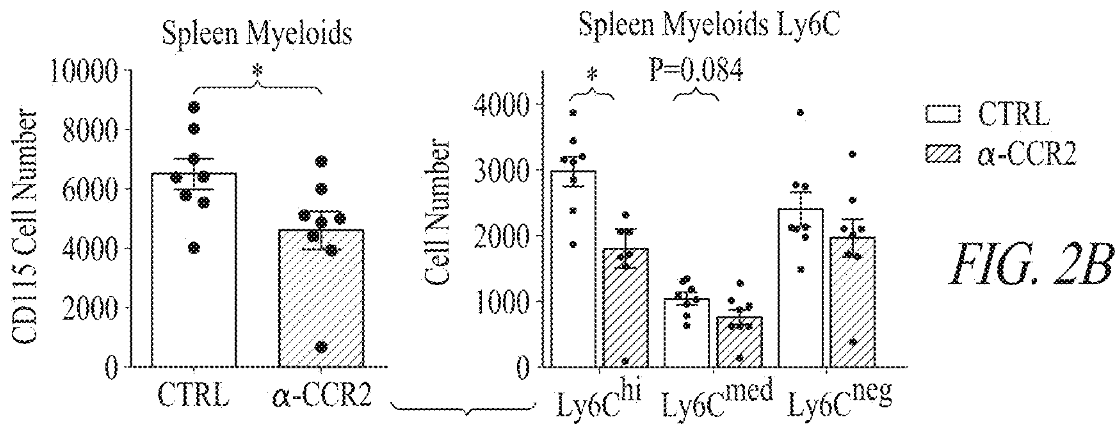
Figure 2C:
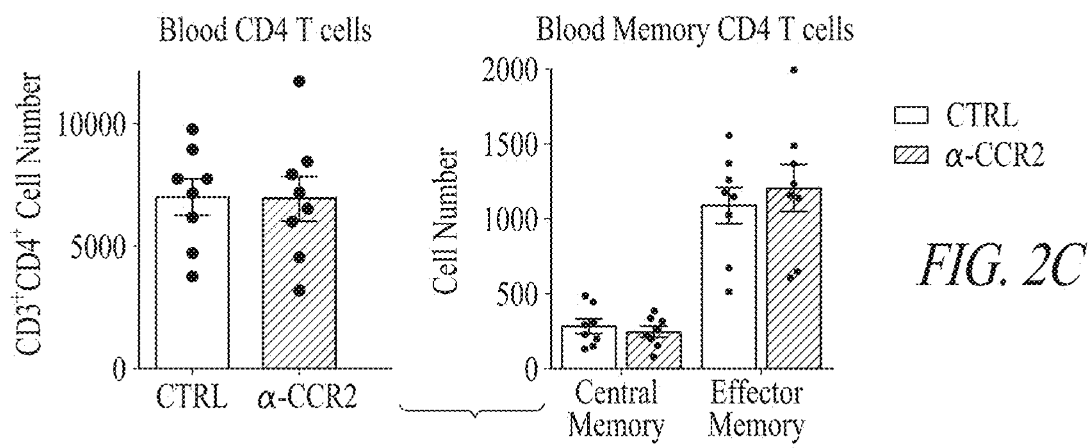
Figure 2D:
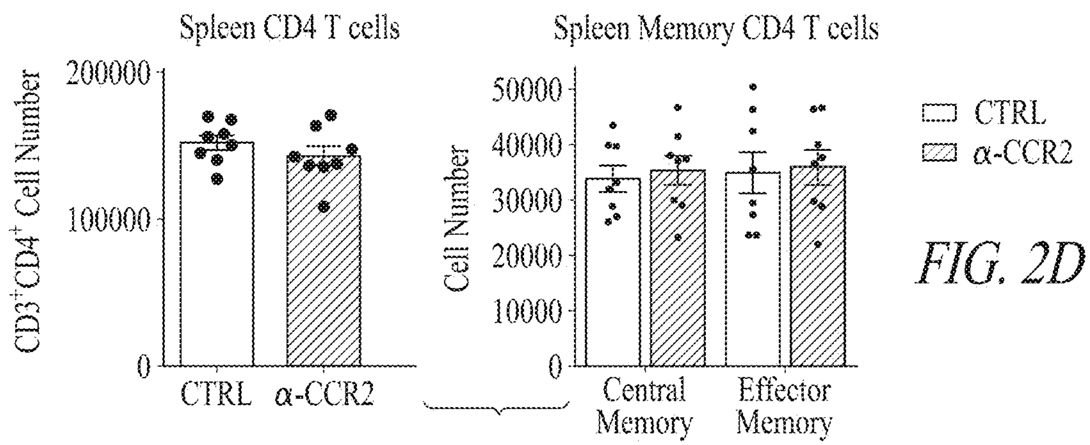

To assess the role of monocyte-derived macrophages in the repair process, induced by anti-PD-L1, DM-hTAU mice were injected anti-CCR2 antibodies (clone MC21) every 3 days starting 3 days prior to PD-L1 antibody administration, up to day 12 following PD-L1 antibody treatment (FIG. 1A). Monocytes home to the brain following anti-PD-1 treatment and their number is higher at 2 weeks relative to 1-week post treatment. In this experiment, 5 groups of animals were included: 1) Will type mice; 2) DM-hTAU treated with 1.5 mg rat IgG2b anti-KLH antibody control; 3) DM-hTAU treated with 1.5 mg rat anti-mouse PD-L1 monoclonal antibody (clone 10F.9G2, BioXCell); 4) DM-hTAU treated repeatedly with anti-CCR2 antibody (MC21) only; and 5) DM-hTAU treated with both anti-CCR2 (MC21) and anti-PD-L1 antibodies. One month after the treatment, all mice were scored for their cognitive performance in three independent paradigms, T-Maze (FIG. 1C), Y-Maze (FIG. 1D) and Novel Object recognition (NOR) (FIG. 1E). Three one-way ANOVAs were performed to analyze the behavioral data. One week prior to the first administration, animals were subjected to a pre-test using a T-maze in order to assess their cognitive performance prior to any therapeutic intervention (FIG. 1B).

A significant main effect of treatment with anti-PD-L1 antibody was detected for each of the cognitive tests (Y-maze: $F(4,52)=12.48$, $p>0.0001$; T-maze: $F(4,56)=9.068$, $p<0.0001$; NOR: $F(4,52)=12.48$, $p<0.0001$). To assess significant difference between the experimental groups, a Tukey's test for multiple comparisons was performed for each of the behavioral tests. A significant difference is represented by: $*p<0.05$, $p<0.01$, $*p<0.001$. Data showed that anti-CCR2 antibody abrogated the effect of PD-L1 therapy. In addition, the anti-CCR2 antibody treatment selectively reduced only monocyte levels, and no other T cell/leukocyte populations in the blood and spleen (FIG. 2A-D). These results indicated that anti-CCR2 antibody abrogated the effect of PD-L1 therapy by selectively reducing monocyte levels.

Figure 3A:
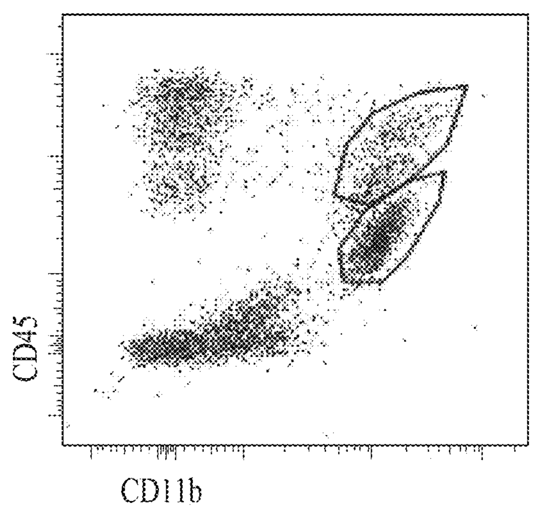
FIG. 3A-B show flow cytometry of brains of DM-hTAU mice treated with either anti-PD-L1 antibodies or IgG antibodies, analyzed for $CD45^{low}/CD11b^{high}$ myeloid cells with FIG. 3A showing the flow cytometry of brain cells gated for $CD45^{low}/CD11\ b^{high}$ and $CD45^{high}/CD11b^{high}$ myeloid cells.
Figure 3B:
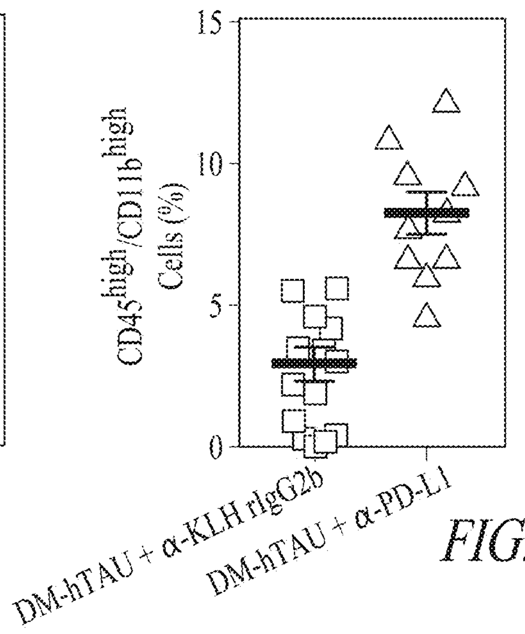

To test whether enhanced trafficking of immune cells to the brain followed an anti-PD-L1 treatment, brain parenchyma tissue from DM-hTAU mice were analyzed by flow cytometry for the presence of $CD45^{high}/CD11b^{high}$ infiltrating myeloid cells. This population is mainly comprised of infiltrating cells, unlike the $CD45^{low}/CD11b^{low}$ or intermediate population, which represent resident microglia. Brains from the same mice were excised 2 weeks after being treated with either rat anti-mouse PD-L1 monoclonal antibody (clone 10F.9G2, BioXCell) (n=10) or rat IgG2b anti-KLH antibody as control (n=16). Cell were harvested from these brains and stained by immunohistochemistry using the fluorochrome-labeled monoclonal antibodies Brilliant-violet 421-conjugated anti-CD45 antibodies, PE-conjugated anti-CD11 b antibodies, FITC-conjugated anti-CD11 b antibodies, and APC-conjugated anti-Ly6C antibodies. Cells were analyzed on an LSRII cytometer (BD Biosciences) using FlowJo software (FIG. 3A). In each experiment, relevant negative control groups, positive controls and single-stained samples for each tissue were used to identify the populations of interest and to exclude other populations. Results are pooled from two independent experiments. Data are shown as mean±s.e.m.; *$P<0.05$, $P<0.01$, *$P<0.001$. Quantitative analysis of brain $CD45^{high}/CD11b^{high}$ cells demonstrated a significant increase of infiltrating $CD45^{high}/CD11b^{high}$ cells in the brains of DM-hTAU mice treated with anti-PD-L1 antibody relative to those treated with the rat IgG2b anti-KLH antibody control (FIG. 3B). The results indicate that an anti-PD-L1 treatment facilitated recruitment of monocyte-derived macrophages ($CD45^{high}/CD11b^{high}$) to the brain parenchyma.

Figure 4A:
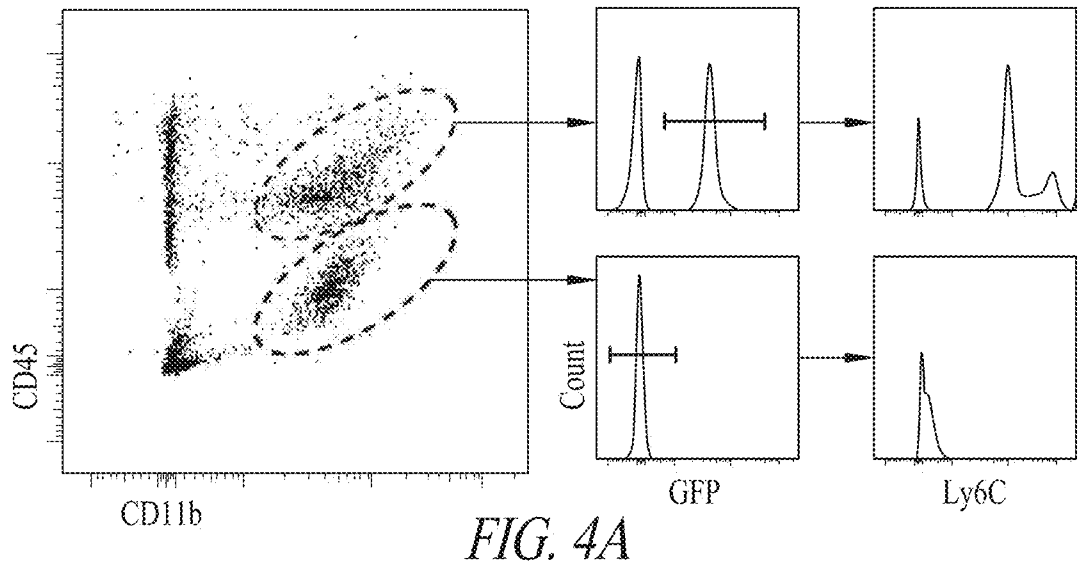
FIG. 4A-B show flow cytometry of brains of GFP-BM-chimeric DM-hTAU mice treated with anti-PD-L1 antibodies or IgG antibodies analyzed for $CD45^{low}/CD11b^{high}$ myeloid cells with FIG. 4A showing the flow cytometry of GFP-labeled brain cells gated from $CD45^{low}/CD11b^{high}$ and $CD45^{high}/CD11b^{high}$ myeloid cells, expressing Ly6C.
Figure 4B:
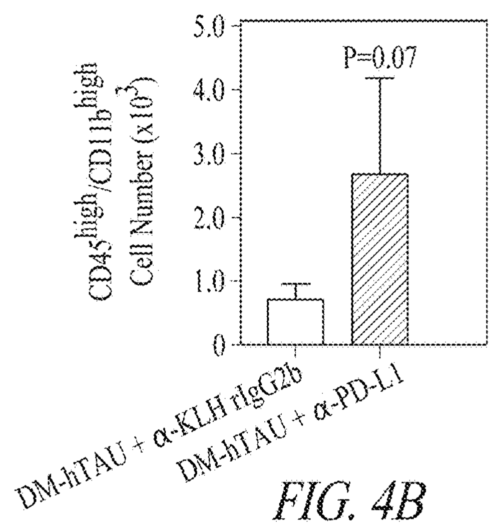

To confirm the observation made based on cell lineage and high expression of CD45 and CD11b, the experiment above was repeated with bone marrow (BM)-chimeric mice, in which the donor BM cells were taken from mice with GFP-labeled hematopoietic cells. To create such chimera, recipient DM-hTAU mice were conditioned with lethal-dose irradiation, with the radiation beam targeting the lower part of the body while avoiding the head, prior to BM transplantation. Following establishment of chimerism, animals were treated with either rat anti-mouse PD-L1 monoclonal antibody (clone 10F.9G2, BioXCell) (n=4) or with rat IgG2b anti-KLH antibody control (n=6). Brains were analyzed 2 weeks after the administration of the antibody. Analysis by flow cytometry, revealed that among the $CD45^{high}CD11b^{high}$ cells, about 50% of the cells were $GFP^{+}$, which was consistent with the extent of the chimerism, and confirmed their identity as infiltrating monocytes, rather than activated resident microglia (FIG. 4A). No $GFP^{+}$ cells were seen among the $CD45^{low}CD11\ b^{+}$ cells. Notably, only $GFP^{+}CD45^{+}CD11\ b^{+}$ myeloid cells were gated; BM-derived cells that were $GFP^{+}CD45^{+}CD11b^{-}$ were not analyzed. Treatment with anti-PD-L1 antibody resulted in an approximately 3-fold increase in the frequency of $GFP^{+}$ $CD45^{high}CD11b^{high}$ cells in animals, relative to IgG-treated controls (FIG. 4B). Notably, this number underestimates the number of homing macrophages since the chimerism was incomplete, and thus about 50% of the infiltrating cells were not GFP-labelled.

Figure 5A:
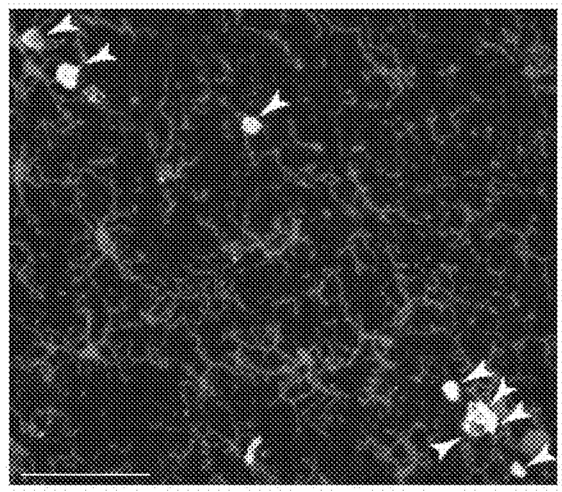
FIG. 5A-B show confocal images of brains from GFP-BM-chimeric DM-hTAU mice treated with anti-PD-L1 antibodies or IgG antibodies analyzed by immunohistochemistry with FIG. 5A showing representative projections of confocal z-axis stacks, indicating co-localization of $GFP^+$ cells (in green) with the myeloid marker IBA-1 (in blue), detected in the cortex of $DM\text{-}hTAU^{GFP/+}$ mice, treated with anti-PD-L1 (see arrowheads, scale bar: 100 μm)
Figure 5B:
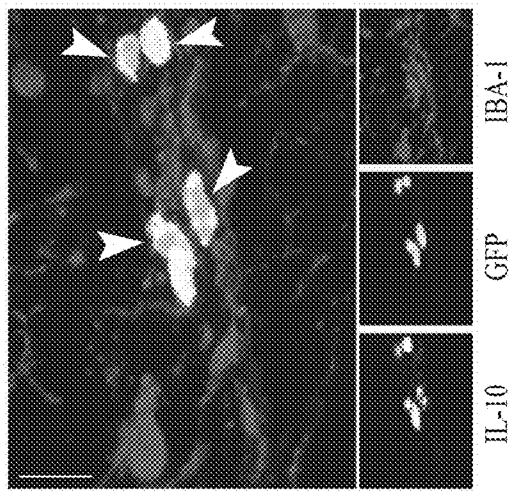

The brains of other mice from the same experiment were excised and processed for immunohistochemistry, which revealed the presence of $GFP^{+}IBA^{-}1^{+}$ myeloid cells in the brain parenchyma (mainly in the cortex) of the anti-PD-L1-treated brains (FIG. 5A). Brain sections from the same animals were also stained for the anti-inflammatory cytokine, IL-10, and observed its co-localization with infiltrating monocyte-derived macrophages, but not with $IBA\text{-}1^{+}GFP^{-}$ microglia (FIG. 5B).

Taken together, these results suggest that systemic immune activation, under conditions of chronic neurodegenerative diseases, facilitates the entry of peripheral monocyte-derived macrophages to the diseased brain. These experiments further indicate that monocyte-derived macrophages in the diseased brain parenchyma can contribute to resolution of the local inflammation, and promote local phagocytic activity, needed for the removal of cellular debris and for clearance of pathological conformations of misfolded and aggregated proteins.

Example 2

Anti-PD-L1 Antibody Treatment Improves Cognitive Performance and Reduces Brain Pathology This example describes experiments demonstrating that an anti-PD-L1 treatment is effective in improving cognitive performance and brain pathology in a 5×FAD mouse model of AD and a DM-h-Tau mouse model for dementia.

Figure 6A:
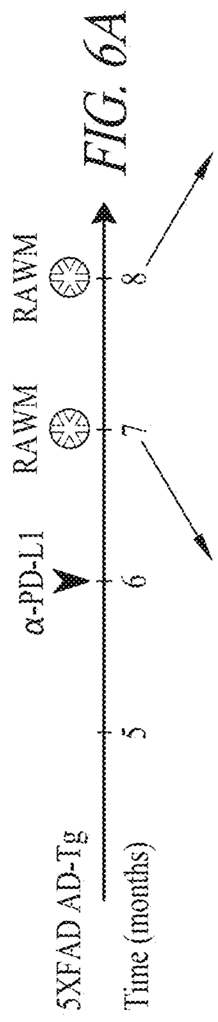
FIG. 6A-C show dose response-dependent effect of anti-PD-L1 on spatial learning and memory in 5×FAD mice, with FIG. 6A illustrating the experimental design with black arrowheads indicate time points of treatment, and illustrations indicate time points of cognitive scoring using a Radial Arm Water Maze (RAWM) assay.
Figure 6B:
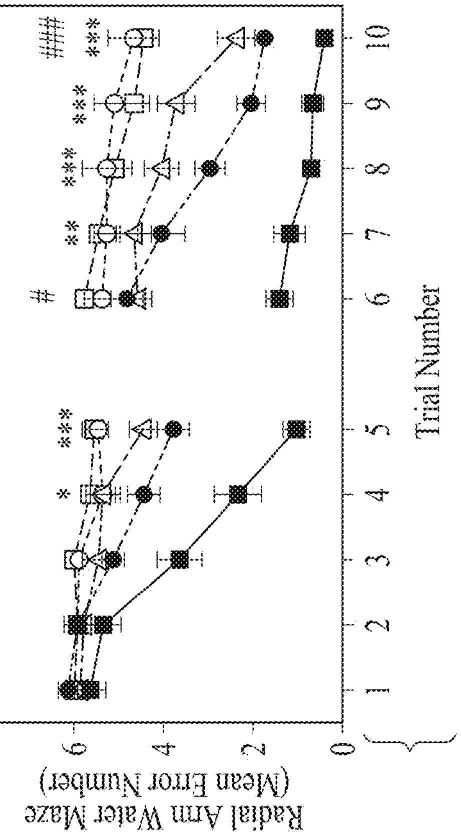
Figure 6C:
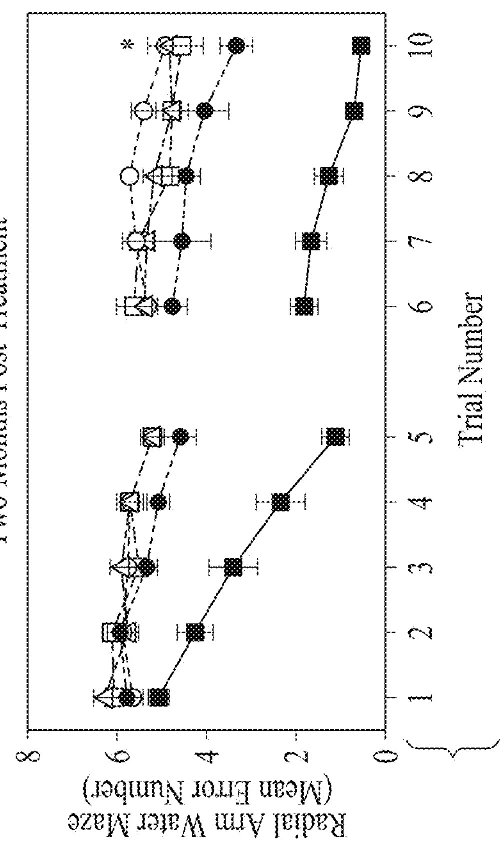

In one series of experiments, a 5×FAD mouse model was used to assess whether an anti-PD-L1 antibody treatment improved cognitive performance. In 5×FAD mice, reduced hippocampal-dependent spatial learning/memory performance relative to age-matched wild-type (WT) mice, using the radial arm water maze (RAWM), can be detected starting from 5 to 6 months of age. Male and female 5×FAD mice (average cohorts aged 6 months) were treated with either 0.1 mg/mouse (n=8), 0.5 mg/mouse (n=9) or 1.5 mg/mouse (n=9), single dose injections of a rat anti-mouse PD-L1 monoclonal antibody (clone 10F.9G2, BioXCell), or 1.5 mg/mouse (n=9) rat IgG2b anti-KLH antibody control (LTF-2 clone; BioXcell) (FIG. 6A). Aged matched wild-type (WT) mice were used as additional control group (n=10). Significance was calculated using two-way repeated-measures ANOVA followed by Dunnett's post-hoc test for multiple comparisons. While 0.1 mg of the anti-PD-L1 antibody did not have any effect on cognitive performance compared to treatment with isotype control antibody (control animals), both 0.5 mg and 1.5 mg doses of the anti-PD-L1 antibody showed a significant beneficial effect in 5×FAD mice relative to control animals (FIG. 6B). Treatment effect was significant at one month following antibody administration and declined at 2-months post treatment (FIG. 6C). Slightly better performance was shown in the 5×FAD mice treated with 1.5 mg/mouse relative to mice treated with 0.5 mg/mouse (FIG. 6B-C).

Figure 7A:
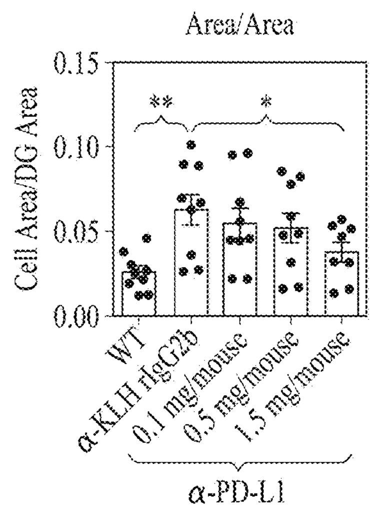
FIG. 7A-C show dose-dependent effect of anti-PD-L1 on hippocampal astrogliosis in 5×FAD mice with FIG. 7A showing area of all detected GFAP$^+$ cells divided by the total selected area of the dentate gyrus (*P<0.05, P<0.01)
Figure 7B:
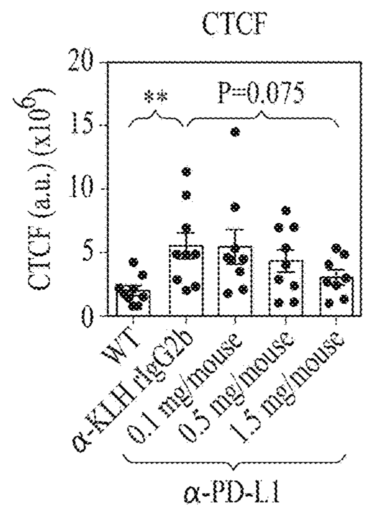
Figure 7C:
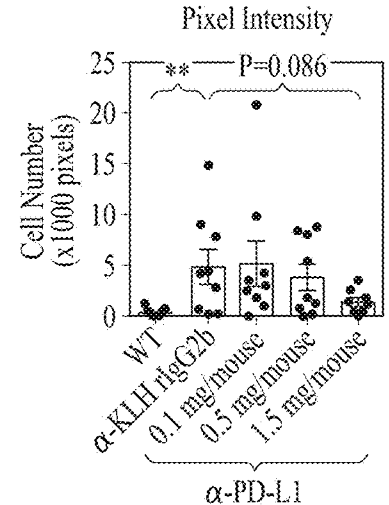

To examine the effect of anti-PD-L1 antibody treatment on brain pathology, brains from 5×FAD mice were analyzed at the end of the study period, 2 months following treatment by immunohistochemistry. Brains were removed after perfusion, 6 μm coronal slices were collected, and 5 sections per mouse were immune-stained for glial fibrillary acidic protein (GFAP) at 4-5 different pre-determined depths throughout the region of interest (dentate gyrus or cerebral cortex). Histogram-based segmentation of positively stained pixels was performed using Image-Pro Plus software (Media Cybernetics, Bethesda, Md., USA). The segmentation algorithm was manually applied to each image, calculating the size of a manually selected area of the dentate gyrus, and locating within it all cells expressing GFAP fluorescence. The algorithm then measures the total area of the detected cells (FIG. 7A), their fluorescence intensity (FIG. 7B), and number of cells which are larger than 1000 pixels (FIG. 7C). The calculation is as follows: "Area/Area" is the area of all detected GFAP$^+$ cells divided by the total selected area of the dentate gyrus; and "CTCF" is the mean fluorescence of the detected cells, corrected to the mean fluorescence of the whole dentate gyrus. Quantification was performed in a blinded fashion to the identity of the treatment groups. Analysis of GFAP immunostaining using a marker for astrogliosis and neuroinflammation showed a clear treatment effect on reducing astrogliosis which was observed as late as 8 weeks following single antibody administration (FIG. 7A-C).

Figure 8A:
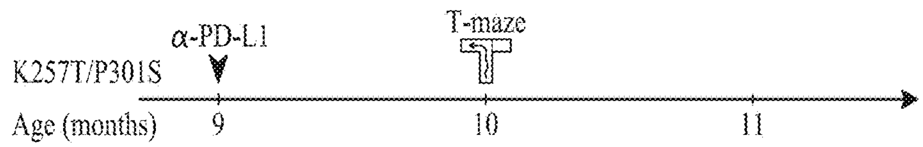
FIG. 8A-B show dose response-dependent effect of anti-PD-L1 on spatial learning and memory in DM-hTAU mice, with FIG. 8A illustrating the experimental design with black arrowheads indicate time points of treatment, and illustrations indicate time points of cognitive scoring using a T-maze assay.
Figure 8B:
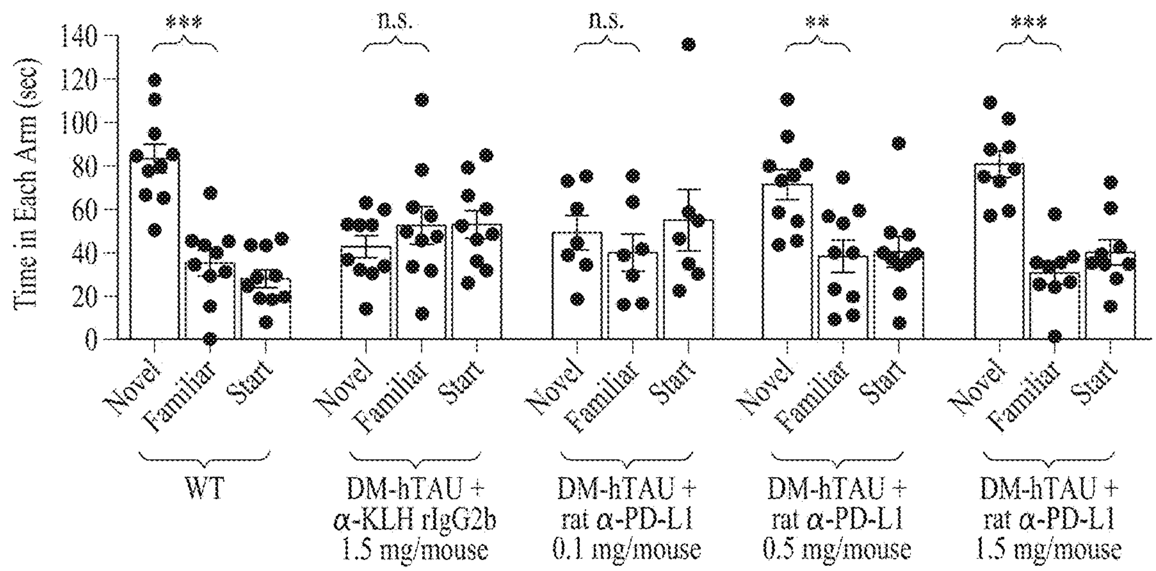

In another series of experiments, a DM-hTAU mouse model was used to assess whether an anti-PD-L1 antibody treatment improved cognitive performance. Male and female DM-hTAU mice (average cohorts aged 9 months) were treated with either 0.1 mg/mouse (n=7), 0.5 mg/mouse (n=9) or 1.5 mg/mouse (n=9), single dose injections of rat anti-mouse PD-L1 monoclonal antibody (clone 10F.9G2, BioXCell), or 1.5 mg/mouse (n=10) a rat IgG2b anti-KLH antibody (clone LTF-2; BioXCell)(FIG. 8A). Aged matched wild-type (WT) mice were used as additional control group (n=10). Cognitive performance was assessed using a T-maze assay. Significance was calculated using one-way ANOVA followed by Fisher's post-hoc test for multiple comparisons. As in the 5×FAD mice, an anti-PD-L1 treatment was found to be effective in DM-hTAU mice following a single administration of 1.5 mg/mouse or 0.5 mg/mouse but not following administration of 0.1 mg/mouse (FIG. 8B).

Figure 9A:
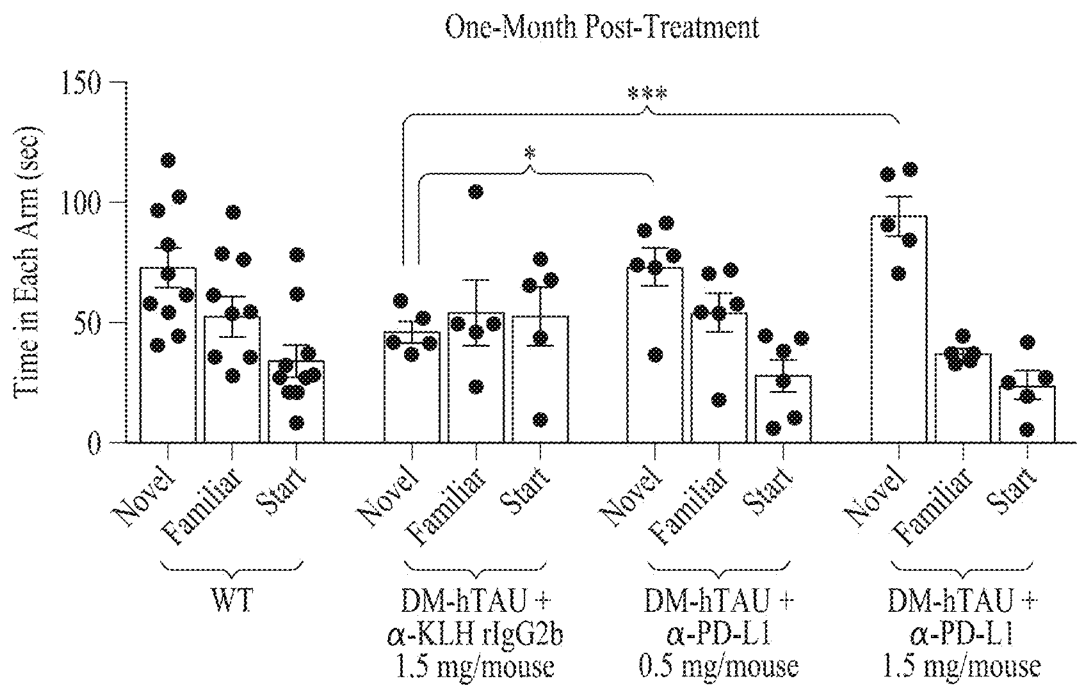
FIG. 9A-B show dose response-dependent and time-dependent effects of anti-PD-L1 on spatial learning and memory in DM-hTAU mice, with FIG. 9A showing T-maze performance one-month after treatment of three groups of DM-hTAU mice, each group treated with a different dose of anti-PD-L1 antibody along with wild-type littermates and anti-IgG2-treated mice, both of which served as controls (*P<0.05, P<0.01, *P<0.001)
Figure 9B:
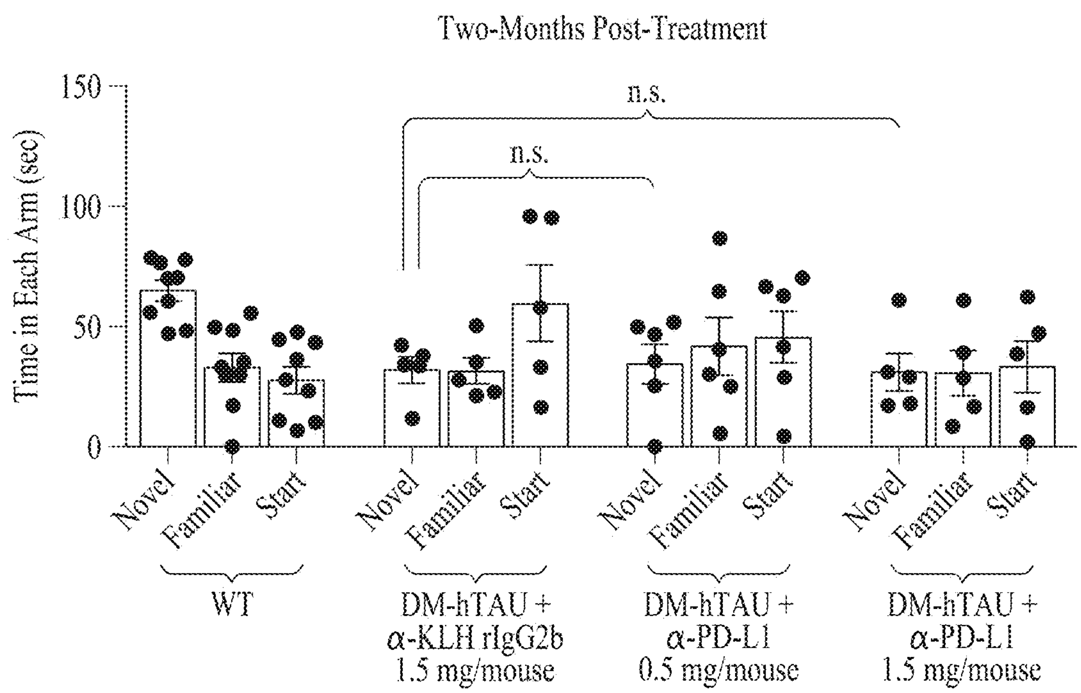

To examine the duration of the treatment effect on behavior following a single antibody administration, DM-hTAU mice were treated with the two effective dosages (0.5 or 1.5 mg/mouse) or with rat IgG2b anti-KLH antibody control, and assessed by a T-maze assay 1 month and 2 months after a single antibody administration. DM-hTAU mice were treated with either 0.5 mg/mouse (n=6) or 1.5 mg/mouse (n=5), single dose injection and aged matched wild-type (WT) mice were used as a control group (n=10). Significance was calculated using one-way ANOVA followed by Fisher's post-hoc test. Treatment effect was observed at 1-month post-injection of 0.5 mg/mouse or the 1.5 mg/mouse dosages (FIG. 9A). The effect on behavior that was observed 1 month after treatment was transient, at 2 months following injection, no significant difference in behavior performance could be observed between anti-PD-L1 and isotype-control treated animals (FIG. 9B).

Figure 10:
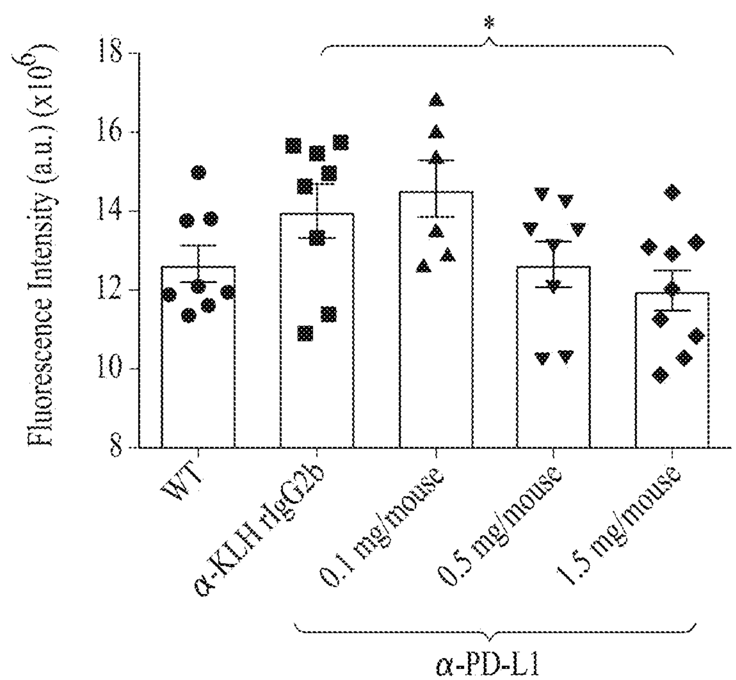
FIG. 10 shows the quantitative distribution of AT-180 immunoreactivity (Phospho-Tau (Thr231) in brains of wild-type mice and DM-hTAU mice treated with rat anti-PD-L1 antibodies or rat anti-KLH as control (both having IgG2b Fc) (error bars represent mean±s.e.m.; *P<0.05).

In addition, the effect of an anti-PD-L1 antibody treatment on brain pathology was examined in the same DM-hTAU mice at the end of the experimental period (2 months after the injection) by immunohistochemistry staining to phosphorylated Tau. DM-hTAU mice with either effective or non-effective dosages of anti-PD-L1 antibody (0.1, 0.5, or 1.5 mg/mouse respectively) were euthanized and their brains processed and analyzed by immunohistochemistry staining for AT-180 (Phospho-Tau Thr231) immunoreactivity, in the hippocampal C1 and CA3 regions. Significance was calculated using one-way ANOVA followed by Fisher's exact test. Immunohistochemical analysis of brain sections from DM-hTAU mice revealed reduced immunoreactivity in staining for the AT-180 epitope in the hippocampal CA1 and CA3 regions, following anti-PD-L1 blockade as compared to the IgG isotype control group (FIG. 10). These results reveled a dose response-dependent effect of anti-PD-L1 on hippocampal tau phosphorylation in DM-hTAU mice.

Levels of the pro-inflammatory cytokine IL-1β were then examined in DM-hTAU mice because elevation in brain-parenchymal of IL-1β levels was previously linked to cognitive decline in murine models of dementia. Using a FRET-based immunoassay change in mean hippocampal IL-1β protein levels, normalized to mg protein measured in each homogenate, was measured in untreated DM-hTAU mice (n=3), DM-hTAU mice treated with either 1.5 mg/mouse of anti-PD-L1 antibody (n=6) or with 1.5 mg/mouse of rat IgG2b anti-KLH antibody (n=6) and wild-type (WT) littermates (n=6) (average cohorts aged 9 months). Significance was calculated using one-way ANOVA and Fisher exact-test.

Figure 11F:
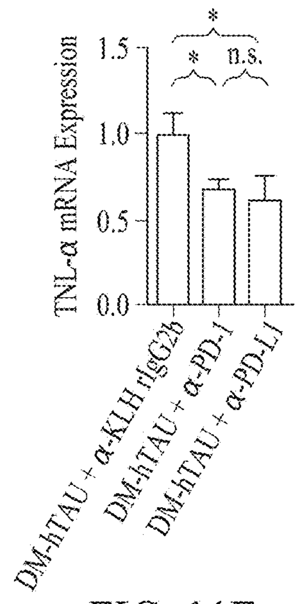

Analysis of brain sections from DM-hTAU mice, treated with either anti-PD-L1 antibodies or rat IgG2b anti-KLH antibody controls revealed IL-1β levels in the brain parenchyma deceased following treatment with anti-PD-L1 antibody as compared with the rat IgG2b anti-KLH antibody control (FIG. 11A-B). Moreover, IL-1β immunoreactivity was found to be co-localized mainly with GFAP expressing cells, a marker of astrocytes, but not with the myeloid cell marker IBA-1, including microglia and monocyte-derived macrophages (FIG. 11C).

To quantify the ability of anti-PD-L1 antibody treatment to decrease IL-1β levels in the brains of the DM-hTAU mouse, experiment were repeated using four groups of mice, including DM-hTAU and wild-type (WT) littermates that were left untreated, compared with DM-hTAU treated with IgG control antibody or treated with anti-PD-L1 antibody. After verifying the effect on behavior, which was tested 1 month following treatment initiation, mice were perfused and their brains excised, with half of each brain used to prepare separate protein extracts from hippocampi and cortices, while the other hemisphere from each brain was processed for histochemistry. The results indicate that significantly higher levels of IL-1β, was found in the hippocampi of DM-hTAU mice relative to age-matched wild type littermates, and a significant reduction in IL-1β levels followed an anti-PD-L1 antibody treatment relative to untreated, or IgGb-treated DM-hTAU mice (FIG. 11D). Moreover, linear regression analysis revealed a correlation in these animals between behavioral outcome and levels of IL-1β (FIG. 11E).

Figure 11G:
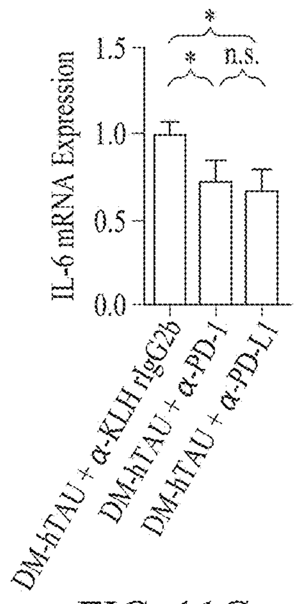
Figure 11H:
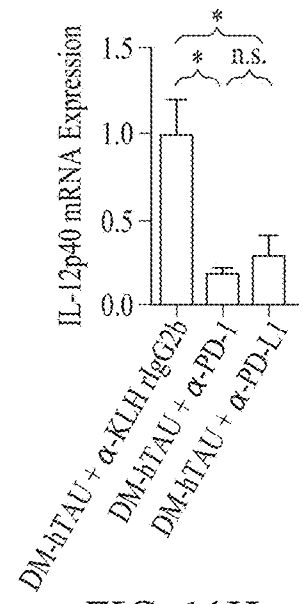
Figure 11I:
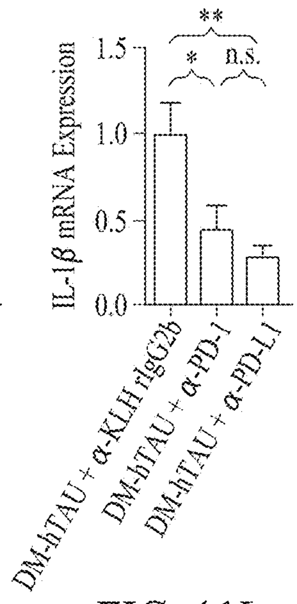

The beneficial effect of PD-1/PD-L1 blockade using antibodies was also evaluated by assessing changes in the inflammatory cytokine profile of the brain. Quantitative determination of mRNA expression levels for the genes tnf-a; il-6, il-12p40, and Il-1β, measured by RT-qPCR, in hippocampi isolated from DM-hTAU mice 1 month after treatment with IgG control (n=6), anti-PD-1 (n=6), or anti-PD-L1 (n=4). Significance was calculated using one-way ANOVA and Fisher exact-test. Quantitative RT-qPCR revealed that both anti-PD-1 and anti-PD-L1 treatment led to a reduction in the expression levels of the inflammatory cytokine genes tnf-a (FIG. 11F), il-6 (FIG. 11G), il-12p40 (FIG. 11H), and Il-1β (FIG. 11I) relative to the IgG-treated control group.

Taken together, these results demonstrate that efficacy in terms of cognitive outcome and brain pathology was shown following a single administration of anti-PD-L1 antibodies in dosages of 0.5 or 1.5 mg/mouse but not with 0.1 mg/mouse, in mouse models of AD and dementia.

Example 3

Anti-PD-L1 Antibody Pharmacokinetics and Pharmacodynamics

Figure 12:
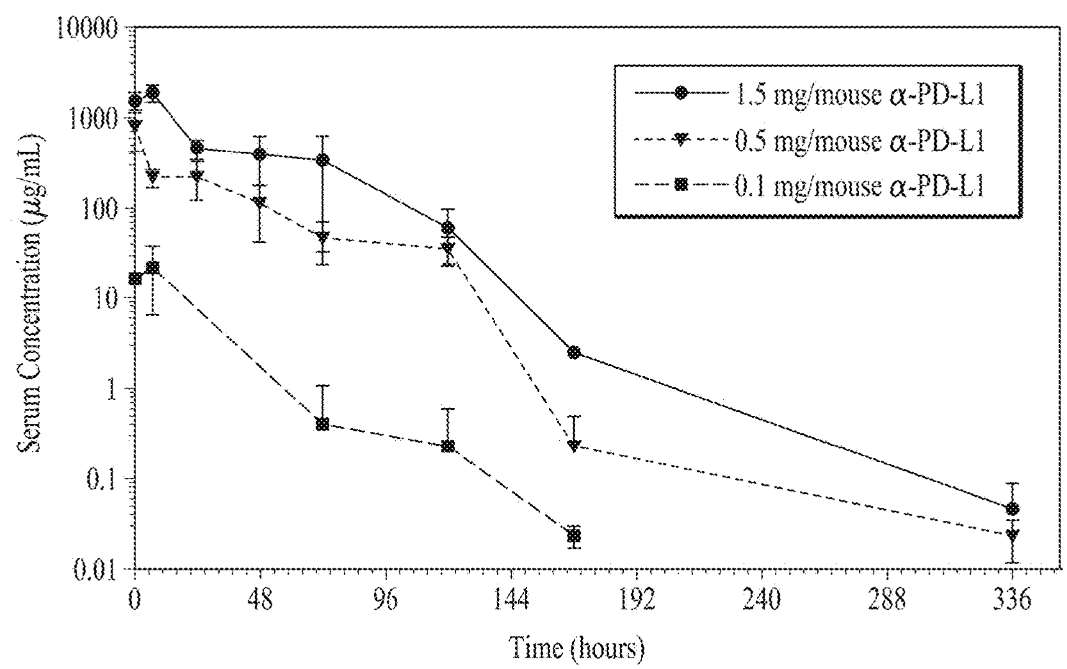
FIG. 12 shows PK profile of anti-PD-L1 antibody in blood sera taken from C57BL/6J mice and quantified using enzyme-linked immunosorbent assay (ELISA).

To learn about pharmacokinetics of an anti-PD-L1 antibody wild-type mice were injected with different dosages of an anti-PD-L1 antibody to determine the half-life of the antibody. Male C57BL/6J mice were injected once i.p. with either 0.1 mg/mouse (n=3), 0.5 mg/mouse (n=3) or 1.5 mg/mouse (n=3), single dose injections of rat anti-mouse PD-L1 monoclonal antibody (clone 10F.9G2, BioXCell). Serum was collected at different time point following injection and serum levels of anti-PD-L1 antibodies were quantified using ELISA. The results of the PK study demonstrate a half-life of about 24 hours for the anti-PD-L1 antibody in each of the treated dosages (Table 3; FIG. 12).

TABLE 3

Half-Life of Rat Anti-Mouse PD-L1 Monoclonal Antibody

| Antibody Dose | $C_{max}$ | $t_{1/2}$ (h) | $AUC_{total}$ (μg/mL · h) | $AUC_{0-7}$ (μg/mL · h) |
|---|---|---|---|---|
| 0.1 mg/mouse | 22.02 | 17.34 | 339 | 123 |
| 0.5 mg/mouse | 828.13 | 22.09 | 11,948 | 3,558 |
| 1.5 mg/mouse | 1886.04 | 21.55 | 60,987 | 10,979 |

Receptor occupancy by anti-PD-L1 antibodies on cells that express PD-L1 block PD-1 from interaction of their ligand, which neutralizes their inhibitory activity, thereby leads to higher levels of PD-1+ effector memory T cells. Thus, in response to antibody administration both receptor occupancy on blood $CD3^+$ T lymphocytes and percentage of $PD-1^+$ effector memory T-cells ($PD-1^+$ memory T cells) were examined at various time points following single injection of 0.1, 0.5 or 1.5 mg/mouse of rat anti-mouse PD-L1 monoclonal antibody. To identify the minimal effective concentration of antibody in the serum, the concentration of the anti-PD-L1 antibody in the serum was correlated to receptor occupancy on blood T lymphocytes. The pharmacodynamics of treatment effect on levels of $PD-1^+$ memory T-cells in the blood was also examined. Male and female 5×FAD and wild-type (WT) mice (average cohorts aged 6 months) were treated with different dosages of rat anti-mouse PD-L1 monoclonal antibody (clone 10F.9G2; BioXcell), or rat IgG2b anti-KLH antibody control (clone LTF-2; BioXcell). Blood was extracted from the mice at different time points post-injection (day 1, 5, 7 or 10) and prepared for flow cytometry analysis. Each sample was equally divided into two tubes, one saturated in-vitro for 30 min on ice with the rat anti-mouse PD-L1 monoclonal antibody (therefore, saturating all PD-L1 molecules with the anti-PD-L1 antibody) and the other with the rat IgG2b anti-KLH antibody control. Cells were then stained for flow cytometry to detect CD3+ cells (T cells) and PD-L1 receptor bound with anti-PD-L1 (using anti-rat IgG2b antibody). Receptor occupancy was evaluated by the ratio of differences in mean florescence intensity of rat IgG2b anti-KLH antibodies bound on CD3 T cells, whereby each sample was compared to its own control of maximal receptor occupancy in the anti-PD-L1 saturated sample. Each dot on the graph represent blood sample of a different mouse. Day 1 and day 10 data is comprised of wild-type (WT) mice, and days 5 and 10 of 5×FAD mice. Significance was calculated using one-way ANOVA followed by Fisher test for multiple comparisons.

Figure 13:
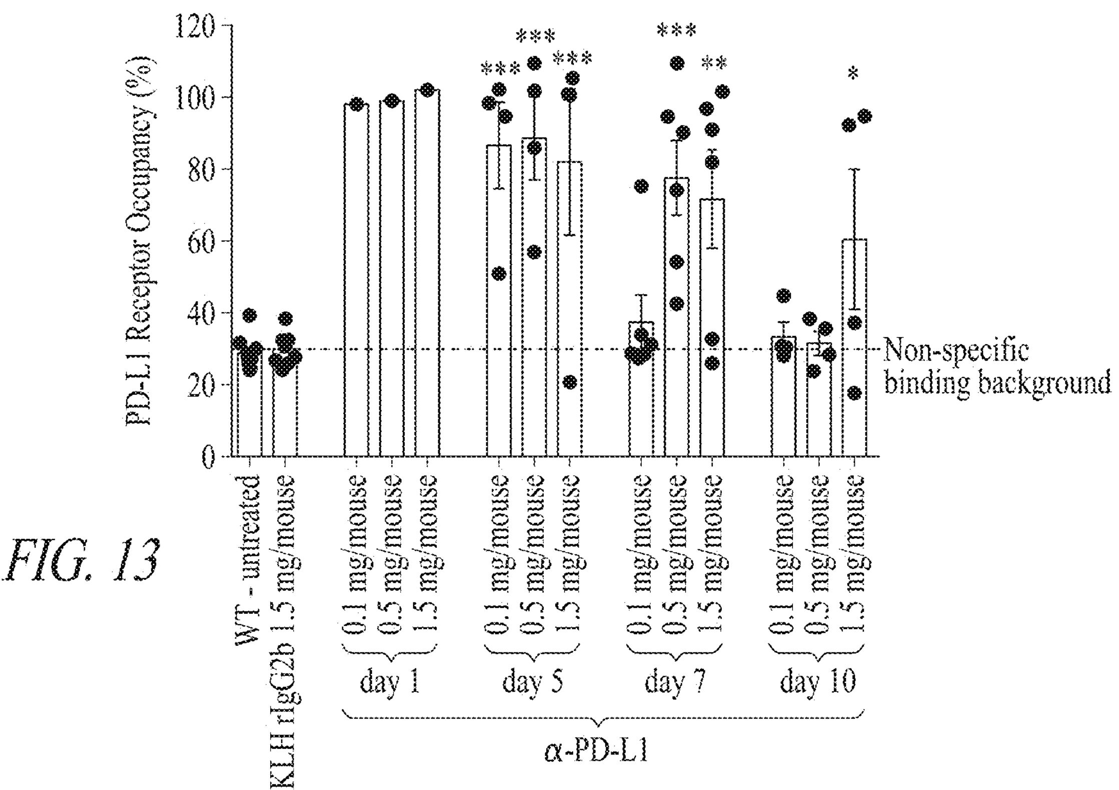
FIG. 13 shows kinetics of PD-L1 receptor occupancy on T cells in the blood from 5×FAD and C57BL/6J wild-type mice following a single injection of different dosages of rat anti-mouse PD-L1 monoclonal antibody (clone 10F. 9G2, BioXCell) vs. rat IgG2b anti-KLH antibody-treated controls (error bars represent mean±s.e.m.; *P<0.05, P<0.01, *P<0.001).

Complete target occupancy of anti-PD-L1 antibody on $CD3^+$ T lymphocytes was observed at 24 hours and persisted up to day 5 post dosing with all dosages of the antibody and was achieved at all serum concentrations above 0.15 μg/mL ($10^{-9}$ M). Receptor occupancy levels reduced gradually, returning to pre-treatment levels concomitantly with the reduction in antibody concentration in the serum to about 1 nM. In line with this, animals in the 0.1, and 0.5 mg/mouse treated groups returned to baseline levels of receptor occupancy at 7-days and 10-days post treatment respectively. Animal group dosed with 1.5 mg/mice showed more than 60% receptor occupancy at day 10 post dosing and serum antibody concentration of 0.5 μg/mL (about $3\times10^{-8}$ M) (FIG. 13).

In another series of experiments, male and female 5×FAD and wild-type (WT) mice (average cohorts aged 6 months) were treated with different dosages (described on the X-axis) of rat anti-mouse PD-L1 monoclonal antibody (clone 10F.9G2; BioXcell), or rat IgG2b anti-KLH antibody control (clone LTF-2; BioXcell). Blood was extracted from the mice at different time points post-injection (day 1, 5, 7 or 10) and prepared for flow cytometry analysis. Cells were stained for the surface markers CD3, CD4, CD44 and PD-1 and analyzed by flow cytometry. Day 1 and day 10 data is comprised of wild-type (WT) mice, and days 5 and 10 of 5×FAD mice. Significance was calculated using one-way ANOVA followed by Fisher test for multiple comparisons.

Figure 14:
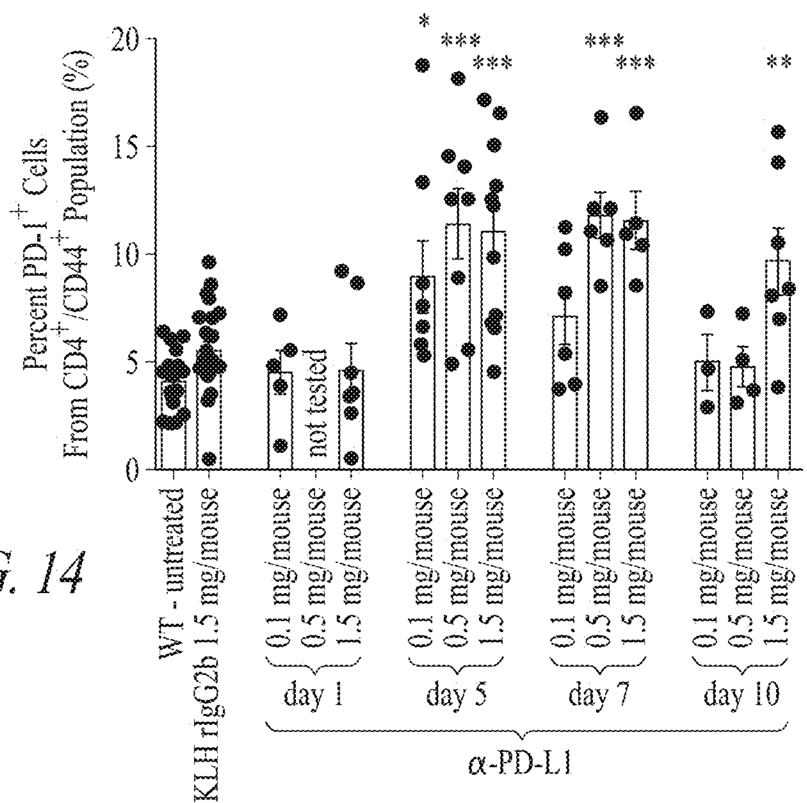
FIG. 14 shows levels of effector memory T cells (CD4$^+$ CD44$^+$ cell population) expressing PD-1+ in 5×FAD and C57BL/6J wild-type (WT) mice following a single injection of multi-dosages of rat anti-mouse PD-L1 monoclonal antibody (clone 10F.9G2, BioXCell) relative to rat anti-KLH antibody-treated mice, with each dot on the graph represent blood sample of a different mouse (error bars represent mean±s.e.m.; *P<0.05, P<0.01, *P<0.001).

Elevated levels of $PD-1^+$ memory T cells were observed using all tested treatment dosages, yet with a different kinetic: on day 1 post-injection, a time point of high antibody serum concentration and full receptor occupancy, no change was observed in the percentage of these cells compared to the pre-treatment levels (FIG. 14). On day 5 post-treatment, a significant elevation in PD-1+ memory T-cell levels was observed using all the dosages. The effect on PD-1+ memory T-cell levels followed the kinetic of the observed effect on receptor occupancy. This is in line with the proposed mechanism of action, of a sequence of events that starts with receptor occupancy in the periphery, continues with the release of recently activated T-cells that are under inhibitory regulation in the lymph nodes, and in turn activates the choroid plexus as a gateway for homing of monocytes to the brain. Notably, while the beneficial effects in the CNS on cognition and brain pathology, lasted between 1 to 2 months (in vivo studies described above), the effect of the treatment effects in the periphery, on receptor occupancy and on levels of PD-1+ memory T-cells, lasted between 7 to 10 days following antibody administration, respectively.

This suggests that for a beneficial effect in AD to be achieved, a transient blockade of PD-1/PD-L1 pathway is needed, as oppose to cancer therapy, in which continuous high receptor occupancy is required to obtain optimal beneficial effect.

Figure 15:
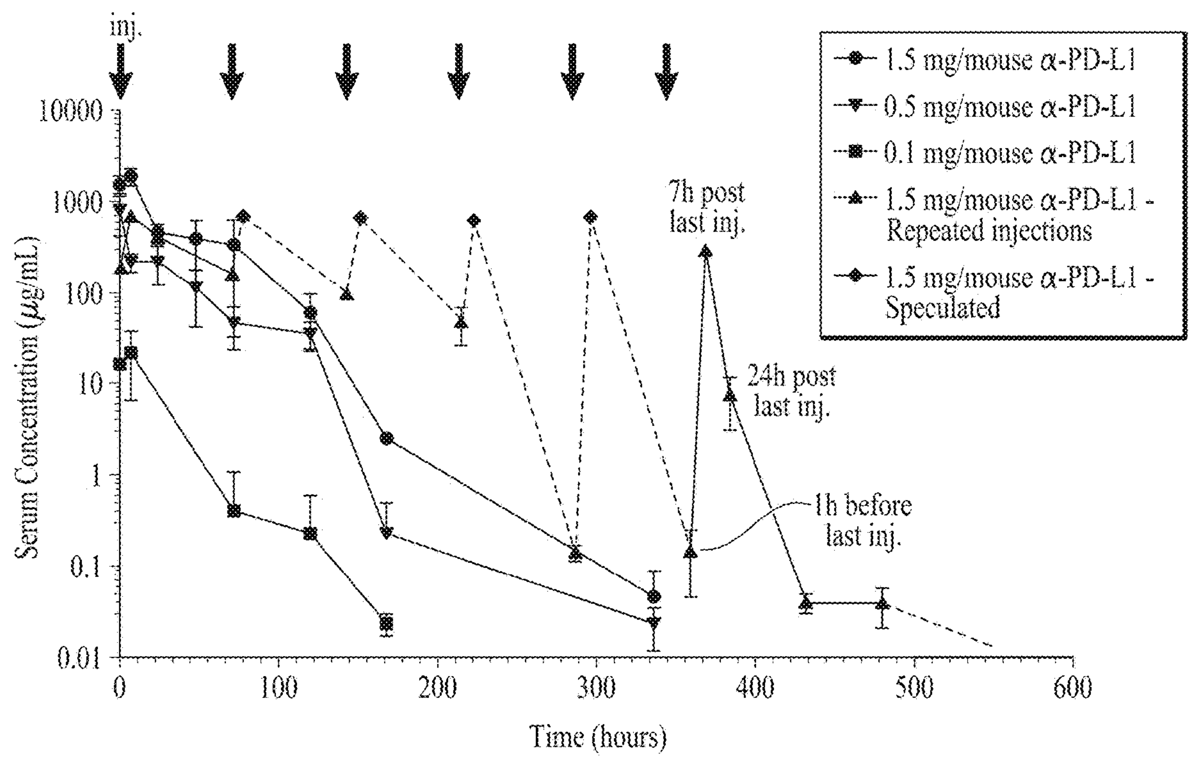
FIG. 15 shows PK profile of rat anti-mouse PD-L1 monoclonal antibody (clone 10F.9G2, BioXCell) in mice quantified using ELISA.

To address the question whether prolonged exposure to the antibody would be more effective or would be longer lasting, the exposure time for an anti-PD-L1 antibody was artificially extended by repeated administrations of the antibody to maintain antibody concentration in the serum above 1 nM, and thereby high receptor occupancy for an extended period. Based on the PK profile of the antibody, a concentration of 1.5 mg/mouse was initially administered, followed by 5 consecutive injections of 1 mg/mouse every 72 hours. A satellite group of wild-type mice was used to determine PK profile in this repeated dosing setup. Male C57BL/6J mice were injected i.p. with either 0.1 mg/mouse (n=3), 0.5 mg/mouse (n=3) or 1.5 mg/mouse (n=3), single dose injections of rat anti-mouse PD-L1 monoclonal antibody (clone 10F.9G2, BioXCell), or with 1.5 mg/mouse at time zero, followed by 1 mg/mouse injections every 72 hours (indicated by black arrows on the upper part of the graph in FIG. 15). Serum was collected at different time points following injection and serum levels of anti-PD-L1 antibodies were quantified using ELISA. Serum levels of anti-PD-L1 antibodies measured for this experiment are shown in FIG. 15.

Figure 16:
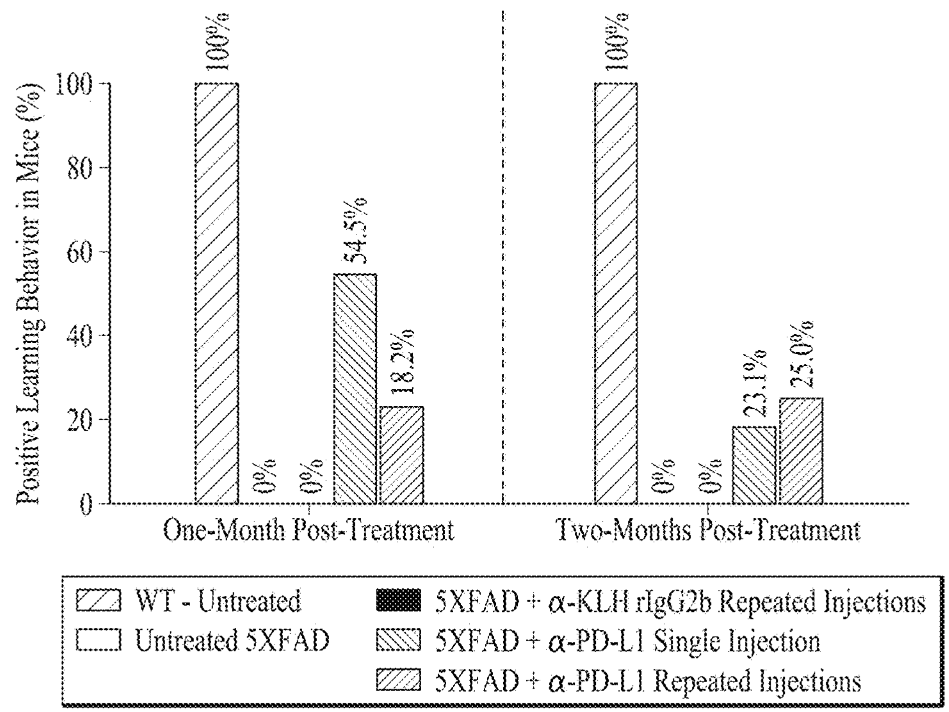
FIG. 16 shows comparison of treatment effect on cognitive performance of a single relative to repeated injections of anti-PD-L1, representing transient relative to continuous exposure to the treatment, respectively, in 5×FAD mice, tested 1 month and 2 months after the first injection. Cognitive performance of 5×FAD mice was tested using the radial arm water maze, and effect following treatment in the different treatment groups is expressed as the percentage of mice that showed positive learning behavior (positive learning was defined as less than 3 mean errors in the last 2 trails of the cognitive task).

Assessment of the effect of treatment on cognitive performance in radial arm water maze one month and two months following the beginning of an anti-PD-L1 antibody treatment revealed that extending the exposure time of the antibody in the serum to about 17 days by repeated dosing showed no advantage upon the shorter exposure in terms of the effect on cognitive performance. On contrary, prolonged exposure was less beneficial at one-month post treatment initiation than shorter exposure (FIG. 16). Extended exposure time not only showed no advantage, but was somewhat less effective than shorter exposure. It was thus concluded that the transient exposure and the relative long period "free of antibody" is needed as part of the mechanism of action of the antibody in Alzheimer's disease. Hence, the physical properties of the antibody, including its high affinity and exclusivity to PD-L1 and fast clearance rate are critical for its beneficial activity i.e. a slow clearance rate may negatively impact efficacy of treatment.

Many factors can influence the clearance of an antibody from serum with the primary determinant being FcRn-mediated recycling. By Fc engineering, the IgG-FcRn interaction can be used to generate a variety of therapeutic antibodies with significantly enhanced clearance from circulation. In addition to the advantage in efficacy, it is expected that the shorter the duration of exposure to the antibody relative to the period with no exposure, the lower the probability of evoking immune-related adverse effects. Important to note, that in cancer patients that are treated with anti PD-L1 antibody and experience immune related adverse events, most of the adverse events resolved by discontinuation of treatment. Thus, intermitted treatment, which includes a short period of exposure to the antibody, followed by a relative long period of no exposure is expected to have a better safety profile than a regimen based on continuous exposure.

Example 4

Analysis of Modified Anti-Human PD-L1 Antibody Atezolizumab

To create anti-PD-L1 antibodies with enhanced clearance rate from the blood, abolished Fc-related effector functions, and improved safety profile, while maintaining therapeutic efficacy for neurodegenerative disease modification, amino acid variants of anti-PD-L1 were developed having the same variable region but possessing amino acid alterations on the Fc heavy chain designed to increase the antibody clearance rate and abolish Fc-related effector function. These variants were examined for beneficial effects in mouse models of Alzheimer and dementia.

Four variants of a recombinant human anti-PD-L1 antibody were produced which comprised the variable regions of the humanized anti-PD-L1 monoclonal antibody atezolizumab (ATZ; Genentech) and an human IgG1 backbone which included the following amino acid substitutions in the heavy chain: 1) Variant 1-ATZ, human IgG1 Fc effector null (L235A, L236A, and K323A substitutions; L234A, L235A, and K322A under the Kabat numbering system generalized for all antibodies); Variant 2-ATZ, human IgG1 Fc effector null substitutions plus a H311A substitution (H310A under the Kabat numbering system generalized for all antibodies); 3) Variant 3-ATZ, human IgG1 Fc effector null substitutions plus a H436Q substitution (H335Q under the Kabat numbering system generalized for all antibodies); and 4) Variant 4-ATZ, human IgG1 Fc effector null substitutions plus H311A and H436Q substitutions (H310A and H435Q under the Kabat numbering system generalized for all antibodies).

These anti-PD-L1 variant antibodies were designed to comprised the light and heavy chain variable regions of the human anti-PD-L1 antibody atezolizumab and an IgG1 backbone in the heavy chain constant region from a human kappa1 light chain and a human IgG1 heavy chain which included the amino acid substitutions. The first group are substitutions, comprising L235A, L236A, and K323A, were made to reduce/eliminate antibody dependent cellular cytotoxicity (ADCC) by reducing/eliminating Fc effector function activity. The second group of substitutions, comprising H311A and/or H436Q, were made to accelerate antibody clearance from the circulation by reducing antibody interaction with the FcRn receptor. Heavy chain and light chain expression constructs were generated by standard gene synthesis and cloning methods (Table 4). The unaltered atezolizumab antibody has a heavy chain amino acid sequence of SEQ ID NO: 98 including a heavy chain variable region SEQ ID NO: 94 and a heavy chain constant region SEQ ID NO: 99 and a light chain amino acid sequence of SEQ ID NO: 97 including a light chain variable region SEQ ID NO: 95 and a light chain constant region SEQ ID NO: 96. Variant 1-ATZ (Fc effector null) has a heavy chain amino acid sequence of SEQ ID NO: 100 including a heavy chain variable region SEQ ID NO: 104, Variant 2-ATZ (Fc effector null-H311A) has a heavy chain amino acid sequence of SEQ ID NO: 101 including a heavy chain variable region SEQ ID NO: 105, Variant 3-ATZ (Fc effector null-H436Q) has a heavy chain amino acid sequence of SEQ ID NO: 102 including a heavy chain variable region SEQ ID NO: 106, and Variant 4-ATZ (Fc effector null-H311A+H436Q) has a heavy chain amino acid sequence of SEQ ID NO: 103 including a heavy chain variable region SEQ ID NO: 107.

TABLE 4

Humanized Anti-PD-L1 Monoclonal Antibody Variants (ATZ)

| ATZ Variant | Light Chain Sequence Amino Acid | Heavy Chain Sequence Amino Acid |
|---|---|---|
| Unaltered Atezolizumab Antibody | 97 | 98 |
| Variant 1-ATZ (Fc effector null) | 97 | 100 |
| Variant 2-ATZ (Fc effector null-H311A) | 97 | 101 |
| Variant 3-ATZ (Fc effector null-H436Q) | 97 | 102 |
| Variant 4-ATZ (Fc effector null-H311A + H436Q) | 97 | 103 |

The antibodies were expressed in a transient HEK293 system by regular co-transfection of the HC and LC expression plasmids. The antibodies were purified from the expression culture supernatants by standard protein A capture and size-exclusion chromatography. The antibody purity was determined by analytical SEC-HPLC and SDS-PAGE and concentration measured by UV280 absorption using the calculated molar extinction coefficient.

Human anti-B12 antibodies served as human IgG1 isotype controls. Besides the unaltered version, designated human IgG1 anti-B12, the following isotype variants were constructed: Variant 1-B12 (an anti-B12 antibody containing a human IgG1 backbone with the Fc effector null substitutions in the Fc portion corresponding to the same substitutions of Variant 1-ATZ), Variant 2-B12 (an anti-B12 antibody containing a human IgG1 backbone with the Fc effector null and H311A substitutions in the Fc portion corresponding to the same substitutions of Variant 2-ATZ), and Variant 3-B12 (an anti-B12 antibody containing a human IgG1 backbone with the Fc effector null and H436Q substitutions in the Fc portion corresponding to the same substitutions of Variant 3-ATZ). These anti-B12 antibody variants were produced using routine methods as discussed above.

Figure 17:
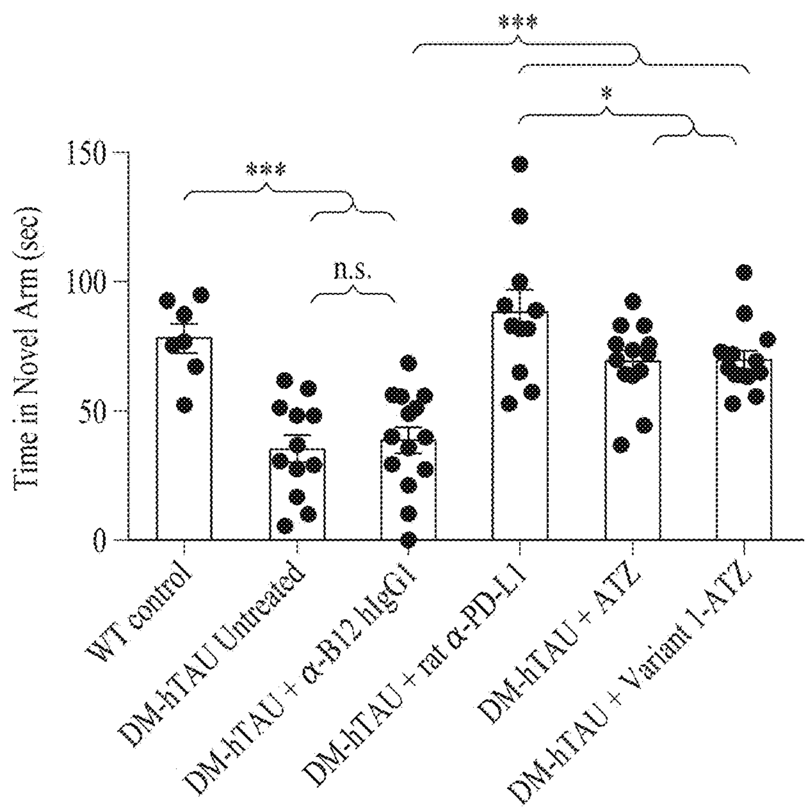
FIG. 17 shows T-maze performance of DM-hTAU mice one month after an anti-PD-L1 antibody treatment with either a rat anti-PD-L1 antibody, a humanized anti-PD-L1 antibody atezolizumab (ATZ; with human IgG1 Fc) or Variant 1-ATZ (Fc effector null) antibody along with wild-type mice, untreated DM-hTAU mice, and mice treated with human anti-B12 antibody as an IgG1 isotype control, each of which served as controls (Error bars represent mean±s.e.m.; *P<0.05, P<0.01, *P<0.001).

In one series of experiments, a DM-hTAU mouse model was used to assess whether treatment using the Variant 1-ATZ (Fc effector-null) antibody maintained the improved cognitive performance observed using a rat anti-mouse PD-L1 monoclonal antibody. Male and female 8-9 months old DM-hTAU mice were treated with 1.5 mg/mouse of either a rat anti-mouse PD-L1 monoclonal antibody (clone 10F.9G2, BioXCell), atezolizumab, Variant 1-ATZ (Fc effector null) or 1.5 mg/mouse (n=10) anti-B12 human IgG1 isotype antibody control. Aged matched wild-type mice and untreated DM-hTAU mice were used as additional control groups. Significance was calculated using one-way ANOVA followed by Fisher's post-hoc test. The results indicated that Variant 1-ATZ (Fc effector null) elicited the same statistically significant beneficial effect as atezolizumab in DM-hTAU mouse model performance in the T-maze assay, measured at 4 weeks following a single IP injection of the effective dose (FIG. 17). In addition, both the Variant 1-ATZ (Fc effector null) antibody and atezolizumab improved cognitive performance in DM-hTAU better than the rat anti-mouse PD-L1 monoclonal antibody (FIG. 17).

Figure 18:
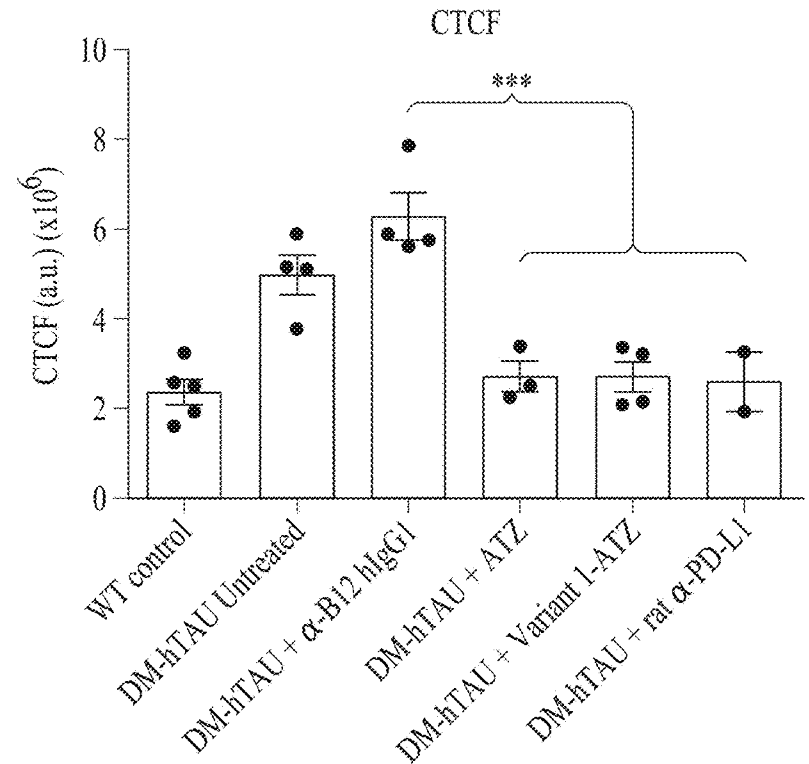
FIG. 18 shows a comparison of anti-PD-L1 antibody effect (rat anti-mouse PD-L1 with rat IgG2b anti-KLH antibody, anti-PD-L1 atezolizumab with human IgG1 backbone, and Variant 1-ATZ (Fc effector null) on hippocampal astrogliosis in DM-hTAU mice based on mean fluorescence of detected GFAP$^+$ cells, corrected to the mean fluorescence (CTCF) of the whole dentate gyrus (error bars represent mean±s.e.m.; *P<0.05, P<0.01, *P<0.001).

To examine the effect of anti-PD-L1 antibody treatment on brain pathology, brains from DM-hTAU mice were analyzed at the end of the cognitive assessment in a T-maze assay by immunohistochemistry. Brains were removed after perfusion, 6 μm coronal slices were collected, and 5 sections per mouse were immune-stained for glial fibrillary acidic protein (GFAP) at 4-5 different pre-determined depths throughout the region of interest (dentate gyrus or cerebral cortex). Histogram-based segmentation of positively stained pixels was performed using Image-Pro Plus software (Media Cybernetics, Bethesda, Md., USA). The segmentation algorithm was manually applied to each image, calculating the size of a manually selected area of the dentate gyrus, and locating within it all cells expressing GFAP fluorescence. The algorithm then measure the fluorescence intensity of cells and "CTCF" calculated as mean fluorescence of the detected cells, corrected to the mean fluorescence of the whole dentate gyrus. Analysis of GFAP immunostaining using a marker for astrogliosis and neuroinflammation showed that Variant 1-ATZ (Fc effector null) antibody elicited the same beneficial effect as atezolizumab and the rat anti-mouse PD-L1 monoclonal antibody (FIG. 18). These experiments show that Fc effector function does not contribute to the therapeutic activity of the treatment with anti-PD-L1 antibody in neurodegenerative disease models, manifested by effect on cognitive performance and brain pathology.

To understand the effects of amino acid substitutions in the Fc portion on the clearance of an anti-PD-L1 antibody from the serum, pharmacokinetic experiments were done to determine the half-life and clearance rate of the antibodies. Male C57BL/6J mice were injected i.p. with 1.5 mg/mouse (n=3), single dose administrations of either atezolizumab or one of the following modified anti-PD-L1 antibodies: Variant 1-ATZ (Fc effector null), Variant 2-ATZ (Fc effector null-H311A), Variant 3-ATZ (Fc effector null-H436Q), or Variant 4-ATZ (Fc effector null-H311A+H436Q). Serum was collected at different time point following injection and serum levels of anti-PD-L1 antibodies were quantified using reverse-sandwich ELISA.

Figure 19:
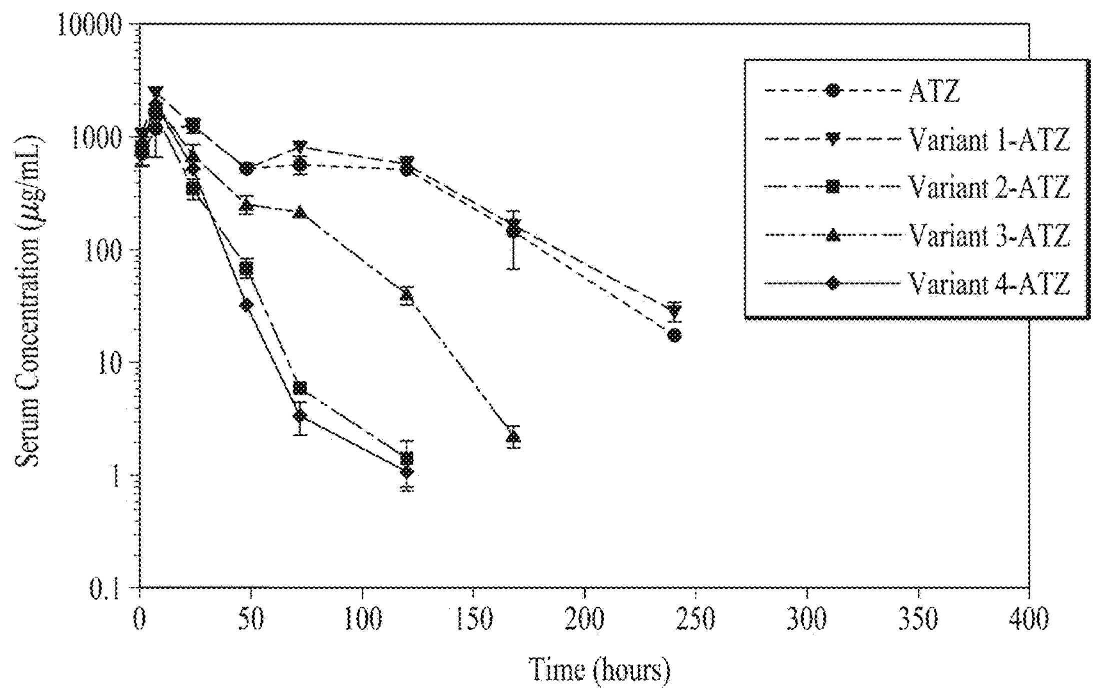
FIG. 19 shows PK profile of anti-human PD-L1 atezolizumab (ATZ) and four ATZ variants in blood sera taken from wild type C57BL/6J mice and quantified using reverse ELISA (error bars represent mean±s.e.m.).

The results of the PK study demonstrate that while the Variant 1-ATZ (Fc effector null) antibody showed a PK profile similar to atezolizumab, the other substitutions significantly accelerated clearance of the antibody as demonstrated by the reduced half-life ($t_{1/2}$) values (Table 5; FIG. 19). The fastest clearance was obtained in Variant 4-ATZ (Fc effector null-H311A+H436Q) antibody, which demonstrated a half-life of about 10 hours. This represented an over 4-fold reduction in the clearance rate relative to atezolizumab (10 hours vs. 44 hours). Variant 2-ATZ (Fc effector null-H311A) also exhibited faster clearance rate compare to atezolizumab (11 hours v. 44 hours), followed by Variant 3-ATZ (Fc effector null-H436Q) (19 hours vs. 44 hours).

TABLE 5

Half-Life of Human Anti-PD-L1 Monoclonal Antibody Variants (Atezolizumab)

| Antibody Dose | $C_{max}$ | $t_{1/2}$ (h) | $AUC_{total}$ (μg/mL · h) | $AUC_{0-7}$ (μg/mL · h) |
|---|---|---|---|---|
| Unaltered Atezolizumab Antibody | 1260.52 | 44.85 | 110,434 | 6,168 |
| Variant 1-ATZ (Fc effector null) | 2519.15 | 44.57 | 141,104 | 11,315 |
| Variant 2-ATZ (Fc effector null-H311A) | 1625.79 | 11.46 | 30,506 | 7,410 |
| Variant 3-ATZ (Fc effector null-H436Q) | 1973.55 | 19.27 | 55,992 | 8,834 |
| Variant 4-ATZ (Fc effector null-H311A + H436Q) | 2004.69 | 10.22 | 38,927 | 10,089 |

To assess the effect of clearance rate on an antibody's beneficial effect in attenuating disease progression, a DM-hTAU mouse model was used to assess whether treatment using the four variant antibodies maintained the improved cognitive performance observed using a rat anti-mouse PD-L1 monoclonal antibody or atezolizumab. Male and female DM-hTAU mice were treated with 1.5 mg/mouse of 1) humanized anti-PD-L1 monoclonal antibody atezolizumab (Genentech) or one of the four atezolizumab variants, or 2) 1.5 mg/mouse Variant 1-B12 (Fc effector null) human IgG1 isotype antibody control. Untreated aged matched wild-type mice were used as additional control group. Cognitive performance was assessed by testing mice using a T-maze at 4 weeks and eight weeks following antibody administration and using a Y-maze cognitive task at 6 weeks following antibody administration. Following the last cognitive scoring (8 weeks post treatment initiation), the animals were sacrificed for brain pathology assessment (cortex and hippocampus from both hemispheres). Significance was calculated using one-way ANOVA followed by Fisher's post-hoc test.

Figure 20A:
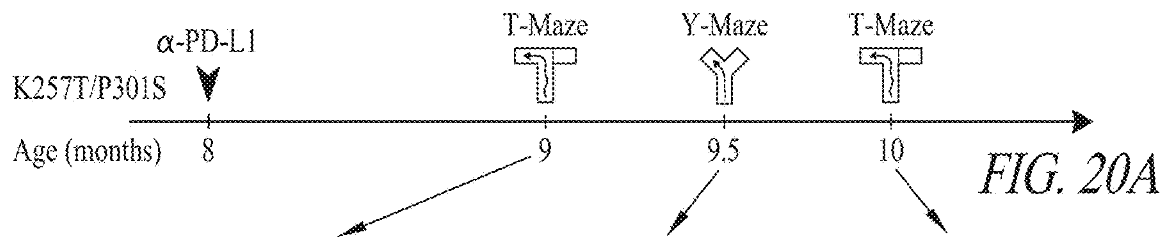
FIG. 20A-D show effect of modified anti-PD-L1 antibody variants on spatial learning and memory in DM-hTAU mice, with FIG. 20A illustrating the experimental design with black arrowheads indicate time points of treatment, and drawings indicate time points of cognitive scoring using a T-maze or Y-maze assay.
Figure 20B:
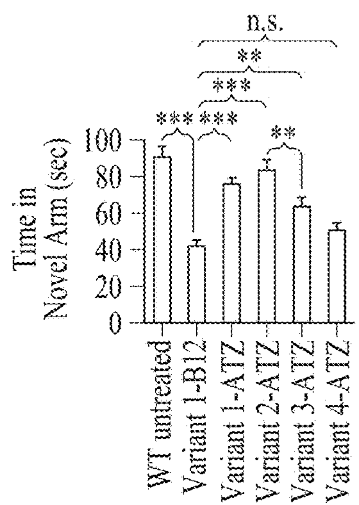
Figure 20C:
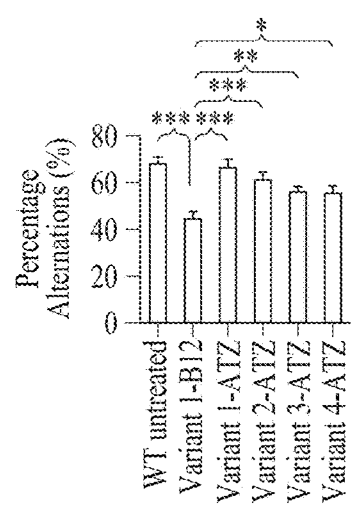
Figure 20D:
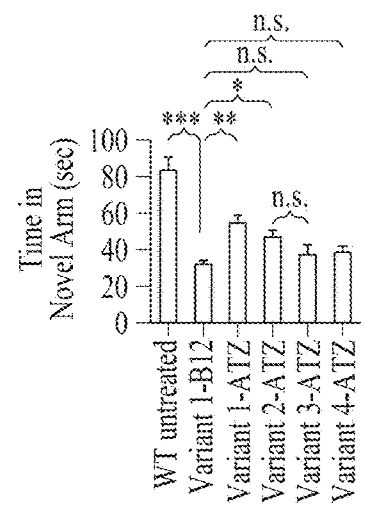

When examined 1-month post-injection, treatment effect was observed in DM-hTAU mice treated with either the Variant 1-ATZ (Fc effector null), Variant 2-ATZ (Fc effector null-H311A) or Variant 3-ATZ (Fc effector null-H436Q) antibodies, though the effect of the Variant 2-ATZ (Fc effector null-H311A) antibody was significantly more pronounced compared to the Variant 3-ATZ (Fc effector null-H436Q) antibody (FIG. 20B). When assessed again by the T-maze task, 2 months following injection, both Variant 1-ATZ (Fc effector null) and Variant 2-ATZ (Fc effector null-H311A) antibodies maintained their effect on cognitive performance, while efficacy was not observed at this time point in mice treated with the Variant 3-ATZ (Fc effector null-H436Q) antibody (FIG. 20D). Animals were also tested using the Y-maze cognitive task, at 6 weeks post-injection, and all variants of the antibody were effective in this test, in which the parameter that is gauged is the frequency of between-arm spontaneous alternations performed by the mouse during the assay timeframe (FIG. 20C). The more spontaneous alternations performed by the mouse (unlike the T-maze, in the Y-maze all the arms of the maze are identical), the greater the normal exploring behavior.

Notably, the concentration of the Variant 2-ATZ (Fc effector null-H311A) antibody in the serum reaches below 1 nM at 5 days post-treatment, while the null variant is cleared to under 1 nM at around 12 days post-treatment (FIG. 19). Yet, both variant antibodies significantly improved cognitive performance to the same extant, as was measured at 4 weeks post treatment using the T-maze system. Moreover, at 8 weeks after treatment both the antibodies with the shorter and longer exposure time still preserved a small but significant beneficial effect in comparison to the animals that were treated with the isotype control antibody.

To further assess the effect of clearance rate on antibody's beneficial effect in attenuating disease progression, a 5×FAD mouse model was used to assess whether treatment using the four variant antibodies maintained the improved cognitive performance observed using a rat anti-mouse PD-L1 monoclonal antibody or atezolizumab. Male and female 5×FAD mice were treated with 1.5 mg/mouse of 1) humanized anti-PD-L1 monoclonal antibody (Genentech) or one of the four atezolizumab variants, or 2) 1.5 mg/mouse anti-B12 human IgG1 isotype antibody control. Untreated aged matched wild-type (WT) mice were used as additional control group. Animals were scored for their cognitive performance one-month post-single injection using the Radial Arm Water Maze (RAWM). Significance was calculated using two-way repeated-measures ANOVA followed by Dunnett's post-hoc test for multiple comparisons.

Figure 21:
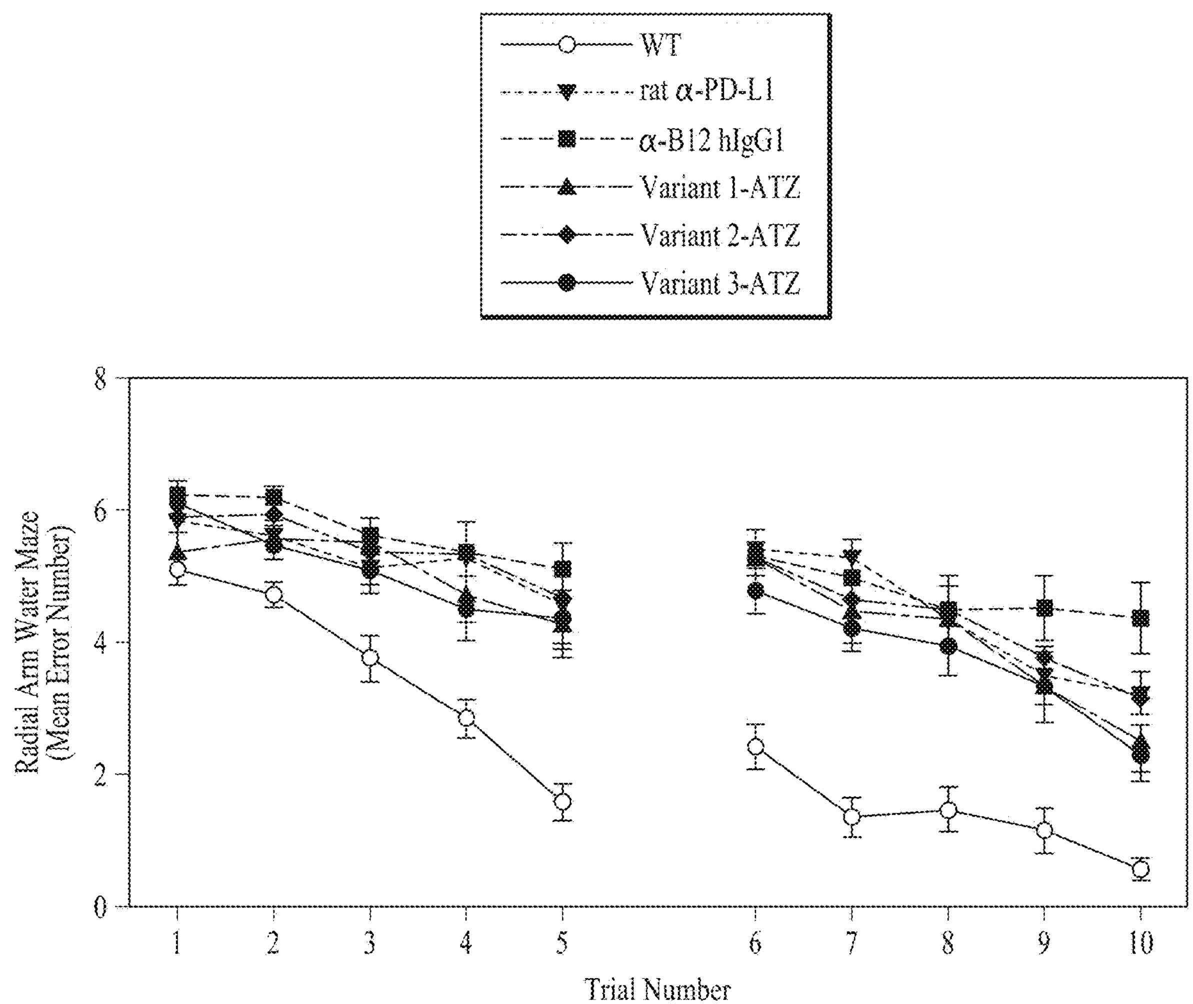
FIG. 21 shows effect of modified anti-PD-L1 antibody variants on spatial learning and memory in 5×FAD mice using a RAWM cognitive task one-month after treatment, each group treated with a different modified anti-PD-L1 antibody variant, or the rat anti-mouse PD-L1 antibody, along with wild-type littermates and anti-B12-treated mice, both of which served as controls (Error bars represent mean±s.e.m.).

Similar results in terms of improved effect on cognitive performance were obtained with 5×FAD mice, using the RAWM cognitive task (FIG. 21). Modified anti-PD-L1 antibodies variants with accelerated clearance properties do not lose their efficacy, and show similar effect on cognitive performance as atezolizumab (Table 6).

TABLE 6

Statistical Analysis

| Comparison | p-value |
|---|---|
| 5XFAD + B12 (hlgG1 isotype control) v. WT (untreated control) | <0.0001 |
| 5XFAD + B12 (hlgG1 isotype control) v. 5XFAD + 10F.9G2 (positive control) | 0.0512 |
| 5XFAD + B12 (hlgG1 isotype control) v. 5XFAD + Variant 1-ATZ (Fc effector null) | 0.0005 |
| 5XFAD + B12 (hlgG1 isotype control) v. 5XFAD + Variant 2-ATZ (Fc effector null-H311A) | 0.0203 |
| 5XFAD + B12 (hlgG1 isotype control) v. 5XFAD + Variant 3-ATZ (Fc effector null-H436Q) | 0.00001 |

In another series of experiments, a multi-dose study was conducted using two of the antibody variants to correlate between efficacy and PK/PD profile. Male C57BL/6J mice were injected i.p. (n=3 per group) with the Variant 2-ATZ (Fc effector null-H311A) antibody or Variant 3-ATZ (Fc effector null-H436Q) antibody. Serum was collected at different time point following injection and serum levels of antibody were quantified using ELISA. Blood was collected at different time point following injection and prepared for flow cytometry analysis. Each sample was equally divided into two tubes, one saturated in-vitro for 30 minutes on ice with the injected anti-PD-L1 antibody and the other with the IgG control. Cells were then stained for the surface markers CD3, CD4, CD44 and PD-1 and analyzed by flow cytometry to detect CD3+ cells (T cells) and PD-L1 receptor bound with anti-PD-L1 (using anti-human Fc). Receptor occupancy was evaluated by the ratio of differences in mean florescence intensity on CD3 T cells, whereby each sample was compared to its own control of maximal receptor occupancy in the anti-PD-L1 saturated sample. The efficacy study was conducted using the DM-hTAU animals as disclosed above and significance calculated using one-way ANOVA and Fisher exact-test post hoc analysis.

Figure 22A:
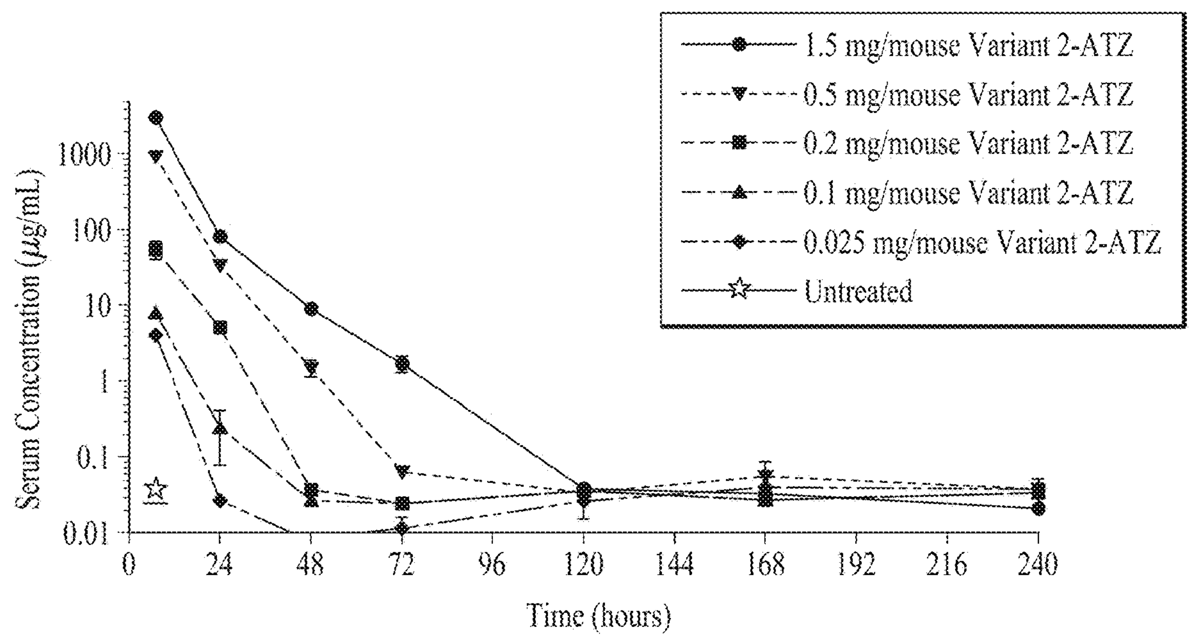
FIG. 22A-B show PK profile using multi-dosages of two different modified anti-PD-L1 antibody variants in blood sera taken from C57BL/6J mice and quantified using ELISA, with FIG. 22A showing the results obtained with the Variant 2-ATZ (Fc effector null-H311A) antibody (error bars represent mean±s.e.m.)
Figure 22B:
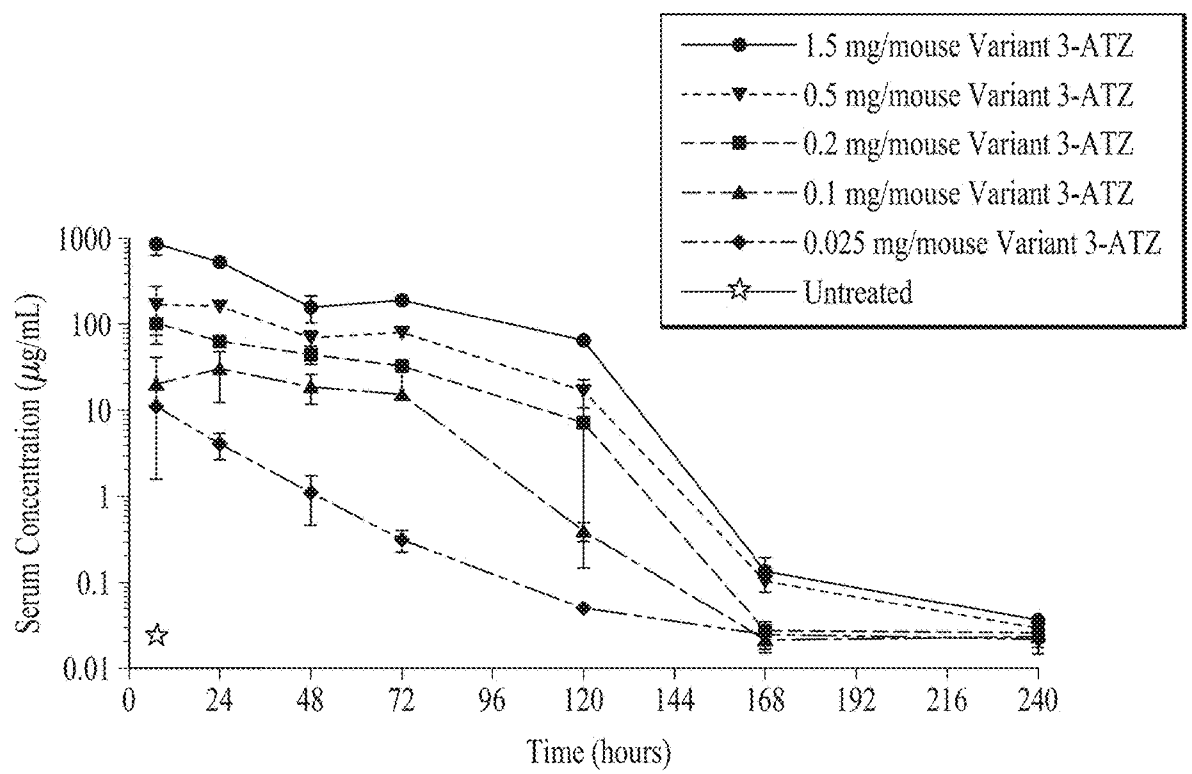
Figure 23A:
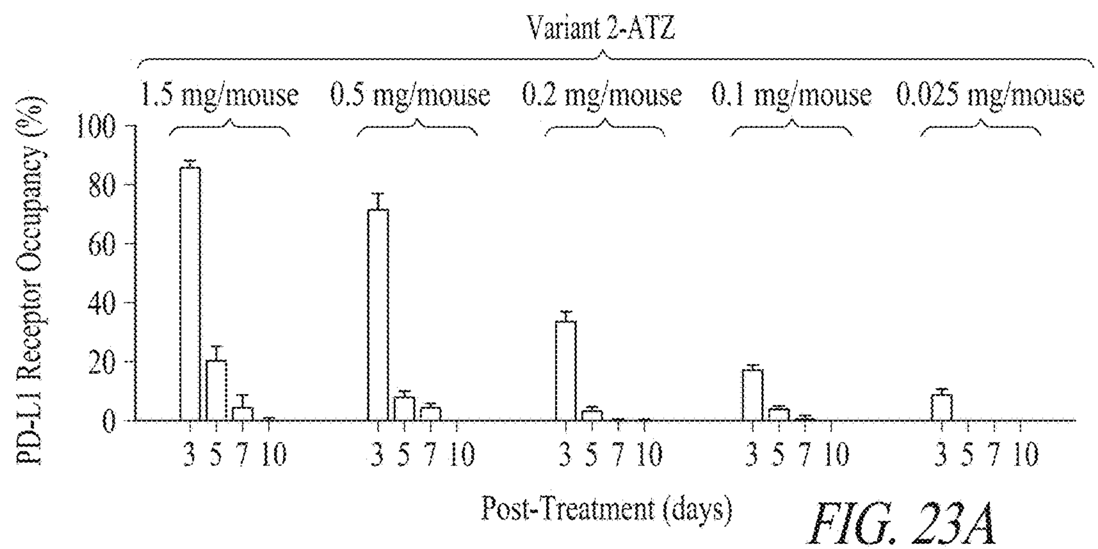
FIG. 23A-B show kinetics of PD-L1 receptor occupancy on T cell in the blood from C57BL/6J wild-type mice following a single injection of two different modified anti-PD-L1 antibody variants, with FIG. 23A showing the results obtained from the Variant 2-ATZ (Fc effector null-H311A) antibody (error bars represent mean±s.e.m.)
Figure 23B:
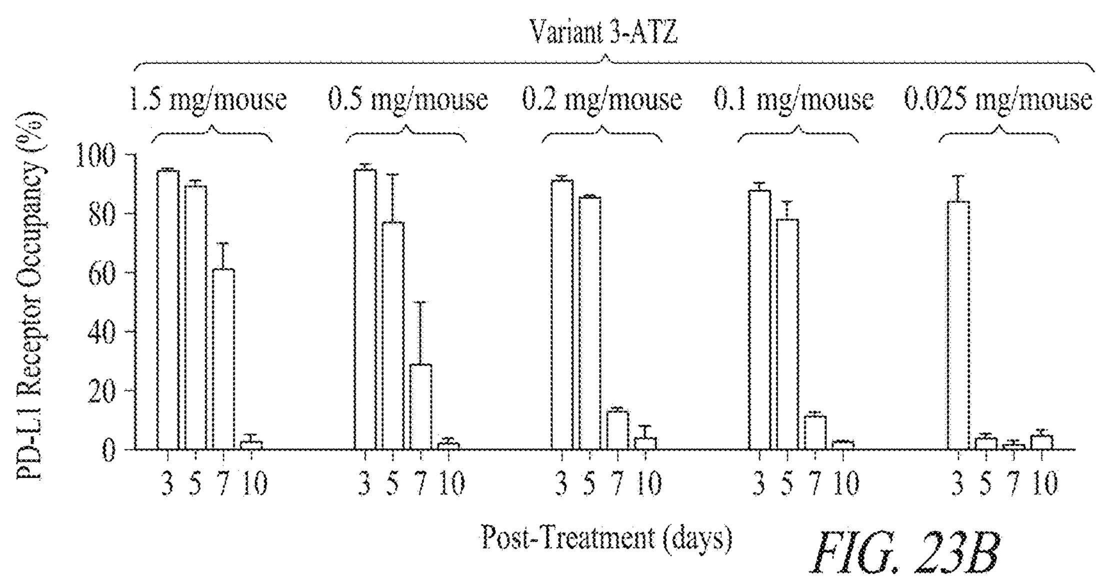
Figure 24A:
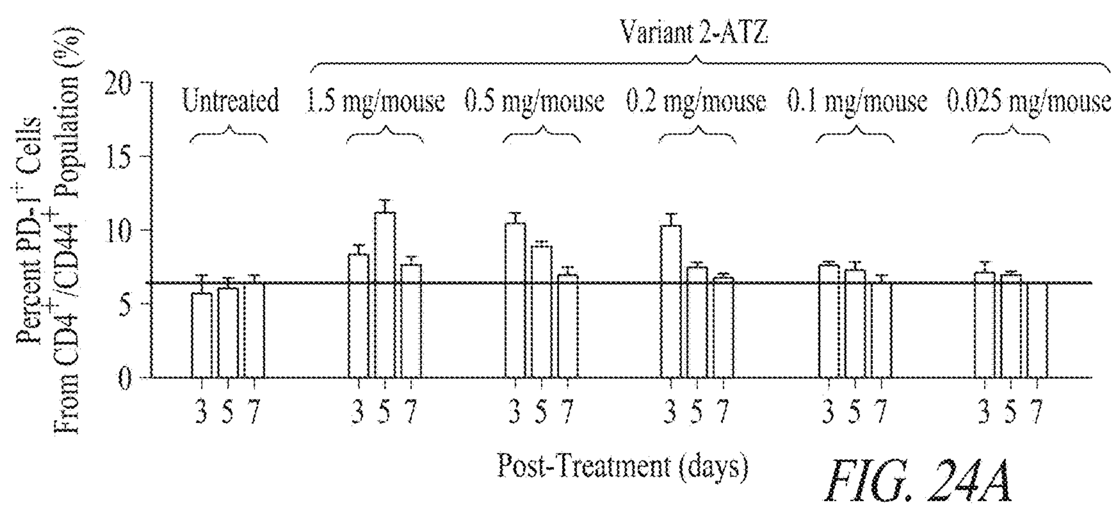
FIG. 24A-B show kinetics of blood levels of PD-$1^+$CD$4^+$ CD$44^+$ T cells in C57BL/6J wild-type mice following a single injection of two different modified anti-PD-L1 antibody variants, with FIG. 24A showing the results obtained with the Variant 2-ATZ (Fc effector null-H311A) antibody (error bars represent mean±s.e.m.)
Figure 24B:
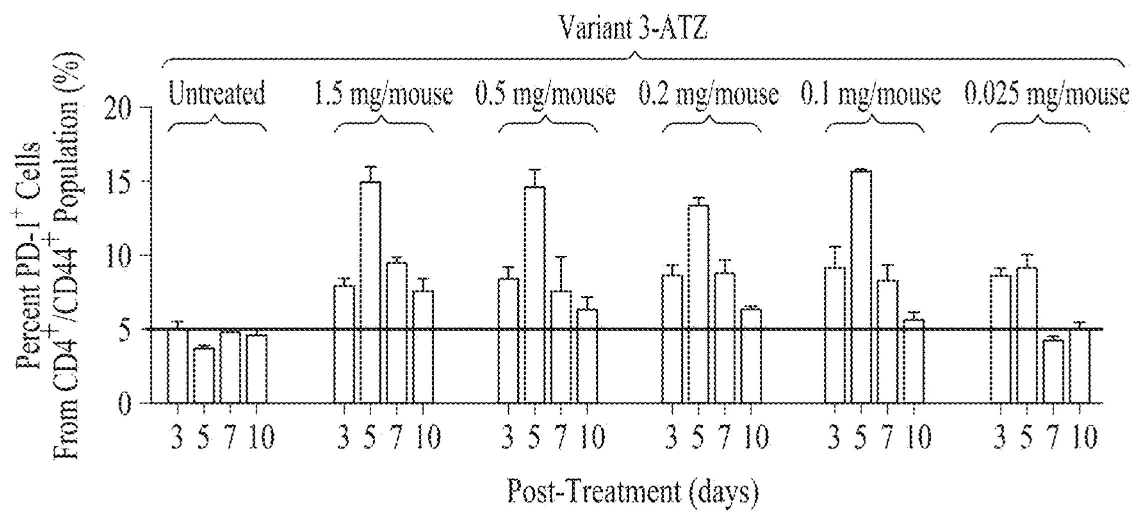

The results of the PK/PD study are shown in Table 7 and FIG. 22, FIG. 23 and FIG. 24. Variant 2-ATZ (Fc effector null-H311A) approximated a dose-dependent half-life range of about 7.5 hours to 11.6 hours while Variant 3-ATZ (Fc effector null-H436Q) exhibited a dose-dependent half-life range of about 13.6 hours to 23.5 hours (Table 6; FIG. 22A-B). The concentration of the antibody variants in serum correlated with receptor occupancy on lymphocytes and elevated levels of PD-1⁺ memory T-cells in the blood (compare FIG. 22A-B with FIG. 23A-B).

These results imply that an average concentration at the range of $C_{max}$ obtained by injection of 0.5 mg/mouse for a short exposure period is sufficient to trigger a cascade of events that attenuates disease progression. In conclusion, an anti-PD-L1 antibody with accelerated clearance properties does not lose its efficacy, assessed by its effect on cognition, demonstrated in both the DM-hTAU and 5×FAD neurodegenerative disease mouse models.

TABLE 7

Half-Life of Human Anti-PD-L1 Monoclonal Antibody Variants (Atezolizumab)

| Antibody Dose | Dose (mg/ mouse) | $C_{max}$ | $t_{1/2}$ (h) | $AUC_{total}$ (μg/mL · h) | $AUC_{0-7}$ (μg/mL · h) |
|---|---|---|---|---|---|
| Variant 2-ATZ (Fc effector null-H311A) | 1.5 | 2974.67 | 7.76 | 11,593 | 10,660 |
| Variant 2-ATZ (Fc effector null-H311A) | 0.5 | 909.33 | 9.3 | 3,610 | 3,284 |
| Variant 2-ATZ (Fc effector null-H311A) | 0.2 | 54.89 | 7.18 | 256 | 208 |
| Variant 2-ATZ (Fc effector null-H311A) | 0.1 | 7.95 | 11.61 | 37 | 29 |
| Variant 2-ATZ (Fc effector null-H311A) | 0.025 | 3.96 | 7.51 | 19 | 14 |
| Variant 3-ATZ (Fc effector null-H436Q) | 1.5 | 853.67 | 21.69 | 19162.93 | 4555.83 |
| Variant 3-ATZ (Fc effector null-H436Q) | 0.5 | 173.50 | 23.49 | 6457.87 | 1095.74 |
| Variant 3-ATZ (Fc effector null-H436Q) | 0.2 | 102.10 | 21.35 | 3055.76 | 547.26 |
| Variant 3-ATZ (Fc effector null-H436Q) | 0.1 | 30.03 | 19.96 | 1214.37 | 194.85 |
| Variant 3-ATZ (Fc effector null-H436Q) | 0.025 | 10.99 | 13.61 | 119.99 | 50.76 |

Figure 25:
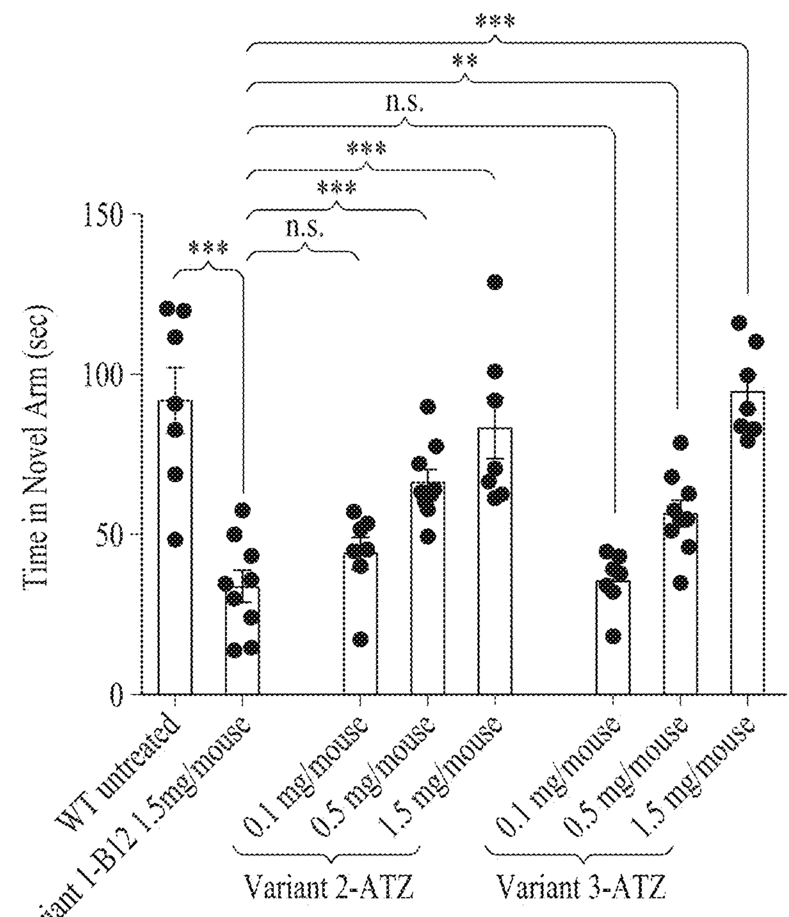
FIG. 25 shows dose dependent effect of two different modified anti-PD-L1 antibody variants on spatial learning and memory in DM-hTAU mice four weeks after treatment (data represented as mean±s.e.m.; *P<0.05, P<0.01, *P<0.001).

To assess whether treatment using a modified anti-PD-L1 variant with faster clearance rates maintained the improved cognitive performance observed using unaltered anti-PD-L1 antibodies, cognitive behavior was examined. Male and female 8-9 months old DM-hTAU mice were treated with 1.5 mg/mouse of either the Variant 2-ATZ (Fc effector null-H311A) antibody, the Variant 3-ATZ (Fc effector null-H436Q) antibody or the Variant 1-B12 (Fc effector null) human IgG1 isotype antibody control. Aged matched wild-type mice were used as an additional control group. Cognitive performance was assessed by testing mice using a T-maze at 2-weeks and 4-weeks following antibody administration. Significance was calculated using one-way ANOVA followed by Fisher's exact-test post-hoc analysis. The results indicated that while no significant improvement in cognitive performance was observed at 2-weeks post-treatment, both the Variant 2-ATZ (Fc effector null-H311A) antibody and the Variant 3-ATZ (Fc effector null-H436Q) elicited statistically significant improvement in cognitive behavior in DM-hTAU mice at four weeks following a single administration of an effective dose (FIG. 25).

Interestingly, there was a delay between the effect on receptor occupancy in the periphery and the effect on cognitive behavior. While both antibody concentration in the serum (FIGS. 22A-B) and receptor occupancy on blood T-lymphocytes (FIGS. 23-A-B) peaked on the first day, and were reduced to undetectable levels at around 7 days following antibody administration (FIGS. 22-A-B; FIGS. 23-A-B), no effect on cognition was found 2-weeks post-treatment yet a significant improvement was observed with the same animals at 4-weeks post-treatment (FIG. 25).

Figure 26A:
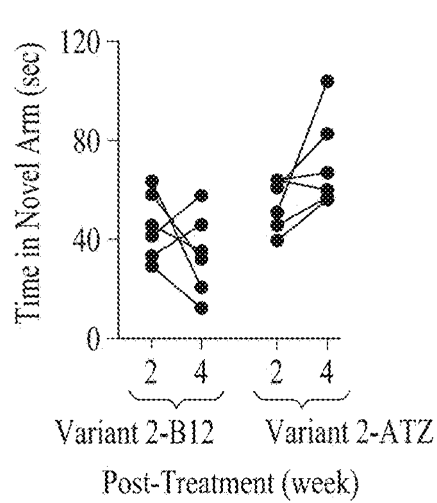
FIG. 26A-C shows longitudinal measures of cognitive performance at 2- and 4-week post 1.5 mg/mouse anti-PD-L1 administration of Variant 2-ATZ (Fc effector null-H311A) or isotype control Variant 2-B12 (an anti-B12 antibody containing the human IgG1 Fc effector null and H311A substitutions in the Fc portion corresponding to the same substitutions of Variant 2-ATZ), with FIG. 26A showing time spent of each individual mouse in the novel arm of the T-maze measured at 2 and at 4 weeks post treatment is presented and connected with solid line.
Figure 26B:
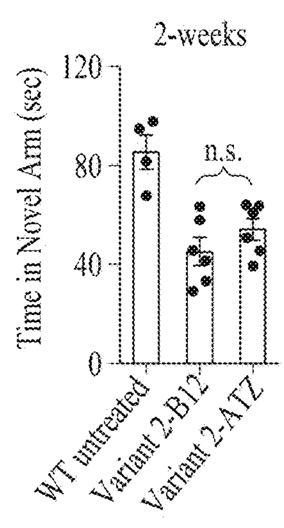
Figure 26C:
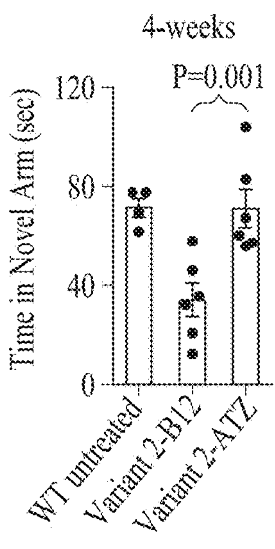

In this study, the same mice were evaluated for their cognitive scoring following the injection of 1.5 mg/mouse of Variant 2-ATZ (Fc effector null-H311A) at 2- and 4 weeks post-injection. While no significant change could be observed at 2-week post-injection, at 4-week post-injection Variant 2-ATZ (Fc effector null-H311A)-treated mice showed significant better cognitive performance, compared to control treated mice (FIG. 26).

Figure 27:
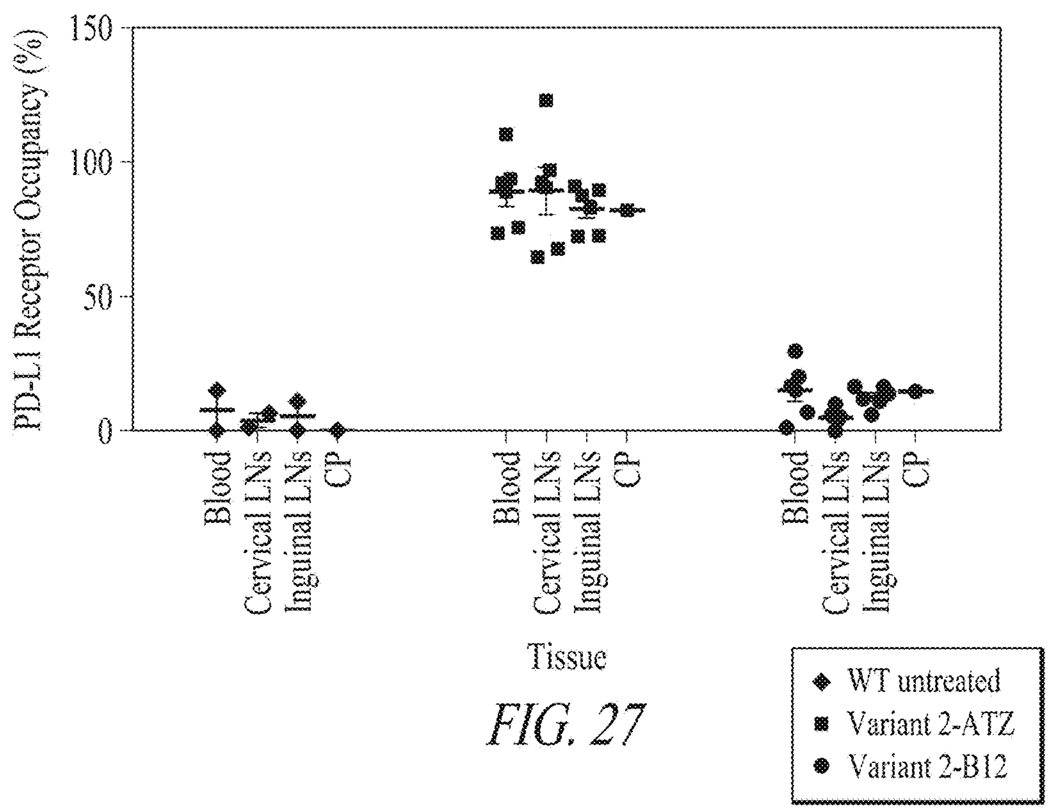
FIG. 27 shows kinetics of PD-L1 receptor occupancy on CD$3^+$ T cells isolated from blood, cervical lymph nodes, inguinal lymph nodes, and choroid plexus (CP) of C57BL/6J wild-type mice 3 days following a single injection of Variant 2-ATZ (Fc effector null-H311A) antibody or isotype control Variant 2-B12 (an anti-B12 antibody containing the human IgG1 Fc effector null and H311A substitutions) (error bars represent mean±s.e.m.).

In another series of experiments, receptor occupancy by immune cells from other peripheral tissues was examined by flow cytometry to determine whether cells from these tissues show a different pharmacodynamics pattern than the blood. Male C57BL/6J mice were injected i.p. with 1.5 mg/mouse of the Variant 2-ATZ (Fc effector null-H311A) antibody. Serum was collected at different time point following injection and serum levels of antibody were quantified using ELISA. Cells were isolated from inguinal lymph nodes, cervical lymph nodes, choroid plexus and blood and prepared for flow cytometry analysis by staining to detect $CD3^+$ cells (T cells) and PD-L1 receptor bound with anti-PD-L1 (using anti-rat IgG2b). CP was isolated from the lateral ventricles of the brain and pooled together from n=6 mice for flow cytometry analysis due to the low number of immune cells in this tissue. Receptor occupancy was evaluated by the ratio of differences in mean florescence intensity of IgG2b expression on $CD3^+$ T cells, whereby each sample was compared to its own control of maximal receptor occupancy in the anti-PD-L1 saturated sample. Each dot on the graph represent blood sample of a different mouse. Significance was calculated using one-way ANOVA followed by Fisher test for multiple comparisons. The results indicate that a similar pharmacodynamics pattern was observed in cells obtained from inguinal lymph nodes, cervical lymph nodes, and choroid plexus when compared to cells obtained from blood (FIG. 27).

Example 5

Cognitive Performance Using Multi-Dose Administration

Single administration of anti-PD-L1 antibody in mice at a dose of 1.5 mg/mouse was shown to be effective in reducing cognitive deficits and aggregated tau levels in the brain of DM-hTau mice. The beneficial effect on cognitive performance upon treatment with the short half-life Variant 2-ATZ (Fc effector null-H311A) was observed at 4 and 6 weeks, but not at 8 weeks post-treatment. To test whether the beneficial effect on cognitive performance and pathology could be extended beyond the 6 weeks observed following a single injection, an experiment was conducted in which the mice received multiple administrations of a modified anti-PD-L1 antibody variant.

Male and female DM-hTau mice at age 6-7 months were given 3 consecutive anti-PD-L1 treatments every 6 weeks by injecting mice with 1.5 mg/mouse of either with the Variant 2-ATZ (Fc effector null-H311A) antibody or the Variant 2-B12 (Fc effector null-H311A) human IgG1 isotype antibody control. Untreated aged matched wild-type (WT) mice were used as an additional control group. The effect on cognitive performance, brain pathology, and pharmacokinetics and pharmacodynamics parameters, were performed at different time points along the study (FIG. 28A). At 4 weeks following each injection, mice were tested using the T-maze cognitive test. In addition, at 3 days following each injection, a cohort of 5 mice were taken from each treatment group, euthanized and blood for isolation of PBMCs and serum/plasma, CSF and brain tissues (cortex and hippocampus were separately excised) were collected (FIG. 28A). The serum/plasma and brain tissues were kept frozen until analysis. PBMCs were freshly assessed for receptor occupancy and PD1+ memory CD4 T cells frequencies. Based on PK/PD data obtained following single administration, at 3 days post injection we expect to see high receptor occupancy as well as elevated levels of PD1+CD4 memory T cells in the blood. In addition, at 2 weeks after the first injection, 5-6 animals per treatment group were assessed using the T-maze test, the same animals were also assessed at 4 weeks and ethnized at 6 weeks post study initiation (3 days after the second injection). Hence, for this group of animals longitudinal readouts of single-administration effect on T-maze performance and on levels of aggregated tau at 6 weeks are available. Also, following the 3rd injection, animals were examined for cognitive performance in T-maze every 2 weeks up to 8 weeks post injection while some of the animals were euthanized at 4 weeks post injection for PK/PD and pathology measures. An additional 4th injection was given at 8 weeks following the third injection for measuring antibody exposure in the serum, peripheral immune response at 4 hours and 3 days after the last antibody administration. Significance was calculated using one-way ANOVA followed by Fisher's post-hoc test.

To assess the effect of the Variant 2-ATZ (Fc effector null-H311A) antibody on cognitive performance mice were tested using a T-maze cognitive task assay at two and four weeks following the first antibody administration, four weeks following the second antibody administration, two and four weeks following the third antibody administration and two and four weeks following the fourth antibody administration (FIG. 28A). The results indicate that while improved cognitive performance was not observed two-weeks post-treatment of the first Variant 2-ATZ (Fc effector null-H311A) antibody administration (FIG. 28B), statistically significant improvement of cognitive performance was measured in DM-hTau mice at all other post-treatment times (FIG. 28C-H).

To assess the effect of the Variant 2-ATZ (Fc effector null-H311A) antibody on pharmacokinetics and pharmacodynamics parameters receptor occupancy by immune cells from various peripheral tissues was examined by flow cytometry. A cohort of five mice were taken from each treatment group at five different time points along the course of the experiment: 1) 72 hours after 1st injection; 2) 72 hours after 2nd injection; 3) 72 hours after 3rd injection; 4) 4 hours after 4th injection; and 1) 72 hours after 4th injection (FIG. 28A). Serum was drawn from these mice and then these animals euthanized and tissue collected. Cells were isolated from inguinal lymph nodes, cervical lymph nodes, choroid plexus and blood and prepared for flow cytometry analysis by staining to detect $CD3^+$ cells (T cells) and PD-L1 receptor bound with anti-PD-L1 (using anti-rat IgG2b). CP was isolated from the lateral ventricles of the brain and pooled together from n=6 mice for flow cytometry analysis due to the low number of immune cells in this tissue. Significance was calculated using one-way ANOVA followed by Fisher's post-hoc test.

Figure 29:
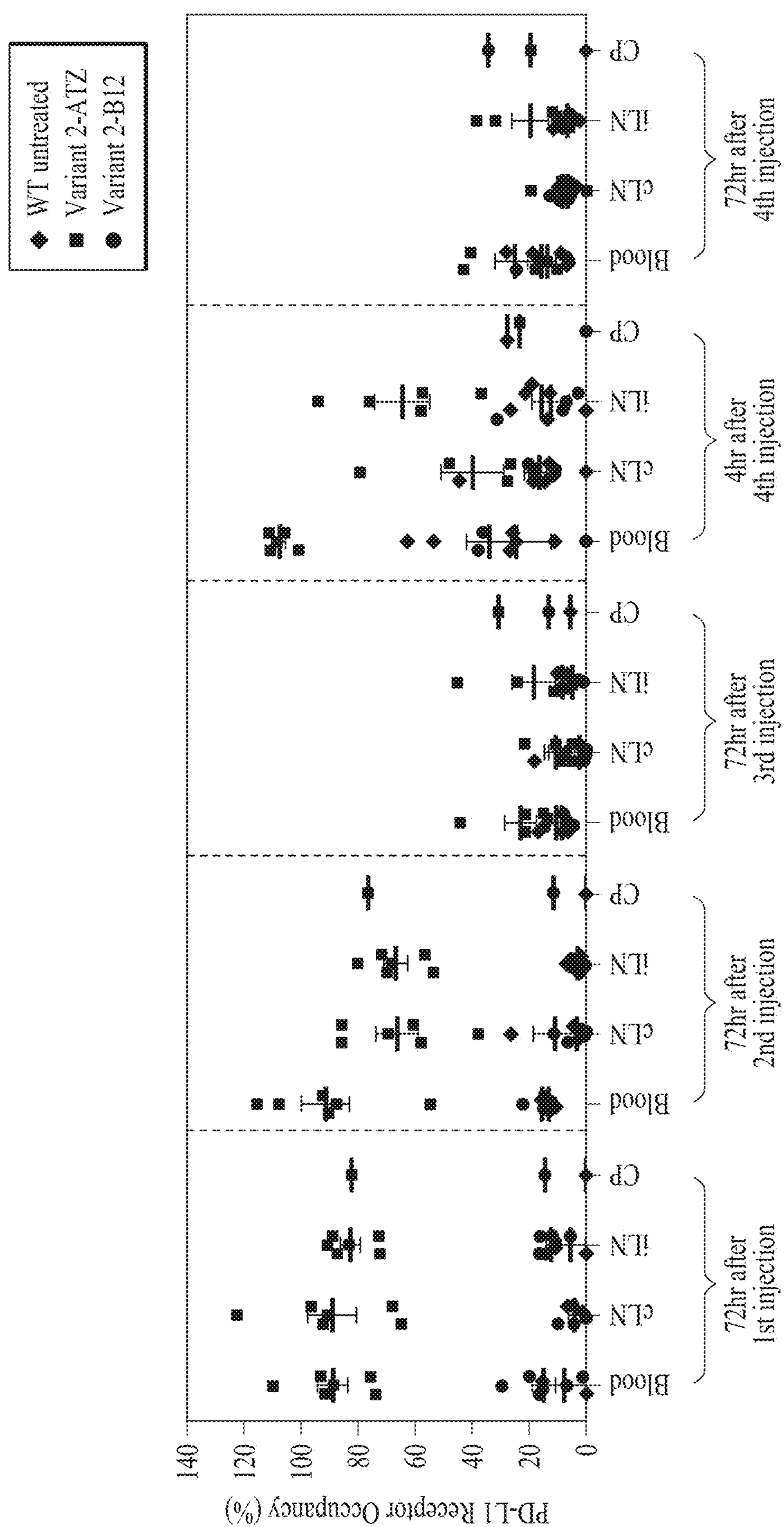
FIG. 29 shows kinetics of PD-L1 receptor occupancy on CD$3^+$ T cells isolated from blood, cervical lymph nodes, inguinal lymph nodes, and choroid plexus (CP) tissues from DM-hTAU mice at various time points following treatment with different dosages of the Variant 2-ATZ (Fc effector null-H311A) or isotype control Variant 2-B12 (an anti-B12 antibody containing the human IgG1 Fc effector null and H311A substitutions in the Fc portion corresponding to the same substitutions of Variant 2-ATZ) (error bars represent mean±s.e.m.).

Results indicate that at 72 hours after the first and second injection of the Variant 2-ATZ (Fc effector null-H311A) antibody (6 weeks interval), full PD-L1 receptor occupancy was observed at on T cells at different tissues, including blood, cervical lymph nodes (cLN), inguinal lymph nodes (iLN) and choroid plexus (CP) (FIG. 29). At 72 hours after the third injection of PD-L1 (additional 6-week interval), PD-L1 receptor occupancy was not observed in any of the tested tissues, nevertheless, elevation of activated T cells was noticed, suggesting faster clearance after repeated injections, but apparently sufficient to evoke an immune response (FIG. 29). Therefore, mice were injected for a 4th time to assess the receptor occupancy using flow cytometry at earlier time point after antibody injection, when antibody concentration in serum is expected to be in its maximum level. Indeed, at 4 hours after injection a full receptor occupancy of the Variant 2-ATZ (Fc effector null-H311A) antibody was observed on blood T-cells, while at 72 hours post-injection no receptor occupancy was detected, suggesting a faster clearance than after first antibody administration (FIG. 29).

Figure 30:
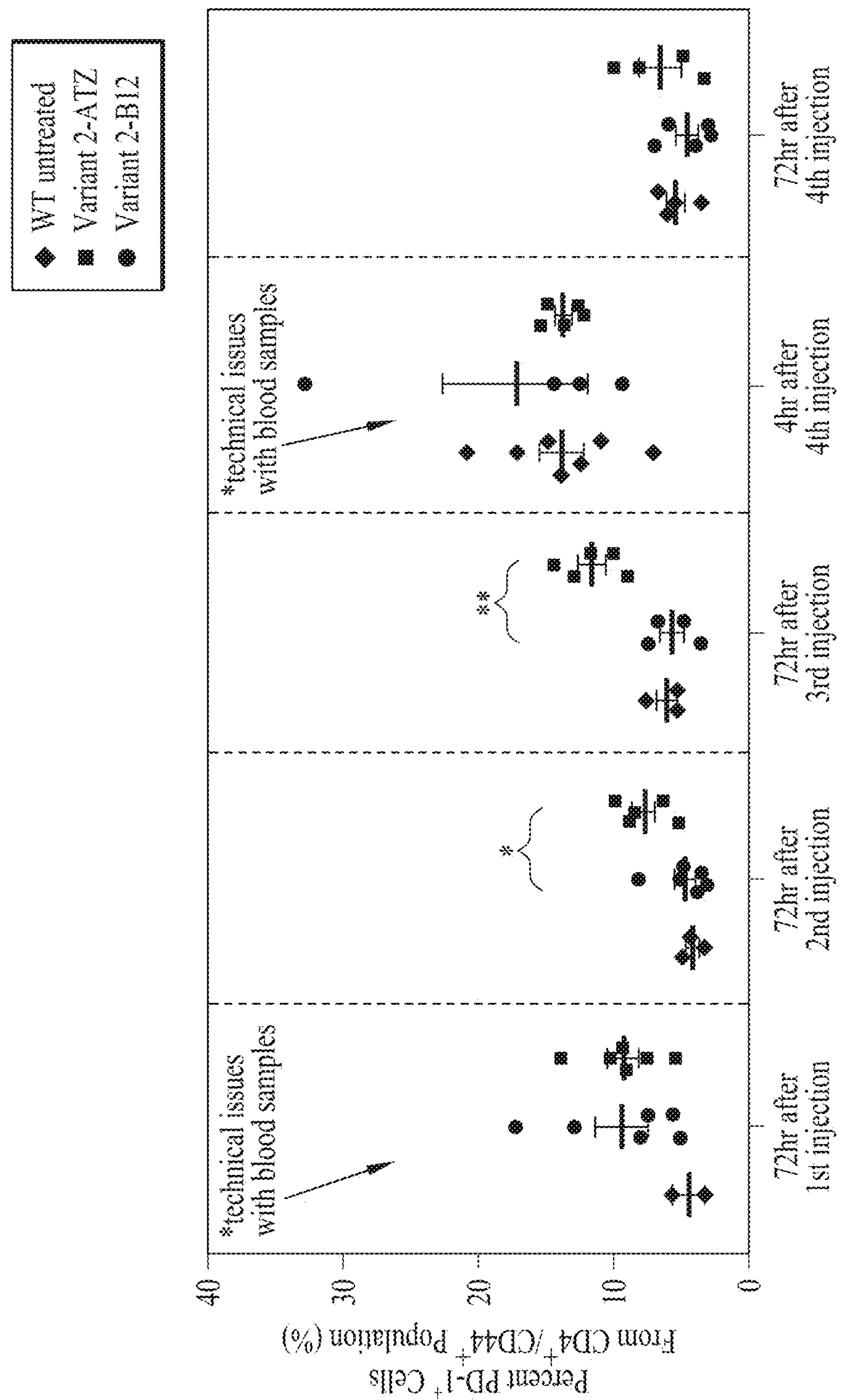
FIG. 30 shows levels of $CD4^+$ memory T lymphocytes expressing PD-1 (percentage of the PD-1+ cells of the total $CD4^+/CD44^+$ population) (error bars represent mean±s.e.m.; *P<0.05, P<0.01, * P<0.001).

In addition, a transient elevation in PD1+ memory T-cells was observed 72 hours after the first, second and third dose administration (see population #3, FIG. 30). These results demonstrate that following each injection, immune cell activation in the form of higher frequencies of memory CD4 T cells which express PD-1 (surface molecule expresses on activated immune cells), could be detected.

Figure 31A:
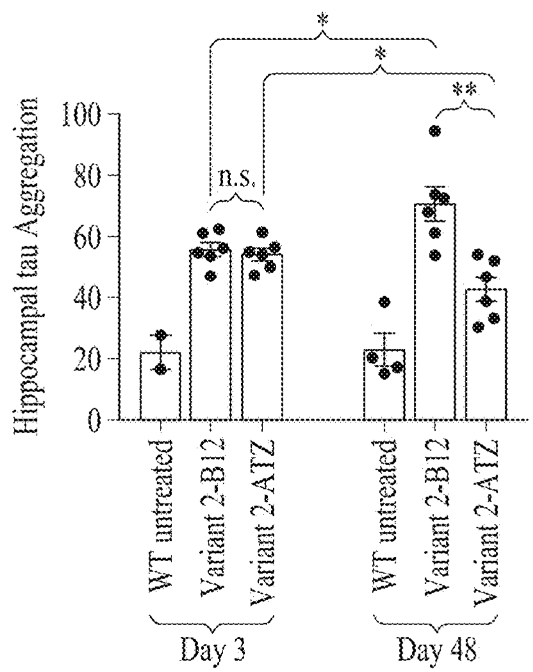
FIG. 31A-B show relative hippocampal aggregated tau (normalized to manufacture's negative control; arbitrary units) in DM-hTau mice with FIG. 31A showing quantitative measurement of aggregated, measured by FRET-based ELISA in hippocampi excised on day 3 and 48 following a single injection (error bars represent mean±s.e.m.; *P<0.05, P<0.01, *P<0.001)
Figure 31B:
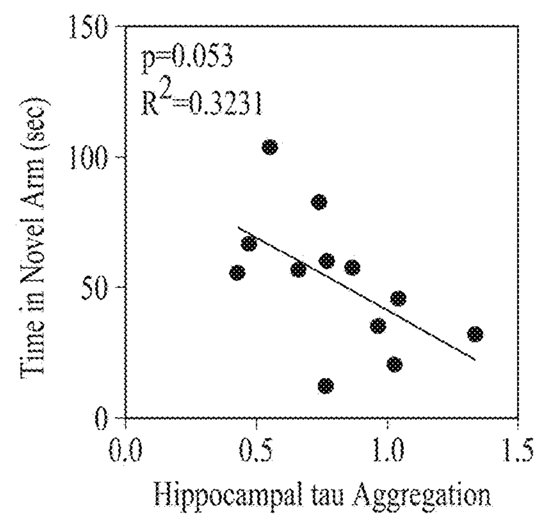

To assess the effect of the Variant 2-ATZ (Fc effector null-H311A) antibody on brain pathology, aggregated tau protein levels were measured in hippocampal brain tissue samples. Brain tissue samples were harvested at day 3 and day 48 of the study (FIG. 28A) and tau aggregation was determined using an FRET-based immunoassay that detects human Tau aggregates (CysBio Kit), according to manufacture instructions. Reduced levels of aggregated tau was observed 48 days after the first injection of the Variant 2-ATZ (Fc effector null-H311A) antibody, but not 3 days following the treatment, relative to IgG treated control (FIG. 31A). In the IgG treated control, a low but a significant elevation in aggregated tau levels was observed between 3 day and 48 days following treatment initiation, as opposed to the significant reduction seen in the Variant 2-ATZ (Fc effector null-H311A) antibody-treated group. A trend towards statistically significant negative correlation was observed between the cognitive score of the mouse at week 4 of the study, and its brain tau aggregation protein levels 2 weeks later (FIG. 31B).

Example 6

Analysis of Modified Anti-Human PD-L1 Monoclonal Antibody 84G09

Modified human anti-PD-L1 antibodies were created using the 84G09 clone for the variable region that exhibit high affinity (Kd<nM) for PD-L1, enhance clearance rate, and abolish Fc-related effector function while maintaining efficacy on disease modification. Four recombinant variants of a human anti-PD-L1 antibody (84G09 clone) with human IgG1 backbone were produced and designated 1) Variant 1-G09, human IgG1 Fc effector null (L239A, L240A, and K327A substitutions; L234A, L235A, and K322A under the Kabat numbering system generalized for all antibodies); Variant 2-G09, human IgG1 Fc effector null substitutions plus a H315A substitution (H310A under the Kabat numbering system generalized for all antibodies); 3) Variant 3-G09, human IgG1 Fc effector null substitutions plus a H440Q substitution (H335Q under the Kabat numbering system generalized for all antibodies); and 4) Variant 4-G09, human IgG1 Fc effector null substitutions plus H315A and H440Q substitutions (H310A and H335Q under the Kabat numbering system generalized for all antibodies). These anti-PD-L1 variant antibodies were designed to comprised the light and heavy chain variable regions of the human anti-PD-L1 antibody 84G09 and an human IgG1 backbone in the heavy chain constant region from a human kappa1 light chain and a human IgG1 heavy chain which included the amino acid substitutions. Human anti-PD-L1 antibody 84G09 is described in, e.g., U.S. Pat. No. 9,617,338 which is hereby incorporated by reference in its entirety. The first group are substitutions, comprising L239A, L240A, and K327A, were made to reduce/eliminate antibody dependent cellular cytotoxicity (ADCC) by reducing/eliminating Fc effector function activity. The second group of substitutions, comprising H315A and/or H440Q, were made to accelerate antibody clearance from the circulation by reducing antibody interaction with the FcRn receptor. A signal peptide was selected and included at the amino-terminal end to ensure proper secretion of the antibody.

These anti-PD-L1 variant antibodies were produced by synthesizing DNA sequences codon optimized for *Cricetulus griseus* which encoded each of the variants (Table 8). The light chain amino acid sequences differ in the signal peptide used with SEQ ID NO: 84 having signal peptide SEQ ID NO: 88 and SEQ ID NO: 85 having signal peptide SEQ ID NO: 89. Similarly, the heavy chain amino acid sequences differ in the signal peptide used with SEQ ID NOs: 66-69 having signal peptide SEQ ID NO: 88 and SEQ ID NOs: 70-73 having signal peptide SEQ ID NO: 90. Thus, DNA sequence SEQ ID NO: 86 comprises SEQ ID NO: 82 encoding the light chain and SEQ ID NO: 74 encoding the signal peptide; and DNA sequence SEQ ID NO: 87 comprises SEQ ID NO: 83 encoding the light chain and SEQ ID NO: 92 encoding the signal peptide. Similarly, DNA sequence SEQ ID NO: 74 comprises SEQ ID NO: 58 encoding the heavy chain and SEQ ID NO: 92 encoding the signal peptide; DNA sequence SEQ ID NO: 75 comprises SEQ ID NO: 59 encoding the heavy chain and SEQ ID NO: 92 encoding the signal peptide; DNA sequence SEQ ID NO: 76 comprises SEQ ID NO: 60 encoding the heavy chain and SEQ ID NO: 92 encoding the signal peptide; DNA sequence SEQ ID NO: 77 comprises SEQ ID NO: 61 encoding the heavy chain and SEQ ID NO: 92 encoding the signal peptide; DNA sequence SEQ ID NO: 78 comprises SEQ ID NO: 62 encoding the heavy chain and SEQ ID NO: 93 encoding the signal peptide; DNA sequence SEQ ID NO: 79 comprises SEQ ID NO: 63 encoding the heavy chain and SEQ ID NO: 93 encoding the signal peptide; DNA sequence SEQ ID NO: 80 comprises SEQ ID NO: 64 encoding the heavy chain and SEQ ID NO: 93 encoding the signal peptide; and DNA sequence SEQ ID NO: 81 comprises SEQ ID NO: 65 encoding the heavy chain and SEQ ID NO: 93 encoding the signal peptide.

The synthetic DNA sequences were subcloned into an expression construct and introduced into CHO or HEK host cells for expression by, e.g., transfection or transduction. The subsequently expressed modified anti-PD-L1 antibody was isolated and examined for activity.

TABLE 8

Human Anti-PD-L1 Monoclonal Antibody Variants (G09)

| G09 Variant | Light Chain Sequence DNA | Light Chain Sequence Amino Acid | Heavy Chain Sequence DNA | Heavy Chain Sequence Amino Acid |
|---|---|---|---|---|
| Variant 1-G09 (Fc effector null) | 86, 87 | 84, 85 | 74, 78 | 66, 70 |
| Variant 2-G09 (Fc effector null-H315A) | 86, 87 | 84, 85 | 75, 79 | 67, 71 |
| Variant 3-G09 (Fc effector null-H440Q) | 86, 87 | 84, 85 | 76, 80 | 68, 72 |
| Variant 4-G09 (Fc effector null-H315A + H44OQ) | 86, 87 | 84, 85 | 77, 81 | 69, 73 |

The physical and biological activities of the antibody, including four antibody variants, were examined ex-vivo and compared to commercially available anti-human PD-L1 antibodies (atezolizumab, durvalumab, avelumab, BMS-936559) as well as anti-human PD-L1 antibody (clone 84G09), which served as benchmarks and tested to determine whether specific modifications of the human IgG1 Fc backbone would change ex-vivo efficacy. Affinity of the antibodies to their ligand, PD-L1, was measured by Surface Plasmon Resonance (SPR) method, and their biological activity was determined by both allogenic and autologous setups of MLR, configurations (testing for immune activation), as well as PD-1/PD-L1 interaction neutralization assay. No significant differences between the antibodies in terms of PD-L1 binding affinity, neutralizing PD-1 binding to PD-L1, and augmenting T-cell responses in human primary cell assays.

TABLE 9

Profile of Benchmark Anti-PD-L1 Antibodies

| mAb Name | hPD-L1 KD (nM) Kinetics | mPD-L1 KD (nM) Kinetics |
|---|---|---|
| Atezolizumab | 0.2 | 3 |
| Durvalumab | 0.1 | n.a. |
| Avelumab | 0.3 | I |
| BMS-936559 | 0.3 | n.a. |
| 84G09 | 0.4 | n.a. |

The human anti-PD-L1 monoclonal antibody 84G09 shows high affinity to human PD-L1 (KD=0.43 nM) and cynomolgus monkey PD-L1 (KD=0.52 nM) (Table 9). In neurodegenerative disease mouse models, anti-PD-L1 antibodies with different clearance properties showed similar results in terms of the intensity and duration of their beneficial effects on cognition and brain pathology. The beneficial effect was shown to be $C_{max}$ dependent and lasted for about 6 weeks regardless of the clearance rate of the antibody. An antibody with fast clearance properties is thus advantageous in terms of tolerability. To examine the effect of these Fc mutations on the PK profile, the PK of the four G09 variants were tested in non-human primates (NHP) using the variable region of the 84G09, with human IgG1 constant region including four Fc mutations.

Naïve cynomolgus monkeys were administered with a single IV infusion of less than 30 minutes of 13 mg/kg of one of the four G09 variant antibodies. Due to technical constrains, this study was divided into two phases (Table 10). Three variants, Variants 1, 2 and 4 that were produced in an expression system using transfected CHO cells, were tested in the first study. Blood (8 mL) for PBMC isolation was collected at least one day prior to dose and 5, 14, 21 and 30-days post-injection. Serum isolation (1 mL) was collected at 0.5, 8, 24, 48, 96 and 168 hours, 14, 21, 28, 35, 42, 49 and 56-days post-injection. All collected blood and serum samples were frozen for subsequent analysis. The second study included testing the PK of two variants; Variant 3, which was missing from the first experiment and Variant 1 as a reference. These antibodies came from a different expression system using transfected HEK cells. Blood (8 mL) for PBMC isolation was collected at least one day prior to dose and 5, 14, 21, 30 and 45-days post-injection. Serum isolation (1 mL) was collected at 0.5, 8, 24, 48, 96 and 168 hours, 14, 21, 28, 35, 42, 49 and 56-days post-injection. All collected blood and serum samples were frozen for subsequent analysis. Serum aliquots were analyzed for antibody concentration in the serum using reverse ELISA assay.

TABLE 10

NHP Study

| Antibody Variant | Phase 1 N Male | Phase 1 N Female | Phase 2 N Male | Phase 2 N Female |
|---|---|---|---|---|
| Variant 1-G09 (Fc effector null) | 0 | 3 | 2 | 0 |
| Variant 2-G09 (Fc effector null-H315A) | 0 | 4 | — | — |
| Variant 3-G09 (Fc effector null-H440Q) | — | — | 2 | 0 |
| Variant 4-G09 (Fc effector null-H315A + H44OQ) | 0 | 3 | — | — |
| Untreated | 6 | 0 | — | — |

Figure 32:
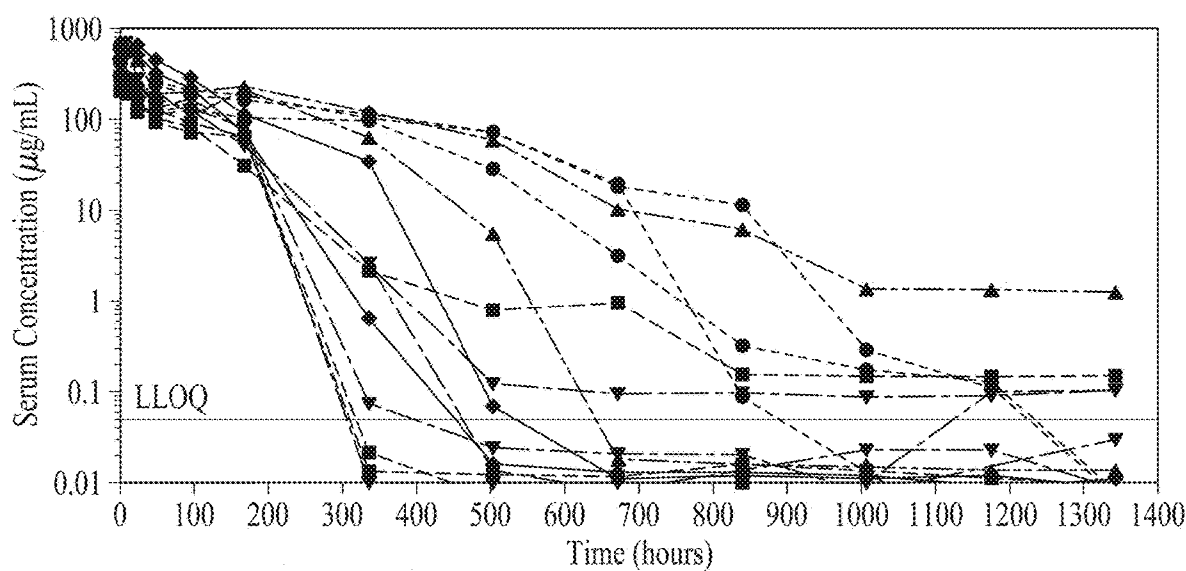
FIG. 32 shows PK profile of modified anti-PD-L1 antibody variants based on 84G09 in blood serum taken from cynomolgus monkeys and quantified using reverse ELISA.
Figure 33A:
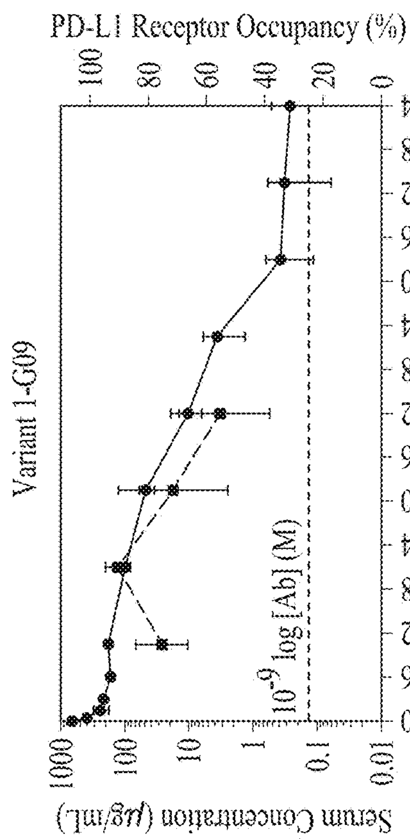
FIG. 33A-D show the correlation between PD-L1 receptor occupancy and serum concentration of the of modified anti-PD-L1 antibody variants based on 84G09 in cynomolgus monkeys, with FIG. 33A showing the correlation between PD-L1 receptor occupancy and serum concentration of the Variant 1-G09 (Fc effector null) antibody.
Figure 33B:
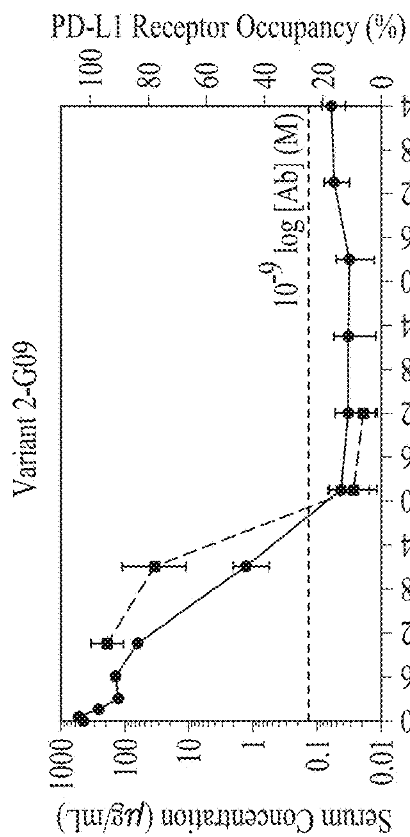
Figure 33C:
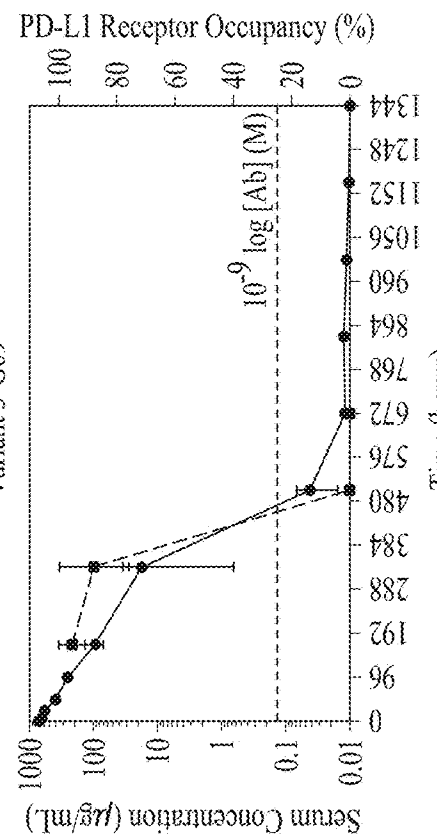
Figure 33D:
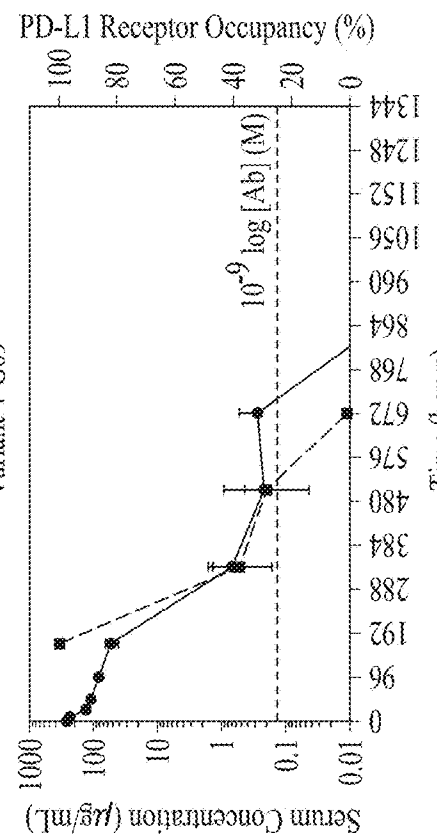

The results of the PK study demonstrate that Variant 1-G09 (Fc effector null) antibodies show similar PK profiles regardless of whether the antibodies were expressed by CHO or HEK cells (FIG. 32). The Variant 4-G09 (Fc effector null-H315A+H440Q) antibody showed the fastest clearance rate, while the differences between Variant 2-G09 (Fc effector null-H315A) and Variant 3-G09 (Fc effector null-H440Q) antibodies were less pronounced than in mice (Table 11).

TABLE 11

Half-Life of Human Anti-PD-L1 Monoclonal Antibody Variants (G09)

| Analyte | Phase | $C_{max}$ (μg/mL) | $T_{max}$ (h) | $T_{last}$ (h) | $AUC_{0-1344}$ (h · μg/mL) | $t_{1/2}$ (h) |
|---|---|---|---|---|---|---|
| Variant 1-G09 (Fc effector null) | 1 | 611 | 0.50 | 1180 | 77700 | 60.5 |
| Variant 2-G09 (Fc effector null-H315A) | 1 | 622 | 8.00 | 336 | 35100 | 54.1 |

TABLE 11-continued

Half-Life of Human Anti-PD-L1 Monoclonal Antibody Variants (G09)

| Analyte | Phase | $C_{max}$ (μg/mL) | $T_{max}$ (h) | $T_{last}$ (h) | $AUC_{0-1344}$ (h · μg/mL) | $t_{1/2}$ (h) |
|---|---|---|---|---|---|---|
| Variant 4-G09 (Fc effector null-H315A + H440Q) | 1 | 289 | 8.00 | 168 | 22400 | 177 |
| Variant 1-G09 (Fc effector null) | 2 | 813 | 0.50 | 840 | 81400 | 64.7 |
| Variant 3-G09 (Fc effector null-H440Q) | 2 | 719 | 0.50 | 420 | 65900 | 29.2 |

Note:
Median values are presented for $T_{max}$.

One day prior to dosing (baseline), and on 5, 14, 21, and 30-days post treatment, 8 mL of whole blood was collected for Peripheral Blood Mononuclear Cell (PBMC) isolation and cryopreservation. In the second study, whole blood was also collected also at 45-days post treatment. Samples were analyzed for PD-L1 receptor occupancy on blood T lymphocytes and for Immunophenotype of different immune cell subpopulations. The percentage of PD-L1 receptor occupancy on blood T-lymphocytes by the antibody was assessed using the same method as described above for receptor occupancy in mice. Tight correlation was found between serum concentration of the antibody and receptor occupancy (FIG. 33A-D). Receptor occupancy declined significantly when antibody concentration fell below $10^{-8}$ M, for all tested variants. Over 80% Receptor Occupancy was detected up to day 12 post administration for all variants except for the double mutant. Less than 20% occupancy was detected by day 20 post administration for all variants except of the null mutant. Variant 2-G09 (Fc effector null-H315A) and Variant 3-G09 (Fc effector null-H440Q) showed similar PD-L1 receptor occupancy profile (compare FIG. 33B with FIG. 33C).

Blood immunophenotyping was performed to examine the in-vivo effect of the different antibodies on the distribution of specific immune subpopulations. Cells were stained with 8 different panels of fluorescently labeled antibodies recognizing naïve T cells, memory T cells, Tregs, myeloid (mDC)/plasmacytoid (pDC), monocytes, and PD-L1 expressing memory T cells (Table 12), and were examined by flow cytometry. Levels of immune populations were normalized to baseline (level prior to antibody administration) for each animal and are presented as % change from baseline. Significance was calculated using Paired Student's t-test.

TABLE 12

Summary of Flow Cytometry Immunophenotyping Panels

| Panel name | Marker combination |
|---|---|
| Naïve T cells | CD3/CD4/CD8/CD95/PD-1 |
| Memory T cells | CD3/CD4/CD95/CD28/PD-1 |
| Tregs | CD3/CD4/CD25/CD127/PD-1 |
| mDC/pDC | CD14/CD16/CD3/CD123/BDCA-1 |
| Monocytes | CD14/CD16/CD20/HLA-DR/PD-L1 |
| Foxp3 Tregs | CD3/CD4/Foxp3/Ki-67/PD-1 |
| Proliferation | CD3/CD95/CD28/Ki-67/PD-1 |
| IFN-γ-producing T cells | CD3/CD4/CD8/PD-1/IFNγ |

Figure 34:
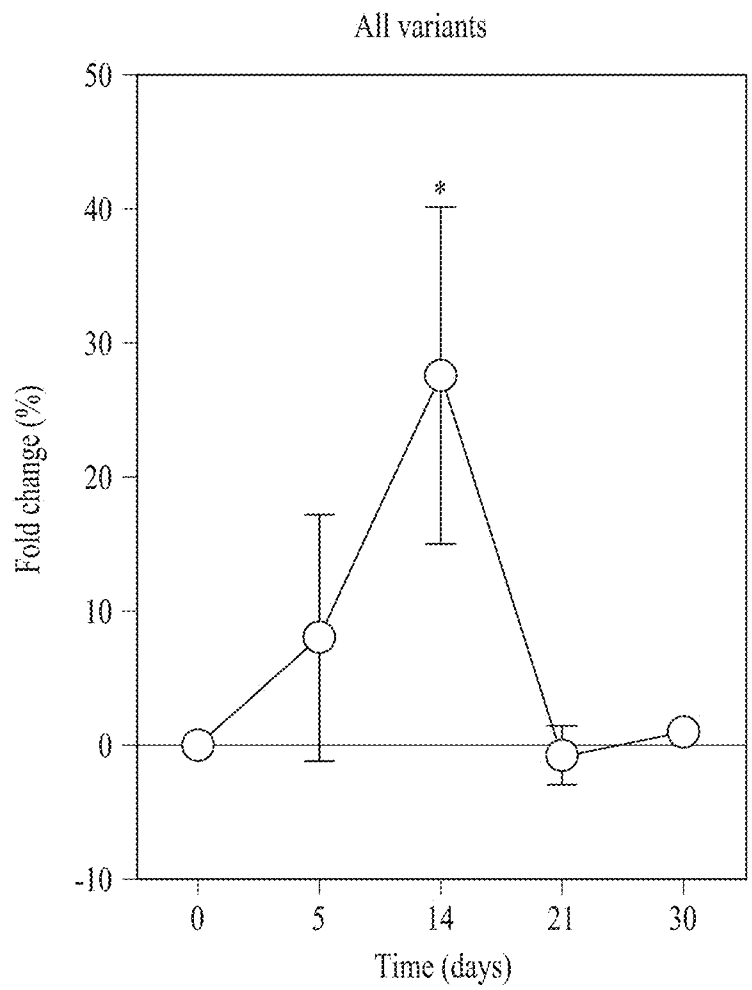
FIG. 34 shows pharmacodynamics changes in PD-1-high expressing effector memory CD4 T cells frequencies in cynomolgus monkeys treated with different modified anti-PD-L1 antibody variants based on 84G09. The values represent the percent fold change in PD-1-high expressing effector memory CD4 T cells normalized to baseline (data represented as mean±s.e.m.; *P<0.05, P<0.01, *P<0.001).

Analysis of the obtained results, identified significant pharmacodynamic changes in several immune-cell subpopulations in the blood. Specifically, upregulation of PD-1 expressing CD4 memory T cells (FIG. 34) were detected following treatment with modified anti-PD-L1 antibodies based on 84G09. Similar changes were observed in mice following injection of the anti-PD-L1 antibody variants based on atezolizumab (FIG. 30), indicating the involvement of similar immune-related mechanisms in both the mouse and primate.

Figure 35A:
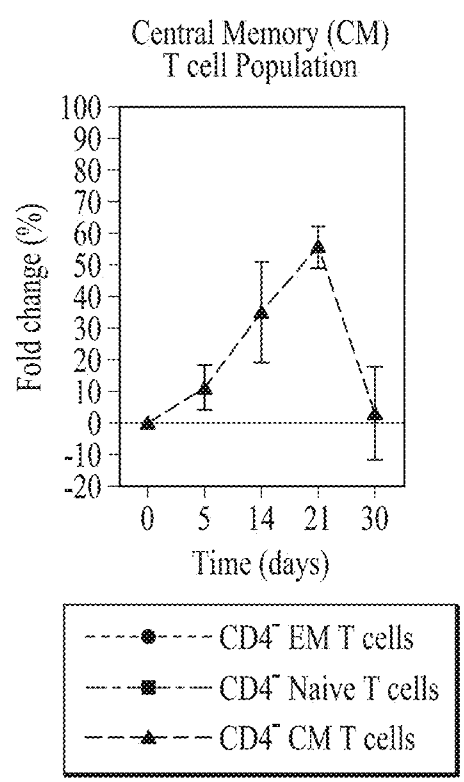
FIG. 35A-B shows pharmacodynamics changes in different T cells subpopulations following treatment with the Variant 2-G09 (Fc effector null-H315A) antibody, with FIG. 35A showing central memory T cells.
Figure 35B:
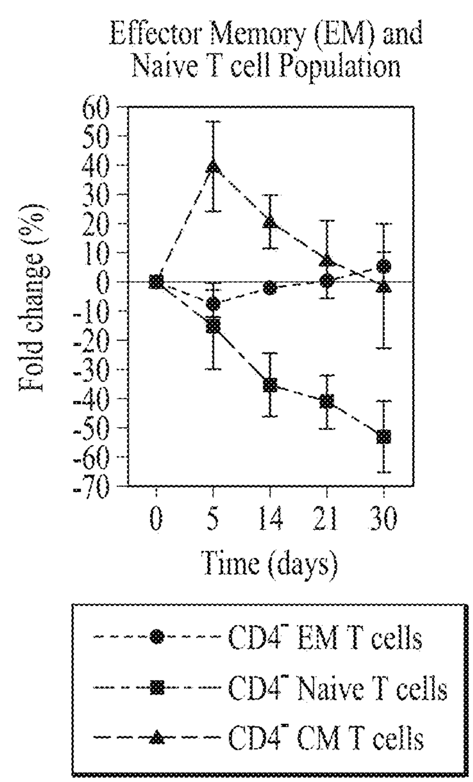

Additional examples for pharmacodynamic changes in immune-cell subpopulation distribution in the blood following treatment with the anti-PD-L1 variants of 84G09 are shown in FIG. 35. These changes include elevation in the abundance of PD-1 and Ki-67 expressing central memory (CM) T cells ($CD3^{+}CD95^{+}CD28^{+}$; FIG. 35A), which represent a subset of proliferating memory T cells. Expression of PD-1 and Ki-67 over CD8 T cells was previously shown to correlate with response to anti-PD-1 treatment in cancer patients (Kamphorst et al, 2017). In addition, increased frequency of $CD4^{-}$ effector memory (EM) T cells was detected following treatment, along with decreased levels of CD4-Naïve T cells (FIG. 35B).

Taken together, these results are consistent with data obtained from PK studies in mice. The anti-PD-L1 antibody Variant 2-G09 (Fc effector null-H315A), Variant 3-G09 (Fc effector null-H440Q) and Variant 4-G09 (Fc effector null-H315A+H440Q) have significantly increased clearance rate compared to Variant 1-G09 (Fc effector null). In addition, tight correlation between antibody serum concentration and receptor occupancy was demonstrated. Furthermore, immunophenotyping results of peripheral immune cells, identified significant changes in the frequencies and activation status of several immune subpopulations following injection of all antibody variants. Specifically, elevated frequencies of PD-1 expressing memory T cells and classical monocytes were detected, similar to those detected in mouse PD data using surrogate antibodies.

Example 7

Antibody Characterization Using an Antibody-Dependent Cell-Mediated Cytotoxicity (ADCC) Assay These experiments functionally characterized the antibody-dependent cell killing potencies of Variant 2-G09 (Fc effector null-H315A) antibodies using in vitro Antibody-Dependent Cell-mediated Cytotoxicity (ADCC) assay. ADCC is a cell-mediated immune response leading to lysis of antibody-coated (opsonized) target cells by immune effector cells. ADCC is triggered by the interaction between the Fc portion of an antibody and Fc-y receptors expressed on the immune cells, ultimately resulting in the release cytotoxic granules which lyse target cells.

Two target cell lines were used in this assay 1) Raji lymphoblast-like-derived target cells with stable CD-20 expression; and 2) CHO-K1-derived target cells with stable PD-L1 expression. These target cells were maintained in corresponding complete medium incubated at 37° C. with 5% $CO_2$ and regularly sub-cultured with suitable medium. Immune effector cells were prepared by pooling blood from more than 20 healthy human volunteers, isolating peripheral blood mononuclear cells (PBMC) from the blood by density gradient centrifugation and culturing the PBMCs in RPMI 1640 complete culture medium.

ADCC assays were performed by harvesting target cells by centrifugation, re-suspending the cells in a buffered solution, adjusting the cell density and then transferring aliquots of the cell suspension to wells of an assay microplate. In the ADCC dose response experiment, the positive control group used Raji as the target cells, PBMC as the effector cells, and Rituxan as the positive control antibody with E/T ratio at 25:1. The experimental group used CHO-K1/PD-L1 as target cells, PBMC as effector cells to evaluate the ADCC effect of antibody samples with E/T ratio at 25:1 according to the E/T optimization assay results. An antibody sample, comprising either a test antibody, a positive control antibody, or a negative control antibody, was added to a well containing the cell suspension aliquot and incubated for 30 minutes at room temperature (about 20° C.). Cell lysis was induced by adding PBMCs to each well containing a target cell/antibody mixture and incubating the assay microplate in cell incubator at 37° C. with 5% $CO_2$ for about 6 hours. After incubation, the assay microplate was centrifuged and the supernatant from each well was transferred to wells of another assay microplate. Cell death was quantified using a commercially-available colorimetric assay based on the spectrophotometric measurement of lactate dehydrogenase (LDH) activity released from the cytosol of damaged cells (Cytotoxicity Detection Kit Plus; Roche, Mannheim, Germany).

Briefly, test samples were prepared by adding an equal amount of an LDH substrate assay solution to a well containing supernatant from a treated target cell and incubated at room temperature for 15 minutes. Control samples included 1) a spontaneous lysis control containing a LDH substrate assay solution and supernatant from untreated target cells incubated with PMBC effector cells; 2) a minimum lysis control containing a LDH substrate assay solution and supernatant from untreated target cells; and 3) a maximum lysis control containing a LDH substrate assay solution, 2% TRITON® X-100 (a polyoxyethylene octyl phenyl ether), and supernatant from untreated target cells. The resulting color reaction was read by spectrophotometry at $OD_{492}$ nm and $OD_{650}$ nm. All procedures were performed in duplicate. The percentage of specific cell lysis was calculated according to the manufacturers instructions using the following formula: $100\times[(A-B)/(C-D)]$, where A represents the absorbance value obtained with test sample (experimental lysis), B represents the absorbance obtained by lysing all of untreated target cells with effector cells (spontaneous lysis), C represents the absorbance obtained by lysing all of untreated target cells with 2% TRITON® X-100 (maximum lysis), and D represents the absorbance obtained with untreated target cells incubated in assay solution (minimum lysis). When this calculation provided a negative value, 0.0% was assigned as the result.

In a first series of experiments, the effector cell/target cell (E/T) ratio was optimized for the ADCC assay. A chimeric anti-CD20 monoclonal antibody (Rituximab) was used as a positive control and tested with Raji lymphoblast-like-derived target cells. This antibody achieved 48.8% as the highest percentage of target cell lysis at the E/T ratio of 25:1. Human IgG at a concentration of 10 mg/mL was used as a negative control and tested with CHO-K1-derived target cells. This antibody achieved the highest percentage of target cell lysis of 18.1% at an E/T ratio 10:1 with no appreciable cell lysis detected at E/T ratios of 25:1 or 50:1. For this reason, the E/T ratio of 25:1 was chosen for further experiments.

In a second series of experiments, the antibody dose response was determined for the ADCC assay using an E/T ratio of 25:1. Variant 2-G09 was assayed over a 7-fold dilution range at the following concentrations: 80 μg/mL, 8 μg/mL, 0.8 μg/mL, 0.08 μg/mL, 0.008 μg/mL, 0.0008 μg/mL, and 0.00008 μg/mL. A biosimilar of atezolizumab, atezolizumab is a commercially available humanized anti-PD-L1 monoclonal antibody (Genentech) known to be deprived of ADCC Fc activity, was assayed over a 7-fold dilution range at the following concentrations: 40 μg/mL, 4 μg/mL, 0.4 μg/mL, 0.04 μg/mL, 0.004 μg/mL, 0.0004 μg/mL, and 0.00004 μg/mL. The positive control antibody Rituximab was assayed over a 7-fold dilution range at the following concentrations: 40 μg/mL, 4 μg/mL, 0.4 μg/mL, 0.04 μg/mL, 0.004 μg/mL, 0.0004 μg/mL, and 0.00004 μg/mL. The negative control antibody Human IgG was assayed over a 7-fold dilution range at the following concentrations: 40 μg/mL, 4 μg/mL, 0.4 μg/mL, 0.04 μg/mL, 0.004 μg/mL, 0.0004 μg/mL, and 0.00004 μg/mL. Dose response experiments examining Variant 2-G09, atezolizumab biosimilar and Human IgG used CHO-K1-derived target cells while experiments testing Rituximab used Raji lymphoblast-like-derived target cells.

Figure 36A:
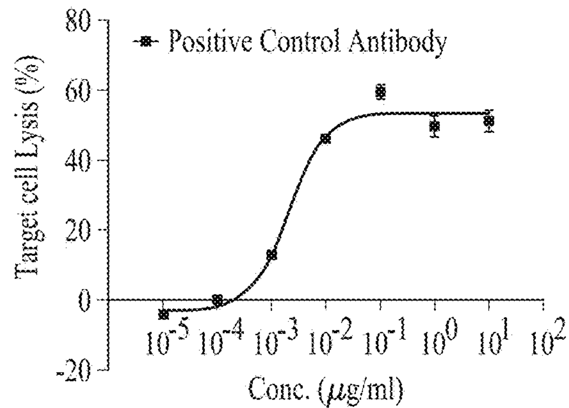
FIG. 36A-E show ADCC dose-response assays, with FIG. 36A showing a dose response ADCC assay of Rituxan, a positive control antibody, with Raji/CD-20 cells.
Figure 36B:
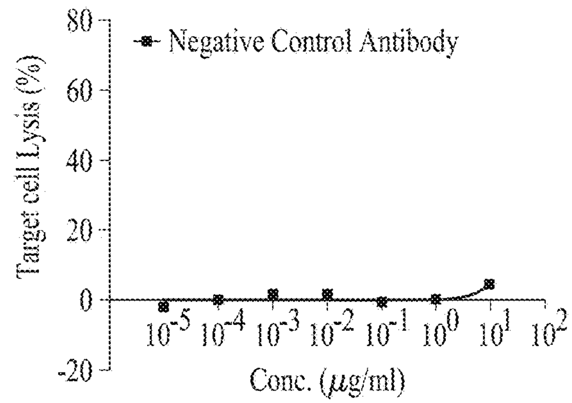
Figure 36C:
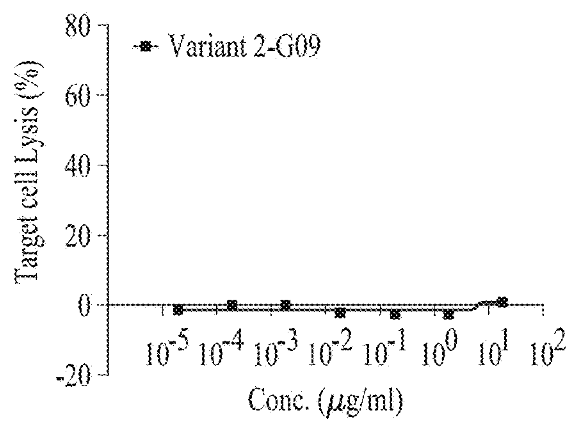

The results show that Variant 2-G09 had no significant cell-mediated cytotoxicity activity. For example, at an E/T ratio of 25:1 Variant 2-G09 did not demonstrate a dose response curve over the entire 7-fold dilution series tested indicating that this antibody could not mediate an ADCC effect against CHO-K1/PD-L1 target cells at any concentration (FIG. 36C). Variant 2-G09 showed an $EC_{50}$ of approximately 7 μg/mL and no appreciable target cell lysis was observed (Table 13). On the other hand, the positive control antibody demonstrated a strong dose response curve over the entire 7-fold dilution series tested indicating that this antibody mediate a significant ADCC effect against Raji lymphoblast-like-derived target cells (FIG. 36A). The positive control antibody exhibited an $EC_{50}$ of approximately $2.1\times10^{-3}$ μg/mL and 53.5% was the highest percentage of target cell lysis observed for this antibody (Table 13). As expected, the negative control did not demonstrate a dose response curve over the entire 7-fold dilution series (FIG. 36B), had no detectable cell lysis, and had an $EC_{50}$ of over $2.2\times10^{5}$ μg/mL (Table 13). Taken together, these results demonstrate that Variant 2-G09 has no significant cell-mediated cytotoxicity activity.

TABLE 13

ADCC Assay for Variant 2-G09

| Parameter | Rituxan | Variant 2-G09 | Human IgG |
|---|---|---|---|
| Target cell lysis | 53.5% | 0.0% | 0.0% |
| $LogEC_{50}$ | −2.7 | 0.8 | 5.3 |
| HillSlope | 1.3 | −65.7 | 1.5 |
| $EC_{50}$, μg/ml | $2.1\times10^{-3}$ | 7.0 | $2.2\times10^{5}$ |

Figure 36D:
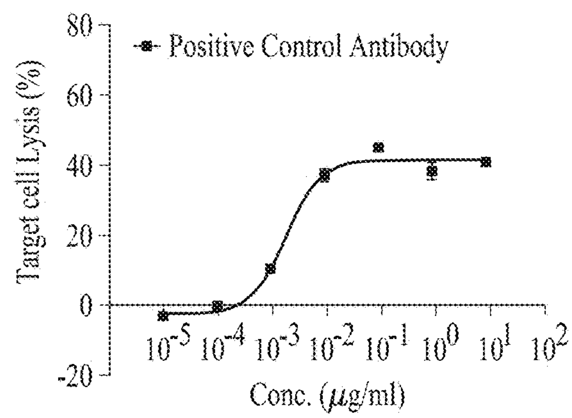
Figure 36E:
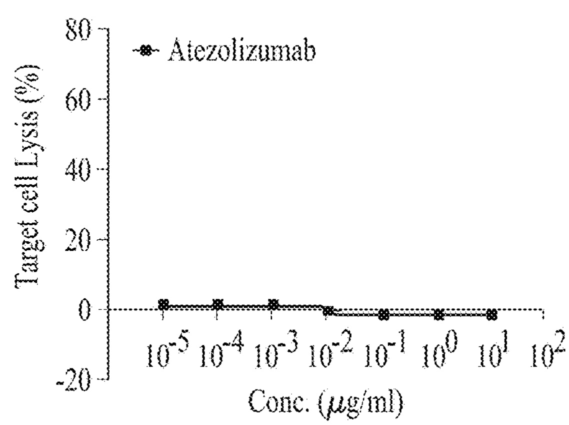

Similar results show that, as expected, the atezolizumab biosimilar also has no significant ADCC activity. For example, at an E/T ratio of 25:1 the atezolizumab biosimilar did not exhibit a dose response curve over the entire 7-fold dilution series tested indicating that this antibody could not mediate an ADCC effect against CHO-K1/PD-L1 target cells at any concentration (FIG. 36E) and approximately 1.4% was the highest percentage of target cell lysis observed (Table 14). In contrast, the positive control antibody demonstrated a strong dose response curve over the entire 7-fold dilution series tested (FIGS. 36A and 36D) and 43.6% was the highest percentage of target cell lysis observed for this antibody (Table 14).

TABLE 14

| ADCC Assay for Atezolizumab Biosimilar | | |
|---|---|---|
| Parameter | Rituxan | Atezolizumab Biosimilar |
| Target cell lysis | 43.6% | 1.4% |
| $LogEC_{50}$ | −2.7 | −2.0 |
| HillSlope | 1.4 | −6.4 |
| $EC_{50}$, μg/ml | $1.9 \times 10^{-3}$ | $9.5 \times 10^{-3}$ |

Example 8

Antibody Characterization Using a Complement-Dependent Cytotoxicity (CDC) Assay

The experiments functionally characterized the antibody-dependent cell killing potencies of Variant 2-G09 (Fc effector null-H315A) antibodies using in vitro Complement-Dependent Cytotoxicity (CDC) assay. CDC is a cell-mediated immune response leading to lysis of antibody-coated (opsonized) target cells by a Membrane Attack Complex (MAC). CDC is triggered by the interaction between the Fc portion of an antibody and serum complement components, particularly C1q, initiating a complement cascade which ultimately leads to ell lysis of target cells expressing the antigen by the insertion of MACs into the cell membrane causing damage and loss of cellular integrity.

Two target cell lines were used in this assay 1) Raji lymphoblast-like-derived target cells with stable CD20 expression; and 2) CHO-K1-derived target cells with stable PD-L1 expression. These target cells were maintained in corresponding complete medium incubated at 37° C. with 5% $CO_2$ and regularly sub-cultured with suitable medium. The complement component was prepared by pooling blood from more than 20 healthy human volunteers and isolating the serum, referred to as Pooled Normal Human Serum (PNHS).

CDC assays were performed by harvesting target cells by centrifugation, re-suspending the cells in a buffered solution, adjusting the cell density and then transferring aliquots of the cell suspension to wells of an assay microplate. An antibody sample, comprising either a test antibody, a positive control antibody, or a negative control antibody, was added to a well containing the cell suspension aliquot and incubated for 30 minutes at room temperature (about 20° C.). Cell lysis was induced by adding PNHS to each well containing a target cell/antibody mixture and incubating the assay microplate in cell incubator at 37° C. with 5% $CO_2$ for about 4 hours. After incubation, the assay microplate was centrifuged and the supernatant from each well was transferred to wells of another assay microplate. Cell death was quantified using a commercially-available luminescent assay based on the spectrophotometric measurement of ATP released from the cytosol of damaged cells (CellTiter-Glo Luminescent Cell Viability Assay; Promega, Wisconsin, United States).

Briefly, test samples were prepared by adding an equal amount of a luciferase/luciferin assay solution to a well containing supernatant from a treated target cell and incubated at room temperature for 10-30 minutes. Control samples included 1) a spontaneous lysis control containing a luciferase/luciferin assay solution and supernatant from untreated target cells incubated with PMBC effector cells; 2) a minimum lysis control containing a luciferase/luciferin assay solution and supernatant from untreated target cells; and 3) a maximum lysis control containing a luciferase/luciferin assay solution, 2% TRITON® X-100 (a polyoxyethylene octyl phenyl ether), and supernatant from untreated target cells and PNHS. The resulting luminescence was read by luminometer. All procedures were performed in duplicate. The percentage of specific cell lysis was calculated according to the manufacturers instructions using the following formula: 100×[(A−C)/(B−C)], where A represents the luminescence value obtained with test sample (experimental lysis), B represents the luminescence value obtained by lysing all of untreated target cells with 2% TRITON® X-100 (maximum lysis), and C represents the luminescence value obtained with untreated target cells incubated in assay solution (minimum lysis). When this calculation provided a negative value, 0.0% was assigned as the result.

In a first series of experiments, the amount of PNHS was optimized for the CDC assay. A chimeric anti-CD20 monoclonal antibody (Rituximab) was used as a positive control and tested with Raji lymphoblast-like-derived target cells. This antibody achieved 98.5% as the highest percentage of target cell lysis using a PNHS concentration of 10%. Human IgG was used as a negative control and tested with CHO-K1-derived target cells. This antibody achieved the highest percentage of target cell lysis of 19.1% using a PNHS concentration of 50% with no appreciable cell lysis detected at PNHS concentration of 10% and 20%. For this reason, a 10% PNHS concentration was used for further experiments.

In a second series of experiments, the antibody dose response was determined for the CDC assay using a PNHS concentration of 10%. Variant 2-G09 was assayed over an 8-fold dilution range at the following concentrations: 20 μg/mL, 2 μg/mL, 0.2 μg/mL, 0.02 μg/mL, 0.002 μg/mL, 0.0002 μg/mL, 0.00002 μg/mL, and 0.000002 μg/mL. A biosimilar of atezolizumab, atezolizumab is a commercially available humanized anti-PD-L1 monoclonal antibody (Genentech) known to be deprived of ADCC Fc activity, was assayed over a 8-fold dilution range at the following concentrations: 10 μg/mL, 1 μg/mL, 0.1 μg/mL, 0.01 μg/mL, 0.001 μg/mL, 0.0001 μg/mL, 0.00001 μg/mL, and 0.000001 μg/mL. The positive control antibody Rituximab was assayed over a 8-fold dilution range at the following concentrations: 10 μg/mL, 2 μg/mL, 0.4 μg/mL, 0.08 μg/mL, 0.016 μg/mL, 0.0032 μg/mL, 0.00064 μg/mL, and 0.000128 μg/mL. The negative control antibody Human IgG was assayed over a 8-fold dilution range at the following concentrations: 10 μg/mL, 1 μg/mL, 0.1 μg/mL, 0.01 μg/mL, 0.001 μg/mL, 0.0001 μg/mL, 0.00001 μg/mL, and 0.000001 μg/mL. Dose response experiments examining Variant 2-G09, atezolizumab biosimilar and Human IgG used CHO-K1-derived target cells while experiments testing Rituximab used Raji lymphoblast-like-derived target cells.

Figures 37A, 37B, 37C, 37D:
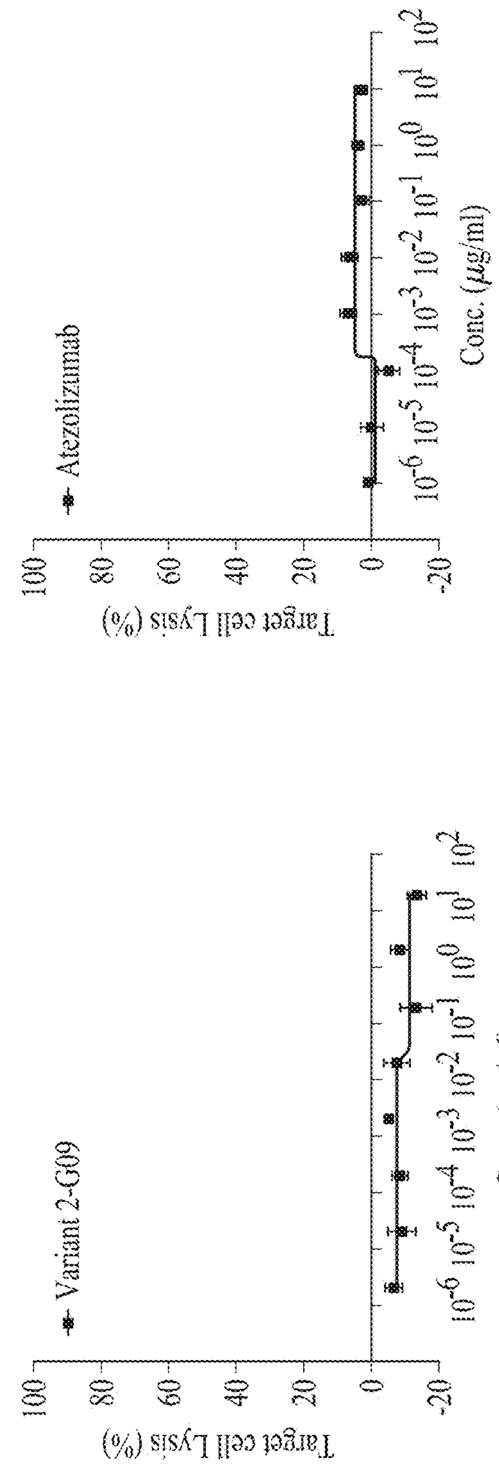
FIG. 37A-D show CDC dose-response assays, with FIG. 36A showing a dose response CDC assay of Rituxan, a positive control antibody, with Raji/CD-20 cells.

The results show that Variant 2-G09 had no significant cell-mediated cytotoxicity activity. For example, at a PNHS concentration of 10% Variant 2-G09 did not demonstrate a dose response curve over the entire 8-fold dilution series tested indicating that this antibody could not mediate a CDC effect against CHO-K1/PD-L1 target cells at any concentration (FIG. 37C). Variant 2-G09 showed an $EC_{50}$ of approximately $2.8\times10^{-2}$ μg/mL and no appreciable target cell lysis was observed (Table 15). Similar results show that, as expected, the atezolizumab biosimilar also has no significant cell-mediated cytotoxicity activity. For example, at a PNHS concentration of 10% the atezolizumab biosimilar did not exhibit a dose response curve over the entire 8-fold dilution series tested indicating that this antibody could not mediate an CDC effect against CHO-K1/PD-L1 target cells at any concentration (FIG. 37D) and approximately 4.7% was the highest percentage of target cell lysis observed (Table 15).

On the other hand, the positive control antibody demonstrated a strong dose response curve over the entire 8-fold dilution series tested indicating that this antibody mediate a significant CDC effect against Raji lymphoblast-like-derived target cells (FIG. 37A). The positive control antibody exhibited an $EC_{50}$ of approximately 0.2 μg/mL and 104.7% was the highest percentage of target cell lysis observed for this antibody (Table 15). As expected, the negative control did not demonstrate a dose response curve over the entire 8-fold dilution series (FIG. 37B), had no detectable cell lysis, and had an $EC_{50}$ of $8.4\times10^{-4}$ μg/mL (Table 15). Taken together, these results demonstrate that Variant 2-G09 had no significant cell-mediated cytotoxicity activity.

TABLE 15

CDC Assay for Variant 2-G09

| Parameter | Rituxan | Human IgG | Variant 2-G09 | Atezolizumab Biosimilar |
|---|---|---|---|---|
| Target cell lysis | 104.7% | 7.9% | 0.0% | 4.7% |
| $LogEC_{50}$ | −0.7 | −3.1 | −1.6 | −3.7 |
| HillSlope | 1.7 | 5.7 | −9.1 | 73.8 |
| $EC_{50}$, μg/ml | 0.2 | $8.4\times10^{-4}$ | $2.8\times10^{-2}$ | $1.8\times10^{-4}$ |

Example 9

Modified Human Anti-PD-L1 84G09 Antibody Exhibit Reduced Rate of Immune-Related Adverse Side Effects Commercially available immune checkpoint inhibitors for treating cancer indications have been associated with significant risk for immune-related adverse events (irAEs) (Tocut et al, 2018). Among these, new onset of insulin dependent diabetes mellitus (DM) occurs in 0.2%-1.0% of patients (Stamatouli et al, 2018; Barroso-Sousa et al, 2018). While the exact mechanism is not yet fully understood, it involves an autoimmune response against pancreatic β-cells, leading to insufficient insulin production. This complication is common for PD-1/PD-L1 checkpoint blockade therapies, and usually develops following a relatively prolonged treatment of repeated cycles of administration, necessary for maintaining high exposure to the antibody (Orlov et al, 2015; de Filette et al, 2016).

Non-obese diabetic (NOD) mice, are a common animal model for type 1 diabetes, which develop insulitis, as a result of leukocytic infiltration into pancreatic islets. Administration of anti-PD-1 or anti-PD-L1 antibodies to prediabetic female NOD mice results in rapid onset of diabetes (Ansari et al, 2003) and reversal of tolerogenic therapies, such as anti-CD3 and tolerogenic peptide infusion (Fife et al, 2006). It was shown that a single injection of ant-PD-L1 to NOD mice in a relatively wide range of ages (4 and 10 weeks) can induce diabetes. In this model, diabetes is defined when a random blood glucose reading of >250 mg/dL is detected for three consecutive days. When anti-PD-L1 is injected at the age of 10 weeks, the onset of disease is expected already at 5 days after treatment, in 80%-100% of the mice. Importantly, it was shown that prolonged exposure to anti-PD-L1 in a regimen of 500 μg on day 0, followed by additional 250 μg every 2 days up until day 10, is needed for diabetes induction (Ansari et al, 2003).

Accordingly, the induction of diabetes in susceptible NOD mice can be used to investigate the relationship between the clearance rate of the antibody and the risk of evoking an autoimmune disease by using variants of the same anti-PD-L1 antibodies that differ in their clearance rates. At the age of 9 weeks, female NOD mice received a single i.p. injection of the tested anti-PD-L1 antibody variants, or were left untreated, according to the following groups: 1) 1.5 mg/mouse of anti-B12 human IgG1 isotype antibody control (n=2); 2) 1.5 mg/mouse of Variant 1-ATZ (Fc effector null) antibody (n=10); and 3) 1.5 mg/mouse of Variant 2-ATZ (Fc effector null-H315A) antibody (n=10). Prior to the single injection, and once daily post-injection, mice were monitored for their blood glucose levels each morning using a glucometer (FreeStyle blood glucose monitoring system). Significance was calculated using log-rank (Mantel-Cox) test of Variant 1 vs. Variant 2. A mouse is defined as diabetic when blood glucose reading >250 mg/dL for three consecutive days.

In mice, the differences in the PK profile of these two variants was significant, i.e. clearance rate of 0.44 mL/hr/kg of the Variant 1-ATZ versus 2.22 mL/hr/kg of the Variant 2-ATZ (Fc effector null-H315A) antibody. The effective dose of both antibody variants, in terms of reduced cognitive deficits and brain pathology in animal AD and dementia models, was the same, ranging between 0.5 to 1.5 mg/mouse. In this experiment diabetes onset in NOD mice was measured following single administration of 1.5 mg/mouse of the two anti-PD-L1 antibody variants.

Figure 38:
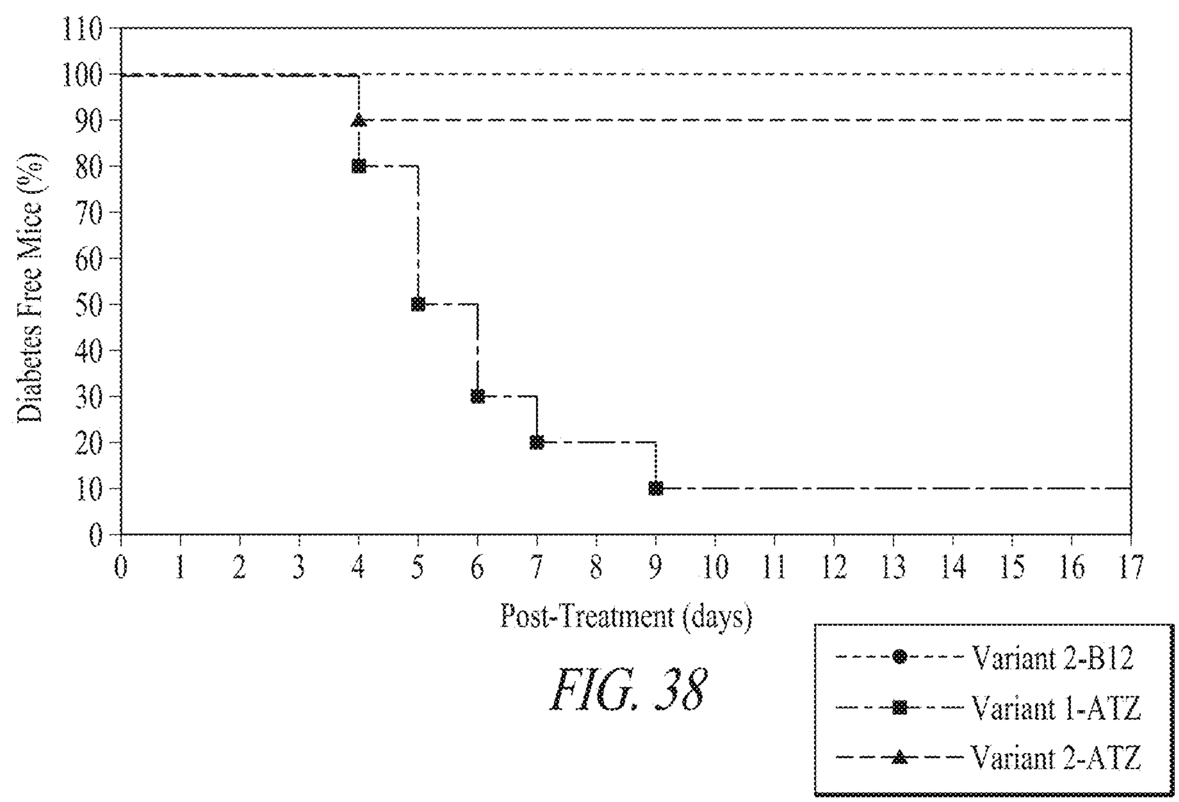
FIG. 38 shows comparison between two modified anti-PD-L1 antibody variants, Variant 1-ATZ (Fc effector null) and 2-ATZ (Fc effector null-H311A) as well as isotype control Variant 2-B12 (an anti-B12 antibody containing the human IgG1 Fc effector null and H311A substitutions in the Fc portion corresponding to the same substitutions of Variant 2-ATZ) on diabetes-free survival after single injection of 1.5 mg/mouse dose to 9-week-old female NOD mice (P value=0.0030).

Daily glucose readings were performed between 8 am to 11 am. Results of daily glucose readings are presented in a Kaplan-Meier survival curve. As shown in Table 16 and FIG. 38, no significant change in levels of glucose weight was observed during the experiment in NOD mice treated with Variant 2-ATZ (Fc effector null-H315A). This contrasts with NOD mice treated with Variant 1-ATZ (Fc effector null); the animals in this group exhibited significant increase in blood glucose levels to levels indicating the onset of diabetes.

TABLE 16

Daily Blood glucose Levels of the NOD Mice

| | | Glucose Level Post-Injection (Days) | | | | | | | | |
|---|---|---|---|---|---|---|---|---|---|---|
| Group | Animal | 0 | 1 | 2 | 3 | 4 | 5 | 6 | 7 | 8 |
| anti-B12 hIgG1 | 1689 | 73 | 85 | 88 | 86 | 80 | 82 | 97 | 82 | 101 |
| (n = 2) | 1690 | 111 | 97 | 65 | 95 | 89 | 93 | 92 | 78 | 101 |
| Variant 1-ATZ | 1168 | 81 | 88 | 97 | 104 | 61 | 70 | 120 | 110 | 90 |
| Fc effector null | 1670 | 113 | 81 | 83 | 100 | 62 | 65 | 139 | 144 | 215 |
| (n = 10) | 1671 | 69 | 76 | 101 | **285** | **336** | **354** | **496** | **>500** | **>500** |
| | 1672 | 77 | 93 | 87 | 136 | **273** | **294** | **468** | **>500** | **>500** |
| | 1673 | 89 | 89 | 77 | 96 | **238** | **273** | **374** | **>500** | **>500** |
| | 1674 | 73 | 101 | **390** | **412** | **454** | **455** | **320** | **>500** | **>500** |

TABLE 16-continued

| Daily Blood glucose Levels of the NOD Mice | | | | | | | | | | |
|---|---|---|---|---|---|---|---|---|---|---|
| | | Glucose Level Post-Injection (Days) | | | | | | | | |
| Group | Animal | 0 | 1 | 2 | 3 | 4 | 5 | 6 | 7 | 8 |
| | 1675 | 66 | 90 | **402** | **485** | **436** | **421** | **220** | **Died** | — |
| | 1676 | 75 | 71 | 83 | **321** | **338** | **342** | **416** | **>500** | **>500** |
| | 1677 | 78 | 67 | 79 | 196 | **332** | **378** | **441** | **>500** | **>500** |
| | 1691 | 90 | 106 | 180 | **345** | **486** | **472** | **500** | **>500** | **>500** |
| Variant 2-ATZ | 1678 | 69 | 84 | 64 | 80 | 84 | 88 | 129 | 109 | 93 |
| Fc effector null-H315A | 1679 | 87 | 88 | 72 | 91 | 58 | 64 | 109 | 72 | 87 |
| (n = 10) | 1680 | 114 | 72 | 88 | 95 | 78 | 71 | 94 | 101 | 91 |
| | 1681 | 75 | 70 | 76 | 74 | 91 | 82 | 105 | 122 | 78 |
| | 1682 | 66 | 98 | 94 | 93 | 64 | 73 | 98 | 119 | 85 |
| | 1684 | 131 | 158 | **316** | **424** | **417** | **422** | **470** | **500** | **500** |
| | 1685 | 92 | 107 | 100 | 68 | 76 | 69 | 107 | 75 | 77 |
| | 1686 | 55 | 87 | 94 | 98 | 83 | 81 | 101 | 116 | 98 |
| | 1687 | 80 | 87 | 101 | 82 | 69 | 73 | 117 | 89 | 111 |
| | 1688 | 89 | 79 | 73 | 78 | 71 | 68 | 120 | 113 | 101 |

Measurements in Bold indicate a diabetic animal.

Figure 39:
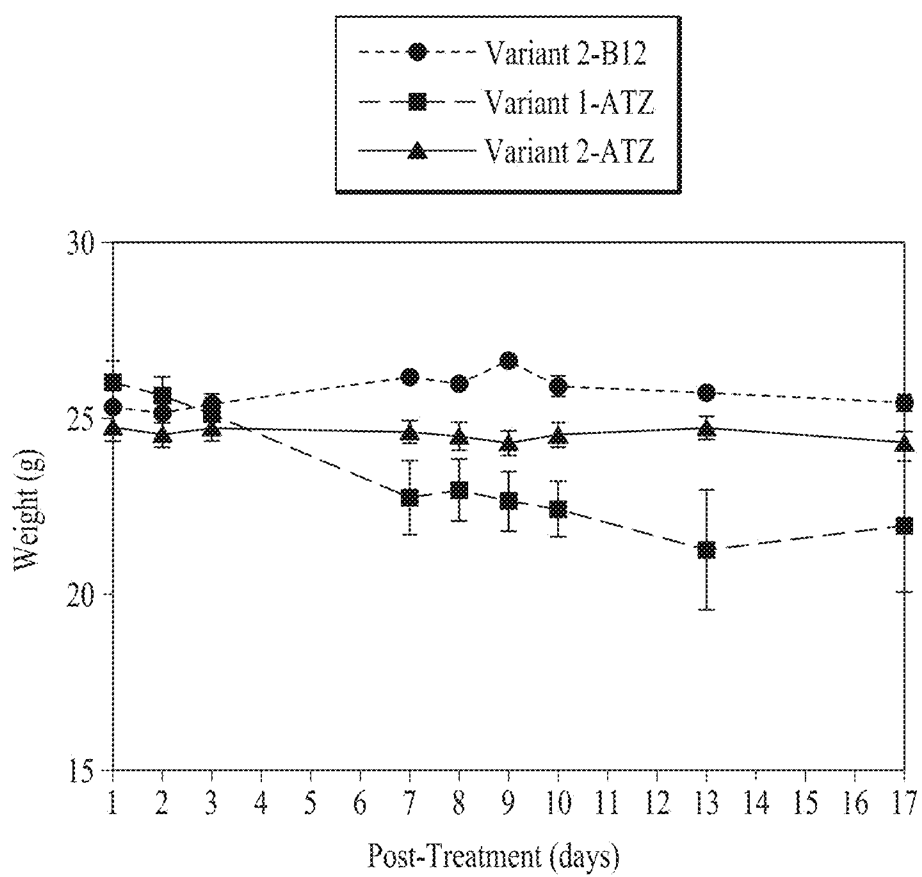
FIG. 39 shows comparison between the two modified anti-PD-L1 antibody variants, Variant 1-ATZ (Fc effector null) and 2-ATZ (Fc effector null-H311A), as well as isotype control Variant 2-B12 (an anti-B12 antibody containing the human IgG1 Fc effector null and H311A substitutions in the Fc portion corresponding to the same substitutions of Variant 2-ATZ) on change in body weight after single injection of 1.5 mg/mouse dose to 9-week-old female NOD mice.

Body weight loss was also monitored in NOD mice. As shown in Table 17 and FIG. 39, no significant change in body weight was observed during the experiment in NOD mice treated with Variant 2-ATZ (Fc effector null-H315A). This contrasts with NOD mice treated with Variant 1-ATZ (Fc effector null); the animals in this group exhibited significant degrees of body weight loss.

TABLE 17

| Percent Weight Loss from Baseline of the NOD mice | | | | | | | | | | |
|---|---|---|---|---|---|---|---|---|---|---|
| | | Percent Weight Loss Post-Injection (Days) | | | | | | | | |
| Group | Animal | 1 | 2 | 3 | 7 | 8 | 9 | 10 | 13 | 17 |
| anti-B12 hIgG1 | 1689 | 0 | −1.2 | 1.2 | 3.5 | 2.8 | 4.7 | 0.8 | 0.8 | 0.8 |
| (n = 2) | 1690 | 0 | 0.0 | −0.4 | 3.2 | 2.4 | 5.6 | 4.0 | 2.4 | 2.0 |
| Variant 1-ATZ | 1168 | 0 | 0.8 | 2.7 | 5.5 | 0.8 | 0.4 | 1.6 | −5.5 | −3.5 |
| Fc effector null | 1670 | 0 | −0.4 | −2.8 | −2.1 | −5.0 | −7.1 | −8.5 | −7.4 | −1.8 |
| (n = 10) | 1671 | 0 | 0.0 | −6.4 | −17.5 | −17.9 | <20% | −16.7 | <20% | <20% |
| | 1672 | 0 | 3.4 | 3.0 | 0.4 | 0.9 | −1.7 | 1.7 | −11.9 | −11.9 |
| | 1673 | 0 | −0.4 | −2.8 | −13.1 | −11.3 | −12.1 | −16.7 | Died | — |
| | 1674 | 0 | −2.8 | −4.0 | <20% | <20% | <20% | <20% | Died | — |
| | 1675 | 0 | −2.8 | −4.0 | Died | — | — | — | — | — |
| | 1676 | 0 | −2.6 | −2.2 | <20% | <20% | <20% | <20% | Died | — |
| | 1677 | 0 | −4.8 | 0.0 | <20% | −15.5 | −16.7 | −16.7 | Died | — |
| | 1691 | 0 | −0.8 | −5.2 | −9.6 | −5.6 | −9.2 | −9.2 | <20% | <20% |
| Variant 2-ATZ | 1678 | 0 | 1.6 | 1.6 | 3.7 | 2.1 | 3.3 | 1.6 | 4.1 | 3.3 |
| Fc effector null-H315A | 1679 | 0 | 1.3 | 2.6 | 2.6 | 3.9 | 4.3 | 7.4 | 6.1 | 5.7 |
| (N = 10) | 1680 | 0 | −0.8 | 0.4 | −1.5 | −1.5 | −6.0 | −.4 | −1.1 | −4.5 |
| | 1681 | 0 | −4.8 | −6.0 | −8.3 | −10.3 | −8.7 | −3.6 | −0.8 | −1.6 |
| | 1682 | 0 | 0.4 | 0.8 | −2.3 | −2.0 | −3.9 | −0.8 | −4.3 | −4.3 |
| | 1684 | 0 | −4.1 | −2.3 | −3.8 | −0.8 | −1.5 | −6.4 | −6.0 | −6.4 |
| | 1685 | 0 | −0.4 | −0.4 | 2.9 | 0.8 | −0.8 | −0.8 | 1.7 | −0.8 |
| | 1686 | 0 | −0.4 | 0.0 | 0.8 | 0.4 | 0.8 | −1.2 | 4.0 | 0.0 |
| | 1687 | 0 | 0.9 | 3.4 | 3.4 | −0.9 | −2.2 | −1.7 | −0.4 | −2.6 |
| | 1688 | 0 | −2.1 | −0.8 | −1.7 | −1.7 | −2.9 | −3.3 | −2.9 | −5.0 |

The only difference between the two anti-PD-L1 antibody variants tested in this study is the H315A single-point mutation on the Fc portion of the antibody, which accelerates antibody clearance from the circulation. The two antibody variants show the same effective dose range in AD and dementia mouse models, and similar effect on peripheral immune activity as reflected by the elevated frequencies of PD-1 expressing memory T-cells in the blood. It is thus suggested that the short exposure time of the Variant 2-ATZ (Fc effector null-H315A) antibody, sufficient for resulting in a beneficial effect in AD and dementia mouse models, is not sufficient to induce autoimmune diabetics in susceptible NOD mice while 80% of the NOD mice developed diabetes upon treatment with the null only variants that exhibit much slower clearance rate. While for treating cancer, the aim is to maintain a constant exposure to the antibody along the treatment period, for AD and dementia a single administration evokes a cascade of self-perpetuating events in the periphery and in the brain that after initiation are not dependent on the levels of antibody in the periphery. Thus, the dosing regimen in AD is determined by the kinetics of the downstream events regardless of the exposure time of the antibody. The mechanism of action of anti-PD-L1 antibody in reducing AD and dementia pathologies enables the use of an antibody with fast clearance properties which makes it safer in terms of immune-related adverse events but without hampering its efficacy.

In closing, it is to be understood that, although aspects of the present specification are highlighted by referring to specific embodiments, one skilled in the art will readily appreciate that these disclosed embodiments are only illustrative of the principles of the subject matter disclosed herein. The specific embodiments are not intended to be exhaustive or to limit the invention to the precise forms disclosed. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the scope of the invention is not to be limited by this detailed description. Furthermore, it is intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified, thus fulfilling the written description of all Markush groups used in the appended claims.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as, e.g., "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising", variations thereof such as, e.g., "comprise" and "comprises", and equivalent open-ended transitional phrases thereof like "including," "containing" and "having", encompass all the expressly recited elements, limitations, steps, integers, and/or features alone or in combination with unrecited subject matter; the named elements, limitations, steps, integers, and/or features are essential, but other unnamed elements, limitations, steps, integers, and/or features may be added and still form a construct within the scope of the claim.

Specific embodiments disclosed herein may be further limited in the claims using the closed-ended transitional phrases "consisting of" or "consisting essentially of" (or variations thereof such as, e.g., "consist of", "consists of", "consist essentially of", and "consists essentially of") in lieu of or as an amendment for "comprising." When used in the claims, whether as filed or added per amendment, the closed-ended transitional phrase "consisting of" excludes any element, limitation, step, integer, or feature not expressly recited in the claims. The closed-ended transitional phrase "consisting essentially of" limits the scope of a claim to the expressly recited elements, limitations, steps, integers, and/or features and any other elements, limitations, steps, integers, and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps, integers, and/or features specifically recited in the claim, whereas the meaning of the closed-ended transitional phrase "consisting essentially of" is being defined as only including those elements, limitations, steps, integers, and/or features specifically recited in the claim and those elements, limitations, steps, integers, and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such, the embodiments described herein or so claimed with the phrase "comprising" expressly and unambiguously provide description, enablement and support for the phrases "consisting essentially of" and "consisting of."

All patents, patent publications, and other references cited and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard is or should be construed as an admission that the inventors are not entitled to antedate such disclosure by virtue of prior invention or for any other reason. All statements as to the date or representation as to the contents of these documents are based on the information available to the applicant and do not constitute any admission as to the correctness of the dates or contents of these documents.

Lastly, the terminology used herein is for the purpose of describing particular embodiments only and is not intended to limit the scope of the present invention, which is defined solely by the claims. Accordingly, the present invention is not limited to that precisely as shown and described.

The invention claimed is:

1. A modified anti-Programmed Death Ligand 1 (PD-L1) antibody, comprising a heavy chain comprising a heavy chain variable region including a CDR1 of SEQ ID NO: 3 or SEQ ID NO: 4, a CDR2 of SEQ ID NO: 5 or SEQ ID NO: 6, and a CDR3 of SEQ ID NO: 7 or SEQ ID NO: 8, and a heavy chain constant region of SEQ ID NO: 55; and a light chain comprising a light chain variable region including CDR1 of SEQ ID NO: 10 or SEQ ID NO: 11, a CDR2 of SEQ ID NO: 12 or SEQ ID NO: 13 and a CDR3 of SEQ ID NO: 14 or SEQ ID NO 15.

2. The modified anti-PD-L1 antibody according to claim 1, wherein the heavy chain variable region is SEQ ID NO: 2.

3. The modified anti-PD-L1 antibody according to claim 2, wherein the heavy chain is SEQ ID NO: 42.

4. The modified anti-PD-L1 antibody according to claim 1, wherein the light chain variable region is SEQ ID NO: 9.

5. The modified anti-PD-L1 antibody according to claim 1, wherein the light chain further comprises a kappa light chain constant region.

6. The modified anti-PD-L1 antibody according to claim 5, wherein the kappa light chain constant region is SEQ ID NO: 16.

7. The modified anti-PD-L1 antibody according to claim 1, wherein the light chain is SEQ ID NO: 21.

8. A pharmaceutical kit comprising a modified anti-PD-L1 antibody as defined in claim 1.

9. A pharmaceutical composition comprising a modified anti-PD-L1 antibody as defined in claim 1.

10. A pharmaceutical kit comprising a pharmaceutical composition as defined in claim 9.

11. A modified anti-Programmed Death Ligand 1 (PD-L1) antibody comprising a heavy chain comprising a heavy chain variable region of SEQ ID NO: 2 and a heavy chain constant region of SEQ ID NO: 55; and a light chain comprising a light chain variable region of SEQ ID NO: 9 and a light chain constant region of SEQ ID NO: 16.

12. The modified anti-PD-L1 antibody according to claim 11, wherein the heavy chain is SEQ ID NO: 42.

13. A pharmaceutical kit comprising a modified anti-PD-L1 antibody as defined in claim 11.

14. A pharmaceutical composition comprising a modified anti-PD-L1 antibody as defined in claim 11.

15. A pharmaceutical kit comprising a pharmaceutical composition as defined in claim 14.

16. A modified anti-Programmed Death Ligand 1 (PD-L1) antibody comprising a heavy chain of SEQ ID NO: 42 and a light chain of SEQ ID NO: 21.

17. A pharmaceutical kit comprising a modified anti-PD-L1 antibody as defined in claim 16.

18. A pharmaceutical composition comprising a modified anti-PD-L1 antibody as defined in claim 16.

19. A pharmaceutical kit comprising a pharmaceutical composition as defined in claim 18.

* * * * *